United States Patent [19]

Yuan et al.

[11] Patent Number: 6,083,735
[45] Date of Patent: Jul. 4, 2000

[54] PROGRAMMED CELL DEATH GENES AND PROTEINS

[75] Inventors: Junying Yuan, Newton; Masayuki Miura, Waltham, both of Mass.

[73] Assignee: The General Hospital Corporation, Boston, Mass.

[21] Appl. No.: 08/258,287

[22] Filed: Jun. 10, 1994

Related U.S. Application Data

[63] Continuation-in-part of application No. 08/080,850, Jun. 24, 1993, abandoned.

[51] Int. Cl.$^7$ ..................................................... C12N 9/64
[52] U.S. Cl. .................. 435/226; 435/320.1; 435/252.3; 424/94.67; 530/350; 536/23.2; 536/23.5
[58] Field of Search .......................... 424/94.67; 435/226, 435/320.1, 240.1, 252.3; 536/23.2, 23.5; 530/350

[56] References Cited

U.S. PATENT DOCUMENTS

5,360,893  11/1994  Owens et al. ............................ 530/350

FOREIGN PATENT DOCUMENTS

| 0 533 350 A1 | 3/1993 | European Pat. Off. . |
| WO 91/15577 | 10/1991 | WIPO . |
| WO 93/05071 | 3/1993 | WIPO . |
| Wo 93/11246 | 6/1993 | WIPO . |
| WO 93/25685 | 12/1993 | WIPO . |
| WO 93/25694 | 12/1993 | WIPO . |
| WO 96/00297 | 1/1996 | WIPO . |

OTHER PUBLICATIONS

Dinarello, C.A., "Interleukin–1$^a$," *Ann N.Y. Acad. Sci.*, 546:122–132 (Dec. 1998).
Sarih, M., et al., "Silica induces apoptosis in macrophages and the release of interleukin–1α and interleukin–1β," *J. Leukoc. Biol.*, 54(3):407–413 (Nov. 1993).
Zychlinsky, A., et al., "Interleukin–1 is released by Murine Macrophages during Apoptosis Induced by *Shigella flexneri*," *J. Clin. Invest.*, 94(3):1328–1332 (Sep. 1994).
Black, R.A., et al., "A Pre–aspertate–specific Protease from Human Leukocytes That Cleaves Pro–interleukin–1β," *J. Biol. Chem.* 264(10):5323–5326 (1989).
Bruno, S., et al., "Inhibitors of Proteases Prevent Endonucleolysis Accompanying Apoptotic Death of HL–60 Leukemic Cells and Normal Thymocytes," *Leukemia* 6(11):1113–1120 (Nov. 1992).
Hockenbery, D., et al., "Bcl–2 is an inner mitochondrial membrane protein that blocks programmed cell death," *Nature* 348:334–336 (1990).
Komiya, T., et al., "Inhibition of Interleukin–1β Converting Enzyme by the Cowpox Virus Serpin CrmA," *J. Biol. Chem.* 269(30):19331–19337 (Jul. 1994).
Tewari, M., and Dixit, V.M., "Fas– and Tumor Necrosis Factor–induced Apoptosis Is Inhibited by the Poxvirus crmA Gene Product," *J. Biol. Chem.* 270(7):3255–3260 (Feb. 1995).

International Search Report for Patent Application No. PCT/US94/06630 (attached cited reference: UEMBL, Accession No. D28492 and D10713, issued Jun. 4, 1994, Kumar et al., "Mouse mRNA for Nedd2 protein"; sequence).
Barinaga, M., "Cell Suicide: By ICE, Not Fire," *Science* 263:754–756 (Feb. 1994).
Barinaga, M., "Death Gives Birth ot the Nervous System. But How?," *Science* 259:762–763 (Feb. 1993).
Bhakdi, S., et al., "Effects of *Escherichia coli* Hemolysin on Human Monocytes. Cytocidal Action and Stimulation of Interleukin 1 Release," *J. Clin. Invest.* 85:1746–1753 (1990).
Black, R.A. et al., "Activation of interleukin–1β by a co–induced protease," *FEBS Letters* 247(2):386–390 (1989).
Cerretti, D.P. et al., "Molecular Cloning of the Interleukin–1β Converting Enzyme," *Science* 256:97–100 (Apr. 3, 1992).
Edgington, S.M., "Looking Death In The Eye: Apoptosis And Cancer Research," *Bio/Technology* 11:787–792 (Jul. 1993).
Ellis, H.M. et al., "Genetic Control of Programmed Cell Death in the Nematode C. elegans," *Cell* 44:817–829 (1986).
Ellis, R.E. et al., "Genes Required for the Engulfment of Cell Corpses During Programmed Cell Death in *Caenorhabditis elegans*," *Genetics* 129:79–94 (1991).
Ellis, R.E. et al., "Two C. elegans genes control the programmed deaths of specific cells in the pharynx," *Development* 112:591–603 (1991).
Gagliardini, V. et al., "Prevention of Vertebrate Neuronal Death by the crmA Gene," *Science* 263:826–828 (Feb. 1994).
Hengartner, M.O. et al., "*Caenorhabditis elegans* gene ced–9 protects cells from programmed cell death," *Nature* 356:494–499 (Apr. 9, 1992).
Hodgson, C.P., "The Vector Void in Gene Therapy," *Bio/Technology* 13:222–225 (Mar. 1995).
Hogquist, K.A. et al., "Interleukin 1 is processed and released during apoptosis," *Proc. Natl. Acad. Sci. USA* 88:8485–8489 (1991).
Jacobson, M.D. et al., "Bcl–2 blocks apoptosis in cells lacking mitochondrial DNA," *Nature* 361:365–369 (Jan. 28, 1993).
Kostura, M.J. et al., "Identification of a monocyte specific pre–interleukin 1β convertase activity," *Proc. Natl. Acad. Sci. USA* 86:5227–5231 (1989).

(List continued on next page.)

*Primary Examiner*—Karen Cochrane Carlson
*Assistant Examiner*—Enrique D. Longton
*Attorney, Agent, or Firm*—Sterne, Kessler, Goldstein & Fox

[57] ABSTRACT

This invention relates to proteins encoded by the cell death genes that are involved in regulating programmed cell death. In particular, the invention describes the cell death protein Ich-1 (Caspase-2) and its alternative splicing products Ich-$1_L$ and Ich-$1_S$. Methods for controlling programmed cell death by regulating the activity of the cell death gene products are also described.

6 Claims, 54 Drawing Sheets

OTHER PUBLICATIONS

Kumar, S. et al., "Identification of a Set of Genes with Developmentally Down–Regulated Expression in the Moues Brain," *Biochem. Biophys. Res. Comm.* 185(3):1155–1161 (Jun. 1992).

Marx, J., "Cell Death Studies Yield Cancer Clues," *Science* 259:760–761 (Feb. 1993).

Miura, M. et al., "Induction of Apoptosis in Fibroblasts by IL–1β–Converting Enzyme, a Mammalian Homolog of the C. elegans Cell Death Gene ced–3," *Cell* 75:653–660 (Nov. 1993).

Miura, M. et al., "Tumor necrosis factor–induced apoptosis is mediated by a CrmA–sensitive cell death pathway," *Proc. Natl. Acad. Sci USA* 92:8318–8322 (Aug. 1995).

Nett, M.A. et al., "Molecular Cloning Of The Murine IL–1β Converting Enzyme cDNA," *J. Immunol.* 149(10):3254–3259 (Nov. 15, 1992).

Nuñez, G. et al., "Deregulated Bcl–2 Gene Expression Selectively Prolongs Survival Of Growth Factor–Deprived Hemopoietic Cell Lines," *J. Immunol.* 144(9)3602–3610 (1990).

Oltvai, Z.N. et al., "Bcl–2 Heterodimerizes In Vivo with a Conserved Homolog, Bax, That Accelerates Programed Cell Death," *Cell* 74:609–619 (Aug. 1993).

Ray, C.A. et al., "Viral Inhibition of Inflammation: Cowpox Virus Encodes an Inhibitor of the Interleukin–1β Converting Enzyme," *Cell* 69:597–604 (May 15, 1992).

Sentman, C.L. et al., "bcl–2 Inhibits Multiple Forms of Apoptosis but Not Negative Selection in Thymocytes," *Cell* 67:879–888 (1991).

Strasser, A. et al., "bcl–2 Transgene Inhibits T Cell Death and Perturbs Thymic Self–Censorship," *Cell* 67:889–899 (1991).

Thornberry, N.A. et al., "A novel heterodimeric cysteine protease is required for interleukin–1β processing in monocytes," *Nature* 356:768–774 (Apr. 30, 1992).

Ulhmann, E. and Peyman, A., "Antisense Oligonucleotides: A New Therapeutic Principle," *Chem. Rev.* 90(4):544–584 (1990).

Vaux, D.L. et al., "Prevention of Programmed Cell Death in *Caenorhabditis elegans* by Human bcl–2," *Science* 258:1955–1957 (Dec. 18, 1992).

Wang, L. et al., "Ich–1, an IceIced–3–Related Gene, Encodes Both Positive and Negative Regulators of Programmed Cell Death," *Cell* 78:739–750 (Sep. 1994).

Yuan, J. et al., "The *Caenorhabditis elegans* cell death gene ced–4 encodes a novel protein and is expressed during the period of extensive programmed cell death," *Development* 116:309–320 (Oct. 1992).

Yuan, J. et al., "The *Caenorhbditis elegans* Genes ced–3 and ced–4 Act Cell Autonomously to Cause Programmed Cell Death," *Developmental Biology* 138:33–41 (1990).

Yuan, J. et al., "The C. elegans Cell Death Gene ced–3 Encodes a Protein Similar to Mammalian Interleukin–1β–Converting Enzyme," *Cell* 75:641–652 (Nov. 1993).

```
   1  AGATCTGAAATAAGGTGATAAATTAATAAATTAAGTGTATTTCTGAGGAAATTTGACTGT
  61  TTTAGCACAATTAATCTTGTTTCAGAAAAAAAGTCCAGTTTTCTAGATTTTTCCGTCTTA
 121  TTGTCGAATTAATATCCCTATTATCACTTTTTCATGCTCATCCTCGAGCGGCACGTCCTC
 181  AAAGAATTGTGAGAGCAAACGCGCTCCCATTGACCTCCACACTCAGCCGCCAAAACAAAC
 241  GTTCGAACATTCGTGTGTTGTGCTCCTTTTCCGTTATCTTGCAGTCATCTTTTGTCGTTT
 301  TTTTCTTTGTTCTTTTTGTTGAACGTGTTGCTAAGCAATTATTACATCAATTGAAGAAAA
 361  GGCTCGCCGATTTATTGTTGCCAGAAAGATTCTGAGATTCTCGAAGTCGATTTTATAATA
 421  TTTAACCTTGGTTTTTGCATTGTTTCGTTTAAAAAAACCACTGTTTATGTGAAAAACGAT
 481  TAGTTTACTAATAAAACTACTTTTAAACCTTTACCTTTACCTCACCGCTCCGTGTTCATG
 541  GCTCATAGATTTTCGATACTCAAATCCAAAAATAAATTTACGAGGGCAATTAATGTGAAA
 601  CAAAAACAATCCTAAGATTTCCACATGTTTGACCTCTCCGGCACCTTCTTCCTTAGCCCC
 661  ACCACTCCATCACCTCTTTGGCGGTGTTCTTCGAAACCCACTTAGGAAAGCAGTGTGTAT
 721  CTCATTTGGTATGCTCTTTTCGATTTTATAGCTCTTTGTCGCAATTTCAATGCTTTAAAC
 781  AATCCAAATCGCATTATATTTGTGCATGGAGGCAAATGACGGGGTTGGAATCTTAGATGA
 841  GATCAGGAGCTTTCAGGGTAAACGCCCGGTTCATTTTGTACCACATTTCATCATTTTCCT
 901  GTCGTCCTTGGTATCCTCAACTTGTCCCGGTTTTGTTTTCGGTACACTCTTCCGTGATGC
 961  CACCTGTCTCCGTCTCAATTATCGTTTAGAAATGTGAACTGTCCAGATGGGTGACTCATA
1021  TTGCTGCTGCTACAATCCACTTTCTTTTCTCATCGGCAGTCTTACGAGCCCATCATAAAC
1081  TTTTTTTCCGCGAAATTTGCAATAAACCGGCCAAAAACTTTCTCCAAATTGTTACGCAA
1141  TATATACAATCCATAAGAATATCTTCTCAATGTTTATGATTTCTTCGCAGCACTTTCTCT
1201  TCGTGTGCTAACATCTTATTTTTATAATATTTCCGCTAAAATTCCGATTTTTGAGTATTA
1261  ATTTATCGTAAAATTATCATAATAGCACCGAAAACTACTAAAAATGGTAAAAGCTCCTTT
                                                            Repeat 1a
                                     ─────────────────────────────────
1321  TAAATCGGCTCGACATTATCGTATTAAGGAATCACAAAATTCTGAGAATGCGTACTGCGC ─────────────────────────────────────────────────────────────
1381  AACATATTTGACGGCAAAATATCTCGTAGCGAAAACTACAGTAATTCTTTAAATGACTAC
                                                        <  Repeat 1a
      ────────────────────────────────>    ─────────────────────
1441  TGTAGCGCTTGTGTCGATTTACGGGCTCAATTTTTGAAAATAATTTTTTTTTTCGAATTT ─────────────────────────────────────────────────────────────
1501  TGATAACCCGTAAATCGTCACAACGCTACAGTAGTCATTTAAAGGATTACTGTAGTTCTA
```

FIG.2A

1561 GCTACGAGATATTTTGCGCGCCAAATATGACTGTAATACGCATTCTCTGAATTTTGTGTT
1621 TCCGTAATAATTTCACAAGATTTTGGCATTCCACTTTAAAGGCGCACAGGATTTATTCCA
1681 ATGGGTCTCGGCACGCAAAAAGTTTGATAGACTTTTAAATTCTCCTTGCATTTTTAATTC
1741 AATTACTAAAATTTTCGTGAATTTTTCTGTTAAAATTTTTAAAATCAGTTTTCTAATATT
1801 TTCCAGGCTGACAAACAGAAACAAAAACACAACAAACATTTTAAAAATCAGTTTTCAAAT
1861 TAAAAATAACGATTTCTCATTGAAAATTGTGTTTTATGTTTGCGAAAATAAAAGAGAACT
1921 GATTCAAAACAATTTTAACAAAAAAAAAACCCCAAAATTCGCCAGAAATCAAGATAAAAAA
1981 TTCAAGAGGGTCAAAATTTTCCGATTTTACTGACTTTCACCTTTTTTTTCGTAGTTCAGT
2041 GCAGTTGTTGGAGTTTTTGACGAAAACTAGGAAAAAAATCGATAAAAATTACTCAAATCG
2101 AGCTGAATTTTGAGGACAATGTTTAAAAAAAAACACTATTTTTCCAATAATTTCACTCAT

2161 `TTTC`AGACTAAATCGAAAATCAAATCGTACTCTGACTACGGGTCAGTAGAGAGGTCAACC
         ▼
2221 ATCAGCCGAAGATGATGCGTCAAGATAGAAGGAGCTTGCTAGAGAGGAACATTATGATGT
              M M R Q D R R S L L E R N I M M F
              1                              10
                        T(n1060)
2281 TCTCTAGTCATCTAAAAGTCGATGAAATTCTCGAAGTTCTCATCGCAAAACAAGTGTTGA
      S S H L K V D E I L E V L I A K Q V L N
          20                    30
2341 ATAGTGATAATGGAGATATGATTAATGTGAGTTTTTAATCGAATAATAATTTTAAAAAAA
      S D N G D M I N
              40
2401 AATTGATAATATAAAGAATATTTTTGCAGTCATGTGGAACGGTTCGCGAGAAGAGACGGG
                            S C G T V R E K R R E
                                           50
                   A(n716)
2461 AGATCGTGAAAGCAGTGCAACGACGGGGAGATGTGGCGTTCGACGCGTTTTATGATGCTC
      I V K A V Q R R G D V A F D A F Y D A L
          60                    70
2521 TTCGCTCTACGGGACACGAAGGACTTGCTGAAGTTCTTGAACCTCTCGCCAGATCGTAGG
      R S T G H E G L A E V L E P L A R S
          80                    90
2581 TTTTTAAAGTTCGGCGCAAAAGCAAGGGTCTCACGGAAAAAAGAGGCGGATCGTAATTTT
2641 GCAACCCACCGGCACGGTTTTTTCCTCCGAAAATCGGAAATTATGCACTTTCCCAAATAT
2701 TTGAAGTGAAATATATTTTATTTACTGAAAGCTCGAGTGATTATTTATTTTTTAACACTA
2761 ATTTTCGTGGCGCAAAAGGCCATTTTGTAGATTTGCCGAAAATACTTGTCACACACACAC
2821 ACACACATCTCCTTCAAATATCCCTTTTTCCAGTGTTGACTCGAATGCTGTCGAATTCGA
                                            V D S N A V E F E
                                                         100
2881 GTGTCCAATGTCACCGGCAAGCCATCGTCGGAGCCGCGCATTGAGCCCCGCCGGCTACAC
      C P M S P A S H R R S R A L S P A G Y T

FIG.2B

```
2941 TTCACCGACCCGAGTTCACCGTGACAGCGTCTCTTCAGTGTCATCATTCACTTCTTATCA
      S  P  T  R  V  H  R  D  S  V  S  S  V  S  S  F  T  S  Y  Q
                       130                           140
3001 GGATATCTACTCAAGAGCAAGATCTCGTTCTCGATCGCGTGCACTTCATTCATCGGATCG
      D  I  Y  S  R  A  R  S  R  S  R  S  R  A  L  H  S  S  D  R
                       150                           160
3061 ACACAATTATTCATCTCCTCCAGTCAACGCATTTCCCAGCCAACCTTCTATGTTGATGCG
      H  N  Y  S  S  P  P  V  N  A  F  P  S  Q  P  S
         Repeat 1b     170
3121 AACACTAAATTCTGAGAATGCGCATTACTCAACATATTTGACGCGCAAATATCTCGTAGC
3181 GAAAAATACAGTAACCCTTTAAATGACTATTGTAGTGTCGATTTACGGGCTCGATTTTCG
     ―――>
3241 AAACGAATATATGCTCGAATTGTGACAACGAATTTTAATTTGTCATTTTTGTGTTTTCTT
                          <       Repeat 1b
3301 TTGATATTTTTGATCAATTAATAAATTATTTCCGTAAACAGACACCAGCGCTACAGTACT
3361 CTTTTAAAGAGTTACAGTAGTTTTCGCTTCAAGATATTTGAAAAGAATTTTAAACATTT
3421 TGAAAAAAAATCATCTAACATGTGCCAAAACGCTTTTTTCAAGTTTCGCAGATTTTTTGA
                           Repeat 2
3481 TTTTTTTCATTCAAGATATGCTTATTAACACATATAATTATCATTAATGTGAATTTCTTG
3541 TAGAAATTTTGGGCTTTTCGTTCTAGTATGCTCTACTTTTGAAATTGCTCAACGAAAAAA
3601 TCATGTGGTTTGTTCATATGAATGACGAAAAATAGCAATTTTTTATATATTTTCCCCTAT
3661 TCATGTTGTGCAGAAAAATAGTAAAAAAGCGCATGCATTTTTCGACATTTTTTACATCGA
     ―――――――――――――――――――――――――――――――――――――――――――――――――――――――――
                                                            ―――>
3721 ACGACAGCTCACTTCACATGCTGAAGACGAGAGACGCGGAGAAATACCACACATCTTTCT
         <     Repeat 2
3781 GCGTCTCTCGTCTTCAGCATGTGAAATGGGATCTCGGTCGATGTAAAAAAATGTCGAATA
3841 ATGTAAAAAATGCATGCGTTTTTTTACACTTTTCTGCACAAATGAATAGGGGGAAAATGT
3901 ATTAAAATACATTTTTTGTATTTTTCAACATCACATGATTAACCCCATTATTTTTTCGTT
3961 GAGCAACTTAAAAAGTAGAGAATATTAGAGCGAAAACCAAAATTTCTTCAAGATATTACC
4021 TTTATTGATAATTATAGATGTTAATAAGCATATCTTGAATGAAAGTCAGCAAAAATATGT
4081 GCGAAACACCTGAAAAAAAATCAAAAATTCTGCGAAAATTGAAAAAATGCATTAAAATACA
4141 TTTTTGCATTTTTCTACATCACATGAATGTAGAAAATTAAAAGGGAAATCAAAATTTCTA
4201 GAGGATATAATTGAATGAAACATTGCCGAAATTAAAATGTGCGAAACGTCAAAAAAGAGGA
4261 AATTTGGGTATCAAAATCGATCCTAAAACCAACACATTTCAGCATCCGCCAACTCTTCAT
                                                       S  A  N  S  S  F
                                                                   180
4321 TCACCGGATGCTCTTCTCTCGGATACAGTTCAAGTCGTAATCGCTCATTCAGCAAAGCTT
      T  G  C  S  S  L  G  Y  S  S  S  R  N  R  S  F  S  K  A  S
                       190                           200
4381 CTGGACCAACTCAATACATATTCCATGAAGAGGATATGAACTTTGTCGATGCACCAACCA
      G  P  T  Q  Y  I  F  H  E  E  D  M  N  F  V  D  A  P  T  I
                       210                           220
4441 TAAGCCGTGTTTTCGACGAGAAAACCATGTACAGAAACTTCTCGAGTCCTCGTGGAATGT
      S  R  V  F  D  E  K  T  M  Y  R  N  F  S  S  P  R  G  M  C
                       230                           240
4501 GCCTCATCATAAATAATGAACACTTTGAGCAGATGCCAACACGGAATGGTACCAAGGCCG
      L  I  I  N  N  E  H  F  E  Q  M  P  T  R  N  G  T  K  A  D
                       250                           260
```

FIG.2C

```
4561 ACAAGGACAATCTTACCAATTTGTTCAGATGCATGGCTATACGGTTATTTGCAAGGACA
      K  D  N  L  T  N  L  F  R  C  M  G  Y  T  V  I  C  K  D  N
               270                         280
4621 ATCTGACGGGAAGGGTACGGCGAAATTATATTACCCAAACGCGAAATTTGCCATTTTGCG
      L  T  G  R
                    ——————Repeat 3——————————>
4681 CCGAAAATGTGGCGCCCGGTCTCGACACGACAATTTGTGTTAAATGCAAAAATGTATAAT
4741 TTTGCAAAAAACAAAATTTTGAACTTCCGCGAAAATGATTTACCTAGTTTCGAAATTTTC
4801 GTTTTTTCCGGCTACATTATGTGTTTTTTCTTAGTTTTTCTATAATATTTGATGTAAAAA
4861 ACCGTTTGTAAATTTTCAGACAATTTTCCGCATACAAAACTTGATAGCACGAAATCAATT
4921 TTCTGAATTTTCAAAATTATCCAAAAATGCACAATTTAAAATTTGTGAAAATTGGCAAAC
4981 GGTGTTTCAATATGAAATGTATTTTTAAAAACTTTAAAAACCACTCCGGAAAAGCAATAA
5041 AAATCAAAACAACGTCACAATTCAAATTCAAAAGTTATTCATCCGATTTGTTTATTTTTG
5101 CAAAATTTGAAAAAATCATGAAGGATTTAGAAAAGTTTTATAACATTTTTTCTAGATTTT
5161 TCAAAATTTTTTTTAACAAATCGAGAAAAAGAGAATGAAAAATCGATTTTAAAAATATCC
     <————Repeat 3————————————————————
5221 ACAGCTTCGAGAGTTTGAAATTACAGTACTCCTTAAAGGCGCACACCCCATTTGCATTGG
5281 ACCAAAAATTTGTCGTGTCGAGACCAGGTACCGTAGTTTTTGTCGCAAAAATTGCACCAT
5341 TGGACAATAAACCTTCCTAATCACCAAAAAGTAAAATTGAAATCTTCGAAAAGCCAAAAA
5401 ATTCAAAAAAAAAGTCGAATTTCGATTTTTTTTTTTGGTTTTTTGGTCCCAAAAACCAAAA
5461 AAATCAATTTTCTGCAAAATACCAAAAAGAAACCCGAAAAAATTTCCCAGCCTTGTTCCT
5521 AATGTAAACTGATATTTAATTTCCAGGGAATGCTCCTGACAATTCGAGACTTTGCCAAAC
                              G  M  L  L  T  I  R  D  F  A  K  H
                                    290                      300
5581 ACGAATCACACGGAGATTCTGCCGATACTCGTGATTCTATCACACGGAGAAGAGAATGTGA
      E  S  H  G  D  S  A  I  L  V  I  L  S  H  G  E  E  N  V  I
                     310                         320
5641 TTATTGGAGTTGATGATATACCGATTAGTACACACGAGATATATGATCTTCTCAACGCGG
      I  G  V  D  D  I  P  I  S  T  H  E  I  Y  D  L  L  N  A  A
                     330                         340
                                                           A(n2433)
                                                           |
5701 CAAATGCTCCCCGTCTGGCGAATAAGCCGAAAATCGTTTTTGTGCAGGCTTGTCGAGGCG
      N  A  P  R  L  A  N  K  P  K  I  V  F  V  Q  A  C  R  G  E
                     350                         360
5761 GTTCGTTTTTTATTTTAATTTTAATATAAATATTTTAAATAAATTCATTTTCAGAACGTC
                                                            R  R
5821 GTGACAATGGATTCCCAGTCTTGGATTCTGTCGACGGAGTTCCTGCATTTCTTCGTCGTG
      D  N  G  F  P  V  L  D  S  V  D  G  V  P  A  F  L  R  R  G
                     370                         380
                                                           T(n1165)
                                                           |
5881 GATGGGACAATCGAGACGGGCCATTGTTCAATTTTCTTGGATGTGTGCGGCCGCAAGTTC
      W  D  N  R  D  G  P  L  F  N  F  L  G  C  V  R  P  Q  V  Q
                     390                         400
```

FIG.2D

5941 AGGTTGCAATTTAATTTCTTGAATGAGAATATTCCTTCAAAAAATCTAAAATAGATTTTT
6001 ATTCCAGAAAGTCCCGATCGAAAAATTGCGATATAATTACGAAATTTGTGATAAAATGAC
<u>     Repeat 4</u>
6061 AAACCAATCAGCATCGTCGATCTCCGCCCACTTCATCGGATTGGTTTGAAAGTGGGCGGA
    ─────────────────────────>
6121 GTGAATTGCTGATTGGTCGCAGTTTTCAGTTTAGAGGGAATTTAAAAATCGCCTTTTCGA 6181 AAATTAAAAATTGATTTTTTCAATTTTTTCGAAAAATATTCCGATTATTTTATATTCTTT
                                                            A(n717)
                                                              |
6241 GGAGCGAAAGCCCCGTCCTGTAAACATTTTTAAATGATAATTAATAAATTTTTGCAGCAA
            T(n1949)                                          Q
              |
6301 GTGTGGAGAAAGAAGCCGAGCCAAGCTGACATTCTGATTCGATACGCAACGACAGCTCAA
      V  W  R  K  K  P  S  Q  A  D  I  L  I  R  Y  A  T  T  A  Q
                    410                             420
            A(n1286)
              |
6361 TATGTTTCGTGGAGAAACAGTGCTCGTGGATCATGGTTCATTCAAGCCGTCTGTGAAGTG
      Y  V  S  W  R  N  S  A  R  G  S  W  F  I  Q  A  V  C  E  V
                    430                             440
            T(n11129,n1164)
              |
6421 TTCTCGACACACGCAAAGGATATGGATGTTGTTGAGCTGCTGACTGAAGTCAATAAGAAG
      F  S  T  H  A  K  D  M  D  V  V  E  L  L  T  E  V  N  K  K
                    450                             460
      T(n2430)                                                A(n2426)
        |                                                       |
6481 GTCGCTTGTGGATTTCAGACATCACAGGGATCGAATATTTTGAAACAGATGCCAGAGGTA
      V  A  C  G  F  Q  T  S  Q  G  S  N  I  L  K  Q  M  P  E
                    470                             480

FIG.2E

```
                                              Repeat 5
6541 CTTGAAACAAACAATGCATGTCTAACTTTTAAGGACACAGAAAAATAGGCAGAGGCTCCT
     ─────────────────────────▶
6601 TTTGCAAGCCTGCCGCGCGTCAACCTAGAATTTTAGTTTTTAGCTAAAATGATTGATTTT
6661 GAATATTTTATGCTAATTTTTTTGCGTTAAATTTTGAAATAGTCACTATTTATCGGGTTT
6721 CCAGTAAAAAATGTTTATTAGCCATTGGATTTTACTGAAAACGAAAATTTGTAGTTTTTC
6781 AACGAAATTTATCGATTTTTAAATGTAAAAAAAAATAGCGAAAATTACATCAACCATCAA
6841 GCATTTAAGCCAAAATTGTTAACTCATTTAAAAATTAATTCAAAGTTGTCCACGAGTATT
        ◀     Repeat 5
6901 ACACGGTTGGCGCGCGGCAAGTTTGCAAAACGACGCTCCGCCTGTTTTTCTGTGCGGCTT
                                                              T(n1163)
                                                              │
6961 GAAAACAAGGGATCGGTTTAGATTTTTCCCCAAAATTTAAATTAAATTTCAGATGACATC
                                                         M  T  S
7021 CCGCCTGCTCAAAAAGTTCTACTTTTGGCCGGAAGCACGAAACTCTGCCGTCTAAAATTC
      R  L  L  K  K  F  Y  F  W  P  E  A  R  N  S  A  V  *
         400                      500
7081 ACTCGTGATTCATTGCCCAATTGATAATTGTCTGTATCTTCTCCCCCAGTTCTCTTTCGC
7141 CCAATTAGTTTAAAACCATGTGTATATTGTTATCCTATACTCATTTCACTTTATCATTCT
7201 ATCATTTCTCTTCCCATTTTCACACATTTCCATTTCTCTACGATAATCTAAAATTATGAC
7261 GTTTGTGTCTCGAACGCATAATAATTTTAATAACTCGTTTTGAATTTGATTAGTTGTTGT
7321 GCCCAGTATATATGTATGTACTATGCTTCTATCAACAAAATAGTTTCATAGATCATCACC
7381 CCAACCCCACCAACCTACCGTACCATATTCATTTTTGCCGGGAATCAATTTCGATTAATT
7441 TTAACCTATTTTTTCGCCACAAAAAATCTAATATTTGAATTAACGAATAGCATTCCCATC
7501 TCTCCCGTGCCGGAATGCCTCCCGGCCTTTTAAAGTTCGGAACATTTGGCAATTATGTAT
7561 AAATTTGTAGGTCCCCCCCATCATTTCCCGCCCATCATCTCAAATTGCATTCTTTTTTCG
7621 CCGTGATATCCCGATTCTGGTCAGCAAAGATCT
```

FIG.2F

Repeat 1

```
              1          10         20         30         40         50         60         70
ced-3(1a,for) GTATTAA-GGAATCACAAAATTCTGAGAATGCGTACTGCCCAACATATTGACGG-CAAAATATCTCGTAGCG
ced-3(1a,rev) ------------AAAATTCAGAGAATGCGTATTACAGTC-ATATTGGCGCGCCAAAATATCTCGTAGCT
ced-3(1b,for) ------------AAATTCTGAGAATGCGCCATTACTCAACATATTGACGCGC-AAATATCTCGTAGCG
ced-3(1b,rev) ---------------------------------------------------TATCTTGAAGCG
fem-1(for)    GTATTAC-GGCAAGCAAATAATTATGAGAATGCCTATTGCCCACCATAGTTGACGCGCAAAATATCTCGTAGCG
fem-1(rev)    GTATAAC-GGTAACACACAATTCTGAGAATGCCTATTGCCACAACACATTGACGCGCAAAATATCTCGTAGCG
hlh-1(for)    CTATTAC-GGGAGTACAAAATTCTGAGAATGCCTACTGCGCCCAACATATTTGACGCGCAAAATATTTCGTATCC
hlh-1(rev)    --------GGGAGCACAAAATTCTGACTATGAGAAT-GCGTATAA---------GCACAAAATATTTCGTAGCG consensus     -TAT-A--GG-A--A-A-AATT--GA-ATG---A-T-C-----A-A-TTG-CG--CAAAATAT-T-G-A-C-

80         90         100        110        120        130        140
ced-3(1a,for) AAAACTACAGTAATTCTTAAATGACTACTGTAGCGC--------TTGTGTCGA-TTTACGGGCTCAATT------
ced-3(1a,rev) AGAACTACAGTAATCCTTAAATGACTACTGTAGCG---------TTGTGACGA-TTTACGGGTTATCAAAATTCGAAA
ced-3(1b,for) AAAA-TACAGTAACCCTTTAAATGACTATGTAG-----------TGTCGA-TTTACGGG---TCGATTTTCGAAA
ced-3(2b,rev) AAAACTACTGTAACTCTTAAAAGAGTACTGTAGCGC--------TGGTGTCTG-TTTACGGAAATAATT------
fem-1(for)    AAAACTACAGTAACTCTTTGAATGACTACTGTAGCGC-------TTGTTTCGA-TTTACGGGCTCGTT-------
fem-1(rev)    AAAACTACAGTGATTCGCTGAATGAATACGGTAGGGTCC-------------------------
hlh-1(for)    AAAACTACAGTAATTCGTTTATTGGCTACTGT-GCG--------TGTTGA-TTTACGGGC---------
hlh-1(rev)    AAAACTACAGTAATTGTCAAGGGACTACTGTAGCTAGCG-CTCGTGTCGA-TTTACGGAGC-TCGATTTT----- consensus     A--AACTAC-GT-A-----A-G--TA-GTAG-------T-GT-------TTTACGG----------TT-GAAA
```

FIG. 2G

Repeat 2

```
                1         10        20        30        40        50        60        70        80
ced-3(for)      TCATTCAAGATATGCTTATTAACACATATAATTATCATTAATGTGAATTCTTGTAGAAATTTTGGGCTTTTCGTTCTAG
ced-3(rev)      TCATTCAAGATATGCTTATTAACATCTATAATTATCATAAGGTAATATCTTGAAGAAATTTTGG--TTTTCGCTCTAA consensus       TCATTCAAGATATGCTTATTAACA--TATAATTATCA-TAA-G--AAT-TCTTG-AGAAATTTTGG--TTTTCG-TCTA- 90       100       110       120       130       140       150       160
ced-3(for)      TATGCTCTACTTTTGAAATGCTCAACGAAAAAAT-----------------CATGTGTTTGTTCATATGAATGACGAAAAATA
ced-3(rev)      TATTCTCTACTTTTTTAAGTTGCTCAACGAAAAAAATAATGGGTTAATCATGTG----------------ATGTGAAAAATA consensus       TAT-CTCTACTTTT--AA-TGCTCAACGAAAAAAT------------------CATGTG------------ATG--GAAAAATA 170       180       190       200       210       220       230       240
ced-3(for)      GCAA------T-TTTTATATATTT-CCCCTATTCATGTGTGCAGAAAAATAGTAAAAAAGCGCATGCATTTT------
ced-3(rev)      CAAAAAATGTATTTAATACATTTCCCCCTATTCAT-TTGTCAGAAAGT-GTAAAAAAACCATGCATTTTTTACAT consensus       --AA------T-TTTT-ATA-ATTTT-CCCCTATTCAT-TTGTCAGAAAA-T-GTAAAAAAA-CCATGCATTTTT---

250       260       270       280       290
ced-3(for)      ------CGACA-TTTTTTACATCGAACGACAGCTCACTTCACATGCTGAAGACGAGAGACG
ced-3(for)      TATTCGACATTTTTTACATCGACCGAGATCCCATTCACATGCTGAAGACGAGAGACG consensus       ------CGACA-TTTTTTACATCGA-CGA-A-C-CA-TTCACATGCTGAAGACGAGAGACG
```

FIG.2H

Repeat 3

```
                1         10        20        30        40        50        60
    ced-3(for)  CAGCTTCGAGAGTTTG-AAATTACAGTACTCCTTAAAGGCGCACACCCCATTTGCATTGG
    ced-3(rev)  ------------------------------------------------------------
    lin-12(for) CAGCAACAAATGTTTG-AAATTACAGTAATCTTTAAAGGCGCACACC-------------
    lin-12(rev) ------------------------------------------------------------
    B0303(1)    CTGCAACGAAAGTCTG-AAATTACAGTACCCCTTAAAGGCGCATA---------------
    B0303(2)    ------------GTTAG-AAACTAGAGTACCTCTTAAAGGCGCACAT—CCTTTCCCACCT
    ZK643(1)    CAGCAACAAAAGTTTG-AAATTACAGTGCTCTTAAAAGGCACACACC-TTTTTACATT-T
    ZK643(2,for)CAGAAGCGAAAATTTG-AAATTACAGTACTCTTTAAACGCTCAA-CCCCGTTTCTATTCA
    ZK643(2,rev)------GATTGTT-GAAAATTACAGTAATCTTTAAAGGCGCACACA-CGTTTGTATTTT
    ZK643(3)    ------------------------------------------------------------
    glp-1(for)  ------------TTTTTAAACTACAGTACTCTTTAGGAGCGCACA---TTTTTTCGCATTT
    glp-1(rev)  --------ACCGTTTG-AAACTACAGTACTCTTTAAAGGCGC------------------
    consensus   C-G----C------T-----AAA-TA-AGT------TTA---GC-CA-A---------TTT--------

70        80        90        100       110
    ced-3(for)  ACCAAAAATTTGTCGTGTCGAGA-CCAGGTA-CCGTAGTTTTTG-TC-------GCAAA
    ced-3(rev)  ---ACAAA-TTGTCGTGTCGAGA-CCGGGCG-CCACA-----------------------
    lin-12(for) ------------------------------------------------------------
    lin-12(rev) AACAAAACTTTGTCGTGTCGAGA-CCGGGTA-CCGTATTTTTAATT-------GCAAA
    B0303(1)    ------------------------------------------------------------
    B0303(2)    ATCGAAAATTTGTCGTGTCGAGA-CCGGGTAGC-TAATTTTATGC-CAAAAA-------
    ZK643(1)    AACAAAAAAGTGTCGCTTCGAGA-CCGGGTA-CCGTGTTTTTGGCGCAAAAATCGCTAT
    ZK643(2,for)ATAGAAAG-TTGTCGTTTCGAGA-CCGGACA-CCGTATTTTTGGCGCAAAATATACCTG
    ZK643(2,rev)ACAGAAAA-TTCTCGTTTCGAGA-CCGAACA-CAGTATTTTTGGCGGAGAAATTCTAAA
    ZK643(3)    -------TTTGTCGTGTCGAGA-CCTGG--------------------------------
    glp-1(for)  AACAAATTTTTGTCGTGGCGAGA-CCTGATA-CCGTATTTTTAGGTCAAGATTACTAGG
    glp-1(rev)  -------GTTTGTCGT--------------------------------------------
    consensus   A----A----T-TCG---CGAGA-CC-------C------TTT--------A--A----
```

FIG.21

Repeat 4

```
              1         10        20        30        40        50        60        70
ced-3         AACCAATCAGCATCGTCGATCTCCGCCCCACTTCATCGGATTGGTTTGAAAGTGGGGGAGTGAATTGCTGATTGGTC
lin-12        AACCAATTAGGGACTTCGGAATTTCCATACTTAATCTGATTGGTTGAAGAATGGGCAGACGGAATTGCTGATTGGCC consensus     AACCAAT-AGC--C-TCG---T--C--ACTT-ATC-GATTGGTT--A-A-TGGGC-GAG-GAATTGCTGATTGG-C
```

FIG. 2J

Repeat 5

```
              1         10        20        30        40        50        60
ced-3(for)    TTTTAAG-GACACAGAAAAATAGGCAGAGGCTCCTTTGCAAGCCTGCCGGCGTCAACC
ced-3(rev)    TTTCAAGCCGCACAGAAAAAGAGGCGGAGCGTCGTTTGCAAACTTGCCGGCGCCAACC consensus     TTT-AAG----CACAGAAAAA-AGGC-GAG---TC-TTTGCAA-C-TGCCGGCGG-CAACC
```

FIG. 2K

```
  1 AACCATCAGCCGAAGATGATGCGTCAAGATAGAAGGAGCTTGCTAGAGAGGAACATTATGATGTTCTCTAGTCATCTAAAAGTCGATGAAATTCTCGAAG
                  M  M  R  Q  D  R  R  S  L  L  E  R  N  I  M  M  F  S  S  H  L  K  V  D  E  I  L  E  V

101 TTCTCATCGCCAAAACAAGTGTTGAATAGTCGAGATATGATTAATTCATGTGAACGGTTCGGGAGAAGACGGGAGATCGTGAAAGCAGTGCA
    L  I  A  K  Q  V  L  N  S  D  N  G  D  M  I  N  S  C  G  T  V  R  E  K  R  R  E  I  V  K  A  V  Q

201 ACGACCGGGAGATGTGGCGTTCGACGCGTTTTATGATGCTCTTCGCCTCACCGGACACCGAAGGACTTGCTGAAGTTCTTGAACCTCGCCAGATCTGTT
    R  P  G  D  V  A  F  D  A  F  Y  D  A  L  R  S  T  G  H  E  G  L  A  E  V  L  E  P  L  A  R  S  V

301 GACTCGAATGCTGTCGAATTCGAGTGTCCAATGTCCAAGCCATCGTCGGAGCCCGCCATTGAGCCCGGCTACACTTCACCGACCGAGTTC
    D  S  N  A  V  E  F  E  C  P  M  S  P  A  S  H  R  R  S  R  A  L  S  P  A  G  Y  T  S  P  T  R  V  H

401 ACCGTGACAGCCTCTCTTCAGTGTCATCATTCACTTCTTATCAGGATATCTACTCAAGAGCAAGATCTCGTTCTCGATCGGTGCACTTCATTCATCGGA
    R  D  S  V  S  S  V  S  S  F  T  S  Y  Q  D  I  Y  S  R  A  R  S  R  S  R  A  L  H  S  S  D

501 TCGACACAATTATTCATCTCCCAGTCAACGGCATTTCCCAGCCAACCTTCATCCGCCAACTCTTCATTCACCGGATGCTCTTCTCTCCGATACAGTTCA
    R  H  N  Y  S  S  P  P  V  N  A  F  P  S  Q  P  S  S  A  N  S  S  F  T  G  C  S  S  L  G  Y  S  S

601 AGTCGTAATCGCTCATTCAGCAAAGCTTCTGGACCAACTCAATACATATTCCATGAAGAGGATATGAACTTTGTCGATGCACCAACCATAAGCCGTGTTT
    S  R  N  R  S  F  S  K  A  S  G  P  T  Q  Y  I  F  H  E  E  D  M  N  F  V  D  A  P  T  I  S  R  V  F
```

FIG. 2M

701  TCGACCGAGAAACCATGTACAGAAACTTCTCCAGTCCTCCTCGTGGAATGTGCCCTCATCATAAATAATGAACACTTTGAGCAGATGCCAACACGGAATGGTAC
       D  E  K  T  M  Y  R  N  F  S  S  P  R  G  M  C  L  I  I  N  N  E  H  F  E  Q  M  P  T  R  N  G  T

801  CAAGGCCGACAAGGACAACATCTTACCAATTGTTCAGATGCATGGCTATACGGTTATTTGCAAGGACAATCTGACCGGAAGGGAATGCTCCTGACAATT
       K  A  D  K  D  N  L  T  N  L  F  R  C  M  G  Y  T  V  I  C  K  D  N  L  T  G  R  G  M  L  L  T  I

901  CGAGACTTTGCCAAACACGAATCACACGGAGATTCTGCCATACTCGTGATTCTATCACACGGAAGAGAATGTGATTATTGGAGTTGATGATATACCGA
       R  D  F  A  K  H  E  S  H  G  D  S  A  I  L  V  I  L  S  H  G  E  E  N  V  I  I  G  V  D  D  I  P  I

1001 TTAGTACACGAGATATATGATCTTCTCAACGCGGCAAATGCTCCCCGCTCGGCGAATAAGCCGAAATCGTTTTTCTGCAGGCTTGTCCAGGCGAACG
       S  T  H  E  I  Y  D  L  L  N  A  A  N  A  P  R  L  A  N  K  P  K  I  V  F  V  Q  A  C  R  G  E  R

1101 TCGTGACAATGGATTCCCAGTCTTGGATTCTGTCGACGGAGTTCCTGCATTCTTCGTCGTGGATGGACAATCGAGACGGGCCATTGTCAATTTTCTT
       R  D  N  G  F  P  V  L  D  S  V  D  G  V  P  A  F  L  R  R  G  W  D  N  R  D  G  P  L  F  N  F  L

1201 GGATGTGTGCGGCCGCAAGTTCAGGCAAGTGTGAGAAAGAAGCCAGCCAAGCTGACATTCGATTCGATACGCAACGACCAGCTCAATATGTTTCGTGGA
       G  C  V  R  P  Q  V  Q  Q  V  W  R  K  K  P  S  Q  A  D  I  L  I  R  Y  A  T  T  A  Q  Y  V  S  W  R

FIG.2N

```
1301 GAAACAGTGCTCGTGGATCATGGTTCATTCAAGCGTCTGTGAAGTGTTCTCGACACGCCAAAGGATATGGATGTTGTTGAGCTGCTGACTGAAGTCAA
      N  S  A  R  G  S  W  F  I  Q  A  V  C  E  V  F  S  T  H  A  K  D  M  D  V  V  E  L  L  T  E  V  N

1401 TAAGAAGGTCGCCTTGTGGATTTCAGACATCACAGGGATCGAATATTTGAAACAGATGCCAGAGATGACATCCCGGCTGCTCAAAAGTTCTACTTTTGG
      K  K  V  A  C  G  F  Q  T  S  Q  G  S  N  I  L  K  Q  M  P  E  M  T  S  R  L  L  K  K  F  Y  F  W

1501 CCGGAAGCACGAAACTCGCCGTCTAAAATTCACTCGTGATTCATTGCCCAATTGATAATGTCTGTATCTTCTCCCCAGTTCTCTTCGCCAATTAG
      P  E  A  R  N  S  A  V  *

1601 TTTAAAACCATGTGTATATTGTTATCCTATACTCATTCACTTTATCATTCTATCATTCTCTCCCATTTCACACATTTCCATTCTCTACGATAATC

1701 TAAAATTATGACGTTTGTGTCTCGAACGCATAATAATTTTAATAACTCGTTTGAATTGATTAGTTGTTGTGCCCAGTATATGTACTATGCTT

1801 CTATCAACAAAATGTTTCATAGATCATCACCCCAACCTCCAACCTACCGTACCATATTCATTTTGCCGGAATCAATTCGATTAATTTTAACCTA

1901 TTTTTCGCCACAAAAAATCTAAATATTTGAATTAACGAATAGCCATTCCCATCTCTCCCGTGCCGGAACTCCCGGCCTTTTAAAGTTCGAACATTTGGCC

2001 AATTATGTATAAAATTTGTAGGTCCCCCCATCATTCCCGCCCATCATCTCAAATTGCATTCTTTTTCGCCGTGATATCCCGATTCGTCAGCCAAA
```

FIG. 20

2101 GATCTTTCTCATAGCCCATTCCATTCGAGCTTTCTAATAGGAATTTGAAAAATTTTCGAAATTCCAGTAATAATATTGGAAAATGGATTTTTCGAGTTTT

2201 CAGCAACACAAATTTACTTGAAACCCCATTTTCCAAAATTTCAATTTTTTCAAATTTCCCGCTATCTTCCAAATACTCTTGTACGTTTATTATATTTCC

2301 CTCGTTTTCTTCCGATTCCTCCTCTCCGGGCACCCAATAAGTTTATATATGTTGAGATTTATATAGCTTGTTATTATAATTATATATTTATAGATTATT

2401 ATAGTTGCTTTCTCGCCGTATGTTTGTGTGTGTGATTGGTATACATAGATAAAAGAAAACAAGTAAAAAAGGAATTC

```
  1   TCTTCACAGTGCCGAAAGAACTGAGGCTTTTTCTCATGGCTGAAAACAAACACCCTGACAAACCACTTAAGGTGTTGGAACAGCTGGGCAAAGAAGTCCTT
                                      M  A  E  N  K  H  P  D  K  P  L  K  V  L  E  Q  L  G  K  E  V  L

101   ACGGAGTACCTAGAAAAATTAGTACAAAGCAATGTACTGAAATTAAAGGAGGAAGATAAACAAAATTTAACAATGCTGAACCAGTGACAAGCGTTGGG
       T  E  Y  L  E  K  L  V  Q  S  N  V  L  K  L  K  E  E  D  K  Q  K  F  N  N  A  E  R  S  D  K  R  W  V

201   TTTTTGTAGATGCCATGAAAAAGAAACACAGCAAAGTAGTGGAAATGCTTCTCCAGACATTCTTCAGTGTGGACCCAGGCAGCCACCATGGTGAAGCTAA
       F  V  D  A  M  K  K  K  H  S  K  V  G  E  M  L  L  Q  T  F  F  S  V  D  P  G  S  H  H  G  E  A  N

301   TCTGGAAATGGAGGAACCAGAAGAATCATTGAACACTCTCAAGCTTTGTTCCCTGAAGAGTTCACAAGGCTTGCAGAGAAAAGACACAAGAAATTTAC
       L  E  M  E  E  P  E  E  S  L  N  T  L  K  L  C  S  P  E  E  F  T  R  L  C  R  E  K  T  Q  E  I  Y

401   CCAATAAAGGAGGCCAATGCCGGTACGAAAGGCTCTTATCATATGCAATACAGAGTTCAAACATCTCTCACTGAGTATGGGCTAAATTTGACATCA
       P  I  K  E  A  N  G  R  T  R  K  A  L  I  I  C  N  T  E  F  K  H  L  S  L  R  Y  G  A  K  F  D  I  I
```

FIG. 6A

```
501  TTGGTATGAAAGGCCCTTCTTGAAGACTTAGGCTACGATGTGGTGGTGAAAGAGGAGCTTACAGCAGAGGGCATGGAGTCAGAGATGAAAGACTTTGCTGC
      G  M  K  G  L  L  E  D  L  G  Y  D  V  V  V  K  E  E  L  T  A  E  G  M  E  S  E  M  K  D  F  A  A

601  ACTCTCAGAACACCAGAGACATCAGATCCATGGCTGTCTAATGTCTCATGCCACACTGCCATTGTGGAACAGTGAAAAAACTCCA
      L  S  E  H  Q  T  S  D  S  T  F  L  V  L  M  S  H  G  T  L  H  G  I  C  G  T  M  H  S  E  K  T  P

701  GATGTGCTACAGTATGATACCATCTATCAGATATTCAACAATTGCCACTGTCCAGGTCATACGAGACAAACCCAAAGTCATCATTGTGCAGGCCTGCAGAG
      D  V  L  Q  Y  D  T  I  Y  Q  I  F  N  N  C  H  C  P  G  L  R  D  K  P  K  V  I  I  V  Q  A  C  R  G

801  GTGGGAACTCTGGAGAAATGTGGATCAGAGAGTCTTCAAAACCCAGTTGTGCAGAGTGTAGATCTACCTAGGAATATGGAAGCTGATGCTGTCAAGCT
      G  N  S  G  E  M  W  I  R  E  S  S  K  P  Q  L  C  R  G  V  D  L  P  R  N  M  E  A  D  A  V  K  L

901  GAGCCACGTGGAGAAGGACTTCATTGCCTTCTACGCTACAACCCCACATCACTTGTCCTACCGAGACAAAACAGGAGGCTCTTACTTCATCACTAGACTC
      S  H  V  E  K  D  F  I  A  F  Y  A  T  T  P  H  H  L  S  Y  R  D  K  T  G  G  S  Y  F  I  T  R  L
```

FIG.6B

```
1001 ATTCCTGCTTCCGGAAACATGCTTGCTCTTGTCATCTCTTGATATATTCCTGAAGGTGCAACAATCATTGAAAAGGCAAGTATTCATTCCCAGATGC
      I  S  C  F  R  K  H  A  C  S  C  H  L  F  D  I  F  L  K  V  Q  Q  S  F  E  K  A  S  I  H  S  Q  M  P

1101 CCACCATTGATCGGGCCAACCTTGACAAGATCACATTCTATCCTCTTTCCTGGCAACTGAGAACAAAGCAACAAGCAACTGAATCTCATTTCTTCAGCTTGAAG
      T  I  D  R  A  T  L  T  R  Y  F  Y  L  F  P  G  N  *

1201 AAGTGATCTTGGCCAAGGATCACATTCTATTCCTGAAATTCCAGAACTAGTGAATTAAGGAAAGAATACTTATGAATTCAAGACCAGCCTAAGCAACAC

1301 AGTGGGATTCTGTTCGATAGACAAGCAAACAAGCAAAAATAAAAAAAAAAA
```

FIG.6C

```
        1                                                           50
MICE1   MADKILRAKR KQFINS..... .VSIGTINGL LDELLEKRVL NQEEMDKIKL
HICE    MADKVLKEKR KLFIRS..... .MGEGTINGL LDELLQTRVL NKEEMEKVKR
MICE2   MAENKHPDKP LKVLEQ..... .LGKEVLTEY LEKLVQSNVL KLKEEDKQKF
Ced3    ....MMRQDR RSLLERNIMM FSSHLKVDEI LEVLIAKQVL NSDNGDMIN.

51                                                          100
MICE1   ANITAMDKAR NLCDHVSKKG APASQ.IFIT YICNEDCYLA GLLELQSAPS
HICE    ENATVMDKTR ALIDSVIPKG AQACQ.ICIT YICEEDSYLA GTLGLSADQT
MICE2   NNAERSDKRW VFVDAMKKKH SKVGE.MLL. .......... ..........
Ced3    SCGTVREKRR EIVKAVQRPG DVAFDAFYDA LRSTGHEGLA EVLEPLARSV 101                                                         150
MICE1   AETFVATEDS KGGHPSSSET KE.EQNKEDG TFPGLTGTLK FCPLEKAQKL
HICE    SGNYLNMQDS QGVLSSFPAP QAVQDNPAMP TSSGSEGNVK LCSLEEAQRI
MICE2   .......... QTFFSVDPGS HHGEANLEME EPEESLNTLK LCSPEEFTRL
Ced3    DSNAVEFECP MSPASHRRSR ALSPAGYTSP TRVHRDSVSS VSSFTSYQDI 151                                                         200
MICE1   WKE....... .......... .......... .......... ..........
HICE    WKQ....... .......... .......... .......... ..........
MICE2   CRE....... .......... .......... .......... ..........
Ced3    YSRARSRSRS RALHSSDRHN YSSPPVNAFP SQPSSANSSF TGCSSLGYSS 201                                                         250
MICE1   .......... .......... .....NPSEI YPIMNTTTRT R.......LA
HICE    .......... .......... .....KSAEI YPIMDKSSRT R.......LA
MICE2   .......... .......... .....KTQEI YPIKEANGRT R.......KA
Ced3    SRNRSFSKAS GPTQYIFHEE DMNFVDAPTI SRVFDEKTMY RNFSSPRGMC 251                                                         300
MICE1   LIICNTEFQH LSPRVGAQVD LREMKLLLED LGYTMKVKEN LTALEMVKEV
HICE    LIICNEEFDS IPRRTGAEVD ITGMTMLLQN LGYSVDVKKN LTASDMTTEL
MICE2   LIICNTEFKH LSLRYGAKFD IIGMKGLLED LGYDVMVKEE LTAEGMESEM
Ced3    LIINNEHFEQ MPTRNGTKAD KDNLTNLFRC MGYTMICKDN LTGRGMLLTI
```

FIG.7

```
         301                                                              350
MICE1   KEFAACPEHK TSDSTFLVFM SHGIQEGICG TTYSNEVSDI .LKVDTIFQM
HICE    EAFAHRPEHK TSDSTFLVFM SHGIREGICG KKHSEQVPDI .LQLNAIFNM
MICE2   KDFAALSEHQ TSDSTFLVLM SHGTLHGICG TMHSEKTPDV .LQYDTIYQI
Ced3    RDFAKHESH. .GDSAILMIL SHGEENVIIG ......VDDI PISTHEIYDL 351                                                              400
MICE1   MNTLKCPSLK DKPKVIILQA CRGEKQGVVL LKDSVRDSEE .DFLTDAIFE
HICE    LNTKNCPSLK DKPKVIIIQA CRGDSPGVVW FKDSVGVSGN LSLPTTEEFE
MICE2   FNNCHCPGLR DKPKVIIVQA CRGGNSGEMW IRESSKPQLC RGVDLPRNME
Ced3    LNAANAPRLA NKPKIVFVQA CRGERRDNGF PVLDSVDGVP AFLRRGWDNR 401                                                              450
MICE1   DDGI...... ..........K KAHIEKDFIA FCSSTPDNVS WRHPVRGSLF
HICE    DDAI...... ..........K KAHIEKDFIA FCSSTPDNVS WRHPTMGSVF
MICE2   ADAV...... ..........K LSHVEKDFIA FYATTPHHLS YRDKTGGSYF
Ced3    DGPLFNFLGC VRPQVQQVWR KKPSQADILI RYATTAQYVS WRNSARGSWF 451                                                              500
MICE1   IESLIKHMKE YAWSCDLEDI F....RKVRF SFEQPEFRLQ MPTTADRVT..
HICE    IGRLIEHMQE YACSCDVEEI F....RKVRF SFEQPDGRAQ MPTTERVT..
MICE2   ITRLTSCFRK HACSCHLFDI F....LKVQQ SFEKASIHSQ MPTIDRAT..
Ced3    IQAVCEVFST HAKDMDVVEL LTEVNKKVAC GFQTSQGSNI LKQMPEMTSR 501       517
MICE1   LTKRFYLFPG H......
HICE    LTRCFYLFPG H......
MICE2   LTRYFYLFPG N*.....
Ced3    LLKKFYFWPE ARNSAV*
```

FIG.7A

```
  1  GAATTCCGCACAAGGAGCTGATGGCCCCTGACAGGGGACCCAGGATATTGGGAGTGTGTGGCATGCATCCTCATCATCAGGAAACTCTAAAAAAGAACCG
        I  P  H  K  E  L  M  A  A  D  R  G  R  R  I  L  G  V  C  G  M  H  P  H  H  Q  E  T  L  K  K  N  R

101  AGTGTGCTAGCCAAACAGCTGTTGTTGAGCGAATTGTTAGAACATCTCTGGAGAAGGACATCATCACCTTGGAAATGAGGGAGCTCATCCAGGCCAAA
        V  V  L  A  K  Q  L  L  S  E  L  L  E  H  L  L  E  K  D  I  I  T  L  E  M  R  E  L  I  Q  A  K

201  GTGGGCAGTTTCAGCCAGAATGTGGAACTCCTCAACTTGCTCCCAAGTTTTGATGCCTTCTGTGAAGCACTGAGGGAGACCAAGC
        V  G  S  F  S  Q  N  V  E  L  L  N  L  L  P  K  R  G  P  Q  A  F  D  A  F  C  E  A  L  R  E  T  K  Q

301  AAGGCCACCTGGAGGATATGTTGCTCACCACCCTTTCTGGGCTTCAGCATGTACTCCCACGTTGAGCTGTGACTACGACTGAGTCTCCCTTTCCGGT
        G  H  L  E  D  M  L  L  T  T  L  S  G  L  Q  H  V  L  P  P  L  S  C  D  Y  D  L  S  L  P  F  P  V

401  GTGTGAGTCCTGTCCCCTTTACAAGAAGCTCCGCCTGTCGACAGATACTGTGGAACACTCCCTAGACAATAAAGATGTCCTGTCTGCCTTCAGGTGAAG
        C  E  S  C  P  L  Y  K  K  L  R  L  S  T  D  T  V  E  H  S  L  D  N  K  D  G  P  V  C  L  Q  V  K
```

FIG.8A

```
501 CCTTGCACTCCTGAATTTTATCAAACACACTTCCAGCTGGCATATAGGTTGCAGTCTCCGGCCTCTGTGGCCTAGCCACTGTGTTGAGCAATGTGCACTTCA
     P  C  T  P  E  F  Y  Q  T  H  F  Q  L  A  Y  R  L  Q  S  R  P  R  G  L  A  L  V  L  S  N  V  H  F  T

601 CTGGAGAGAAAGAACTGGAATTTCGCTCTGGAGGGGATGTGGACCACAGTACTCTAGTCACCCTCTTCAAGCTTTTGGGCTATGACGTCCATGTTCTATG
     G  E  K  E  L  E  F  R  S  G  G  D  V  D  H  S  T  L  V  T  L  F  K  L  L  G  Y  D  V  H  V  L  C

701 TGACCAGACTGCACAGGAAATGCAAGAGAAACTGCAGAATTTTGCACAGTTACCTGCACACCGAGTCACGGACTCCTGCATCGTGGCACTCCTCTCGCAT
     D  Q  T  A  Q  E  M  Q  E  K  L  Q  N  F  A  Q  L  P  A  H  R  V  T  D  S  C  I  V  A  L  L  S  H

801 GGTGTGGAGGGCGCCATCTATGGTGTGGATGGGAAACTGCTCCAGCTCCAAGAGGTTTTTCAGCTCTTTGACAACGCCAACTGCCCAAGCTACAGAACA
     G  V  E  G  A  I  Y  G  V  D  G  K  L  L  Q  L  Q  E  V  F  Q  L  F  D  N  A  N  C  P  S  L  Q  N  K

901 AACCAAAAATGTTCTTCATCCAGGCCTGCCGTGGAGATGAGACTGATCGTGGGGTTGACCAACAAGATGAAAGAACCACCAGGATCCCCTGGGTGCCGA
     P  K  M  F  F  I  Q  A  C  R  G  D  E  T  D  R  G  V  D  Q  Q  D  G  K  N  H  A  G  S  P  G  C  E
```

FIG.8B

```
1001 GGAGAGTGATGCCGGTAAAGAAAAGTTGCCGAAGATGAGACTGCCCACGCGCTCAGACACATGATATGCGGCTATGCCTGCCTGCCTCAAAGGGACTGCCGCCATG
      E  S  D  A  G  K  E  K  L  P  K  M  R  L  P  T  R  S  D  M  I  C  G  Y  A  C  L  K  G  T  A  A  M

1101 CGGAACACCAAAACGAGGTTCCTGGTACATCGAGGCTCTTGCTCAAGTGTTTCTGAGCGGGCTTGTGATATGCACGTGGCCGACATGCTGGTTAAGGTGA
      R  N  T  K  R  G  S  W  Y  I  E  A  L  A  Q  V  F  S  E  R  A  C  D  M  H  V  A  D  M  L  V  K  V  N

1201 ACGCACTTATCAAGGATCGGGAAGGTTATGCCTCCTGGCACACCCTCCCATGATGTCACCTCCCATCATCCACCCCAAGTGGAAGCCACTGGACACCAGGAGGTGTGATAGAGCCTTTGATCTT
      A  L  I  K  D  R  E  G  Y  A  P  G  T  E  F  H  R  C  K  E  M  S  E  Y  C  S  T  L  C  R  H  L  Y

1301 CCTGTTCCCAGGACACCCTCCCACTGAGTCACCTCCCATGATGTCACCTCCCATCATCCACCCCAAGTGGAAGCCACTGGACACCAGGAGGTGTGATAGAGCCTTTGATCTT
      L  F  P  G  H  P  P  T  *

1401 CAGGATGCACGGTTTCTGCGTTCTGCCCCCTCAGGGATGTGGGAATCTCCCAGACTGTTCCTGGAATTCCAGGCCTGTGAAGGGCCTGGGACTGATTTC

1501 TAATGGGCACCTTGATGAATCAGGTCTGTTTGTTTGTTTCAAAAATTGAGAACCTTTCTGGGTTCTCTCTTAGAATATGCCTCCTGGGCCCAGTTGATCCAGCCTTTAT

1601 TTTCATTCTCTTGGCTTTGGCTACCTTATCAGTGCTAAAATATATATTTAGAGCTCGGAAATTATATGAGAATCACTCTGGCATTGTCT
```

FIG.8C

1701 TATTACAGAGCAGGTAGCTGAAGCTGGAGAGGTTTTTTCCTAGAGTCTCAAAACTATGAAGTTAGGGAACTGGAATCCAGATTTAAGTCAGCTTGTGCC

1801 CAATCCAGTACTCTTTTCACTTCATCACACCGTCTGTCAGAATTTATTCTGTATATAATCATCCCTTGACCTCCACAGGTGTTGGTGCCA

1901 CCTACTTTTTAGTGGCTCTACCTGTTCATTGGCTGTGTGACTTTGAGCAAATTATGTAACCTCTTCATGCTTCAGTTTCTGATCAGAAGGAAATAGGGT

2001 AAGAATAATACCTACTTGATAGAATTACTGCAAGGATTTACAATAACATACAAGTGAAGTGCTTGGCACAGGTGAAGTGCTGGCACATGC

2101 TCAGTAAATGTCAACTTATTTCTAGTAATAGACTGTTTCAGATACTTGCTTTCTTTAAGTGTCTAGAGTCATGAAATATTTTAAAAGGACAGTTAAAAT

2201 AAGTGTTTTCTCAAAAAAACCTACATTATAATTTTCCTTCAGGGGCTCAGGAGGCAAATTTAGAGCAATGAGTTTCAAATTGTTCAGAGCTTAGAGTTAC

2301 CATGCCTTGAGTTTCCAGACACATGATTATCTGTCTTATAAATGAGAAACAGTTTTACTAGTAGAAAATGACTTTATTGGATTATATAATATAAATTCAC

2401 TATAAGCATACACATCCATAAAAAAGCTATATAGAAGTAAGCCTAATAAACTTGTAAATGGATGTTATTTTAATTGCATACTGGGAATTC

FIG. 8D

```
            TTCTGGTAGCTCCAAGAGGTTTTTCGACTTTTTGACAATGCTAACTGTCCAAGTCTACAG
     1141 ——————+——————+——————+——————+——————+——————+ 1200 a        F W * L Q E V F R L F D N A N C P S L Q     -
  b         S G S S K R F F D F L T M L T V Q V Y R    -
  c          L V A P R G F S T F * Q C * L S K S T E   -

AACAAGCCAAAAATGTTCTTCATCCAAGCATGTCGTGGAGGTGCTATTGGATCCCTTGGG
     1201 ——————+——————+——————+——————+——————+——————+ 1260 a        N K P K M F F I Q A C R G G A I G S L G     -
  b         T S Q K C S S S K H V V E V L L D P L G    -
  c          Q A K N V L H P S M S W R C Y W I P W A   -
```

FIG.9

```
251  ATGAAAGTGCATTTTTATATCTTTATGCTGTACACTTCACTCACTGTAAT 300
                        | | |  |||    |
  1  .............................GAATTCCGCACAAGGAGCTGA 21

301  GGTGGGTAAGTTTAGTGAGCAATAGGTCACTATGGTGACCCATGTCACAC 350
       | |        |   ||| | |    |  |||   ||||    |
 22  TGGCCGCTGACAGGGGACGCAGGATATTGGGAGTGTGTGGCATGCATCCT 71

351  AGCCTGAATGTTATGGTAAAATATACTC......TGCTAAATAAATTAGT 394
       | || |   |||| | | |        ||||| |||       |
 72  CATCATCAGGAAACTCTAAAAAAGAACCGAGTGGTGCTAGCCAAACAGCT 121

395  CCATTATTTAAATTCAACCTCAAGTTTTCAGAATATAGACGACTGCGTCC 444
         |  ||      |   |||| | |  |||  |  |
122  GTTGTTGAGCGAATTGTTAGAACATCTTCTGGAGAAGGACATCATCACCT 171

445  AATTCCTCACCAAAGTAGGACACAAGCTGAGTTCTCATTAAAGTCCTTGA 494
       |   |    ||          ||       || ||  |
172  TGGAAATGAGGGAGCTCATCCAGGCCAAAGTGGGCAGTTTCAGCCAGAAT 221

495  TCTGTTCTAGGATCTATTGAGCCTAGCCTGTGTCTTCATTTTTCTTAATT 544
       | ||    |    |||||    | ||| ||   || | |
222  GTGGAACTCCTCAACTTGCTGCCTAAGAGGGGTCCCCAAGCTTTTGATGC 271

545  AACACTTGGGTGTCTTGAAAACCCACTAAAATTGCCCCTGAAGCCCTGCT 594
        ||   ||    | |    ||   | |||| ||       |
272  CTTCTGTGAAGCACTGAGGGAGACCAAGCAAGGCCACCTGGAGGATATGT 321

595  TAGAGCATTCTGGGCTTTTTAGCCTGCAGCTTCTAATTCTCCCATATTCC 644
       | || |   |||||| | || |||| | || |   || |
322  T...GCTCACCACCCTTTCTGGGCTTCAGCATGTACTCCCACCGTTGAGC 368

645  TCCAACAAACTAGTTCCAATGGCCTATGAACCATGTGGAAAGATTATGGC 694
       | |||   |   | |||    ||||     |
369  TGTGACTACGACTTGAGTCTCCCTTTTCCGGTGTGTGAGTCCTGTCCCCT 418

695  TGTATTGACCCCAAACTGGCATAAGTTTTCAGTATTGGTTTTCTTGGACT 744
       |  ||  |  |  |    |  | ||||      | | |||
419  TTACAAGAAGCTCCGCCTGTCGACAGATACTGTGGAACACTCCCTAGACA 468
```

FIG. 10A

```
745   GAGACCAAAAATTCTTAACGAGAAACAGTTTGTTTTGGCTCCTTGTTTGA 794
      ||    |    |    | |||   ||| |
469   ATAAAGATGGTCCTGTCTGCCTTCAGGTGAAGCCTTGCACTCCTGAATTT 518

795   CAATATAAGCCCCCGTGGCAAGAAGCCAGCTCTCCAGTGGAGACAGGAGC 844
      | | | |    || || ||| |        || | |
519   TATCAAACACACTTCCAGCTGGCATATAGGTTGCAGTCTCGGCCTCGTGG 568

845   AGTAGGCTTCTTGTATTTGGGTAAATTGTGTAGCATAAAAGAAGAGATGC 894
      |||  | ||  ||| | ||  ||    ||  ||| |    |
569   CCTAGCACTGGTG...TTGAGCAATGTGCACTTCACTGGAGAGAAAGAAC 615

895   TGGCATGTCTGGCTTTCTTTGCCCCAACCCTTTCAGTCTGGGTTCCAGGT 944
      ||| || ||  ||      |          | |||   |||
616   TGGAATTTCGCTCTGGAGGGG..............ATGTGGACCACAGTA 651

945   CTTTCCTCCTCAGTTAATTCTTTCTGGAAATTCAATACCCTCAAAAATAA 994
      || |  ||  |   |    || |||   || ||    ||
652   CTCTAGTCACCCTCTTCAAGCTTTTGGGCTATGACGTCCATGTTCTATGT 701

995   ACTAAGTGTATCTCCCAAGTGACTGTAAATCTAGTCCAGTTGACAAGATC 1044
      ||  |    || ||  | || ||     ||| ||  |
702   GACCAGACTGCACAGGAAATGCAAGAGAAACTGCAGAATTTTGCA....C 747

1045  AGCTATCTCCCTACCTTTCAGATGAAGGTTGAATTTGTATGTGTTAGACT 1094
      || || || |  |||       ||    || ||       ||
748   AGTTACCTGCACACCGAGTCACGGACTCCTGCAT...CGTGGCACTCCTC 794

1095  TCAAGAGGTCTCACTGGCTACCTAACTTCCCCTCTCCCTTATTTGTTTCT 1144
      ||   ||| |    |||  ||  |          |  | ||||
795   TCGCATGGTGTGGAGGGCGCCATCTATGGTGTGGATGGGAAACTGCTCC. 843

1145  GGTAGCTCCAAGAGGTTTTTCGACTTTTTGACAATGCTAACTGTCCAAGT 1194
      |||||||||||||||| ||  |||||||| ||  |||||  |||||
844   ...AGCTCCAAGAGGTTTTTCAGCTCTTTGACAACGCCAACTGCCCAAGC 890

1195  CTACAGAACAAGCCAAAAATGTTCTTCATCCAAGCATGTCGTGGAGGTGC 1244
      ||||||||||| |||||||||||||||||||| ||  || |||||||
891   CTACAGAACAAACCAAAAATGTTCTTCATCCAGGCCTGCCGTGGAG.... 936
```

FIG. 10B

```
1295  TTGCTCTATGAGACAGATAGAGGTGTCGACCAGCAAGATGGAAAGAACCA 1344
      |||||||  |||  |  ||  ||  ||||||  |||||||||||||||||
 937  .......ATGAGACTGATCGTGGGGTTGACCAACAAGATGGAAAGAACCA 979

1345  CACACAATCCCCTGGATGTGAGGAGAGTGATGCTGGCAAAGAGGAGTTGA 1394
      |  ||   ||||||||||  || |||||||||||||  |||||   |||||
 980  CGCAGGATCCCCTGGGTGCGAGGAGAGTGATGCCGGTAAAGAAAAGTTGC 1029

1395  TGAAGATGAGACTGCCTACTCGCTCAGACATGATATGTGGCTATGCTTGC 1444
      |||||||||||||||  || ||||||||||||||||||  |||||||  |||
1030  CGAAGATGAGACTGCCCACGCGCTCAGACATGATATGCGGCTATGCCTGC 1079

1445  CTTAAAGGTAATGCTGCCATGCGGAACACCAAACGGGGTTCCTGGTACAT 1494
      || |||||  |  ||| |||||||||||||||||||| ||||||||||||
1080  CTCAAAGGGACTGCCGCCATGCGGAACACCAAACGAGGTTCCTGGTACAT 1129

1495  TGAGGCCCTCACTCAGGTGTTCTCTGAAAGAGCTTGTGACATGCACGTGG 1544
      |||||  ||||  |||||  ||||| |  ||||||||| |||||||||||
1130  CGAGGCTCTTGCTCAAGTGTTTTCTGAGCGGGCTTGTGATATGCACGTGG 1179

1545  CCGACATGCTTGTTAAGGTGAATGCCCTTATCAAGGAGCGTGAAGGCTAT 1594
      |||||||||  ||||||||||||  || ||||||||||| |||  |||| |||
1180  CCGACATGCTGGTTAAGGTGAACGCACTTATCAAGGATCGGGAAGGTTAT 1229

1595  GCCCCTGGCACAGAATTCCACCGATGCAAGGAGATGTCTGAGTACTGTAG 1644
      || |||||||||||||||||||||  ||||||||  ||||||| ||||| ||
1230  GCTCCTGGCACAGAATTCCACCGGTGCAAGGAAATGTCTGAATACTGCAG 1279

1645  TACTCTGTGCCAGCAACTCTACCTGTTCCCAGGCTACCCACCCACGTGAT 1694
      |||||||||||  ||||||| |||||||||||||||||    |||| ||||
1280  CACTCTGTGCCGCCACCTCTACCTGTTCCCAGGACACCCTCCCACATGAT 1329

1695  GCCGCCTGCTATTC......CTGCTGTTGGAGGCCACTGGACCACTGGGGG 1739
      | | ||| |  ||       |  | |||| |||||||||||||| || ||
1330  GTCACCTCCCCATCATCCACGCCAAGTGGAAGCCACTGGACCACAGGAGG 1379

1740  CACAATGGAGACTT..CTCTTCAGAATGGTTTTTGTTCTGTCTACCCTCT 1787
      || ||| |||    |||||||| |||        | |   |||  ||| ||
1380  TGTGATAGAGCCTTTGATCTTCAGGATGCACGGTTTCTGTTCTGCCCCCT 1429
```

FIG. 10C

```
1788  CAGGGATATGAGATTCTCCCAGGCTTGTTTCCTGTCA.GCCATCTCTGTC  1836
      |||||||| || || |||||||||| ||||||||||||  |  |||   ||||
1430  CAGGGATGTGGGAATCTCCCAGACTTGTTTCCTGGAATTCCAGGCCTGTG  1479

1837  TTTGGGTATGAAACATAAGGATGGCTCCTCCGGTGTCGTGTTCTCTACCT  1886
             |||  || |             | ||||   |   | ||
1480  AAGGGGCTTGGGA................CTGATTTCTAATGGGCACCTT  1513

1887  ATAGAGCCAGCTCTGAATGGATGTGTTACCAGAAGCATTTTAGCTACAGC  1936
         ||  |||||  |                ||||  | ||  |  |  |   |
1514  GATGAATCAGCTGTTTTGTTTCAAAAATTGAGAACCTTTCTGGGTTC.TC  1562

1937  CTAGAAAATGACATTGTGAACACAGTATTATTGTGGGAAGAGGGCATTTG  1986
      ||||| |||    || |              ||    ||      ||||
1563  TTAGAATATGCTCCTGGG.........CCAGTTGATCCAGCCTTTATTTT  1603

1987  GATTTCTCAATGTTTGTGATATTTTTGTTCCCAAGGCATCTTAGGAGTAC  2036
      |||        || |   |  || |  ||    | ||   ||    |||
1604  CATTCTCTTGCTTTGGCTACCTTATCAGTGCTAAAATATATATTTAGCAA  1653

2037  TTGGATCATAGCTTTTTTTTTTTTTCCTAAATCAGTTAAGGAGTCTCAGA  2086
       |   |  ||||         ||| ||       |||||   |  ||| |
1654  TATATTTAGAGCTCGGAAATTATAT.GAGAATCACTCTGGCATTGTCTTA  1702

2087  GATCATCTCCTTTTTTTTCCATATCTACAACCTCATTTTTCCCACAGTGG  2136
       ||    |   |  |   |  | |   ||    |   |||     |   |
1703  TTACA.GAGCAGGTAGCTGAAGCTGGAGAGGTTTTTTTCCTAGAGTCTCA  1751

2137  AGATTTGGAAGATGTCCCAATTTAATGTAGGTGTTTTCATCTGTCATGAA  2186
       |||  ||||  |     ||  ||| |   | ||||   |  |
1752  AAACTATGAAGTTAGGGAACTGGAATCCA...GATTTAAGTCAGCTTGTG  1798

2187  GGGACAGATGAGATCCTACTACTTGCGAAGTTTCTATGCATACCTTTAAG  2236
        |    | |||| ||||       |        || ||   ||||
1799  CCCAATCCAGTACTCTTTTCACTTCATCACACCGTCTGTCAGAATTTA..  1846

2237  TTCAGGCCCTAGGTGAAGGACAGTCCCTCAGCCTTTCCATTGGTTCCTTT  2286
         | || | |  |||||| | ||  ||| |  |||
1847  ........TTCTGTATATAATCATCCCTTA.CCACTCCTTGACCTCCACA  1887
```

FIG.10D

```
2287  GTGTTCAGTGCACCCAGCCTTTGAACAGAGCCTAGGGTCTGTATGCCATG  2336
       |   |  ||||  ||  ||||  |   | |        ||   |  || ||
1888  GGTGTTGGTGCCACCTACTTTTTAGTGGCTCTACCTGTTCATTGGCTGTG  1937

2337  ACACTGGAAGTCATAGAAATTTCCCTGGTCATGCTTTGTTTGAACTGTCA  2386
       |||   || ||  |   |  |  |||  ||||||||| ||  ||
1938  TGACTTTGAG.CAAATTATGTAACCTCTTCATGCTTCAGTT...TCTTGAT  1984

2387  CTGAATGAACCTTATCGGGCATAACTACATGAAAATGCAGTGACAGCTGA  2436
       | |||  |||         | ||||    |      ||   | || ||
1985  CAGAAGGAAATAGGGTAAGAATAATACCTACTTGATAGAATTAC......  2028

2437  GTGTGCTGTGTCTCACACTATCACCCGTCATCAGGATGTCTCTCCTTCCT  2486
          |||   |  |  |||| ||  |       |   ||
2029  ...TGCAAGGATTTACAATAACATACAATAACATACAAGTGAAGTGCTTG  2075

2487  TACTGTGGCTTCTGCATGCACTTACACTGTACTTGACGGCTGGCCTCCAG  2536
         |    |||  ||||  |   | |  |||    ||   ||
2076  GCACAGGTGAAGTGCTGGCACATGCTCAGTAAATGTCAACT.........  2116

2537  GGTCTCTCTTGCTTTGTACTGGTTCCCCTCTTTACCTTCACCA..TTCGC  2584
       |  |||  |    ||||  |||   |  |  || |   |  |
2117  ..TATTTCTAGTAATAGACTGTTTCAGATACTTGCTTTCTTTAAGTGTCT  2164

2585  TGCTTCTGCCAAGTCTGTGAAGCCGTCCTTTGTAGGATGTTTCTTGCCAC  2634
       |  ||   ||   | ||   |  ||   |   | |  ||| | ||  ||
2165  AGAGTCATGAAATATTTTTAAAAGGACAGTTAAAATAAGTGTTTTCTCAA  2214

2635  TTACGCTGTACTGTAGTTGCTTATTCTTTCTGCCTTCTGCCTTCAGCGTGA  2684
       |  ||  |  |  ||               ||||  |    |||    |
2215  AAAACCTACATTATAAT.........TTTCCTTCAGGGGCTCAGGAGGCA  2255

2685  GGCTTCTTTGGTTTTCTGTGGCAGCGTCTCCCTTCTCATTGTTTCTCTG.  2733
       ||      |    |   |   ||     || |   ||| |  | ||
2256  AATTTAGAGCAATGAGTTTCAAATTTGTTCAGAGCTTAGAGTTACCATGC  2305

2734  .TGTTTTAGTGGGGATAGTACCATATGTGATATAACCTAGAAGCACTTGT  2782
       || ||  | |       || |||  ||||  ||||||  ||||  || |
2306  TTGAGTTTCCAGACACATGATTATCTGTCTTATAAATGAGAAACAGTTTT  2355
```

FIG.10E

```
2783  CTCTGCTCTTATGAAACTTGCTTATTCTTGAAAACCTTCTGCATTTCCAT  2832
       |    |   | ||  |   ||  |  ||  |         |  |
2356  ACTAGTAGAAAATGACTTTATTGGATTTATATAATATAAATTCACTATAA  2405

2833  TTTTTCCTCTCTTCCAATTTATTCTCCATGTAACAGAGTAGTTTGGTTTT  2882
       | |  ||    ||     | |  |       ||  || |     || |
2406  GCATACACATCCATAAAAAAGCTATATAGAAGTAAGCCTAATAAACTTGT  2455

2883  TAAAATATCTGGTGATGTCATTCTCTTGCTTAGAACACTAGCTTCCTGTT  2932
       ||   ||| |  |    |||  || || |||    |
2456  AAATGGATGTTAT.TTTTAATTTGCATACTGGGAATTC............  2492
```

FIG.10F

```
Ced-3   1   ................MMRQDRRSLLERNIMMFSSHLKVDEILEVL131
                            |:..:..  |..|  ::::..:| :.|:|| |:
ICE3    1   IPHKELMAADRGRRILGVCGMHPHHQETLKKNRVVLAKQLLLSELLEHLL50

Ced-3   32  AKQVLNSDNGDMINSCGTVREKRREIVKAVQRPGDVAFDAFYDALRSTGH81
            .|::::  :  ::|.. .. ... |::.  ::.:|.. |||||::|||.| :
ICE3    51  EKDIITLEMRELIQAKVGSFSQNVELLNLLPKRGPQAFDAFCEALRETKQ100

Ced-3   82  -EGLAEVLEPLARSVDSNAVEFECPMSPASHRRSRALSPAGYTSPTRVHRD131
               : |.::|
ICE3    101 GHLEDML......................................107

Ced-3   132 SVSSVSSFTSYQDIYSRARSRSRSRALHSSDRHNYSSPPVNAFPSQPSSA181
                   :......:.|.:                      :|. .:.
ICE3    108 ....LTTLSGLQHV......................LPPLSCDY125

Ced-3   182 NSSFTGCSSLGYSSSRNRSFSKASGPTQYIFHEEDMNFVDAPTISRVFDE231
            : |:. . ::. :. .:|..... . ::::: : |... .:.
ICE3    126 DLSLPFPVCESCPLYKKLRLSTDTVEHSLDNKDGPVCLQVKPCTPEFYQT175

Ced-3   232 ..KTMYRNFSSPRGMCLIINNEHF...EQMPTRNGTKADKDNLTNLFRCM276
              . || |.|||:.|::.| ||   .::. |.|...|...|..||: :
ICE3    176 HFQLAYRLQSRPRGLALVLSNVHFTGEKELEFRSGGDVDHSTLVTLFKLL225

Ced-3   277 GYTVICKDNLTGRGMLLTIRDFAKHESH..GDSAILVILSHGEENVIIGV324
            ||.| . : |::| ..::|| ...| .||.|:::|||| |..|.||
ICE3    226 GYDVHVLCDQTAQEMQEKLQNFAQLPAHRVTDSCIVALLSHGVEGAIYGV275

Ced-3   325 DDIPISTHEIYDLLNAANAPRLANKPKIVFVQACRGERRDNGFPVLDSVD374
            |: : :|:::|:::.||.|.|.|||::|||||: |.|.. |
ICE3    276 DGKLLQLQEVFQLFDNANCPSLQNKPKMFFIQACRGDETDRGVDQQD...322

Ced-3   375 GVPAFLRRGWDNRDGPLFNFLGCVRPQVQQVWRKKPSQADILIRYATTAQ424

ICE3    323 ........GKNHAGSPGCEESDAGKEKLPKMR..LPTRSDMICGYACLKG362

Ced-3   425 YVSWRNSARGSWFIQAVCEVFSTHAKDMDVVELLTEVNK...KVACGFQTS472
            .. ||. ||||:|:|:..|||.:| ||.|.::|..||   |    |:...:
ICE3    363 TAAMRNTKRGSWYIEALAQVFSERACDMHVADMLVKVNALIKDREGYAPG412

Ced-3   473 QGSNILKQMPEMTSRLLKKFYFWPEARNSAV*504
            :: : |:|.| .| | :..:|::|:
ICE3    413 TEFHRCKEMSEYCSTLCRHLYLFPGHPPT*...442
```

FIG. 11

```
ICE     1 ......................MADKVLKEKRKLFIRSMGEGTINGLLD  27
                                :..||..:   ::  :     :.:||:
ICE3    1 IPHKELMAADRGRRILGVCGMHPHHQETLKKNRVVLAKQL...LLSELLE  47

ICE    28 ELLQTRVLNKEEMEKVKRENATVMDKTRALIDSVIPKGAQACQICITYIC  77
          .||:. ::.  ||  .:  ......  :....  .|:: :  .:|:||  :  ..  :
ICE3   48 HLLEKDIITL.EMRELIQAKVGSFSQNVELLNLLPKRGPQAFDAFCEALR  96

ICE    78 E.EDSYLAGTLGLSADQTSGNYLNMQDSQGVLSSFPAPQAVQDNPAMPTS 126
          |  .:::.|.:  |           ..:  |  ||...:...  .:    :::...
ICE3   97 ETKQGHLEDML..........LTTLSGLQHVLPPLSCDYDLSLPFPVCES 136

ICE   127 SGSEGNVKLCSLEEAQRIWKQKSAEIYPIMDKS................S 160
          :.    .::| |  |:...::  :...|.....:    :...:                  |
ICE3  137 CPLYKKLRL.STDTVEHSLDNKDGPVCLQVKPCTPEFYQTHFQLAYRLQS 185

ICE   161 RTR.LALIICNEEFDS...IPRRTGAEVDITGMTMLLQNLGYSVDVKKNL 206
          |.| |||:::|  .|.:    :.  |.|::||  ....  |:.  |||.|.|   :
ICE3  186 RPRGLALVLSNVHFTGEKELEFRSGGDVDHSTLVTLFKLLGYDVHVLCDQ 235

ICE   207 TASDMTTELEAFAHRPEHKTSDSTFLVFMSHGIREGICGKKHSEQVPDIL 256
          || :|  ..|:..||:   |.|:..||.:::.:::|||   :::|:|  .         ...:|
ICE3  236 TAQEMQEKLQNFAQLPAHRVTDSCIVALLSHGVEGAIYGVD.....GKLL 280

ICE   257 QLNAIFNMLNTKNCPSLKDKPKVIIIQACRGDSPGVVWFKDSVGVSGNLS 306

ICE3  281 QLQEVFQLFDNANCPSLQNKPKMFFIQACRGDETD...RGVDQQDGKNHAG 328

ICE   307 LPTTEEFEDDAIK....KAHIEKDFIAFCSSTPDNVSWRHPTMGSVFIGR 352

ICE3  329 SPGCEESDAGKEKLPKMRLPTRSDMICGYACLKGTAAMRNTKRGSWYIEA 378

ICE   353 LIEHMQEYACSCDVEEIFRKVRFSFEQPDGRAQMPTTERV........TL 394
          |  :  :  |  ||.  .|.:::  ||.   :...:|  |.  ...  .|.           ||
ICE3  379 LAQVFSERACDMHVADMLVKVNALIKDREGYAPGTEFHRCKEMSEYCSTL 428

ICE   395 TRCFYLFPGH....  404
          .|  :||||||
ICE3  429 CRHLYLFPGHPPT*  442
```

FIG.11A

```
  1  GCACAAGGAGCTGATGGCCCGCTGACAGGGGACGCAGGATATTGGGAGTGTGTGGCATGCATCCTCATCATCAGGAAACTC
     ———|————|————|————|————|————|————|————|
           M  A  A  D  R  G  R  R  I  L  G  V  C  G  M  H  P  H  H  Q  E  T  L

81  TAAAAAAGAACCGAGTGGTGCTAGCCAAACAGCTGTTGTTGAGCGAATTGTTAGAACATCTTCTGGAGAAGGACATCATC
     ———|————|————|————|————|————|————|————|
      K  K  N  R  V  V  L  A  K  Q  L  L  L  S  E  L  L  E  H  L  L  E  K  D  I  I

161  ACCTTGGAAATGAGGGAGCTCATCCAGGCCAAAGTGGGCAGTTTCAGCCAGAATGTGGAACTCCTCAACTTGCTGCCTAA
     ———|————|————|————|————|————|————|————|
      T  L  E  M  R  E  L  I  Q  A  K  V  G  S  F  S  Q  N  V  E  L  L  N  L  L  P  K

241  GAGGGGTCCCCAAGCTTTTGATGCCTTCTGTGAAGCACTGAGGGAGACCAAGCAAGGCCACCTGGAGGATATGTTGCTCA
     ———|————|————|————|————|————|————|————|
      R  G  P  Q  A  F  D  A  F  C  E  A  L  R  E  T  K  Q  G  H  L  E  D  M  L  L  T

321  CCACCCTTTCTGGGCTTCAGCATGTACTCCCACCGTTGAGCTGTGACTACGACTTGAGTCTCCCTTTTCCGGTGTGTGAG
     ———|————|————|————|————|————|————|————|
      T  L  S  G  L  Q  H  V  L  P  P  L  S  C  D  Y  D  L  S  L  P  F  P  V  C  E

401  TCCTGTCCCCTTTACAAGAAGCTCCGCCTGTCGACAGATACTGTGGAACACTCCCTAGACAATAAAGATGGTCCTGTCTG
     ———|————|————|————|————|————|————|————|
      S  C  P  L  Y  K  K  L  R  L  S  T  D  T  V  E  H  S  L  D  N  K  D  G  P  V  C

481  CCTTCAGGTGAAGCCTTGCACTCCTGAATTTTATCAAACACACTTCCAGCTGGCATATAGGTTGCAGTCTCGGCCTCGTG
     ———|————|————|————|————|————|————|————|
      L  Q  V  K  P  C  T  P  E  F  Y  Q  T  H  F  Q  L  A  Y  R  L  Q  S  R  P  R  G

561  GCCTAGCACTGGTGTTGAGCAATGTGCACTTCACTGGAGAGAAAGAACTGGAATTTCGCTCTGGAGGGGATGTGGACCAC
     ———|————|————|————|————|————|————|————|
      L  A  L  V  L  S  N  V  H  F  T  G  E  K  E  L  E  F  R  S  G  G  D  V  D  H

641  AGTACTCTAGTCACCCTCTTCAAGCTTTTGGGCTATGACGTCCATGTTCTATGTGACCAGACTGCACAGGAAATGCAAGA
     ———|————|————|————|————|————|————|————|
      S  T  L  V  T  L  F  K  L  L  G  Y  D  V  H  V  L  C  D  Q  T  A  Q  E  M  Q  E

721  GAAACTGCAGAATTTTGCACAGTTACCTGCACACCGAGTCACGGACTCCTGCATCGTGGCACTCCTCTCGCATGGTGTGG
     ———|————|————|————|————|————|————|————|
      K  L  Q  N  F  A  Q  L  P  A  H  R  V  T  D  S  C  I  V  A  L  L  S  H  G  V  E

801  AGGGCGCCATCTATGGTGTGGATGGGAAACTGCTCCAGCTCCAAGAGGTTTTTCAGCTCTTTGACAACGCCAACTGCCCA
     ———|————|————|————|————|————|————|————|
      G  A  I  Y  G  V  D  G  K  L  L  Q  L  Q  E  V  F  Q  L  F  D  N  A  N  C  P
```

FIG.12A

```
 881 AGCCTACAGAACAAACCAAAAATGTTCTTCATCCAGGCCTGCCGTGGAGATGAGACTGATCGTGGGGTTGACCAACAAGA
      |-------|-------|-------|-------|-------|-------|-------|-------|
      S  L  Q  N  K  P  K  M  F  F  I  Q  A  C  R  G  D  E  T  D  R  G  V  D  Q  Q  D

961 TGGAAAGAACCACGCAGGATCCCCTGGGTGCGAGGAGAGTGATGCCGGTAAAGAAAAGTTGCCGAAGATGAGACTGCCCA
      |-------|-------|-------|-------|-------|-------|-------|-------|
      G  K  N  H  A  G  S  P  G  C  E  E  S  D  A  G  K  E  K  L  P  K  M  R  L  P  T

1041 CGCGCTCAGACATGATATGCGGCTATGCCTGCCTCAAAGGGACTGCCGCCATGCGGAACACCAAACGAGGTTCCTGGTAC
      |-------|-------|-------|-------|-------|-------|-------|-------|
      R  S  D  M  I  C  G  Y  A  C  L  K  G  T  A  A  M  R  N  T  K  R  G  S  W  Y

1121 ATCGAGGCTCTTGCTCAAGTGTTTTCTGAGCGGGCTTGTGATATGCACGTGGCCGACATGCTGGTTAAGGTGAACGCACT
      |-------|-------|-------|-------|-------|-------|-------|-------|
      I  E  A  L  A  Q  V  F  S  E  R  A  C  D  M  H  V  A  D  M  L  V  K  V  N  A  L

1201 TATCAAGGATCGGGAAGGTTATGCTCCTGGCACAGAATTCCACCGGTGCAAGGAAATGTCTGAATACTGCAGCACTCTGT
      |-------|-------|-------|-------|-------|-------|-------|-------|
      I  K  D  R  E  G  Y  A  P  G  T  E  F  H  R  C  K  E  M  S  E  Y  C  S  T  L  C

1281 GCCGCCACCTCTACCTGTTCCCAGGACACCCTCCCACATGATGTCACCTCCCCATCATCCACGCCAAGTGGAAGCCACTG
      |-------|-------|-------|-------|-------|-------|-------|-------|
      R  H  L  Y  L  F  P  G  H  P  P  T  *

1361 GACCACAGGAGGTGTGATAGAGCCTTTGATCTTCAGGATGCACGGTTTCTGTTCTGCCCCCTCAGGGATGTGGGAATCTC
      |-------|-------|-------|-------|-------|-------|-------|-------|

1441 CCAGACTTGTTTCCTGGAATTCCAGGCCTGTGAAGGGGCTTGGGACTGATTTCTAATGGGCACCTTGATGAATCAGCTGT
      |-------|-------|-------|-------|-------|-------|-------|-------|

1521 TTTGTTTCAAAAATTGAGAACCTTTCTGGGTTCTCTTAGAATATGCTCCTGGGCCAGTTGATCCAGCCTTTATTTTCATT
      |-------|-------|-------|-------|-------|-------|-------|-------|

1601 CTCTTGCTTTGGCTACCTTATCAGTGCTAAAATATATATTTAGCAATATATTTAGAGCTCGGAAATTATATGAGAATCAC
      |-------|-------|-------|-------|-------|-------|-------|-------|

1681 TCTGGCATTGTCTTATTACAGAGCAGGTAGCTGAAGCTGGAGAGGTTTTTTTCCTAGAGTCTCAAAACTATGAAGTTAGG
      |-------|-------|-------|-------|-------|-------|-------|-------|

1761 GAACTGGAATCCAGATTTAAGTCAGCTTGTGCCCAATCCAGTACTCTTTTCACTTCATCACACCGTCTGTCAGAATTTAT
      |-------|-------|-------|-------|-------|-------|-------|-------|
```

FIG.12B

1841 TCTGTATATAATCATCCCTTACCACTCCTTGACCTCCACAGGTGTTGGTGCCACCTACTTTTTAGTGGCTCTACCTGTTC

1921 ATTGGCTGTGTGACTTTGAGCAAATTATGTAACCTCTTCATGCTTCAGTTTCTTGATCAGAAGGAAATAGGGTAAGAATA

2001 ATACCTACTTGATAGAATTACTGCAAGGATTTACAATAACATACAATAACATACAAGTGAAGTGCTTGGCACAGGTGAAG

2081 TGCTGGCACATGCTCAGTAAATGTCAACTTATTTCTAGTAATAGACTGTTTCAGATACTTGCTTTCTTTAAGTGTCTAGA

2161 GTCATGAAATATTTTTAAAAGGACAGTTAAAATAAGTGTTTTCTCAAAAAACCTACATTATAATTTTCCTTCAGGGGCTC

2241 AGGAGGCAAATTTAGAGCAATGAGTTTCAAATTTGTTCAGAGCTTAGAGTTACCATGCTTGAGTTTCCAGACACATGATT

2321 ATCTGTCTTATAAATGAGAAACAGTTTTACTAGTAGAAAATGACTTTATTGGATTTATATAATATAAATTCACTATAAGC

2401 ATACACATCCATAAAAAAGCTATATAGAAGTAAGCCTAATAAACTTGTAAATGGATGTTATTTTTAATTTGCATACTGGG

2481 AATTC

FIG.12C

```
1   AGAGGGAGGGAACGATTTAAGGAGCGAATACTACTGGTAAACTAATGGAAGAAATCTGCTGCACCACTGGATATTGGGAG
    |-------|-------|-------|-------|-------|-------|-------|-------|-------|-------|

81  TGTGTGGCATGCATCCTCATCATCAGGAAACTCTAAAAAAGAACCGAGTGGTGCTAGCCAAACAGCTGTTGTTGAGCGAA
    |-------|-------|-------|-------|-------|-------|-------|-------|-------|-------|
            M  H  P  H  H  Q  E  T  L  K  K  N  R  V  V  L  A  K  Q  L  L  L  S  E

161 TTGTTAGAACATCTTCTGGAGAAGGACATCATCACCTTGGAAATGAGGGAGCTCATCCAGGCCAAAGTGGGCAGTTTCAG
    |-------|-------|-------|-------|-------|-------|-------|-------|-------|-------|
     L  L  E  H  L  L  E  K  D  I  I  T  L  E  M  R  E  L  I  Q  A  K  V  G  S  F  S

241 CCAGAATGTGGAACTCCTCAACTTGCTGCCTAAGAGGGGTCCCCAAGCTTTTGATGCCTTCTGTGAAGCACTGAGGGAGA
    |-------|-------|-------|-------|-------|-------|-------|-------|-------|-------|
     Q  N  V  E  L  L  N  L  L  P  K  R  G  P  Q  A  F  D  A  F  C  E  A  L  R  E  T

321 CCAAGCAAGGCCACCTGGAGGATATGTTGCTCACCACCCTTTCTGGGCTTCAGCATGTACTCCCACCGTTGAGCTGTGAC
    |-------|-------|-------|-------|-------|-------|-------|-------|-------|-------|
     K  Q  G  H  L  E  D  M  L  L  T  T  L  S  G  L  Q  H  V  L  P  P  L  S  C  D

401 TACGACTTGAGTCTCCCTTTTCCGGTGTGTGAGTCCTGTCCCCTTTACAAGAAGCTCCGCCTGTCGACAGATACTGTGGA
    |-------|-------|-------|-------|-------|-------|-------|-------|-------|-------|
     Y  D  L  S  L  P  F  P  V  C  E  S  C  P  L  Y  K  K  L  R  L  S  T  D  T  V  E

481 ACACTCCCTAGACAATAAAGATGGTCCTGTCTGCCTTCAGGTGAAGCCTTGCACTCCTGAATTTTATCAAACACACTTCC
    |-------|-------|-------|-------|-------|-------|-------|-------|-------|-------|
      H  S  L  D  N  K  D  G  P  V  C  L  Q  V  K  P  C  T  P  E  F  Y  Q  T  H  F  Q

561 AGCTGGCATATAGGTTGCAGTCTCGGCCTCGTGGCCTAGCACTGGTGTTGAGCAATGTGCACTTCACTGGAGAGAAAGAA
    |-------|-------|-------|-------|-------|-------|-------|-------|-------|-------|
      L  A  Y  R  L  Q  S  R  P  R  G  L  A  L  V  L  S  N  V  H  F  T  G  E  K  E

641 CTGGAATTTCGCTCTGGAGGGGATGTGGACCACAGTACTCTAGTCACCCTCTTCAAGCTTTTGGGCTATGACGTCCATGT
    |-------|-------|-------|-------|-------|-------|-------|-------|-------|-------|
     L  E  F  R  S  G  G  D  V  D  H  S  T  L  V  T  L  F  K  L  L  G  Y  D  V  H  V

721 TCTATGTGACCAGACTGCACAGGAAATGCAAGAGAAACTGCAGAATTTTGCACAGTTACCTGCACACCGAGTCACGGACT
    |-------|-------|-------|-------|-------|-------|-------|-------|-------|-------|
      L  C  D  Q  T  A  Q  E  M  Q  E  K  L  Q  N  F  A  Q  L  P  A  H  R  V  T  D  S

801 CCTGCATCGTGGCACTCCTCTCGCATGGTGTGGAGGGCGCCATCTATGGTGTGGATGGGAAACTGCTCCAGCTCCAAGAG
    |-------|-------|-------|-------|-------|-------|-------|-------|-------|-------|
       C  I  V  A  L  L  S  H  G  V  E  G  A  I  Y  G  V  D  G  K  L  L  Q  L  Q  E
```

FIG.12D

```
881  GTTTTTCAGCTCTTTGACAACGCCAACTGCCCAAGCCTACAGAACAAACCAAAAATGTTCTTCATCCAGGCCTGCCGTGG
      ———|———|———|———|———|———|———|———|———|———|———|———|———|———|———|———|
      V  F  Q  L  F  D  N  A  N  C  P  S  L  Q  N  K  P  K  M  F  F  I  Q  A  C  R  G

961  AGGTGCTATTGGATCCCTTGGGCACCTCCTTCTGTTCACTGCTGCCACCGCCTCTCTTGCTCTATGAGACTGATCGTGGG
      ———|———|———|———|———|———|———|———|———|———|———|———|———|———|———|———|
      G  A  I  G  S  L  G  H  L  L  L  F  T  A  A  T  A  S  L  A  L  *

1041 GTTGACCAACAAGATGGAAAGAACCACGCAGGATCCCCTGGGTGCGAGGAGAGTGATGCCGGTAAAGAAAAGTTGCCGAA
      ———|———|———|———|———|———|———|———|———|———|———|———|———|———|———|———|

1121 GATGAGACTGCCCACGCGCTCAGACATGATATGCGGCTATGCCTGCCTCAAAGGGACTGCCGCCATGCGGAACACCAAAC
      ———|———|———|———|———|———|———|———|———|———|———|———|———|———|———|———|

1201 GAGGTTCCTGGTACATCGAGGCTCTTGCTCAAGTGTTTTCTGAGCGGGCTTGTGATATGCACGTGGCCGACATGCTGGTT
      ———|———|———|———|———|———|———|———|———|———|———|———|———|———|———|———|

1281 AAGGTGAACGCACTTATCAAGGATCGGGAAGGTTATGCTCCTGGCACAGAATTCCACCGGTGCAAGGAGATGTCTGAATA
      ———|———|———|———|———|———|———|———|———|———|———|———|———|———|———|———|

1361 CTGCAGCACTCTGTGCCGCCACCTCTACCTGTTCCCAGGACACCCTCCCACATGATGTCACCTCCCCATCATCCACGCCA
      ———|———|———|———|———|———|———|———|———|———|———|———|———|———|———|———|

1441 AGTGGAAGCCACTGGACCACAGGAGGTGTGATAGAGCCTTTGATCTTCAGGATGCACGGTTTCTGTTCTGCCCCCTCAGG
      ———|———|———|———|———|———|———|———|———|———|———|———|———|———|———|———|

1521 GATGTGGGAATCTTCCAGACTTGTTTCCTGTGCCCATCATCTCTGCCTTTGAGTGTGGGACTCCAGGCCAGCTCCTTTTC
      ———|———|———|———|———|———|———|———|———|———|———|———|———|———|———|———|

1601 TGTGAAGCCCTTTGCCTGTAGAGCCAGCCTTGGTTGGACCTATTGCCAGGAATGTTTCAGCTGCAGTTGAAGAGCCTGAC
      ———|———|———|———|———|———|———|———|———|———|———|———|———|———|———|———|

1681 AAGTGAAGTTGTAAACACAGTGTGGTTATGGGGAGAGGGCATATAAATTCCCCATATTTGTGTTCAGTTCCAGCTTTTGT
      ———|———|———|———|———|———|———|———|———|———|———|———|———|———|———|———|

1761 AGATGGCACTTTAGTGATTGCTTTTATTACATTAGTTAAGATGTCTTGAGAGACCATCTCCTATCTTTTATTTCATTCAT
      ———|———|———|———|———|———|———|———|———|———|———|———|———|———|———|———|
```

FIG.12E

```
1841 ATCCTCCGCCCTTTTTGTCCTAGAGTGAGAGTTTGGAAGGTGTCCAAATTTAATGTAGACATTATCTTTTGGCTCTGAAG
     ————|————|————|————|————|————|————|————|

1921 AAGCAAACATGACTAGAGACGCACCTTGCTGCAGTGTCCAGAAGCGGCCTGTGCGTTCCCTTCAGTACTGCAGCGCCACC
     ————|————|————|————|————|————|————|————|

2001 CAGTGGAAGGACACTCTTGGCTCGTTTGGGCTCAAGGCACCGCAGCCTGTCAGCCAACATTGCCTTGCATTTGTACCTTA
     ————|————|————|————|————|————|————|————|

2081 TTGATCTTTGCCCATGGAAGTCTCAAAGATCTTTCGTTGGTTGTTTCTCTGAGCTTTGTTACTGAAATGAGCCTCGTGGG
     ————|————|————|————|————|————|————|————|

2161 GAGCATCGGAATTC
     ————|———
```

FIG.12F

| | | |
|---|---|---|
| ICH-1S | ..............MHPHQETLKKNRVVLAKQLLLSELLEHLLEKDIITLEMRELIQ.AKVGSFSQNVELLNLL | 60 |
| ICH-1L | MAADRGRRILGVCGMHPHQETLKKNRVVLAKQLLLSELLEHLLEKDIITLEMRELIQ.AKVGSFSQNVELLNLL | 74 |
| hICE | MAD..........KVLKEKRKLFIRS.....MGEGTINGLLDELLQTRVLNKEEMEKVKRENATVMDKTRALIDSV | 61 |
| mICE | MAD..........KILRAKRKQFINS.....VSIGTINGLLDELLEKRVLNQEEMDKIKLANITAMDKARNLCDHV | 61 |
| Ced-3 | ..........MRQDRRSLLERNIMFSSHLKVDEILEVLIAKQVLNSDNGDMIN.SCGTVREKRREIVKAV | 61 |

| | | |
|---|---|---|
| ICH-1S | PKRGPQAFDAFCEALRETKQGHLEDML................................................. | 88 |
| ICH-1L | PKRGPQAFDAFCEALRETKQGHLEDML................................................. | 102 |
| hICE | IPKGAQACQ.ICITYICEEDSYLAGTLGLSADQTSGNYLMQ..............................DSQGVL | 108 |
| mICE | SKKGAPASQ.IFITYICNEDCYLAGILELQSAPSAETFVATE.............................DSKGGH | 108 |
| Ced-3 | QRPGDVAFDAFYDALRSTGHEGLAEVLEPLARSVDSNAVEFECPMSPASHRRSRALSPAGYTSPTRVHRDSVSSV | 136 |

| | | |
|---|---|---|
| ICH-1S | TTLSGLQHVL.........................................PPLSCDYDLSLPFPVCESCPLYKKLRLSTDTVEHS | 133 |
| ICH-1L | TTLSGLQHVL.........................................PPLSCDYDLSLPFPVCESCPLYKKLRLSTDTVEHS | 147 |
| hICE | SSFPAPQAVQ................DNPAMPTSSGSEGNVKLC..........SLEEA....QRI | 144 |
| mICE | PSSSETKE.E................QNKEDGTFPGLTGTLKFC..........PLEKA....QKL | 143 |
| Ced-3 | SSFTSYQDIYSRARSRSRSRSRALHSSDRHNYSSPPVNAFPSQPSSANSSFTGCSSLGYSSSRNRSFSKASGPTQYI | 211 |

F

| | | |
|---|---|---|
| ICH-1S | LDNKDGPVCLQVKPCTPEFYQTHFQLAYRLQSRPRGLALVLSNVHFTGEKELEFRSGGDVDHSTLVTLFKLLLGYD | 208 |
| ICH-1L | LDNKDGPVCLQVKPCTPEFYQTHFQLAYRLQSRPRGLALVLSNVHFTGEKELEFRSGGDVDHSTLVTLFKLLLGYD | 222 |
| hICE | WKQ......KSAEIYPIMDKSSR...TR......LALIICNEEF...DSIPRRTGAEVDITGMTMLLQNLGYS | 199 |
| mICE | WKE......NPSEIYPIMNTTTR...TR......LALIICNTEF...QHLSPRVGAQVDLREMKLLLEDLGYT | 198 |
| Ced-3 | FHEEDMNFVDAPTISRVFDEKTM....YRNFSSPRGMCLIINNEHF...EQMPTRNGTKADKDNLTNLFRCMGYT | 279 |

FIG.14A

```
Nedd-2   	                                              MLTVQV.YRTSQK......CSSSKHVVEVLLDPLGTSFC.SL	 34
ICH-1S   	VHVLCDQTAQEMQEKLQNFAQLPAHRVTDSCIVALLSHCVEGAIYG........VDGKLLQLQEVFQLFDNANCPSL	277
ICH-1L   	VHVLCDQTAQEMQEKLQNFAQLPAHRVTDSCIVALLSHCVEGAIYG........VDGKLLQLQEVFQLFDNANCPSL	291
hICE     	VDVKKNLTASDMTTELEAFAHRPEHKTSDSTFLVFMSHGIREGICGKKHSEQVPDI.LQLNAIFNMLNTKNCPSL	273
mICE     	VKVKENLTALEMVKEVKEFAACPEHKTSDSTFLVFMSHGIQEGICGTTYSNEVSDI.LKVDTIFQMMNTLKCPSL	272
Ced-3    	VICKDNLTGRGMLLTIRDFAKHESH..GDSAILVILSHGEENVIIG.......VDDIPISTHEIYDLLNAANAPRL	346

T

Nedd-2   	LPPPLLLY........ETDRGVDQQDGKNHTQSP..........GCEESDAG......KEELMKMRLPTRSDMICGYAC	 89
ICH-1S   	QNKPKMFFIQACRGGAIGSLGHLLLLFTAATASL...........AL*                                	312
ICH-1L   	QNKPKMFFIQACRGDETDRGVDQQDGKNHAGSP..........GCEESDAG......KEKLPKMRLPTRSDMICGYAC	353
hICE     	KDKPKVIIIQACRGDSPGVVW.FKDSV.................GVSGNLSLPTTEEFEDDAI.KKAHIEKDFIAFCSS	333
mICE     	KDKPKVIIIQACRGEKQGVVL.LKDSV................RDSEE.DFLTDAIFEDDGI.KKAHIEKDFIAFCSS	331
Ced-3    	ANKPKIVFVQACRGERRDNGFPVLDSVDGVPAFLRRGWDNRDGPLFNFLGCVRPQVQQWRKKPSQADILIRYAT	421

S

Nedd-2   	LKGNAAMRNTKRGSWYIEALTQVFSERACDMHVADMLVKVNALIK.EREGYAPGTEFHRCKEMSEYCSTLCQQLY	163
ICH-1L   	LKGTAAMRNTKRGSWYIEALAQVFSERACDMHVADMLVKVNALIK.DREGYAPGTEFHRCKEMSEYCSTLCRHLY	427
hICE     	TPDNVSWRHPTMGSVFIGRLIEHMQEYACSCDVEEIF......RKVRFSFEQPDGRAQMPTTERVT.....LTRCFY	399
mICE     	TPDNVSWRHPVRGSLFIESLIKHMKEYAWSCDLEDIF.....RKVRFSFEQPEFRLQMPTADRVT.....LTKRFY	397
Ced-3    	TAQYVSWRNSARGSWFIQAVCEVFSTHAKDMDVVELLTEVNKKVVACGFQTSQGSNILKQMPEMTSR...LLKKFY	493

Nedd-2   	LFPGYPPT*       171
ICH-1L   	LFPGHPPT*       435
hICE     	LFPGH*          404
mICE     	LFPGH*          402
Ced-3    	FWPEARNSAV*     503
```

FIG.14B

```
  1   CTTTTTTTTTTTTTTTTTTTTTATGTCCTGGAGTCCTGCACAGCC ATG GCG GCC AGG AGG   59
                                                    M   A   A   R   R

60   ACA CAT GAA AGA GAT CCA ATC TAC AAG ATC AAA GGT TTG GCC AAG GAC ATG CTG GAT GGG  119
       T   H   E   R   D   P   I   Y   K   I   K   G   L   A   K   D   M   L   D   G

120   GTT TTT GAT GAC CTG GTG GAG AAG AAT GTT TTA AAT GGA GAT GAG TTA CTC AAA ATA GGG  179
       V   F   D   D   L   V   E   K   N   V   L   N   G   D   E   L   L   K   I   G

180   GAA AGT GCG AGT TTC ATC CTG AAC AAG GCT GAG AAT CTG GTT GAG AAC TTC TTA GAG AAA  239
       E   S   A   S   F   I   L   N   K   A   E   N   L   V   E   N   F   L   E   K

240   ACA GAC ATG GCA GGA AAA ATA TTT GCT GGC CAC ATT GCC AAT TCC CAG GAA CAG CTG AGT  299
       T   D   M   A   G   K   I   F   A   G   H   I   A   N   S   Q   E   Q   L   S

300   TTA CAA TTT TCT AAT GAT GAG GAT GAT GGA CCT CAG AAG ATA TGT ACA CCT TCT TCT CCA  359
       L   Q   F   S   N   D   E   D   D   G   P   Q   K   I   C   T   P   S   S   P

360   TCA GAA TCC AAG AGA AAA GTA GAG GAT GAT GAA ATG GAG GTA AAT GCT GGA TTG GCC CAT  419
       S   E   S   K   R   K   V   E   D   D   E   M   E   V   N   A   G   L   A   H

420   GAA TCA CAT CTA ATG CTG ACA GCT CCT CAT GGA CTC CAG AGC TCA GAA GTC CAA GAT ACA  479
       E   S   H   L   M   L   T   A   P   H   G   L   Q   S   S   E   V   Q   D   T

480   CTG AAG CTT TGT CCA CGT GAT CAG TTT TGT AAG ATA AAG ACA GAA AGG GCA AAA GAG ATA  539
       L   K   L   C   P   R   D   Q   F   C   K   I   K   T   E   R   A   K   E   I

540   TAT CCA GTG ATG GAG AAG GAG GGA CGA ACA CGT CTG GCT CTC ATC ATC TGC AAC AAA AAG  599
       Y   P   V   M   E   K   E   G   R   T   R   L   A   L   I   I   C   N   K   K

600   TTT GAC TAC CTT TTT GAT AGA GAT AAT GCT GAT ACT GAC ATT TTG AAC ATG CAA GAA CTA  659
       F   D   Y   L   F   D   R   D   N   A   D   T   D   I   L   N   M   Q   E   L

660   CTT GAA AAT CTT GGA TAC TCT GTG GTG TTA AAA GAA AAC CTT ACA GCT CAG GAA ATG GAG  719
       L   E   N   L   G   Y   S   V   V   L   K   E   N   L   T   A   Q   E   M   E
```

FIG.16

```
720  ACA GAG TTA ATG CAG TTT GCT GGC CGT CCA GAG CAC CAG TCC TCA GAC AGC ACA TTC CTG 779
      T   E   L   M   Q   F   A   G   R   P   E   H   Q   S   S   D   S   T   F   L

780  GTG TTT ATG TCC CAT GGC ATC CTG GAA GGA ATC TGT GGG GTG AAG CAC CGA AAC AAA AAG 839
      V   F   M   S   H   G   I   L   E   G   I   C   G   V   K   H   R   N   K   K

840  CCA GAT GTT CTT CAT GAT GAC ACT ATC TTC AAA ATT TTC AAC AAC TCT AAC TGT CGG AGT 899
      P   D   V   L   H   D   D   T   I   F   K   I   F   N   N   S   N   C   R   S

900  CTG AGA AAC AAA CCC AAG ATT CTC ATC ATG CAG GCC TGC AGA GGC AGA TAT AAT GGA ACT 959
      L   R   N   K   P   K   I   L   I   M   Q   A   C   R   G   R   Y   N   G   T

960  ATT TGG GTA TCC ACA AAC AAA GGG ATA GCC ACT GCT GAT ACA GAT GAG GAA CGT GTG TTG 1019
      I   W   V   S   T   N   K   G   I   A   T   A   D   T   D   E   E   R   V   L

1020 AGC TGT AAA TGG AAT AAT AGT ATA ACA AAG GCC CAT GTG GAG ACA GAT TTC ATT GCT TTC 1079
      S   C   K   W   N   N   S   I   T   K   A   H   V   E   T   D   F   I   A   F

1080 AAA TCT TCT ACC CCA CAT AAT ATT TCT TGG AAG GTA GGC AAG ACT GGT TCC CTC TTC ATT 1139
      K   S   S   T   P   H   N   I   S   W   K   V   G   K   T   G   S   L   F   I

1140 TCC AAA CTC ATT GAC TGC TTC AAA AAG TAC TGT TGG TGT TAT CAT TTG GAG GAA ATT TTT 1199
      S   K   L   I   D   C   F   K   K   Y   C   W   C   Y   H   L   E   E   I   F

1200 CGA AAG GTT CAA CAC TCA TTT GAG GTC CCA GGT GAA CTG ACC CAG ATG CCC ACT ATT GAG 1259
      R   K   V   Q   H   S   F   E   V   P   G   E   L   T   Q   M   P   T   I   E

1260 AGA GTA TCC ATG ACA CGC TAT TTC TAC CTT TTT CCC GGG AAT TAG CAC AGG CAA CTC TCA 1319
      R   V   S   M   T   R   Y   F   Y   L   F   P   G   N   *

1320 TGC AGT TCA CAG TCA AGT ATT GCT GTA GCT GAG AAG AAA AGA AAA TTC CAA GAT CCC AGG 1379

1380 ATT TTT AAA TGT GTA AAA CTT TT
```

FIG.16A

```
             1                                                      50
    Ice4     .......... ..........M AARRTHERDP IYKIKGLAKD MLDGVFDDLV
     Ice     .......... .......... MADKILRAKR KQFINSVSIG TINGLLDELL
    Ice2     .......... .......... MAENKHPDKP LKVLEQLGKE VLTEYLEKLV
    Ice3     IPHKELMAAD RGRRILGVCG MHPHHQETLK KNRVVLAKQL LLSELLEHLL
    Ced3     .......... .........M MRQDRRSLLE RNIMMFSSHL KVDEILEVLI 51                                                    100
    Ice4     EKNVLNGDEL LKIGESASFI LNKAENLVEN FLEKTDMAGK IFAGHI.ANS
     Ice     EKRVLNQEEM DKIKLANITA MDKARNLCDH VSKKGAPASQ IFITYI.CNE
    Ice2     QSNVLKLKEE DKQKFNNAER SDKRWVFVDA MKKKHSKVGE MLL.......
    Ice3     EKDIITLEMR ELIQ.AKVGS FSQNVELLNL LPKRGPQAFD AFCEALRETK
    Ced3     AKQVLNSDNG DMIN.SCGTV REKRREIVKA VQRPGDVAFD AFYDALRSTG 101                                                   150
    Ice4     QEQLSLQF.. .......... .......... .......... ..........
     Ice     DCYLAGIL.. .......... .......... .......... ..........
    Ice2     .......... .......... .......... .......... ..........
    Ice3     QGHLEDML.. .......... .......... .......... ..........
    Ced3     HEGLAEVLEP LARSVDSNAV EFECPMSPAS HRRSRALSPA GYTSPTRVHR 151                                                   200
    Ice4     ....SNDEDD GPQKICTPSS PS........ .......... ....ESKRKV
     Ice     ....ELQSAP SAETFVATED SK........ .......... ....GGHPSS
    Ice2     .......... ..QTFFSVD. .P........ .......... ....GSHHGE
    Ice3     .....LTTLS GLQHV..... .......... .......... ...LPPLSCD
    Ced3     DSVSSVSSFT SYQDIYSRAR SRSRSRALHS SDRHNYSSPP VNAFPSQPSS 201                                                   250
    Ice4     EDDEMEVNAG LAHESHL... MLTAPHGLQS SEVQDTLKLC PRDQFCKIKT
     Ice     SETKEEQNKE DGTFPGL... T......... ....GTLKFC PLEKAQKLWK
    Ice2     ANLEMEEPEE S......... L......... ....NTLKLC SPEEFTRLCR
    Ice3     YDLSLPFPVC ESCPLYKKLR LSTDTVEHSL DNKDGPVCLQ VKPCTPEFYQ
    Ced3     ANSSFTGCSS LGYSSSRNRS FSKASGPTQY IFHEEDMNFV DAPTISRVFD 251                                                   300
    Ice4     ERAKEIYPVM EKEGRTRLAL IICNKKF... DYLFDRDNAD TDILNMQELL
     Ice     ENPSEIYPIM NTTTRTRLAL IICNTEF... QHLSPRVGAQ VDLREMKLLL
    Ice2     EKTQEIYPIK EANGRTRKAL IICNTEF... KHLSLRYGAK FDIIGMKGLL
    Ice3     THFQLAYRLQ SR..PRGLAL VLSNVHFTGE KELEFRSGGD VDHSTLVTLF
    Ced3     E..KTMYRNF SS..PRGMCL IINNEHF... EQMPTRNGTK ADKDNLTNLF
```

FIG.17

```
       301                                                    350
Ice4   ENLGYSVVLK  ENLTAQEMET  ELMQFAGRPE  HQSSDSTPGV  YVPWHPGRNL
Ice    EDLGYTVKVK  ENLTALEMVK  EVKEFAACPE  HKTSDSTFLV  FMSHGIQEGI
Ice2   EDLGYDVVVK  EELTAEGMES  EMKDFAALSE  HQTSDSTFLV  LMSHGTLHGI
Ice3   KLLGYDVHVL  CDQTAQEMQE  KLQNFAQLPA  HRVTDSCIVA  LLSHGVEGAI
Ced3   RCMGYTVICK  DNLTGRGMLL  TIRDFAKHES  H...GDSAILV  ILSHGEENVI 351                                                    400
Ice4   WGEAPKQK.P  DVLHDDTIFK  IFNNSNCRSL  RNKPKILIMQ  ACRGRYNGTI
Ice    CGTTYSNEVS  DILKVDTIFQ  MMNTLKCPSL  KDKPKVIIIQ  ACRGEKQGVV
Ice2   CGTMHSEKTP  DVLQYDTIYQ  IFNNCHCPGL  RDKPKVIIVQ  ACRGGNSGEM
Ice3   YGVD.....G  KLLQLQEVFQ  LFDNANCPSL  QNKPKMFFIQ  ACRGDETDRG
Ced3   IGVD.....D  IPISTHEIYD  LLNAANAPRL  ANKPKIVFVQ  ACRGERRDNG 401                                                    450
Ice4   WVSTNKGIAT  A....DTDEE  RVLSCKWNNS  ITKAHVET..  .......DFI
Ice    LLKDSVRD..  .....SEEDF  LTDAIFEDDG  IKKAHIEK..  .......DFI
Ice2   WIRESSKPQL  C....RGVDL  PRN..MEADA  VKLSHVEK..  .......DFI
Ice3   VDQQD.....  ......GKNH  AGSPGCEESD  AGKEKLPKMR  ..LPTRSDMI
Ced3   FPVLDSVDGV  PAFLRRGWDN  RDGPLFNFLG  CVRPQVQQVW  RKKPSQADIL 451                                                    500
Ice4   AFKSSTPHNI  SWKVGKTGSL  FISKLIDCKF  KYCWCYHLEE  IFRKVQHSFE
Ice    AFCSSTPDNV  SWRHPVRGSL  FIESLIKHMK  EYAWSCDLED  IFRKVRFSFE
Ice2   AFYATTPHHL  SYRDKTGGSY  FITRLISCFR  KHACSCHLFD  IFLKVQQSFE
Ice3   CGYACLKGTA  AMRNTKRGSW  YIEALAQVFS  ERACDMHVAD  MLVKVNALIK
Ced3   IRYATTAQYV  SWRNSARGSW  FIQAVCEVFS  THAKDMDVVE  LLTEVNK..K 501                               540
Ice4   VPGELTQMPT  IERV......  ..SMTRYFYL  FPGN*.....
Ice    QPEFRLQMPT  ADRV......  ..TLTKRFYL  FPGH......
Ice2   KASIHSQMPT  IDRA......  ..TLTRYFYL  FPGN*.....
Ice3   DREGYAPCTE  FHRCKEMSEY  CSTLCRHLYL  FPGHPPT...
Ced3   VACGFQTSQG  SNILKQMPEM  TSRLLKKFYF  WPEARNSAV*
```

FIG.17A

SEQUENCE LISTING (1) GENERAL INFORMATION:

(iii) NUMBER OF SEQUENCES: 85

(2) INFORMATION FOR SEQ ID NO:1:

(i) SEQUENCE CHARACTERISTICS:
      (A) LENGTH: 7653 base pairs
      (B) TYPE: nucleic acid
      (C) STRANDEDNESS: both
      (D) TOPOLOGY: both (ix) FEATURE:
      (A) NAME/KEY: CDS
      (B) LOCATION: join(2232..2366, 2430..2576, 2855..3109, 4305
         ..4634, 5547..5759, 5817..5942, 6298..6537, 7012
         ..7075)

(xi) SEQUENCE DESCRIPTION: SEQ ID NO:1:

```
AGATCTGAAA TAAGGTGATA AATTAATAAA TTAAGTGTAT TTCTGAGGAA ATTTGACTGT      60

TTTAGCACAA TTAATCTTGT TTCAGAAAAA AAGTCCAGTT TTCTAGATTT TTCCGTCTTA     120

TTGTCGAATT AATATCCCTA TTATCACTTT TTCATGCTCA TCCTCGAGCG GCACGTCCTC     180

AAAGAATTGT GAGAGCAAAC GCGCTCCCAT TGACCTCCAC ACTCAGCCGC CAAAACAAAC     240

GTTCGAACAT TCGTGTGTTG TGCTCCTTTT CCGTTATCTT GCAGTCATCT TTTGTCGTTT     300

TTTTCTTTGT TCTTTTTGTT GAACGTGTTG CTAAGCAATT ATTACATCAA TTGAAGAAAA     360

GGCTCGCCGA TTTATTGTTG CCAGAAAGAT TCTGAGATTC TCGAAGTCGA TTTTATAATA     420

TTTAACCTTG GTTTTTGCAT TGTTTCGTTT AAAAAAACCA CTGTTTATGT GAAAAACGAT     480

TAGTTTACTA ATAAAACTAC TTTTAAACCT TTACCTTTAC CTCACCGCTC CGTGTTCATG     540

GCTCATAGAT TTTCGATACT CAAATCCAAA AATAAATTTA CGAGGGCAAT TAATGTGAAA     600

CAAAAACAAT CCTAAGATTT CCACATGTTT GACCTCTCCG GCACCTTCTT CCTTAGCCCC     660

ACCACTCCAT CACCTCTTTG GCGGTGTTCT TCGAAACCCA CTTAGGAAAG CAGTGTGTAT     720
```

-continued

```
CTCATTTGGT ATGCTCTTTT CGATTTTATA GCTCTTTGTC GCAATTTCAA TGCTTTAAAC   780
AATCCAAATC GCATTATATT TGTGCATGGA GGCAAATGAC GGGGTTGGAA TCTTAGATGA   840
GATCAGGAGC TTTCAGGGTA AACGCCCGGT TCATTTTGTA CCACATTTCA TCATTTTCCT   900
GTCGTCCTTG GTATCCTCAA CTTGTCCCGG TTTTGTTTTC GGTACACTCT TCCGTGATGC   960
CACCTGTCTC CGTCTCAATT ATCGTTTAGA AATGTGAACT GTCCAGATGG GTGACTCATA  1020
TTGCTGCTGC TACAATCCAC TTTCTTTTCT CATCGGCAGT CTTACGAGCC ATCATAAAC   1080
TTTTTTTTCC GCGAAATTTG CAATAAACCG GCCAAAAACT TTCTCCAAAT TGTTACGCAA  1140
TATATACAAT CCATAAGAAT ATCTTCTCAA TGTTTATGAT TCTTCGCAG CACTTTCTCT   1200
TCGTGTGCTA ACATCTTATT TTTATAATAT TTCCGCTAAA ATTCCGATTT TGAGTATTA   1260
ATTTATCGTA AAATTATCAT AATAGCACCG AAAACTACTA AAATGGTAA AAGCTCCTTT   1320
TAAATCGGCT CGACATTATC GTATTAAGGA ATCACAAAAT TCTGAGAATG CGTACTGCGC  1380
AACATATTTG ACGGCAAAAT ATCTCGTAGC GAAAACTACA GTAATTCTTT AAATGACTAC  1440
TGTAGCGCTT GTGTCGATTT ACGGGCTCAA TTTTTGAAAA TAATTTTTTT TTTCGAATTT  1500
TGATAACCCG TAAATCGTCA CAACGCTACA GTAGTCATTT AAAGGATTAC TGTAGTTCTA  1560
GCTACGAGAT ATTTTGCGCG CCAAATATGA CTGTAATACG CATTCTCTGA ATTTGTGTT   1620
TCCGTAATAA TTTCACAAGA TTTTGGCATT CCACTTTAAA GGCGCACAGG ATTTATTCCA  1680
ATGGGTCTCG GCACGCAAAA AGTTGATAG ACTTTTAAAT TCTCCTTGCA TTTTTAATTC   1740
AATTACTAAA ATTTTCGTGA ATTTTTCTGT TAAAATTTTT AAAATCAGTT TTCTAATATT  1800
TTCCAGGCTG ACAAACAGAA ACAAAAACAC AACAAACATT TTAAAAATCA GTTTTCAAAT  1860
TAAAAATAAC GATTTCTCAT TGAAAATTGT GTTTTATGTT TGCGAAAATA AAGAGAACT   1920
GATTCAAAAC AATTTTAACA AAAAAAAACC CCAAAATTCG CCAGAAATCA AGATAAAAAA  1980
TTCAAGAGGG TCAAAATTTT CCGATTTTAC TGACTTTCAC CTTTTTTTTC GTAGTTCAGT  2040
GCAGTTGTTG GAGTTTTTGA CGAAAACTAG GAAAAAAATC GATAAAAATT ACTCAAATCG  2100
AGCTGAATTT TGAGGACAAT GTTTAAAAAA AAACACTATT TTTCCAATAA TTTCACTCAT  2160
TTTCAGACTA AATCGAAAAT CAAATCGTAC TCTGACTACG GGTCAGTAGA GAGGTCAACC  2220
ATCAGCCGAA G ATG ATG CGT CAA GAT AGA AGG AGC TTG CTA GAG AGG AAC   2270
            Met Met Arg Gln Asp Arg Arg Ser Leu Leu Glu Arg Asn
              1               5                   10
ATT ATG ATG TTC TCT AGT CAT CTA AAA GTC GAT GAA ATT CTC GAA GTT   2318
Ile Met Met Phe Ser Ser His Leu Lys Val Asp Glu Ile Leu Glu Val
         15                  20                  25
CTC ATC GCA AAA CAA GTG TTG AAT AGT GAT AAT GGA GAT ATG ATT AAT   2366
Leu Ile Ala Lys Gln Val Leu Asn Ser Asp Asn Gly Asp Met Ile Asn
 30                  35                  40                  45
GTGAGTTTTT AATCGAATAA TAATTTTAAA AAAAAATTGA TAATATAAAG AATATTTTTG  2426
CAG TCA TGT GGA ACG GTT CGC GAG AAG AGA CGG GAG ATC GTG AAA GCA   2474
    Ser Cys Gly Thr Val Arg Glu Lys Arg Arg Glu Ile Val Lys Ala
                 50                  55                  60
GTG CAA CGA CGG GGA GAT GTG GCG TTC GAC GCG TTT TAT GAT GCT CTT   2522
Val Gln Arg Arg Gly Asp Val Ala Phe Asp Ala Phe Tyr Asp Ala Leu
             65                  70                  75
CGC TCT ACG GGA CAC GAA GGA CTT GCT GAA GTT CTT GAA CCT CTC GCC   2570
Arg Ser Thr Gly His Glu Gly Leu Ala Glu Val Leu Glu Pro Leu Ala
         80                  85                  90
AGA TCG TAGGTTTTTA AAGTTCGGCG CAAAAGCAAG GGTCTCACGG AAAAAAGAGG   2626
Arg Ser
```

```
CGGATCGTAA TTTTGCAACC CACCGGCACG GTTTTTTCCT CCGAAAATCG GAAATTATGC        2686

ACTTTCCCAA ATATTTGAAG TGAAATATAT TTTATTTACT GAAAGCTCGA GTGATTATTT        2746

ATTTTTTAAC ACTAATTTTC GTGGCGCAAA AGGCCATTTT GTAGATTTGC CGAAAATACT        2806

TGTCACACAC ACACACACAC ATCTCCTTCA AATATCCCTT TTTCCAGT GTT GAC TCG        2863
                                                      Val Asp Ser
                                                           95

AAT GCT GTC GAA TTC GAG TGT CCA ATG TCA CCG GCA AGC CAT CGT CGG         2911
Asn Ala Val Glu Phe Glu Cys Pro Met Ser Pro Ala Ser His Arg Arg
         100                 105                 110

AGC CGC GCA TTG AGC CCC GCC GGC TAC ACT TCA CCG ACC CGA GTT CAC         2959
Ser Arg Ala Leu Ser Pro Ala Gly Tyr Thr Ser Pro Thr Arg Val His
        115                 120                 125

CGT GAC AGC GTC TCT TCA GTG TCA TCA TTC ACT TCT TAT CAG GAT ATC         3007
Arg Asp Ser Val Ser Ser Val Ser Ser Phe Thr Ser Tyr Gln Asp Ile
130                 135                 140                 145

TAC TCA AGA GCA AGA TCT CGT TCT CGA TCG CGT GCA CTT CAT TCA TCG         3055
Tyr Ser Arg Ala Arg Ser Arg Ser Arg Ser Arg Ala Leu His Ser Ser
                150                 155                 160

GAT CGA CAC AAT TAT TCA TCT CCT CCA GTC AAC GCA TTT CCC AGC CAA         3103
Asp Arg His Asn Tyr Ser Ser Pro Pro Val Asn Ala Phe Pro Ser Gln
                165                 170                 175

CCT TCT ATGTTGATGC GAACACTAAA TTCTGAGAAT GCGCATTACT CAACATATTT         3159
Pro Ser
GACGCGCAAA TATCTCGTAG CGAAAAATAC AGTAACCCTT TAAATGACTA TTGTAGTGTC       3219

GATTTACGGG CTCGATTTTC GAAACGAATA TATGCTCGAA TTGTGACAAC GAATTTTAAT       3279

TTGTCATTTT TGTGTTTTCT TTTGATATTT TTGATCAATT AATAAATTAT TTCCGTAAAC       3339

AGACACCAGC GCTACAGTAC TCTTTTAAAG AGTTACAGTA GTTTTCGCTT CAAGATATTT       3399

TGAAAAGAAT TTTAAACATT TTGAAAAAAA ATCATCTAAC ATGTGCCAAA ACGCTTTTTT       3459

CAAGTTTCGC AGATTTTTTG ATTTTTTTCA TTCAAGATAT GCTTATTAAC ACATATAATT       3519

ATCATTAATG TGAATTTCTT GTAGAAATTT TGGGCTTTTC GTTCTAGTAT GCTCTACTTT       3579

TGAAATTGCT CAACGAAAAA ATCATGTGGT TTGTTCATAT GAATGACGAA AAATAGCAAT       3639

TTTTTATATA TTTTCCCCTA TTCATGTTGT GCAGAAAAAT AGTAAAAAAG CGCATGCATT       3699

TTTCGACATT TTTTACATCG AACGACAGCT CACTTCACAT GCTGAAGACG AGAGACGCGG       3759

AGAAATACCA CACATCTTTC TGCGTCTCTC GTCTTCAGCA TGTGAAATGG GATCTCGGTC       3819

GATGTAAAAA AATGTCGAAT AATGTAAAAA ATGCATGCGT TTTTTTACAC TTTTCTGCAC       3879

AAATGAATAG GGGGAAAATG TATTAAAATA CATTTTTTGT ATTTTTCAAC ATCACATGAT       3939

TAACCCCATT ATTTTTTCGT TGAGCAACTT AAAAAGTAGA GAATATTAGA GCGAAAACCA       3999

AAATTTCTTC AAGATATTAC CTTTATTGAT AATTATAGAT GTTAATAAGC ATATCTTGAA       4059

TGAAAGTCAG CAAAAATATG TGCGAAACAC CTGAAAAAAA TCAAAAATTC TGCGAAAATT       4119

GAAAAAATGC ATTAAAATAC ATTTTTGCAT TTTTCTACAT CACATGAATG TAGAAAATTA       4179

AAAGGGAAAT CAAAATTTCT AGAGGATATA ATTGAATGAA ACATTGCGAA ATTAAAATGT       4239

GCGAAACGTC AAAAAGAGG AAATTTGGGT ATCAAAATCG ATCCTAAAAC CAACACATTT       4299

CAGCA TCC GCC AAC TCT TCA TTC ACC GGA TGC TCT TCT CTC GGA TAC          4346
      Ser Ala Asn Ser Ser Phe Thr Gly Cys Ser Ser Leu Gly Tyr
          180                 185                 190

AGT TCA AGT CGT AAT CGC TCA TTC AGC AAA GCT TCT GGA CCA ACT CAA         4394
Ser Ser Ser Arg Asn Arg Ser Phe Ser Lys Ala Ser Gly Pro Thr Gln
         195                 200                 205

TAC ATA TTC CAT GAA GAG GAT ATG AAC TTT GTC GAT GCA CCA ACC ATA         4442
```

-continued

```
Tyr Ile Phe His Glu Glu Asp Met Asn Phe Val Asp Ala Pro Thr Ile
210                 215                 220                 225

AGC CGT GTT TTC GAC GAG AAA ACC ATG TAC AGA AAC TTC TCG AGT CCT      4490
Ser Arg Val Phe Asp Glu Lys Thr Met Tyr Arg Asn Phe Ser Ser Pro
                230                 235                 240

CGT GGA ATG TGC CTC ATC ATA AAT AAT GAA CAC TTT GAG CAG ATG CCA      4538
Arg Gly Met Cys Leu Ile Ile Asn Asn Glu His Phe Glu Gln Met Pro
                245                 250                 255

ACA CGG AAT GGT ACC AAG GCC GAC AAG GAC AAT CTT ACC AAT TTG TTC      4586
Thr Arg Asn Gly Thr Lys Ala Asp Lys Asp Asn Leu Thr Asn Leu Phe
                260                 265                 270

AGA TGC ATG GGC TAT ACG GTT ATT TGC AAG GAC AAT CTG ACG GGA AGG      4634
Arg Cys Met Gly Tyr Thr Val Ile Cys Lys Asp Asn Leu Thr Gly Arg
        275                 280                 285

GTACGGCGAA ATTATATTAC CCAAACGCGA AATTTGCCAT TTTGCGCCGA AAATGTGGCG    4694

CCCGGTCTCG ACACGACAAT TTGTGTTAAA TGCAAAAATG TATAATTTTG CAAAAACAA     4754

AATTTTGAAC TTCCGCGAAA ATGATTTACC TAGTTTCGAA ATTTTCGTTT TTTCCGGCTA    4814

CATTATGTGT TTTTTCTTAG TTTTTCTATA ATATTTGATG TAAAAAACCG TTTGTAAATT    4874

TTCAGACAAT TTTCCGCATA CAAAACTTGA TAGCACGAAA TCAATTTTCT GAATTTTCAA    4934

AATTATCCAA AAATGCACAA TTTAAAATTT GTGAAAATTG GCAAACGGTG TTTCAATATG    4994

AAATGTATTT TTAAAAACTT TAAAAACCAC TCCGGAAAAG CAATAAAAAT CAAAACAACG    5054

TCACAATTCA AATTCAAAAG TTATTCATCC GATTTGTTTA TTTTTGCAAA ATTTGAAAAA    5114

ATCATGAAGG ATTTAGAAAA GTTTTATAAC ATTTTTTCTA GATTTTTCAA AATTTTTTTT    5174

AACAAATCGA GAAAAGAGA ATGAAAAATC GATTTTAAAA ATATCCACAG CTTCGAGAGT     5234

TTGAAATTAC AGTACTCCTT AAAGGCGCAC ACCCCATTTG CATTGGACCA AAAATTTGTC    5294

GTGTCGAGAC CAGGTACCGT AGTTTTTGTC GCAAAAATTG CACCATTGGA CAATAAACCT    5354

TCCTAATCAC CAAAAAGTAA AATTGAAATC TTCGAAAAGC CAAAAAATTC AAAAAAAAAG    5414

TCGAATTTCG ATTTTTTTTT TGGTTTTTTG GTCCCAAAAA CCAAAAAAAT CAATTTTCTG    5474

CAAAATACCA AAAAGAAACC CGAAAAAATT TCCCAGCCTT GTTCCTAATG TAAACTGATA    5534

TTTAATTTCC AG GGA ATG CTC CTG ACA ATT CGA GAC TTT GCC AAA CAC       5582
              Gly Met Leu Leu Thr Ile Arg Asp Phe Ala Lys His
              290                 295                 300

GAA TCA CAC GGA GAT TCT GCG ATA CTC GTG ATT CTA TCA CAC GGA GAA      5630
Glu Ser His Gly Asp Ser Ala Ile Leu Val Ile Leu Ser His Gly Glu
                305                 310                 315

GAG AAT GTG ATT ATT GGA GTT GAT GAT ATA CCG ATT AGT ACA CAC GAG      5678
Glu Asn Val Ile Ile Gly Val Asp Asp Ile Pro Ile Ser Thr His Glu
        320                 325                 330

ATA TAT GAT CTT CTC AAC GCG GCA AAT GCT CCC CGT CTG GCG AAT AAG      5726
Ile Tyr Asp Leu Leu Asn Ala Ala Asn Ala Pro Arg Leu Ala Asn Lys
335                 340                 345

CCG AAA ATC GTT TTT GTG CAG GCT TGT CGA GGC G GTTCGTTTT TTATTTAAT    5779
Pro Lys Ile Val Phe Val Gln Ala Cys Arg Gly Glu
350                 355                 360

TTTAATATAA ATATTTTAAA TAAATTCATT TTCAG AA CGT CGT GAC AAT GGA TTC    5834
                                        Arg Arg Asp Asn Gly Phe
                                                        365

CCA GTC TTG GAT TCT GTC GAC GGA GTT CCT GCA TTT CTT CGT CGT GGA      5882
Pro Val Leu Asp Ser Val Asp Gly Val Pro Ala Phe Leu Arg Arg Gly
        370                 375                 380

TGG GAC AAT CGA GAC GGG CCA TTG TTC AAT TTT CTT GGA TGT GTG CGG      5930
Trp Asp Asn Arg Asp Gly Pro Leu Phe Asn Phe Leu Gly Cys Val Arg
```

-continued

```
             385                 390                 395
CCG CAA GTT CAG GTTGCAATTT AATTTCTTGA ATGAGAATAT TCCTTCAAAA              5982
Pro Gln Val Gln
400

AATCTAAAAT AGATTTTTAT TCCAGAAAGT CCCGATCGAA AAATTGCGAT ATAATTACGA        6042

AATTTGTGAT AAAATGACAA ACCAATCAGC ATCGTCGATC TCCGCCCACT TCATCGGATT        6102

GGTTTGAAAG TGGGCGGAGT GAATTGCTGA TTGGTCGCAG TTTTCAGTTT AGAGGGAATT        6162

TAAAAATCGC CTTTTCGAAA ATTAAAAATT GATTTTTTCA ATTTTTTCGA AAATATTCC         6222

GATTATTTTA TATTCTTTGG AGCGAAAGCC CCGTCCTGTA ACATTTTTA AATGATAATT         6282

AATAAATTTT TGCAG CAA GTG TGG AGA AAG AAG CCG AGC CAA GCT GAC ATT        6333
          Gln Val Trp Arg Lys Lys Pro Ser Gln Ala Asp Ile
                    405                 410                 415

CTG ATT CGA TAC GCA ACG ACA GCT CAA TAT GTT TCG TGG AGA AAC AGT         6381
Leu Ile Arg Tyr Ala Thr Thr Ala Gln Tyr Val Ser Trp Arg Asn Ser
            420                 425                 430

GCT CGT GGA TCA TGG TTC ATT CAA GCC GTC TGT GAA GTG TTC TCG ACA         6429
Ala Arg Gly Ser Trp Phe Ile Gln Ala Val Cys Glu Val Phe Ser Thr
            435                 440                 445

CAC GCA AAG GAT ATG GAT GTT GTT GAG CTG CTG ACT GAA GTC AAT AAG         6477
His Ala Lys Asp Met Asp Val Val Glu Leu Leu Thr Glu Val Asn Lys
            450                 455                 460

AAG GTC GCT TGT GGA TTT CAG ACA TCA CAG GGA TCG AAT ATT TTG AAA         6525
Lys Val Ala Cys Gly Phe Gln Thr Ser Gln Gly Ser Asn Ile Leu Lys
            465                 470                 475

CAG ATG CCA GAG GTACTTGAAA CAAACAATGC ATGTCTAACT TTTAAGGACA             6577
Gln Met Pro Glu
480

CAGAAAAATA GGCAGAGGCT CCTTTTGCAA GCCTGCCGCG CGTCAACCTA GAATTTTAGT       6637

TTTTAGCTAA AATGATTGAT TTTGAATATT TTATGCTAAT TTTTTTGCGT TAAATTTGA        6697

AATAGTCACT ATTTATCGGG TTTCCAGTAA AAAATGTTTA TTAGCCATTG GATTTTACTG       6757

AAAACGAAAA TTTGTAGTTT TTCAACGAAA TTTATCGATT TTTAAATGTA AAAAAAAATA       6817

GCGAAAATTA CATCAACCAT CAAGCATTTA AGCCAAAATT GTTAACTCAT TTAAAAATTA       6877

ATTCAAAGTT GTCCACGAGT ATTACACGGT TGGCGCGCGG CAAGTTTGCA AAACGACGCT       6937

CCGCCTGTTT TTCTGTGCGG CTTGAAAACA AGGGATCGGT TTAGATTTTT CCCCAAAATT       6997

TAAATTAAAT TTCAG ATG ACA TCC CGC CTG CTC AAA AAG TTC TAC TTT TGG       7048
             Met Thr Ser Arg Leu Leu Lys Lys Phe Tyr Phe Trp
                         485                 490                 495

CCG GAA GCA CGA AAC TCT GCC GTC TAAAATTCAC TCGTGATTCA TTGCCCAATT        7102
Pro Glu Ala Arg Asn Ser Ala Val
                500

GATAATTGTC TGTATCTTCT CCCCCAGTTC TCTTTCGCCC AATTAGTTTA AAACCATGTG       7162

TATATTGTTA TCCTATACTC ATTTCACTTT ATCATTCTAT CATTTCTCTT CCCATTTTCA       7222

CACATTTCCA TTTCTCTACG ATAATCTAAA ATTATGACGT TTGTGTCTCG AACGCATAAT       7282

AATTTTAATA ACTCGTTTTG AATTTGATTA GTTGTTGTGC CCAGTATATA TGTATGTACT       7342

ATGCTTCTAT CAACAAAATA GTTTCATAGA TCATCACCCC AACCCCACCA ACCTACCGTA       7402

CCATATTCAT TTTTGCCGGG AATCAATTTC GATTAATTTT AACCTATTTT TTCGCCACAA       7462

AAAATCTAAT ATTTGAATTA ACGAATAGCA TTCCCATCTC TCCCGTGCCG GAATGCCTCC       7522

CGGCCTTTTA AAGTTCGGAA CATTTGGCAA TTATGTATAA ATTTGTAGGT CCCCCCCATC       7582

ATTTCCCGCC CATCATCTCA AATTGCATTC TTTTTTCGCC GTGATATCCC GATTCTGGTC       7642
```

AGCAAAGATC T                                                                7653

(2) INFORMATION FOR SEQ ID NO:2:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO:2:

```
Met Met Arg Gln Asp Arg Arg Ser Leu Leu Glu Arg Asn Ile Met Met
 1               5                  10                  15

Phe Ser Ser His Leu Lys Val Asp Glu Ile Leu Glu Val Leu Ile Ala
                20                  25                  30

Lys Gln Val Leu Asn Ser Asp Asn Gly Asp Met Ile Asn Ser Cys Gly
            35                  40                  45

Thr Val Arg Glu Lys Arg Arg Glu Ile Val Lys Ala Val Gln Arg Arg
    50                  55                  60

Gly Asp Val Ala Phe Asp Ala Phe Tyr Asp Ala Leu Arg Ser Thr Gly
 65                  70                  75                  80

His Glu Gly Leu Ala Glu Val Leu Glu Pro Leu Ala Arg Ser Val Asp
                85                  90                  95

Ser Asn Ala Val Glu Phe Glu Cys Pro Met Ser Pro Ala Ser His Arg
                100                 105                 110

Arg Ser Arg Ala Leu Ser Pro Ala Gly Tyr Thr Ser Pro Thr Arg Val
            115                 120                 125

His Arg Asp Ser Val Ser Ser Val Ser Ser Phe Thr Ser Tyr Gln Asp
    130                 135                 140

Ile Tyr Ser Arg Ala Arg Ser Arg Ser Arg Ala Leu His Ser
145                 150                 155                 160

Ser Asp Arg His Asn Tyr Ser Ser Pro Pro Val Asn Ala Phe Pro Ser
                165                 170                 175

Gln Pro Ser Ser Ala Asn Ser Ser Phe Thr Gly Cys Ser Ser Leu Gly
                180                 185                 190

Tyr Ser Ser Arg Asn Arg Ser Phe Ser Lys Ala Ser Gly Pro Thr
            195                 200                 205

Gln Tyr Ile Phe His Glu Glu Asp Met Asn Phe Val Asp Ala Pro Thr
    210                 215                 220

Ile Ser Arg Val Phe Asp Glu Lys Thr Met Tyr Arg Asn Phe Ser Ser
225                 230                 235                 240

Pro Arg Gly Met Cys Leu Ile Ile Asn Asn Glu His Phe Glu Gln Met
                245                 250                 255

Pro Thr Arg Asn Gly Thr Lys Ala Asp Lys Asp Asn Leu Thr Asn Leu
                260                 265                 270

Phe Arg Cys Met Gly Tyr Thr Val Ile Cys Lys Asp Asn Leu Thr Gly
            275                 280                 285

Arg Gly Met Leu Leu Thr Ile Arg Asp Phe Ala Lys His Glu Ser His
    290                 295                 300

Gly Asp Ser Ala Ile Leu Val Ile Leu Ser His Gly Glu Glu Asn Val
305                 310                 315                 320

Ile Ile Gly Val Asp Asp Ile Pro Ile Ser Thr His Glu Ile Tyr Asp
                325                 330                 335

Leu Leu Asn Ala Ala Asn Ala Pro Arg Leu Ala Asn Lys Pro Lys Ile
```

```
                340              345              350
Val Phe Val Gln Ala Cys Arg Gly Glu Arg Arg Asp Asn Gly Phe Pro
            355              360              365

Val Leu Asp Ser Val Asp Gly Val Pro Ala Phe Leu Arg Arg Gly Trp
    370              375              380

Asp Asn Arg Asp Gly Pro Leu Phe Asn Phe Leu Gly Cys Val Arg Pro
385              390              395              400

Gln Val Gln Gln Val Trp Arg Lys Pro Ser Gln Ala Asp Ile Leu
                405              410              415

Ile Arg Tyr Ala Thr Thr Ala Gln Tyr Val Ser Trp Arg Asn Ser Ala
            420              425              430

Arg Gly Ser Trp Phe Ile Gln Ala Val Cys Glu Val Phe Ser Thr His
            435              440              445

Ala Lys Asp Met Asp Val Val Glu Leu Leu Thr Glu Val Asn Lys Lys
    450              455              460

Val Ala Cys Gly Phe Gln Thr Ser Gln Gly Ser Asn Ile Leu Lys Gln
465              470              475              480

Met Pro Glu Met Thr Ser Arg Leu Leu Lys Lys Phe Tyr Phe Trp Pro
                485              490              495

Glu Ala Arg Asn Ser Ala Val
                500

(2) INFORMATION FOR SEQ ID NO:3:

(i) SEQUENCE CHARACTERISTICS:
        (A) LENGTH: 132 base pairs
        (B) TYPE: nucleic acid
        (C) STRANDEDNESS: both
        (D) TOPOLOGY: both (xi) SEQUENCE DESCRIPTION: SEQ ID NO:3:

GTATTAAGGA ATCACAAAAT TCTGAGAATG CGTACTGCGC AACATATTTG ACGGCAAAAT      60

ATCTCGTAGC GAAAACTACA GTAATTCTTT AAATGACTAC TGTAGCGCTT GTGTCGATTT     120

ACGGGCTCAA TT                                                         132

(2) INFORMATION FOR SEQ ID NO:4:

(i) SEQUENCE CHARACTERISTICS:
        (A) LENGTH: 125 base pairs
        (B) TYPE: nucleic acid
        (C) STRANDEDNESS: both
        (D) TOPOLOGY: both (xi) SEQUENCE DESCRIPTION: SEQ ID NO:4:

AAAATTCAGA GAATGCGTAT TACAGTCATA TTTGGCGCGC AAAATATCTC GTAGCTAGAA      60

CTACAGTAAT CCTTTAAATG ACTACTGTAG CGTTGTGACG ATTTACGGGT TATCAAAATT     120

CGAAA                                                                 125

(2) INFORMATION FOR SEQ ID NO:5:

(i) SEQUENCE CHARACTERISTICS:
        (A) LENGTH: 116 base pairs
        (B) TYPE: nucleic acid
        (C) STRANDEDNESS: both
        (D) TOPOLOGY: both (xi) SEQUENCE DESCRIPTION: SEQ ID NO:5:

AAATTCTGAG AATGCGCATT ACTCAACATA TTTGACGCGC AAATATCTCG TAGCGAAAAT      60
```

-continued

ACAGTAACCC TTTAAATGAC TATTGTAGTG TCGATTTACG GGCTCGATTT TCGAAA        116

(2) INFORMATION FOR SEQ ID NO:6:

(i) SEQUENCE CHARACTERISTICS:
        (A) LENGTH: 73 base pairs
        (B) TYPE: nucleic acid
        (C) STRANDEDNESS: both
        (D) TOPOLOGY: both (xi) SEQUENCE DESCRIPTION: SEQ ID NO:6:

TATCTTGAAG CGAAAACTAC TGTAACTCTT TAAAAGAGTA CTGTAGCGCT GGTGTCTGTT        60

TACGGAAATA ATT        73

(2) INFORMATION FOR SEQ ID NO:7:

(i) SEQUENCE CHARACTERISTICS:
        (A) LENGTH: 132 base pairs
        (B) TYPE: nucleic acid
        (C) STRANDEDNESS: both
        (D) TOPOLOGY: both (xi) SEQUENCE DESCRIPTION: SEQ ID NO:7:

GTATTACGGC AAGAAATAAT TATGAGAATG CCTATTGCGC ACCATAGTTG ACGCGCAAAA        60

TATCTCGTAG CGAAAACTAC AGTAACTCTT TGAATGACTA CTGTAGCGCT TGTTTCGATT       120

TACGGGCTCG TT        132

(2) INFORMATION FOR SEQ ID NO:8:

(i) SEQUENCE CHARACTERISTICS:
        (A) LENGTH: 111 base pairs
        (B) TYPE: nucleic acid
        (C) STRANDEDNESS: both
        (D) TOPOLOGY: both (xi) SEQUENCE DESCRIPTION: SEQ ID NO:8:

GTATAACGGT AACACACAAT TCTGAGAATG CGTATTGCAC AACACATTTG ACGCGCAAAA        60

TATCTCGTAG CGAAAACTAC AGTGATTCGC TGAATGAATA CGGTAGGGTC G                111

(2) INFORMATION FOR SEQ ID NO:9:

(i) SEQUENCE CHARACTERISTICS:
        (A) LENGTH: 122 base pairs
        (B) TYPE: nucleic acid
        (C) STRANDEDNESS: both
        (D) TOPOLOGY: both (xi) SEQUENCE DESCRIPTION: SEQ ID NO:9:

CTATTACGGG AGTACAAAAT TCTGAGAATG CGTACTGCGC AACATATTTG ACGCGCAAAA        60

TATTTCGTAT CGAAAACTAC AGTAATTCGT TTATTGGCTA CTGTGCGTGT TGATTTACGG       120

GC        122

(2) INFORMATION FOR SEQ ID NO:10:

(i) SEQUENCE CHARACTERISTICS:
        (A) LENGTH: 124 base pairs
        (B) TYPE: nucleic acid
        (C) STRANDEDNESS: both
        (D) TOPOLOGY: both (xi) SEQUENCE DESCRIPTION: SEQ ID NO:10:

GGGAGCACAA AATTCTGACT ATGAGAATGC GTATAAGCAC AAAATATTTC GTAGCGAAAA        60

```
CTACAGTAAT TTGTCAAGGG ACTACTGTAG CTAGCGCTTG TGTCGATTTA CGGAGCTCGA        120

TTTT                                                                    124

(2) INFORMATION FOR SEQ ID NO:11:

(i) SEQUENCE CHARACTERISTICS:
        (A) LENGTH: 74 base pairs
        (B) TYPE: nucleic acid
        (C) STRANDEDNESS: both
        (D) TOPOLOGY: both (xi) SEQUENCE DESCRIPTION: SEQ ID NO:11:

TATAGGAAAA ATTGAATGAT CAATTGCGCA AAATATTGAC AAACTACGTA AGTAGTAGTG         60

TTTTACGGTT GAAA                                                          74

(2) INFORMATION FOR SEQ ID NO:12:

(i) SEQUENCE CHARACTERISTICS:
        (A) LENGTH: 269 base pairs
        (B) TYPE: nucleic acid
        (C) STRANDEDNESS: both
        (D) TOPOLOGY: both (xi) SEQUENCE DESCRIPTION: SEQ ID NO:12:

TCATTCAAGA TATGCTTATT AACACATATA ATTATCATTA ATGTGAATTT CTTGTAGAAA         60

TTTTGGGCTT TTCGTTCTAG TATGCTCTAC TTTTGAAATT GCTCAACGAA AAAATCATGT        120

GGTTTGTTCA TATGAATGAC GAAAAATAGC AATTTTTTAT ATATTTTCCC CTATTCATGT        180

TGTGCAGAAA AATAGTAAAA AGCGCATGCA TTTTTCGACA TTTTTTACAT CGAACGACAG        240

CTCACTTCAC ATGCTGAAGA CGAGAGACG                                         269

(2) INFORMATION FOR SEQ ID NO:13:

(i) SEQUENCE CHARACTERISTICS:
        (A) LENGTH: 280 base pairs
        (B) TYPE: nucleic acid
        (C) STRANDEDNESS: both
        (D) TOPOLOGY: both (xi) SEQUENCE DESCRIPTION: SEQ ID NO:13:

TCATTCAAGA TATGCTTATT AACATCTATA ATTATCAATA AAGGTAATAT CTTGAAGAAA         60

TTTTGGTTTT CGCTCTAATA TTCTCTACTT TTTAAGTTGC TCAACGAAAA AATAATGGGG        120

TTAATCATGT GATGTTGAAA AATACAAAAA ATGTATTTTA ATACATTTTC CCCTATTCA         180

TTTGTGCAGA AAAGTGAAAA AAACGCATGCA TTTTTTACAT TATTCGACAT TTTTTTACA        240

TCGACCGAGAT CCCATTTCAC ATGCTGAAGA CGAGAGACG                             280

(2) INFORMATION FOR SEQ ID NO:14:

(i) SEQUENCE CHARACTERISTICS:
        (A) LENGTH: 226 base pairs
        (B) TYPE: nucleic acid
        (C) STRANDEDNESS: both
        (D) TOPOLOGY: both (xi) SEQUENCE DESCRIPTION: SEQ ID NO:14:

TCATTCAAGA TATGCTTATT AACATATAAT TATCATAAGA ATTCTTGAGA AATTTTGGTT         60

TTCGTCTATA TCTCTACTTT TAATTGCTCA ACGAAAAAAT CATGTGATGG AAAAATAAAT       120

TTTTATAATT TTCCCCTATT CATTTGTGCA GAAAATGTAA AAACGCATG CATTTTTCGA        180

CATTTTTTAC ATCGACGAAC CATTCACATG CTGAAGACGA GAGACG                      226
```

(2) INFORMATION FOR SEQ ID NO:15:

(i) SEQUENCE CHARACTERISTICS:
        (A) LENGTH: 108 base pairs
        (B) TYPE: nucleic acid
        (C) STRANDEDNESS: both
        (D) TOPOLOGY: both (xi) SEQUENCE DESCRIPTION: SEQ ID NO:15:

```
CAGCTTCGAG AGTTTGAAAT TACAGTACTC CTTAAAGGCG CACACCCCAT TTGCATTGGA        60

CCAAAAATTT GTCGTGTCGA GACCAGGTAC CGTAGTTTTT GTCGCAAA                   108
```

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: both
        (D) TOPOLOGY: both (xi) SEQUENCE DESCRIPTION: SEQ ID NO:16:

```
ACAAATTGTC GTGTCGAGAC CGGGCGCCAC A                                      31
```

(2) INFORMATION FOR SEQ ID NO:17:

(i) SEQUENCE CHARACTERISTICS:
        (A) LENGTH: 46 base pairs
        (B) TYPE: nucleic acid
        (C) STRANDEDNESS: both
        (D) TOPOLOGY: both (xi) SEQUENCE DESCRIPTION: SEQ ID NO:17:

```
CAGCAACAAA TGTTTGAAAT TACAGTAATC TTTAAAGGCG CACACC                      46
```

(2) INFORMATION FOR SEQ ID NO:18:

(i) SEQUENCE CHARACTERISTICS:
        (A) LENGTH: 49 base pairs
        (B) TYPE: nucleic acid
        (C) STRANDEDNESS: both
        (D) TOPOLOGY: both (xi) SEQUENCE DESCRIPTION: SEQ ID NO:18:

```
AACAAAACTT TGTCGTGTCG AGACCGGGTA CCGTATTTTT AATTGCAAA                   49
```

(2) INFORMATION FOR SEQ ID NO:19:

(i) SEQUENCE CHARACTERISTICS:
        (A) LENGTH: 43 base pairs
        (B) TYPE: nucleic acid
        (C) STRANDEDNESS: both
        (D) TOPOLOGY: both (xi) SEQUENCE DESCRIPTION: SEQ ID NO:19:

```
CTGCAACGAA AGTCTGAAAT TACAGTACCC TTAAAGGCGC ATA                         43
```

(2) INFORMATION FOR SEQ ID NO:20:

(i) SEQUENCE CHARACTERISTICS:
        (A) LENGTH: 95 base pairs
        (B) TYPE: nucleic acid
        (C) STRANDEDNESS: both
        (D) TOPOLOGY: both (xi) SEQUENCE DESCRIPTION: SEQ ID NO:20:

```
GTTAGAAACT AGAGTACCTC TTAAAGGCGC ACATCCTTTC CCACCTATCG AAAATTTGTC    60

GTGTCGAGAC CGGGTAGCTA ATTTTATGCC AAAAA                              95

(2) INFORMATION FOR SEQ ID NO:21:

(i) SEQUENCE CHARACTERISTICS:
        (A) LENGTH: 114 base pairs
        (B) TYPE: nucleic acid
        (C) STRANDEDNESS: both
        (D) TOPOLOGY: both (xi) SEQUENCE DESCRIPTION: SEQ ID NO:21:

CAGCAACAAA AGTTTGAAAT TACAGTGCTC TTTAAAGGCA CACACCTTTT TACATTTAAC    60

AAAAAAGTGT CGCTTCGAGA CCGGGTACCG TGTTTTTGGC GCAAAAATCG CTAT         114

(2) INFORMATION FOR SEQ ID NO:22:

(i) SEQUENCE CHARACTERISTICS:
        (A) LENGTH: 114 base pairs
        (B) TYPE: nucleic acid
        (C) STRANDEDNESS: both
        (D) TOPOLOGY: both (xi) SEQUENCE DESCRIPTION: SEQ ID NO:22:

CAGAAGCGAA AATTTGAAAT TACAGTACTC TTTAAACGCT CAACCCCGTT TCTATTCAAT    60

AGAAAGTTGT CGTTTCGAGA CCGGACACCG TATTTTTGGC GCAAAATATA CCTG         114

(2) INFORMATION FOR SEQ ID NO:23:

(i) SEQUENCE CHARACTERISTICS:
        (A) LENGTH: 107 base pairs
        (B) TYPE: nucleic acid
        (C) STRANDEDNESS: both
        (D) TOPOLOGY: both (xi) SEQUENCE DESCRIPTION: SEQ ID NO:23:

GATTGTTGAA AATTACAGTA ATCTTTAAAG GCGCACACAC GTTTGTATTT TACAGAAAAT    60

TCTCGTTTCG AGACCGAACA CAGTATTTTT GGCGGAGAAA TTCTAAA                 107

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:24:

TTTGTCGTGT CGAGACCTGG                                                20

(2) INFORMATION FOR SEQ ID NO:25:

(i) SEQUENCE CHARACTERISTICS:
        (A) LENGTH: 103 base pairs
        (B) TYPE: nucleic acid
        (C) STRANDEDNESS: both
        (D) TOPOLOGY: both (xi) SEQUENCE DESCRIPTION: SEQ ID NO:25:

TTTTTAAACT ACAGTACTCT TTAGGAGCGC ACATTTTTTC GCATTTAACA AATTTTTGTC    60

GTGGCGAGAC CTGATACCGT ATTTTTAGGT CAAGATTACT AGG                     103

(2) INFORMATION FOR SEQ ID NO:26:
```

(i) SEQUENCE CHARACTERISTICS:
            (A) LENGTH: 42 base pairs
            (B) TYPE: nucleic acid
            (C) STRANDEDNESS: both
            (D) TOPOLOGY: both (xi) SEQUENCE DESCRIPTION: SEQ ID NO:26:

ACCGTTTGAA ACTACAGTAC TCTTTAAAGG CGCGTTTGTC GT                              42

(2) INFORMATION FOR SEQ ID NO:27:

(i) SEQUENCE CHARACTERISTICS:
            (A) LENGTH: 42 base pairs
            (B) TYPE: nucleic acid
            (C) STRANDEDNESS: both
            (D) TOPOLOGY: both (xi) SEQUENCE DESCRIPTION: SEQ ID NO:27:

CGCTAAATAA GTTTAGCCAA TTTAATTCGC GAGACCCTTT AA                              42

(2) INFORMATION FOR SEQ ID NO:28:

(i) SEQUENCE CHARACTERISTICS:
            (A) LENGTH: 77 base pairs
            (B) TYPE: nucleic acid
            (C) STRANDEDNESS: both
            (D) TOPOLOGY: both (xi) SEQUENCE DESCRIPTION: SEQ ID NO:28:

AACCAATCAG CATCGTCGAT CTCCGCCCAC TTCATCGGAT TGGTTTGAAA GTGGGCGGAG           60

TGAATTGCTG ATTGGTC                                                         77

(2) INFORMATION FOR SEQ ID NO:29:

(i) SEQUENCE CHARACTERISTICS:
            (A) LENGTH: 77 base pairs
            (B) TYPE: nucleic acid
            (C) STRANDEDNESS: both
            (D) TOPOLOGY: both (xi) SEQUENCE DESCRIPTION: SEQ ID NO:29:

AACCAATTAG CGACTTCGGA ATTTCCATAC TTAATCTGAT TGGTTGAAGA ATGGGCAGAG           60

CGAATTGCTG ATTGGCC                                                         77

(2) INFORMATION FOR SEQ ID NO:30:

(i) SEQUENCE CHARACTERISTICS:
            (A) LENGTH: 56 base pairs
            (B) TYPE: nucleic acid
            (C) STRANDEDNESS: both
            (D) TOPOLOGY: both (xi) SEQUENCE DESCRIPTION: SEQ ID NO:30:

AACCAATAGC CTCGTCACTT ATCGATTGGT TAATGGGCGA GGAATTGCTG ATTGGC              56

(2) INFORMATION FOR SEQ ID NO:31:

(i) SEQUENCE CHARACTERISTICS:
            (A) LENGTH: 59 base pairs
            (B) TYPE: nucleic acid
            (C) STRANDEDNESS: both
            (D) TOPOLOGY: both (xi) SEQUENCE DESCRIPTION: SEQ ID NO:31:

TTTTAAGGAC ACAGAAAAAT AGGCAGAGGC TCCTTTTGCA AGCCTGCCGC GCGTCAACC           59

(2) INFORMATION FOR SEQ ID NO:32:

(i) SEQUENCE CHARACTERISTICS:
        (A) LENGTH: 60 base pairs
        (B) TYPE: nucleic acid
        (C) STRANDEDNESS: both
        (D) TOPOLOGY: both (xi) SEQUENCE DESCRIPTION: SEQ ID NO:32:

```
TTTCAAGCCG CACAGAAAAA GAGGCGGAGC GTCGTTTTGC AAACTTGCCG CGCGCCAACC        60
```

(2) INFORMATION FOR SEQ ID NO:33:

(i) SEQUENCE CHARACTERISTICS:
        (A) LENGTH: 48 base pairs
        (B) TYPE: nucleic acid
        (C) STRANDEDNESS: both
        (D) TOPOLOGY: both (xi) SEQUENCE DESCRIPTION: SEQ ID NO:33:

```
TTTAAGCACA GAAAAAGGC GAGTCTTTTG CAACTGCCGC GCGCAACC                     48
```

(2) INFORMATION FOR SEQ ID NO:34:

(i) SEQUENCE CHARACTERISTICS:
        (A) LENGTH: 2483 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 16..1527

(xi) SEQUENCE DESCRIPTION: SEQ ID NO:34:

```
AACCATCAGC CGAAG ATG ATG CGT CAA GAT AGA AGG AGC TTG CTA GAG AGG        51
                Met Met Arg Gln Asp Arg Arg Ser Leu Leu Glu Arg
                  1               5                  10

AAC ATT ATG ATG TTC TCT AGT CAT CTA AAA GTC GAT GAA ATT CTC GAA         99
Asn Ile Met Met Phe Ser Ser His Leu Lys Val Asp Glu Ile Leu Glu
          15                  20                  25

GTT CTC ATC GCA AAA CAA GTG TTG AAT AGT GAT AAT GGA GAT ATG ATT        147
Val Leu Ile Ala Lys Gln Val Leu Asn Ser Asp Asn Gly Asp Met Ile
 30                  35                  40

AAT TCA TGT GGA ACG GTT CGC GAG AAG AGA CGG GAG ATC GTG AAA GCA        195
Asn Ser Cys Gly Thr Val Arg Glu Lys Arg Arg Glu Ile Val Lys Ala
 45                  50                  55                  60

GTG CAA CGA CCG GGA GAT GTG GCG TTC GAC GCG TTT TAT GAT GCT CTT        243
Val Gln Arg Pro Gly Asp Val Ala Phe Asp Ala Phe Tyr Asp Ala Leu
                 65                  70                  75

CGC TCT ACG GGA CAC GAA GGA CTT GCT GAA GTT CTT GAA CCT CTC GCC        291
Arg Ser Thr Gly His Glu Gly Leu Ala Glu Val Leu Glu Pro Leu Ala
             80                  85                  90

AGA TCT GTT GAC TCG AAT GCT GTC GAA TTC GAG TGT CCA ATG TCA CCG        339
Arg Ser Val Asp Ser Asn Ala Val Glu Phe Glu Cys Pro Met Ser Pro
         95                 100                 105

GCA AGC CAT CGT CGG AGC CGC GCA TTG AGC CCC GCC GGC TAC ACT TCA        387
Ala Ser His Arg Arg Ser Arg Ala Leu Ser Pro Ala Gly Tyr Thr Ser
 110                 115                 120

CCG ACC CGA GTT CAC CGT GAC AGC GTC TCT TCA GTG TCA TCA TTC ACT        435
Pro Thr Arg Val His Arg Asp Ser Val Ser Ser Val Ser Ser Phe Thr
125                 130                 135                 140

TCT TAT CAG GAT ATC TAC TCA AGA GCA AGA TCT CGT TCT CGA TCG CGT        483
```

```
Ser Tyr Gln Asp Ile Tyr Ser Arg Ala Arg Ser Arg Ser Arg
                145                 150                 155

GCA CTT CAT TCA TCG GAT CGA CAC AAT TAT TCA TCT CCT CCA GTC AAC       531
Ala Leu His Ser Ser Asp Arg His Asn Tyr Ser Ser Pro Pro Val Asn
            160                 165                 170

GCA TTT CCC AGC CAA CCT TCA TCC GCC AAC TCT TCA TTC ACC GGA TGC       579
Ala Phe Pro Ser Gln Pro Ser Ser Ala Asn Ser Ser Phe Thr Gly Cys
        175                 180                 185

TCT TCT CTC GGA TAC AGT TCA AGT CGT AAT CGC TCA TTC AGC AAA GCT       627
Ser Ser Leu Gly Tyr Ser Ser Ser Arg Asn Arg Ser Phe Ser Lys Ala
    190                 195                 200

TCT GGA CCA ACT CAA TAC ATA TTC CAT GAA GAG GAT ATG AAC TTT GTC       675
Ser Gly Pro Thr Gln Tyr Ile Phe His Glu Glu Asp Met Asn Phe Val
205                 210                 215                 220

GAT GCA CCA ACC ATA AGC CGT GTT TTC GAC GAG AAA ACC ATG TAC AGA       723
Asp Ala Pro Thr Ile Ser Arg Val Phe Asp Glu Lys Thr Met Tyr Arg
                225                 230                 235

AAC TTC TCG AGT CCT CGT GGA ATG TGC CTC ATC ATA AAT AAT GAA CAC       771
Asn Phe Ser Ser Pro Arg Gly Met Cys Leu Ile Ile Asn Asn Glu His
            240                 245                 250

TTT GAG CAG ATG CCA ACA CGG AAT GGT ACC AAG GCC GAC AAG GAC AAT       819
Phe Glu Gln Met Pro Thr Arg Asn Gly Thr Lys Ala Asp Lys Asp Asn
        255                 260                 265

CTT ACC AAT TTG TTC AGA TGC ATG GGC TAT ACG GTT ATT TGC AAG GAC       867
Leu Thr Asn Leu Phe Arg Cys Met Gly Tyr Thr Val Ile Cys Lys Asp
    270                 275                 280

AAT CTG ACG GGA AGG GGA ATG CTC CTG ACA ATT CGA GAC TTT GCC AAA       915
Asn Leu Thr Gly Arg Gly Met Leu Leu Thr Ile Arg Asp Phe Ala Lys
285                 290                 295                 300

CAC GAA TCA CAC GGA GAT TCT GCG ATA CTC GTG ATT CTA TCA CAC GGA       963
His Glu Ser His Gly Asp Ser Ala Ile Leu Val Ile Leu Ser His Gly
                305                 310                 315

GAA GAG AAT GTG ATT ATT GGA GTT GAT GAT ATA CCG ATT AGT ACA CAC       1011
Glu Glu Asn Val Ile Ile Gly Val Asp Asp Ile Pro Ile Ser Thr His
            320                 325                 330

GAG ATA TAT GAT CTT CTC AAC GCG GCA AAT GCT CCC CGT CTG GCG AAT       1059
Glu Ile Tyr Asp Leu Leu Asn Ala Ala Asn Ala Pro Arg Leu Ala Asn
        335                 340                 345

AAG CCG AAA ATC GTT TTT GTG CAG GCT TGT CGA GGC GAA CGT CGT GAC       1107
Lys Pro Lys Ile Val Phe Val Gln Ala Cys Arg Gly Glu Arg Arg Asp
    350                 355                 360

AAT GGA TTC CCA GTC TTG GAT TCT GTC GAC GGA GTT CCT GCA TTT CTT       1155
Asn Gly Phe Pro Val Leu Asp Ser Val Asp Gly Val Pro Ala Phe Leu
365                 370                 375                 380

CGT CGT GGA TGG GAC AAT CGA GAC GGG CCA TTG TTC AAT TTT CTT GGA       1203
Arg Arg Gly Trp Asp Asn Arg Asp Gly Pro Leu Phe Asn Phe Leu Gly
                385                 390                 395

TGT GTG CGG CCG CAA GTT CAG CAA GTG TGG AGA AAG AAG CCG AGC CAA       1251
Cys Val Arg Pro Gln Val Gln Gln Val Trp Arg Lys Lys Pro Ser Gln
            400                 405                 410

GCT GAC ATT CTG ATT CGA TAC GCA ACG ACA GCT CAA TAT GTT TCG TGG       1299
Ala Asp Ile Leu Ile Arg Tyr Ala Thr Thr Ala Gln Tyr Val Ser Trp
        415                 420                 425

AGA AAC AGT GCT CGT GGA TCA TGG TTC ATT CAA GCC GTC TGT GAA GTG       1347
Arg Asn Ser Ala Arg Gly Ser Trp Phe Ile Gln Ala Val Cys Glu Val
    430                 435                 440

TTC TCG ACA CAC GCA AAG GAT ATG GAT GTT GTT GAG CTG CTG ACT GAA       1395
Phe Ser Thr His Ala Lys Asp Met Asp Val Val Glu Leu Leu Thr Glu
445                 450                 455                 460
```

```
GTC AAT AAG AAG GTC GCT TGT GGA TTT CAG ACA TCA CAG GGA TCG AAT       1443
Val Asn Lys Lys Val Ala Cys Gly Phe Gln Thr Ser Gln Gly Ser Asn
                465                 470                 475

ATT TTG AAA CAG ATG CCA GAG ATG ACA TCC CGC CTG CTC AAA AAG TTC       1491
Ile Leu Lys Gln Met Pro Glu Met Thr Ser Arg Leu Leu Lys Lys Phe
            480                 485                 490

TAC TTT TGG CCG GAA GCA CGA AAC TCT GCC GTC TAAAATTCAC TCGTGATTCA     1544
Tyr Phe Trp Pro Glu Ala Arg Asn Ser Ala Val
        495                 500

TTGCCCAATT GATAATTGTC TGTATCTTCT CCCCCAGTTC TCTTTCGCCC AATTAGTTTA     1604

AAACCATGTG TATATTGTTA TCCTATACTC ATTTCACTTT ATCATTCTAT CATTTCTCTT     1664

CCCATTTTCA CACATTTCCA TTTCTCTACG ATAATCTAAA ATTATGACGT TGTGTCTCG      1724

AACGCATAAT AATTTTAATA ACTCGTTTTG AATTTGATTA GTTGTTGTGC CCAGTATATA     1784

TGTATGTACT ATGCTTCTAT CAACAAAATA GTTTCATAGA TCATCACCCC AACCCCACCA     1844

ACCTACCGTA CCATATTCAT TTTTGCCGGG AATCAATTTC GATTAATTTT AACCTATTTT     1904

TTCGCCACAA AAAATCTAAT ATTTGAATTA ACGAATAGCA TTCCCATCTC TCCCGTGCCG     1964

GAACTCCCGG CCTTTTAAAG TTCGGAACAT TTGGCCAATT ATGTATAAAA TTTTGTAGGT     2024

CCCCCCCATC ATTTCCCGCC CATCATCTCA AATTGCATTC TTTTTTCGCC GTGATATCCC     2084

GATTCTGGTC AGCAAAGATC TTTCTCATAG CCCATTCCAT TCGAGCTTTC TAATAGGAAT     2144

TTGAAAATTT TCGAAATTCC AGTAAATAAT ATTGGAAAAT GGATTTTTCG AGTTTTCAGC     2204

AACACAAATT TACTTGAAAC CCCATTTTCC AAAATTTCAA TTTTTTCAAA TTTCCCGCTA     2264

TCTTCCAAAA TACTCTTGTA CGTTTATTAT ATTTCCCTCG TTTTTCTTCG ATTCCTCCTC     2324

TCCGCGCACC CAATAAGTTT TATATATGTT GAGATTTATA TAGCTTGTTA TTATAATTAT     2384

ATATTTATAG ATTATTATAG TTGCTTTTCT CGCCGTATGT TTGTGTGTGT GTGATTGGTA     2444

TACATAGATA AAGAAAACA AGGTAAAAAA AGGAATTCC                             2483

(2) INFORMATION FOR SEQ ID NO:35:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO:35:

Met Met Arg Gln Asp Arg Arg Ser Leu Leu Glu Arg Asn Ile Met Met
  1               5                  10                  15

Phe Ser Ser His Leu Lys Val Asp Glu Ile Leu Glu Val Leu Ile Ala
                20                  25                  30

Lys Gln Val Leu Asn Ser Asp Asn Gly Asp Met Ile Asn Ser Cys Gly
            35                  40                  45

Thr Val Arg Glu Lys Arg Arg Glu Ile Val Lys Ala Val Gln Arg Pro
        50                  55                  60

Gly Asp Val Ala Phe Asp Ala Phe Tyr Asp Leu Arg Ser Thr Gly
 65                  70                  75                  80

His Glu Gly Leu Ala Glu Val Leu Glu Pro Leu Ala Arg Ser Val Asp
                85                  90                  95

Ser Asn Ala Val Glu Phe Glu Cys Pro Met Ser Pro Ala Ser His Arg
               100                 105                 110

Arg Ser Arg Ala Leu Ser Pro Ala Gly Tyr Thr Ser Pro Thr Arg Val
           115                 120                 125
```

His Arg Asp Ser Val Ser Ser Val Ser Ser Phe Thr Ser Tyr Gln Asp
            130                 135                 140

Ile Tyr Ser Arg Ala Arg Ser Arg Ser Arg Ala Leu His Ser
145                 150                 155                 160

Ser Asp Arg His Asn Tyr Ser Pro Pro Val Asn Ala Phe Pro Ser
                165                 170                 175

Gln Pro Ser Ser Ala Asn Ser Ser Phe Thr Gly Cys Ser Ser Leu Gly
                180                 185                 190

Tyr Ser Ser Arg Asn Arg Ser Phe Ser Lys Ala Ser Gly Pro Thr
            195                 200                 205

Gln Tyr Ile Phe His Glu Glu Asp Met Asn Phe Val Asp Ala Pro Thr
            210                 215                 220

Ile Ser Arg Val Phe Asp Glu Lys Thr Met Tyr Arg Asn Phe Ser Ser
225                 230                 235                 240

Pro Arg Gly Met Cys Leu Ile Ile Asn Asn Glu His Phe Glu Gln Met
                245                 250                 255

Pro Thr Arg Asn Gly Thr Lys Ala Asp Lys Asp Asn Leu Thr Asn Leu
                260                 265                 270

Phe Arg Cys Met Gly Tyr Thr Val Ile Cys Lys Asp Asn Leu Thr Gly
            275                 280                 285

Arg Gly Met Leu Leu Thr Ile Arg Asp Phe Ala Lys His Glu Ser His
            290                 295                 300

Gly Asp Ser Ala Ile Leu Val Ile Leu Ser His Gly Glu Glu Asn Val
305                 310                 315                 320

Ile Ile Gly Val Asp Asp Ile Pro Ile Ser Thr His Glu Ile Tyr Asp
                325                 330                 335

Leu Leu Asn Ala Ala Asn Ala Pro Arg Leu Ala Asn Lys Pro Lys Ile
                340                 345                 350

Val Phe Val Gln Ala Cys Arg Gly Glu Arg Arg Asp Asn Gly Phe Pro
            355                 360                 365

Val Leu Asp Ser Val Asp Gly Val Pro Ala Phe Leu Arg Arg Gly Trp
            370                 375                 380

Asp Asn Arg Asp Gly Pro Leu Phe Asn Phe Leu Gly Cys Val Arg Pro
385                 390                 395                 400

Gln Val Gln Gln Val Trp Arg Lys Lys Pro Ser Gln Ala Asp Ile Leu
                405                 410                 415

Ile Arg Tyr Ala Thr Thr Ala Gln Tyr Val Ser Trp Arg Asn Ser Ala
            420                 425                 430

Arg Gly Ser Trp Phe Ile Gln Ala Val Cys Glu Val Phe Ser Thr His
            435                 440                 445

Ala Lys Asp Met Asp Val Val Glu Leu Leu Thr Glu Val Asn Lys Lys
450                 455                 460

Val Ala Cys Gly Phe Gln Thr Ser Gln Gly Ser Asn Ile Leu Lys Gln
465                 470                 475                 480

Met Pro Glu Met Thr Ser Arg Leu Leu Lys Lys Phe Tyr Phe Trp Pro
                485                 490                 495

Glu Ala Arg Asn Ser Ala Val
            500

(2) INFORMATION FOR SEQ ID NO:36:

(i) SEQUENCE CHARACTERISTICS:
        (A) LENGTH: 503 amino acids
        (B) TYPE: amino acid (D) TOPOLOGY: both (xi) SEQUENCE DESCRIPTION: SEQ ID NO:36:

```
Met Met Arg Gln Asp Arg Trp Ser Leu Leu Glu Arg Asn Ile Leu Glu
1               5                   10                  15

Phe Ser Ser Lys Leu Gln Ala Asp Leu Ile Leu Asp Val Leu Ile Ala
            20                  25                  30

Lys Gln Val Leu Asn Ser Asp Asn Gly Asp Met Ile Asn Ser Cys Arg
            35                  40                  45

Thr Glu Arg Asp Asn Glu Lys Glu Ile Val Lys Ala Val Gln Arg Arg
50                  55                  60

Gly Asp Glu Ala Phe Asp Ala Phe Tyr Asp Ala Leu Arg Asp Thr Gly
65                  70                  75                  80

His Asn Asp Leu Ala Asp Val Leu Met Pro Leu Ser Arg Pro Asn Pro
                85                  90                  95

Val Pro Met Glu Cys Pro Met Ser Pro Ser Ser His Arg Arg Ser Arg
            100                 105                 110

Ala Leu Ser Pro Pro Gly Tyr Ala Ser Pro Thr Arg Val His Arg Asp
            115                 120                 125

Ser Ile Ser Ser Val Ser Ser Phe Thr Ser Thr Tyr Gln Asp Val Tyr
130                 135                 140

Ser Arg Ala Arg Ser Ser Ser Arg Ser Ser Arg Pro Leu Gln Ser Ser
145                 150                 155                 160

Asp Arg His Asn Tyr Met Ser Ala Ala Thr Ser Phe Pro Ser Gln Pro
                165                 170                 175

Ser Ser Ala Asn Ser Ser Phe Thr Gly Cys Ala Ser Leu Gly Tyr Ser
            180                 185                 190

Ser Ser Arg Asn Arg Ser Phe Ser Lys Thr Ser Ala Gln Ser Gln Tyr
            195                 200                 205

Ile Phe His Glu Glu Asp Met Asn Tyr Val Asp Ala Pro Thr Ile His
            210                 215                 220

Arg Val Phe Asp Glu Lys Thr Met Tyr Arg Asn Phe Ser Ser Pro Arg
225                 230                 235                 240

Gly Leu Cys Leu Ile Ile Asn Asn Glu His Phe Glu Gln Met Pro Thr
                245                 250                 255

Arg Asn Gly Thr Lys Ala Asp Lys Asp Asn Leu Thr Asn Ile Phe Arg
            260                 265                 270

Cys Met Gly Tyr Thr Val Ile Cys Lys Asp Asn Leu Thr Gly Arg Glu
            275                 280                 285

Met Leu Ser Thr Ile Arg Ser Phe Gly Arg Asn Asp Met His Gly Asp
290                 295                 300

Ser Ala Ile Leu Val Ile Leu Ser His Gly Glu Glu Asn Val Ile Ile
305                 310                 315                 320

Gly Val Asp Asp Val Ser Val Asn Val His Glu Ile Tyr Asp Leu Leu
                325                 330                 335

Asn Ala Ala Asn Ala Pro Arg Leu Ala Asn Lys Pro Lys Leu Val Phe
            340                 345                 350

Val Gln Ala Cys Arg Gly Glu Arg Arg Asp Asn Gly Phe Pro Val Leu
            355                 360                 365

Asp Ser Val Asp Gly Val Pro Ser Leu Ile Arg Arg Gly Trp Asp Asn
370                 375                 380

Arg Asp Gly Pro Leu Phe Asn Phe Leu Gly Cys Val Arg Pro Gln Val
385                 390                 395                 400
```

-continued

```
Gln Gln Val Trp Arg Lys Lys Pro Ser Gln Ala Asp Met Leu Ile Ala
                405                 410                 415

Tyr Ala Thr Thr Ala Gln Tyr Val Ser Trp Arg Asn Ser Ala Arg Gly
            420                 425                 430

Ser Trp Phe Ile Gln Ala Val Cys Glu Val Phe Ser Leu His Ala Lys
        435                 440                 445

Asp Met Asp Val Val Glu Leu Leu Thr Glu Val Asn Lys Lys Val Ala
    450                 455                 460

Cys Gly Phe Gln Thr Ser Gln Gly Ser Asn Ile Leu Lys Gln Met Pro
465                 470                 475                 480

Glu Leu Thr Ser Arg Leu Leu Lys Lys Phe Tyr Phe Trp Pro Glu Asp
                485                 490                 495

Arg Gly Arg Asn Ser Ala Val
            500
```

(2) INFORMATION FOR SEQ ID NO:37:

(i) SEQUENCE CHARACTERISTICS:
        (A) LENGTH: 497 amino acids
        (B) TYPE: amino acid
        (D) TOPOLOGY: both (xi) SEQUENCE DESCRIPTION: SEQ ID NO:37:

```
Met Met Arg Gln Asp Arg Arg Asn Leu Leu Glu Arg Asn Ile Leu Val
1               5                   10                  15

Phe Ser Asn Lys Leu Gln Ser Glu Gln Ile Leu Glu Val Leu Ile Ala
                20                  25                  30

Lys Gln Ile Leu Asn Ala Asp Asn Gly Asp Val Ile Asn Ser Cys Arg
            35                  40                  45

Thr Glu Arg Asp Lys Arg Lys Glu Gln Val Lys Ala Val Gln Arg Arg
        50                  55                  60

Gly Asp Val Ala Phe Asp Arg Phe Tyr Asp Ala Leu Arg Asp Thr Gly
65                  70                  75                  80

His His Glu Leu Ala Ala Val Leu Glu Pro Leu Ala Arg Thr Asp Leu
                85                  90                  95

Gly Cys Pro Met Ser Pro Ala Ser His Arg Arg Ser Arg Ala Leu Ser
                100                 105                 110

Pro Ser Thr Phe Ser Ser Pro Thr Arg Val His Arg Asp Ser Val Ser
            115                 120                 125

Ser Val Ser Ser Phe Thr Ser Thr Tyr Gln Asp Val Tyr Thr Arg Ala
        130                 135                 140

Arg Ser Thr Ser Arg Ser Ser Arg Pro Leu His Thr Ser Asp Arg His
145                 150                 155                 160

Asn Tyr Val Ser Pro Ser Asn Ser Phe Gln Ser Gln Pro Ala Ser Ala
                165                 170                 175

Asn Ser Ser Phe Thr Gly Ser Ser Leu Gly Tyr Ser Ser Ser Arg
            180                 185                 190

Thr Arg Ser Tyr Ser Lys Ala Ser Ala His Ser Gln Tyr Ile Phe His
        195                 200                 205

Glu Glu Asp Met Asn Tyr Val Asp Ala Pro Thr Ile His Arg Val Phe
    210                 215                 220

Asp Glu Lys Thr Met Tyr Arg Asn Phe Ser Thr Pro Arg Gly Leu Cys
225                 230                 235                 240

Leu Ile Ile Asn Asn Glu His Phe Glu Gln Met Pro Thr Arg Asn Gly
                245                 250                 255
```

```
Thr Lys Pro Asp Lys Asp Asn Ile Ser Asn Leu Phe Arg Cys Met Gly
            260                 265                 270

Tyr Ile Val His Cys Lys Asp Asn Leu Thr Gly Arg Met Met Leu Thr
            275                 280                 285

Ile Arg Asp Phe Ala Lys Asn Glu Thr His Gly Asp Ser Ala Ile Leu
            290                 295                 300

Val Ile Leu Ser His Gly Glu Glu Asn Val Ile Ile Gly Val Asp Asp
305                 310                 315                 320

Val Ser Val Asn Val His Glu Ile Tyr Asp Leu Leu Asn Ala Ala Asn
            325                 330                 335

Ala Pro Arg Leu Ala Asn Lys Pro Lys Leu Val Phe Val Gln Ala Cys
            340                 345                 350

Arg Gly Glu Arg Arg Asp Val Gly Phe Pro Val Leu Asp Ser Val Asp
            355                 360                 365

Gly Val Pro Ala Leu Ile Arg Arg Gly Trp Asp Lys Gly Asp Gly Pro
            370                 375                 380

Asn Phe Leu Gly Cys Val Arg Pro Gln Ala Gln Val Trp Arg Lys
385                 390                 395                 400

Lys Pro Ser Gln Ala Asp Ile Leu Ile Ala Tyr Ala Thr Thr Ala Gln
            405                 410                 415

Tyr Val Ser Trp Arg Asn Ser Ala Arg Gly Ser Trp Phe Ile Gln Ala
            420                 425                 430

Val Cys Glu Val Phe Ser Leu His Ala Lys Asp Met Asp Val Val Glu
            435                 440                 445

Leu Leu Thr Glu Val Asn Lys Lys Val Ala Cys Gly Phe Gln Thr Ser
450                 455                 460

Gln Gly Ala Asn Ile Leu Lys Gln Met Pro Glu Leu Thr Ser Arg Leu
465                 470                 475                 480

Leu Lys Lys Phe Tyr Phe Trp Pro Glu Asp Arg Asn Arg Ser Ser Ala
            485                 490                 495

Val (2) INFORMATION FOR SEQ ID NO:38:

(i) SEQUENCE CHARACTERISTICS:
        (A) LENGTH: 402 amino acids
        (B) TYPE: amino acid
        (D) TOPOLOGY: both (xi) SEQUENCE DESCRIPTION: SEQ ID NO:38:

Met Ala Asp Lys Ile Leu Arg Ala Lys Arg Lys Gln Phe Ile Asn Ser
1               5                   10                  15

Val Ser Ile Gly Thr Ile Asn Gly Ile Leu Asp Glu Leu Leu Glu Lys
            20                  25                  30

Arg Val Leu Asn Gln Glu Glu Met Asp Lys Ile Lys Leu Ala Asn Ile
            35                  40                  45

Thr Ala Met Asp Lys Ala Arg Asp Leu Cys Asp His Val Ser Lys Lys
            50                  55                  60

Gly Pro Gln Ala Ser Gln Ile Phe Ile Thr Tyr Ile Cys Asn Glu Asp
65                  70                  75                  80

Cys Tyr Leu Ala Gly Ile Leu Glu Leu Gln Ser Ala Pro Ser Ala Glu
            85                  90                  95

Thr Phe Val Ala Thr Glu Asp Ser Lys Gly His Pro Ser Ser Ser
            100                 105                 110

Glu Thr Lys Glu Glu Gln Asn Lys Glu Asp Gly Thr Phe Pro Gly Leu
```

-continued

```
                115                 120                 125
Thr Gly Thr Leu Lys Glu Cys Pro Leu Glu Lys Ala Gln Lys Leu Trp
        130                 135                 140
Lys Glu Asn Pro Ser Glu Ile Tyr Pro Ile Met Asn Thr Thr Thr Arg
145                 150                 155                 160
Thr Arg Leu Ala Leu Ile Ile Cys Asn Thr Glu Phe Gln His Leu Ser
                165                 170                 175
Pro Arg Val Gly Ala Gln Val Asp Leu Arg Glu Met Lys Leu Leu Leu
                180                 185                 190
Glu Asp Leu Gly Tyr Thr Val Lys Val Lys Glu Asn Leu Thr Ala Leu
                195                 200                 205
Glu Met Val Lys Glu Val Lys Glu Phe Ala Ala Cys Pro Glu His Lys
        210                 215                 220
Thr Ser Asp Ser Thr Phe Leu Val Phe Met Ser His Gly Ile Gln Glu
225                 230                 235                 240
Gly Ile Cys Gly Thr Thr Tyr Ser Asn Glu Val Ser Asp Ile Leu Lys
                245                 250                 255
Val Asp Thr Ile Phe Gln Met Met Asn Thr Leu Lys Cys Pro Ser Leu
            260                 265                 270
Lys Asp Lys Pro Lys Val Ile Ile Gln Ala Cys Arg Gly Glu Lys
            275                 280                 285
Gln Gly Val Val Leu Leu Lys Asp Ser Val Arg Asp Ser Glu Glu Asp
        290                 295                 300
Phe Leu Thr Asp Ala Ile Phe Glu Asp Asp Gly Ile Lys Lys Ala His
305                 310                 315                 320
Ile Glu Lys Asp Phe Ile Ala Phe Cys Ser Ser Thr Pro Asp Asn Val
                325                 330                 335
Ser Trp Arg His Pro Val Arg Gly Ser Leu Phe Ile Glu Ser Leu Ile
                340                 345                 350
Lys His Met Lys Glu Tyr Ala Trp Ser Cys Asp Leu Glu Asp Ile Phe
        355                 360                 365
Arg Lys Val Arg Phe Ser Phe Glu Gln Pro Glu Phe Arg Leu Gln Met
        370                 375                 380
Pro Thr Ala Asp Arg Val Thr Leu Leu Lys Arg Phe Tyr Leu Phe Pro
385                 390                 395                 400
Gly His (2) INFORMATION FOR SEQ ID NO:39:

(i) SEQUENCE CHARACTERISTICS:
        (A) LENGTH: 404 amino acids
        (B) TYPE: amino acid
        (D) TOPOLOGY: both (xi) SEQUENCE DESCRIPTION: SEQ ID NO:39:

Met Ala Asp Lys Val Leu Lys Glu Lys Arg Lys Leu Phe Ile Arg Ser
1               5                   10                  15
Met Gly Glu Gly Thr Ile Asn Gly Leu Leu Asp Glu Leu Leu Gln Thr
                20                  25                  30
Arg Val Leu Asn Lys Glu Glu Met Glu Lys Val Lys Arg Glu Asn Ala
            35                  40                  45
Thr Val Met Asp Lys Thr Arg Ala Leu Ile Asp Ser Val Ile Pro Lys
        50                  55                  60
Gly Ala Gln Ala Cys Gln Ile Cys Ile Thr Tyr Ile Cys Glu Glu Asp
65                  70                  75                  80
```

```
Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Ile Ser Ser Phe Pro
            100                 105                 110

Ala Pro Gln Ala Val Gln Asp Asn Pro Ala Met Pro Thr Ser Ser Gly
        115                 120                 125

Ser Glu Gly Asn Val Lys Leu Cys Ser Ile Glu Ala Gln Arg Ile
    130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Phe Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
        195                 200                 205

Ser Asp Met Thr Thr Glu Leu Glu Ala Phe Ala His Arg Pro Glu His
    210                 215                 220                 225

Lys Thr Ser Asp Ser Thr Phe Leu Val Phe Met Ser His Gly Ile Arg
                230                 235                 240

Glu Gly Ile Cys Gly Lys Lys His Ser Glu Gln Val Pro Asp Ile Leu
            245                 250                 255

Gln Leu Asn Ala Ile Phe Asn Met Leu Asn Thr Lys Asn Cys Pro Ser
        260                 265                 270

Leu Lys Asp Lys Pro Lys Val Ile Ile Ile Gln Ala Cys Arg Gly Asp
    275                 280                 285

Ser Pro Gly Val Val Trp Phe Lys Asp Ser Val Gly Val Ser Gly Asn
290                 295                 300                 305

Leu Ser Leu Pro Thr Thr Glu Glu Phe Glu Asp Asp Ala Ile Lys Lys
                310                 315                 320

Ala His Ile Glu Lys Asp Phe Ile Ala Phe Cys Ser Ser Thr Pro Asp
            325                 330                 335

Asn Val Ser Trp Arg His Pro Thr Met Gly Ser Val Phe Ile Gly Arg
        340                 345                 350

Leu Ile Glu His Met Gln Glu Tyr Ala Cys Ser Cys Asp Val Glu Glu
    355                 360                 365

Ile Phe Arg Lys Val Arg Phe Ser Phe Glu Gln Pro Asp Gly Arg Ala
370                 375                 380                 385

Gln Met Pro Thr Thr Glu Arg Val Thr Leu Thr Arg Cys Phe Tyr Leu
                390                 395                 400

Phe Pro Gly His (2) INFORMATION FOR SEQ ID NO:40:

(i) SEQUENCE CHARACTERISTICS:
        (A) LENGTH: 171 amino acids
        (B) TYPE: amino acid
        (D) TOPOLOGY: both (xi) SEQUENCE DESCRIPTION: SEQ ID NO:40:

Met Leu Thr Val Gln Val Tyr Arg Thr Ser Gln Lys Cys Ser Ser Ser
1               5                   10                  15

Lys His Val Val Glu Val Ile Leu Asp Pro Leu Gly Thr Ser Phe Cys
            20                  25                  30
```

```
Ser Leu Leu Pro Pro Leu Leu Leu Tyr Glu Thr Asp Arg Gly Val
            35                  40                  45

Asp Gln Gln Asp Gly Lys Asn His Thr Gln Ser Pro Gly Cys Glu Glu
        50                  55                  60

Ser Asp Ala Gly Lys Glu Glu Leu Met Lys Met Arg Ile Pro Thr Arg
65                  70                  75                  80

Ser Asp Met Ile Cys Gly Tyr Ala Cys Leu Lys Gly Asn Ala Ala Met
                85                  90                  95

Arg Asn Thr Lys Arg Gly Ser Trp Tyr Ile Glu Ala Leu Thr Gln Val
            100                 105                 110

Phe Ser Glu Arg Ala Cys Asp Met His Val Ala Asp Met Leu Val Lys
        115                 120                 125

Val Asn Ala Leu Ile Lys Glu Arg Glu Gly Tyr Ala Pro Gly Thr Glu
    130                 135                 140

Phe His Arg Cys Lys Glu Met Ser Glu Tyr Cys Ser Thr Leu Cys Gln
145                 150                 155                 160

Gln Leu Tyr Leu Phe Pro Gly Tyr Pro Pro Thr
                165                 170
```

(2) INFORMATION FOR SEQ ID NO:41:

(i) SEQUENCE CHARACTERISTICS:
        (A) LENGTH: 1350 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 35..1156

(xi) SEQUENCE DESCRIPTION: SEQ ID NO:41:

```
TCTTCACAGT GCGAAAGAAC TGAGGCTTTT TCTC ATG GCT GAA AAC AAA CAC          52
                                     Met Ala Glu Asn Lys His
                                      1               5

CCT GAC AAA CCA CTT AAG GTG TTG GAA CAG CTG GGC AAA GAA GTC CTT       100
Pro Asp Lys Pro Leu Lys Val Leu Glu Gln Leu Gly Lys Glu Val Leu
            10                  15                  20

ACG GAG TAC CTA GAA AAA TTA GTA CAA AGC AAT GTA CTG AAA TTA AAG       148
Thr Glu Tyr Leu Glu Lys Leu Val Gln Ser Asn Val Leu Lys Leu Lys
        25                  30                  35

GAG GAA GAT AAA CAA AAA TTT AAC AAT GCT GAA CGC AGT GAC AAG CGT       196
Glu Glu Asp Lys Gln Lys Phe Asn Asn Ala Glu Arg Ser Asp Lys Arg
    40                  45                  50

TGG GTT TTT GTA GAT GCC ATG AAA AAG AAA CAC AGC AAA GTA GGT GAA       244
Trp Val Phe Val Asp Ala Met Lys Lys Lys His Ser Lys Val Gly Glu
55                  60                  65                  70

ATG CTT CTC CAG ACA TTC TTC AGT GTG GAC CCA GGC AGC CAC CAT GGT       292
Met Leu Leu Gln Thr Phe Phe Ser Val Asp Pro Gly Ser His His Gly
                75                  80                  85

GAA GCT AAT CTG GAA ATG GAG GAA CCA GAA GAA TCA TTG AAC ACT CTC       340
Glu Ala Asn Leu Glu Met Glu Glu Pro Glu Glu Ser Leu Asn Thr Leu
            90                  95                  100

AAG CTT TGT TCC CCT GAA GAG TTC ACA AGG CTT TGC AGA GAA AAG ACA       388
Lys Leu Cys Ser Pro Glu Glu Phe Thr Arg Leu Cys Arg Glu Lys Thr
        105                 110                 115

CAA GAA ATT TAC CCA ATA AAG GAG GCC AAT GGC CGT ACA CGA AAG GCT       436
Gln Glu Ile Tyr Pro Ile Lys Glu Ala Asn Gly Arg Thr Arg Lys Ala
    120                 125                 130

CTT ATC ATA TGC AAT ACA GAG TTC AAA CAT CTC TCA CTG AGG TAT GGG       484
```

```
Leu Ile Ile Cys Asn Thr Glu Phe Lys His Leu Ser Leu Arg Tyr Gly
135                 140                 145                 150

GCT AAA TTT GAC ATC ATT GGT ATG AAA GGC CTT CTT GAA GAC TTA GGC        532
Ala Lys Phe Asp Ile Ile Gly Met Lys Gly Leu Leu Glu Asp Leu Gly
                155                 160                 165

TAC GAT GTG GTG GTG AAA GAG GAG CTT ACA GCA GAG GGC ATG GAG TCA        580
Tyr Asp Val Val Val Lys Glu Glu Leu Thr Ala Glu Gly Met Glu Ser
            170                 175                 180

GAG ATG AAA GAC TTT GCT GCA CTC TCA GAA CAC CAG ACA TCA GAC AGC        628
Glu Met Lys Asp Phe Ala Ala Leu Ser Glu His Gln Thr Ser Asp Ser
        185                 190                 195

ACA TTC CTG GTG CTA ATG TCT CAT GGC ACA CTG CAT GGC ATT TGT GGA        676
Thr Phe Leu Val Leu Met Ser His Gly Thr Leu His Gly Ile Cys Gly
    200                 205                 210

ACA ATG CAC AGT GAA AAA ACT CCA GAT GTG CTA CAG TAT GAT ACC ATC        724
Thr Met His Ser Glu Lys Thr Pro Asp Val Leu Gln Tyr Asp Thr Ile
215                 220                 225                 230

TAT CAG ATA TTC AAC AAT TGC CAC TGT CCA GGT CTA CGA GAC AAA CCC        772
Tyr Gln Ile Phe Asn Asn Cys His Cys Pro Gly Leu Arg Asp Lys Pro
                235                 240                 245

AAA GTC ATC ATT GTG CAG GCC TGC AGA GGT GGG AAC TCT GGA GAA ATG        820
Lys Val Ile Ile Val Gln Ala Cys Arg Gly Gly Asn Ser Gly Glu Met
            250                 255                 260

TGG ATC AGA GAG TCT TCA AAA CCC CAG TTG TGC AGA GGT GTA GAT CTA        868
Trp Ile Arg Glu Ser Ser Lys Pro Gln Leu Cys Arg Gly Val Asp Leu
        265                 270                 275

CCT AGG AAT ATG GAA GCT GAT GCT GTC AAG CTG AGC CAC GTG GAG AAG        916
Pro Arg Asn Met Glu Ala Asp Ala Val Lys Leu Ser His Val Glu Lys
    280                 285                 290

GAC TTC ATT GCC TTC TAC GCT ACA ACC CCA CAT CAC TTG TCC TAC CGA        964
Asp Phe Ile Ala Phe Tyr Ala Thr Thr Pro His His Leu Ser Tyr Arg
295                 300                 305                 310

GAC AAA ACA GGA GGC TCT TAC TTC ATC ACT AGA CTC ATT TCC TGC TTC       1012
Asp Lys Thr Gly Gly Ser Tyr Phe Ile Thr Arg Leu Ile Ser Cys Phe
                315                 320                 325

CGG AAA CAT GCT TGC TCT TGT CAT CTC TTT GAT ATA TTC CTG AAG GTG       1060
Arg Lys His Ala Cys Ser Cys His Leu Phe Asp Ile Phe Leu Lys Val
            330                 335                 340

CAA CAA TCA TTT GAA AAG GCA AGT ATT CAT TCC CAG ATG CCC ACC ATT       1108
Gln Gln Ser Phe Glu Lys Ala Ser Ile His Ser Gln Met Pro Thr Ile
        345                 350                 355

GAT CGG GCA ACC TTG ACA AGA TAT TTC TAC CTC TTT CCT GGC AAC TGAGAACA 1163
Asp Arg Ala Thr Leu Thr Arg Tyr Phe Tyr Leu Phe Pro Gly Asn
    360                 365                 370

GCAACAAGCA ACTGAATCTC ATTTCTTCAG CTTGAAGAAG TGATCTTGGC CAAGGATCAC    1223

ATTCTATTCC TGAAATTCCA GAACTAGTGA AATTAAGGAA AGAATACTTA TGAATTCAAG    1283

ACCAGCCTAA GCAACACAGT GGGATTCTGT TCGATAGACA AGCAAACAAG CAAAAATAAA    1343

AAAAAAA                                                              1350

(2) INFORMATION FOR SEQ ID NO:42:

(i) SEQUENCE CHARACTERISTICS:
        (A) LENGTH: 373 amino acids
        (B) TYPE: amino acid
        (D) TOPOLOGY: linear (ii) MOLECULE TYPE: protein (xi) SEQUENCE DESCRIPTION: SEQ ID NO:42:
```

-continued

```
Met Ala Glu Asn Lys His Pro Asp Lys Pro Leu Lys Val Leu Glu Gln
  1               5                  10                  15

Leu Gly Lys Glu Val Leu Thr Glu Tyr Leu Glu Lys Leu Val Gln Ser
             20                  25                  30

Asn Val Leu Lys Leu Lys Glu Glu Asp Lys Gln Lys Phe Asn Asn Ala
                 35                  40                  45

Glu Arg Ser Asp Lys Arg Trp Val Phe Val Asp Ala Met Lys Lys Lys
         50                  55                  60

His Ser Lys Val Gly Glu Met Leu Leu Gln Thr Phe Phe Ser Val Asp
 65                  70                  75                  80

Pro Gly Ser His His Gly Glu Ala Asn Leu Glu Met Glu Glu Pro Glu
                 85                  90                  95

Glu Ser Leu Asn Thr Leu Lys Leu Cys Ser Pro Glu Glu Phe Thr Arg
                100                 105                 110

Leu Cys Arg Glu Lys Thr Gln Glu Ile Tyr Pro Ile Lys Glu Ala Asn
            115                 120                 125

Gly Arg Thr Arg Lys Ala Leu Ile Ile Cys Asn Thr Glu Phe Lys His
        130                 135                 140

Leu Ser Leu Arg Tyr Gly Ala Lys Phe Asp Ile Ile Gly Met Lys Gly
145                 150                 155                 160

Leu Leu Glu Asp Leu Gly Tyr Asp Val Val Lys Glu Glu Leu Thr
                165                 170                 175

Ala Glu Gly Met Glu Ser Glu Met Lys Asp Phe Ala Ala Leu Ser Glu
                180                 185                 190

His Gln Thr Ser Asp Ser Thr Phe Leu Val Leu Met Ser His Gly Thr
            195                 200                 205

Leu His Gly Ile Cys Gly Thr Met His Ser Glu Lys Thr Pro Asp Val
    210                 215                 220

Leu Gln Tyr Asp Thr Ile Tyr Gln Ile Phe Asn Asn Cys His Cys Pro
225                 230                 235                 240

Gly Leu Arg Asp Lys Pro Lys Val Ile Ile Val Gln Ala Cys Arg Gly
                245                 250                 255

Gly Asn Ser Gly Glu Met Trp Ile Arg Glu Ser Ser Lys Pro Gln Leu
                260                 265                 270

Cys Arg Gly Val Asp Leu Pro Arg Asn Met Glu Ala Asp Ala Val Lys
            275                 280                 285

Leu Ser His Val Glu Lys Asp Phe Ile Ala Phe Tyr Ala Thr Thr Pro
    290                 295                 300

His His Leu Ser Tyr Arg Asp Lys Thr Gly Gly Ser Tyr Phe Ile Thr
305                 310                 315                 320

Arg Leu Ile Ser Cys Phe Arg Lys His Ala Cys Ser Cys His Leu Phe
                325                 330                 335

Asp Ile Phe Leu Lys Val Gln Gln Ser Phe Glu Lys Ala Ser Ile His
                340                 345                 350

Ser Gln Met Pro Thr Ile Asp Arg Ala Thr Leu Thr Arg Tyr Phe Tyr
            355                 360                 365

Leu Phe Pro Gly Asn
        370
```

(2) INFORMATION FOR SEQ ID NO:43:

(i) SEQUENCE CHARACTERISTICS:
        (A) LENGTH: 2492 base pairs
        (B) TYPE: nucleic acid
        (C) STRANDEDNESS: both (D) TOPOLOGY: both (ix) FEATURE:
    (A) NAME/KEY: CDS
    (B) LOCATION: 3..1328

(xi) SEQUENCE DESCRIPTION: SEQ ID NO:43:

| | |
|---|---|
| GA ATT CCG CAC AAG GAG CTG ATG GCC GCT GAC AGG GGA CGC AGG ATA<br>   Ile Pro His Lys Glu Leu Met Ala Ala Asp Arg Gly Arg Arg Ile<br>    1            5                10             15 | 47 |
| TTG GGA GTG TGT GGC ATG CAT CCT CAT CAT CAG GAA ACT CTA AAA AAG<br>Leu Gly Val Cys Gly Met His Pro His His Gln Glu Thr Leu Lys Lys<br>                20                25             30 | 95 |
| AAC CGA GTG GTG CTA GCC AAA CAG CTG TTG TTG AGC GAA TTG TTA GAA<br>Asn Arg Val Val Leu Ala Lys Gln Leu Leu Leu Ser Glu Leu Leu Glu<br>         35                40                45 | 143 |
| CAT CTT CTG GAG AAG GAC ATC ATC ACC TTG GAA ATG AGG GAG CTC ATC<br>His Leu Leu Glu Lys Asp Ile Ile Thr Leu Glu Met Arg Glu Leu Ile<br>      50               55              60 | 191 |
| CAG GCC AAA GTG GGC AGT TTC AGC CAG AAT GTG GAA CTC CTC AAC TTG<br>Gln Ala Lys Val Gly Ser Phe Ser Gln Asn Val Glu Leu Leu Asn Leu<br> 65                70                75 | 239 |
| CTG CCT AAG AGG GGT CCC CAA GCT TTT GAT GCC TTC TGT GAA GCA CTG<br>Leu Pro Lys Arg Gly Pro Gln Ala Phe Asp Ala Phe Cys Glu Ala Leu<br> 80                85                90             95 | 287 |
| AGG GAG ACC AAG CAA GGC CAC CTG GAG GAT ATG TTG CTC ACC ACC CTT<br>Arg Glu Thr Lys Gln Gly His Leu Glu Asp Met Leu Leu Thr Thr Leu<br>           100              105            110 | 335 |
| TCT GGG CTT CAG CAT GTA CTC CCA CCG TTG AGC TGT GAC TAC GAC TTG<br>Ser Gly Leu Gln His Val Leu Pro Pro Leu Ser Cys Asp Tyr Asp Leu<br>         115               120              125 | 383 |
| AGT CTC CCT TTT CCG GTG TGT GAG TCC TGT CCC CTT TAC AAG AAG CTC<br>Ser Leu Pro Phe Pro Val Cys Glu Ser Cys Pro Leu Tyr Lys Lys Leu<br>     130               135             140 | 431 |
| CGC CTG TCG ACA GAT ACT GTG GAA CAC TCC CTA GAC AAT AAA GAT GGT<br>Arg Leu Ser Thr Asp Thr Val Glu His Ser Leu Asp Asn Lys Asp Gly<br>   145               150             155 | 479 |
| CCT GTC TGC CTT CAG GTG AAG CCT TGC ACT CCT GAA TTT TAT CAA ACA<br>Pro Val Cys Leu Gln Val Lys Pro Cys Thr Pro Glu Phe Tyr Gln Thr<br>160                165             170             175 | 527 |
| CAC TTC CAG CTG GCA TAT AGG TTG CAG TCT CGG CCT CGT GGC CTA GCA<br>His Phe Gln Leu Ala Tyr Arg Leu Gln Ser Arg Pro Arg Gly Leu Ala<br>           180              185            190 | 575 |
| CTG GTG TTG AGC AAT GTG CAC TTC ACT GGA GAG AAA GAA CTG GAA TTT<br>Leu Val Leu Ser Asn Val His Phe Thr Gly Glu Lys Glu Leu Glu Phe<br>        195              200             205 | 623 |
| CGC TCT GGA GGG GAT GTG GAC CAC AGT ACT CTA GTC ACC CTC TTC AAG<br>Arg Ser Gly Gly Asp Val Asp His Ser Thr Leu Val Thr Leu Phe Lys<br>         210              215             220 | 671 |
| CTT TTG GGC TAT GAC GTC CAT GTT CTA TGT GAC CAG ACT GCA CAG GAA<br>Leu Leu Gly Tyr Asp Val His Val Leu Cys Asp Gln Thr Ala Gln Glu<br>   225               230             235 | 719 |
| ATG CAA GAG AAA CTG CAG AAT TTT GCA CAG TTA CCT GCA CAC CGA GTC<br>Met Gln Glu Lys Leu Gln Asn Phe Ala Gln Leu Pro Ala His Arg Val<br>240                245             250             255 | 767 |
| ACG GAC TCC TGC ATC GTG GCA CTC CTC TCG CAT GGT GTG GAG GGC GCC<br>Thr Asp Ser Cys Ile Val Ala Leu Leu Ser His Gly Val Glu Gly Ala<br>           260              265            270 | 815 |
| ATC TAT GGT GTG GAT GGG AAA CTG CTC CAG CTC CAA GAG GTT TTT CAG<br>Ile Tyr Gly Val Asp Gly Lys Leu Leu Gln Leu Gln Glu Val Phe Gln<br>        275              280             285 | 863 |

```
CTC TTT GAC AAC GCC AAC TGC CCA AGC CTA CAG AAC AAA CCA AAA ATG     911
Leu Phe Asp Asn Ala Asn Cys Pro Ser Leu Gln Asn Lys Pro Lys Met
        290                 295                 300

TTC TTC ATC CAG GCC TGC CGT GGA GAT GAG ACT GAT CGT GGG GTT GAC     959
Phe Phe Ile Gln Ala Cys Arg Gly Asp Glu Thr Asp Arg Gly Val Asp
        305                 310                 315

CAA CAA GAT GGA AAG AAC CAC GCA GGA TCC CCT GGG TGC GAG GAG AGT     1007
Gln Gln Asp Gly Lys Asn His Ala Gly Ser Pro Gly Cys Glu Glu Ser
320                 325                 330                 335

GAT GCC GGT AAA GAA AAG TTG CCG AAG ATG AGA CTG CCC ACG CGC TCA     1055
Asp Ala Gly Lys Glu Lys Leu Pro Lys Met Arg Leu Pro Thr Arg Ser
                340                 345                 350

GAC ATG ATA TGC GGC TAT GCC TGC CTC AAA GGG ACT GCC GCC ATG CGG     1103
Asp Met Ile Cys Gly Tyr Ala Cys Leu Lys Gly Thr Ala Ala Met Arg
                355                 360                 365

AAC ACC AAA CGA GGT TCC TGG TAC ATC GAG GCT CTT GCT CAA GTG TTT     1151
Asn Thr Lys Arg Gly Ser Trp Tyr Ile Glu Ala Leu Ala Gln Val Phe
        370                 375                 380

TCT GAG CGG GCT TGT GAT ATG CAC GTG GCC GAC ATG CTG GTT AAG GTG     1199
Ser Glu Arg Ala Cys Asp Met His Val Ala Asp Met Leu Val Lys Val
        385                 390                 395

AAC GCA CTT ATC AAG GAT CGG GAA GGT TAT GCT CCT GGC ACA GAA TTC     1247
Asn Ala Leu Ile Lys Asp Arg Glu Gly Tyr Ala Pro Gly Thr Glu Phe
400                 405                 410                 415

CAC CGG TGC AAG GAA ATG TCT GAA TAC TGC AGC ACT CTG TGC CGC CAC     1295
His Arg Cys Lys Glu Met Ser Glu Tyr Cys Ser Thr Leu Cys Arg His
                420                 425                 430

CTC TAC CTG TTC CCA GGA CAC CCT CCC ACA TGATGTCACC TCCCCATCAT       1345
Leu Tyr Leu Phe Pro Gly His Pro Pro Thr
                435                 440

CCACGCCAAG TGGAAGCCAC TGGACCACAG GAGGTGTGAT AGAGCCTTTG ATCTTCAGGA   1405

TGCACGGTTT CTGTTCTGCC CCCTCAGGGA TGTGGGAATC TCCCAGACTT GTTTCCTGGA   1465

ATTCCAGGCC TGTGAAGGGG CTTGGGACTG ATTTCTAATG GGCACCTTGA TGAATCAGCT   1525

GTTTTGTTTC AAAAATTGAG AACCTTTCTG GGTTCTCTTA GAATATGCTC CTGGGCCAGT   1585

TGATCCAGCC TTTATTTTCA TTCTCTTGCT TTGGCTACCT TATCAGTGCT AAAATATATA   1645

TTTAGCAATA TATTTAGAGC TCGGAAATTA TATGAGAATC ACTCTGGCAT TGTCTTATTA   1705

CAGAGCAGGT AGCTGAAGCT GGAGAGGTTT TTTTCCTAGA GTCTCAAAAC TATGAAGTTA   1765

GGGAACTGGA ATCCAGATTT AAGTCAGCTT GTGCCCAATC CAGTACTCTT TTCACTTCAT   1825

CACACCGTCT GTCAGAATTT ATTCTGTATA TAATCATCCC TTACCACTCC TTGACCTCCA   1885

CAGGTGTTGG TGCCACCTAC TTTTTAGTGG CTCTACCTGT TCATTGGCTG TGTGACTTTG   1945

AGCAAATTAT GTAACCTCTT CATGCTTCAG TTTCTTGATC AGAAGGAAAT AGGGTAAGAA   2005

TAATACCTAC TTGATAGAAT TACTGCAAGG ATTTACAATA ACATACAATA ACATACAAGT   2065

GAAGTGCTTG GCACAGGTGA AGTGCTGGCA CATGCTCAGT AAATGTCAAC TTATTTCTAG   2125

TAATAGACTG TTTCAGATAC TTGCTTTCTT AAGTGTCTA GAGTCATGAA ATATTTTTAA    2185

AAGGACAGTT AAAATAAGTG TTTTCTCAAA AAACCTACAT TATAATTTTC CTTCAGGGGC   2245

TCAGGAGGCA AATTTAGAGC AATGAGTTTC AAATTTGTTC AGAGCTTAGA GTTACCATGC   2305

TTGAGTTTCC AGACACATGA TTATCTGTCT TATAAATGAG AAACAGTTTT ACTAGTAGAA   2365

AATGACTTTA TTGGATTTAT ATAATATAAA TTCACTATAA GCATACACAT CCATAAAAAA   2425

GCTATATAGA AGTAAGCCTA ATAAACTTGT AAATGGATGT TATTTTTAAT TTGCATACTG   2485
```

GGAATTC                                                                    2492

(2) INFORMATION FOR SEQ ID NO:44:

(i) SEQUENCE CHARACTERISTICS:
        (A) LENGTH: 441 amino acids
        (B) TYPE: amino acid
        (D) TOPOLOGY: linear (ii) MOLECULE TYPE: protein (xi) SEQUENCE DESCRIPTION: SEQ ID NO:44:

Ile Pro His Lys Glu Leu Met Ala Ala Asp Arg Gly Arg Arg Ile Leu
 1               5                  10                  15

Gly Val Cys Gly Met His Pro His His Gln Glu Thr Leu Lys Lys Asn
            20                  25                  30

Arg Val Val Leu Ala Lys Gln Leu Leu Leu Ser Glu Leu Leu Glu His
        35                  40                  45

Leu Leu Glu Lys Asp Ile Ile Thr Leu Glu Met Arg Glu Leu Ile Gln
    50                  55                  60

Ala Lys Val Gly Ser Phe Ser Gln Asn Val Glu Leu Leu Asn Leu Leu
65                  70                  75                  80

Pro Lys Arg Gly Pro Gln Ala Phe Asp Ala Phe Cys Glu Ala Leu Arg
                85                  90                  95

Glu Thr Lys Gln Gly His Leu Glu Asp Met Leu Leu Thr Thr Leu Ser
            100                 105                 110

Gly Leu Gln His Val Leu Pro Pro Leu Ser Cys Asp Tyr Asp Leu Ser
        115                 120                 125

Leu Pro Phe Pro Val Cys Glu Ser Cys Pro Leu Tyr Lys Lys Leu Arg
    130                 135                 140

Leu Ser Thr Asp Thr Val Glu His Ser Leu Asp Asn Lys Asp Gly Pro
145                 150                 155                 160

Val Cys Leu Gln Val Lys Pro Cys Thr Pro Glu Phe Tyr Gln Thr His
                165                 170                 175

Phe Gln Leu Ala Tyr Arg Leu Gln Ser Arg Pro Arg Gly Leu Ala Leu
            180                 185                 190

Val Leu Ser Asn Val His Phe Thr Gly Glu Lys Glu Leu Glu Phe Arg
        195                 200                 205

Ser Gly Gly Asp Val Asp His Ser Thr Leu Val Thr Leu Phe Lys Leu
    210                 215                 220

Leu Gly Tyr Asp Val His Val Leu Cys Asp Gln Thr Ala Gln Glu Met
225                 230                 235                 240

Gln Glu Lys Leu Gln Asn Phe Ala Gln Leu Pro Ala His Arg Val Thr
                245                 250                 255

Asp Ser Cys Ile Val Ala Leu Leu Ser His Gly Val Glu Gly Ala Ile
            260                 265                 270

Tyr Gly Val Asp Gly Lys Leu Leu Gln Leu Gln Glu Val Phe Gln Leu
        275                 280                 285

Phe Asp Asn Ala Asn Cys Pro Ser Leu Gln Asn Lys Pro Lys Met Phe
    290                 295                 300

Phe Ile Gln Ala Cys Arg Gly Asp Glu Thr Asp Arg Gly Val Asp Gln
305                 310                 315                 320

Gln Asp Gly Lys Asn His Ala Gly Ser Pro Gly Cys Glu Glu Ser Asp
                325                 330                 335

Ala Gly Lys Glu Lys Leu Pro Lys Met Arg Leu Pro Thr Arg Ser Asp
            340                 345                 350

```
Met Ile Cys Gly Tyr Ala Cys Leu Lys Gly Thr Ala Ala Met Arg Asn
            355                 360                 365

Thr Lys Arg Gly Ser Trp Tyr Ile Glu Ala Leu Ala Gln Val Phe Ser
        370                 375                 380

Glu Arg Ala Cys Asp Met His Val Ala Asp Met Leu Val Lys Val Asn
385                 390                 395                 400

Ala Leu Ile Lys Asp Arg Glu Gly Tyr Ala Pro Gly Thr Glu Phe His
                405                 410                 415

Arg Cys Lys Glu Met Ser Glu Tyr Cys Ser Thr Leu Cys Arg His Leu
            420                 425                 430

Tyr Leu Phe Pro Gly His Pro Pro Thr
            435                 440
```

(2) INFORMATION FOR SEQ ID NO:45:

(i) SEQUENCE CHARACTERISTICS:
        (A) LENGTH: 120 base pairs
        (B) TYPE: nucleic acid
        (C) STRANDEDNESS: both
        (D) TOPOLOGY: both (ix) FEATURE:
        (A) NAME/KEY: CDS
        (B) LOCATION: join(1..6, 10..118)

(xi) SEQUENCE DESCRIPTION: SEQ ID NO:45:

```
TTC TGG TAG CTC CAA GAG GTT TTT CGA CTT TTT GAC AAT GCT AAC TGT      48
Phe Trp     Leu Gln Glu Val Phe Arg Leu Phe Asp Asn Ala Asn Cys
  1           5                  10                  15

CCA AGT CTA CAG AAC AAG CCA AAA ATG TTC TTC ATC CAA GCA TGT CGT      96
Pro Ser Leu Gln Asn Lys Pro Lys Met Phe Phe Ile Gln Ala Cys Arg
             20                  25                  30

GGA GGT GCT ATT GGA TCC CTT GGG                                     120
Gly Gly Ala Ile Gly Ser Leu Gly
            35
```

(2) INFORMATION FOR SEQ ID NO:46:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:46:

```
Phe Trp Leu Gln Glu Val Phe Arg Leu Phe Asp Asn Ala Asn Cys Pro
  1               5                  10                  15

Ser Leu Gln Asn Lys Pro Lys Met Phe Phe Ile Gln Ala Cys Arg Gly
             20                  25                  30

Gly Ala Ile Gly Ser Leu Gly
            35
```

(2) INFORMATION FOR SEQ ID NO:47:

(i) SEQUENCE CHARACTERISTICS:
        (A) LENGTH: 120 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 2..119

(xi) SEQUENCE DESCRIPTION: SEQ ID NO:47:

```
T TCT GGT AGC TCC AAG AGG TTT TTC GAC TTT TTG ACA ATG CTA ACT        46
  Ser Gly Ser Ser Lys Arg Phe Phe Asp Phe Leu Thr Met Leu Thr
  1               5                   10                  15

GTC CAA GTC TAC AGA ACA AGC CAA AAA TGT TCT TCA TCC AAG CAT GTC      94
Val Gln Val Tyr Arg Thr Ser Gln Lys Cys Ser Ser Ser Lys His Val
                20                  25                  30

GTG GAG GTG CTA TTG GAT CCC TTG GG                                   120
Val Glu Val Leu Leu Asp Pro Leu Gly
            35
```

(2) INFORMATION FOR SEQ ID NO:48:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:48:

```
Ser Gly Ser Ser Lys Arg Phe Phe Asp Phe Leu Thr Met Leu Thr Val
1               5                   10                  15

Gln Val Tyr Arg Thr Ser Gln Lys Cys Ser Ser Ser Lys His Val Val
                20                  25                  30

Glu Val Leu Leu Asp Pro Leu Gly
            35                  40
```

(2) INFORMATION FOR SEQ ID NO:49:

(i) SEQUENCE CHARACTERISTICS:
        (A) LENGTH: 120 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 3..120

(xi) SEQUENCE DESCRIPTION: SEQ ID NO:49:

```
TT CTG GTA GCT CCA AGA GGT TTT TCG ACT TTT TGA CAA TGC TAA CTG       47
   Leu Val Ala Pro Arg Gly Phe Ser Thr Phe     Gln Cys     Leu
   1               5                   10                  15

TCC AAG TCT ACA GAA CAA GCC AAA AAT GTT CTT CAT CCA AGC ATG TCG      95
Ser Lys Ser Thr Glu Gln Ala Lys Asn Val Leu His Pro Ser Met Ser
                20                  25                  30

TGG AGG TGC TAT TGG ATC CCT TGG G                                    120
Trp Arg Cys Tyr Trp Ile Pro Trp Ala
            35
```

(2) INFORMATION FOR SEQ ID NO:50:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:50:

```
Leu Val Ala Pro Arg Gly Phe Ser Thr Phe Gln Cys Leu Ser Lys Ser
1               5                   10                  15

Thr Glu Gln Ala Lys Asn Val Leu His Pro Ser Met Ser Trp Arg Cys
```

20              25              30
Tyr Trp Ile Pro Trp Ala
        35

(2) INFORMATION FOR SEQ ID NO:51:

(i) SEQUENCE CHARACTERISTICS:
        (A) LENGTH: 2632 base pairs
        (B) TYPE: nucleic acid
        (C) STRANDEDNESS: both
        (D) TOPOLOGY: both (xi) SEQUENCE DESCRIPTION: SEQ ID NO:51:

| | | | | | |
|---|---|---|---|---|---|
| ATGAAAGTGC | ATTTTTATAT | CTTTATGCTG | TACACTTCAC | TCACTGTAAT | GGTGGGTAAG | 60 |
| TTTAGTGAGC | AATAGGTCAC | TATGGTGACC | CATGTCACAC | AGCCTGAATG | TTATGGTAAA | 120 |
| ATATACTCTG | CTAAATAAAT | TAGTCCATTA | TTTAAATTCA | ACCTCAAGTT | TTCAGAATAT | 180 |
| AGACGACTGC | GTCCAATTCC | TCACCAAAGT | AGGACACAAG | CTGAGTTCTC | ATTAAAGTCC | 240 |
| TTGATCTGTT | CTAGGATCTA | TTGAGCCTAG | CCTGTGTCTT | CATTTTTCTT | AATTAACACT | 300 |
| TGGGTGTCTT | GAAAACCCAC | TAAAATTGCC | CCTGAAGCCC | TGCTTAGAGC | ATTCTGGGCT | 360 |
| TTTTAGCCTG | CAGCTTCTAA | TTCTCCCATA | TTCCTCCAAC | AAACTAGTTC | CAATGGCCTA | 420 |
| TGAACCATGT | GGAAAGATTA | TGGCTGTATT | GACCCCAAAC | TGGCATAAGT | TTTCAGTATT | 480 |
| GGTTTTCTTG | GACTGAGACC | AAAAATTCTT | AACGAGAAAC | AGTTTGTTTT | GGCTCCTTGT | 540 |
| TTGACAATAT | AAGCCCCCGT | GGCAAGAAGC | CAGCTCTCCA | GTGGAGACAG | GAGCAGTAGG | 600 |
| CTTCTTGTAT | TTGGGTAAAT | TGTGTAGCAT | AAAAGAAGAG | ATGCTGGCAT | GTCTGGCTTT | 660 |
| CTTTGCCCCA | ACCCTTTCAG | TCTGGGTTCC | AGGTCTTTCC | TCCTCAGTTA | ATTCTTTCTG | 720 |
| GAAATTCAAT | ACCCTCAAAA | ATAAACTAAG | TGTATCTCCC | AAGTGACTGT | AAATCTAGTC | 780 |
| CAGTTGACAA | GATCAGCTAT | CTCCCTACCT | TTCAGATGAA | GGTTGAATTT | GTATGTGTTA | 840 |
| GACTTCAAGA | GGTCTCACTG | GCTACCTAAC | TTCCCCTCTC | CCTTATTTGT | TTCTGGTAGC | 900 |
| TCCAAGAGGT | TTTTCGACTT | TTTGACAATG | CTAACTGTCC | AAGTCTACAG | AACAAGCCAA | 960 |
| AAATGTTCTT | CATCCAAGCA | TGTCGTGGAG | GTGCTTGCTC | TATGAGACAG | ATAGAGGTGT | 1020 |
| CGACCAGCAA | GATGGAAAGA | ACCACACACA | ATCCCCTGGA | TGTGAGGAGA | GTGATGCTGG | 1080 |
| CAAAGAGGAG | TTGATGAAGA | TGAGACTGCC | TACTCGCTCA | GACATGATAT | GTGGCTATGC | 1140 |
| TTGCCTTAAA | GGTAATGCTG | CCATGCGGAA | CACCAAACGG | GGTTCCTGGT | ACATTGAGGC | 1200 |
| CCTCACTCAG | GTGTTCTCTG | AAAGAGCTTG | TGACATGCAC | GTGGCCGACA | TGCTTGTTAA | 1260 |
| GGTGAATGCC | CTTATCAAGG | AGCGTGAAGG | CTATGCCCCT | GGCACAGAAT | CCACCGATG | 1320 |
| CAAGGAGATG | TCTGAGTACT | GTAGTACTCT | GTGCCAGCAA | CTCTACCTGT | TCCCAGGCTA | 1380 |
| CCCACCCACG | TGATGCCGCC | TGCTATTCCT | GCTGTTGGAG | GCCACTGGAC | CACTGGGGGC | 1440 |
| ACAATGGAGA | CTTCTCTTCA | GAATGGTTTT | TGTTCTGTCT | ACCCTCTCAG | GGATATGAGA | 1500 |
| TTCTCCCAGG | CTTGTTTCCT | GTCAGCCATC | TCTGTCTTTG | GTATGAAAC | ATAAGGATGG | 1560 |
| CTCCTCCGGT | GTCGTGTTCT | CTACCTATAG | AGCCAGCTCT | GAATGGATGT | GTTACCAGAA | 1620 |
| GCATTTAGC | TACAGCCTAG | AAAATGACAT | TGTGAACACA | GTATTATTGT | GGGAAGAGGG | 1680 |
| CATTTGGATT | TCTCAATGTT | TGTGATATTT | TTGTTCCCAA | GGCATCTTAG | GAGTACTTGG | 1740 |
| ATCATAGCTT | TTTTTTTTTT | TCCTAAATCA | GTTAAGGAGT | CTCAGAGATC | ATCTCCTTTT | 1800 |
| TTTTCCATAT | CTACAACCTC | ATTTTTCCCA | CAGTGGAGAT | TTGGAAGATG | TCCCAATTTA | 1860 |
| ATGTAGGTGT | TTTCATCTGT | CATGAAGGGA | CAGATGAGAT | CCTACTACTT | GCGAAGTTTC | 1920 |

```
TATGCATACC TTTAAGTTCA GGCCCTAGGT GAAGGACAGT CCCTCAGCCT TTCCATTGGT     1980

TCCTTTGTGT TCAGTGCACC CAGCCTTTGA ACAGAGCCTA GGGTCTGTAT GCCATGACAC     2040

TGGAAGTCAT AGAAATTTCC CTGGTCATGC TTTGTTTGAA CTGTCACTGA ATGAACCTTA     2100

TCGGGCATAA CTACATGAAA ATGCAGTGAC AGCTGAGTGT GCTGTGTCTC ACACTATCAC     2160

CCGTCATCAG GATGTCTCTC CTTCCTTACT GTGGCTTCTG CATGCACTTA CACTGTACTT     2220

GACGGCTGGC CTCCAGGGTC TCTCTTGCTT TGTACTGGTT CCCCTCTTTA CCTTCACCAT     2280

TCGCTGCTTC TGCCAAGTCT GTGAAGCCGT CCTTTGTAGG ATGTTTCTTG CCACTTACGC     2340

TGTACTGTAG TTGCTTATTC TTTCTGCCTT CTGCTTCAGC GTGAGGCTTC TTTGGTTTTC     2400

TGTGGCAGCG TCTCCCTTCT CATTGTTTCT CTGTGTTTTA GTGGGATAG TACCATATGT      2460

GATATAACCT AGAAGCACTT GTCTCTGCTC TTATGAAACT TGCTTATTCT TGAAAACCTT     2520

CTGCATTTCC ATTTTTTCCT CTCTTCCAAT TTATTCTCCA TGTAACAGAG TAGTTTGGTT     2580

TTTAAAATAT CTGGTGATGT CATTCTCTTG CTTAGAACAC TAGCTTCCTG TT             2632

(2) INFORMATION FOR SEQ ID NO:52:

(i) SEQUENCE CHARACTERISTICS:
        (A) LENGTH: 2485 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 14..1316

(xi) SEQUENCE DESCRIPTION: SEQ ID NO:52:

GCACAAGGAG CTG ATG GCC GCT GAC AGG GGA CGC AGG ATA TTG GGA GTG           49
            Met Ala Ala Asp Arg Gly Arg Arg Ile Leu Gly Val
              1               5                  10

TGT GGC ATG CAT CCT CAT CAT CAG GAA ACT CTA AAA AAG AAC CGA GTG          97
Cys Gly Met His Pro His His Gln Glu Thr Leu Lys Lys Asn Arg Val
      15                  20                  25

GTG CTA GCC AAA CAG CTG TTG TTG AGC GAA TTG TTA GAA CAT CTT CTG         145
Val Leu Ala Lys Gln Leu Leu Leu Ser Glu Leu Leu Glu His Leu Leu
 30                  35                  40

GAG AAG GAC ATC ATC ACC TTG GAA ATG AGG GAG CTC ATC CAG GCC AAA         193
Glu Lys Asp Ile Ile Thr Leu Glu Met Arg Glu Leu Ile Gln Ala Lys
 45                  50                  55                  60

GTG GGC AGT TTC AGC CAG AAT GTG GAA CTC CTC AAC TTG CTG CCT AAG         241
Val Gly Ser Phe Ser Gln Asn Val Glu Leu Leu Asn Leu Leu Pro Lys
             65                  70                  75

AGG GGT CCC CAA GCT TTT GAT GCC TTC TGT GAA GCA CTG AGG GAG ACC         289
Arg Gly Pro Gln Ala Phe Asp Ala Phe Cys Glu Ala Leu Arg Glu Thr
         80                  85                  90

AAG CAA GGC CAC CTG GAG GAT ATG TTG CTC ACC ACC CTT TCT GGG CTT         337
Lys Gln Gly His Leu Glu Asp Met Leu Leu Thr Thr Leu Ser Gly Leu
     95                  100                 105

CAG CAT GTA CTC CCA CCG TTG AGC TGT GAC TAC GAC TTG AGT CTC CCT         385
Gln His Val Leu Pro Pro Leu Ser Cys Asp Tyr Asp Leu Ser Leu Pro
 110                 115                 120

TTT CCG GTG TGT GAG TCC TGT CCC CTT TAC AAG AAG CTC CGC CTG TCG         433
Phe Pro Val Cys Glu Ser Cys Pro Leu Tyr Lys Lys Leu Arg Leu Ser
125                 130                 135                 140

ACA GAT ACT GTG GAA CAC TCC CTA GAC AAT AAA GAT GGT CCT GTC TGC         481
```

```
                Thr Asp Thr Val Glu His Ser Leu Asp Asn Lys Asp Gly Pro Val Cys
                                145                 150                 155

CTT CAG GTG AAG CCT TGC ACT CCT GAA TTT TAT CAA ACA CAC TTC CAG                 529
Leu Gln Val Lys Pro Cys Thr Pro Glu Phe Tyr Gln Thr His Phe Gln
            160                 165                 170

CTG GCA TAT AGG TTG CAG TCT CGG CCT CGT GGC CTA GCA CTG GTG TTG                 577
Leu Ala Tyr Arg Leu Gln Ser Arg Pro Arg Gly Leu Ala Leu Val Leu
        175                 180                 185

AGC AAT GTG CAC TTC ACT GGA GAG AAA GAA CTG GAA TTT CGC TCT GGA                 625
Ser Asn Val His Phe Thr Gly Glu Lys Glu Leu Glu Phe Arg Ser Gly
    190                 195                 200

GGG GAT GTG GAC CAC AGT ACT CTA GTC ACC CTC TTC AAG CTT TTG GGC                 673
Gly Asp Val Asp His Ser Thr Leu Val Thr Leu Phe Lys Leu Leu Gly
205                 210                 215                 220

TAT GAC GTC CAT GTT CTA TGT GAC CAG ACT GCA CAG GAA ATG CAA GAG                 721
Tyr Asp Val His Val Leu Cys Asp Gln Thr Ala Gln Glu Met Gln Glu
                225                 230                 235

AAA CTG CAG AAT TTT GCA CAG TTA CCT GCA CAC CGA GTC ACG GAC TCC                 769
Lys Leu Gln Asn Phe Ala Gln Leu Pro Ala His Arg Val Thr Asp Ser
            240                 245                 250

TGC ATC GTG GCA CTC CTC TCG CAT GGT GTG GAG GGC GCC ATC TAT GGT                 817
Cys Ile Val Ala Leu Leu Ser His Gly Val Glu Gly Ala Ile Tyr Gly
        255                 260                 265

GTG GAT GGG AAA CTG CTC CAG CTC CAA GAG GTT TTT CAG CTC TTT GAC                 865
Val Asp Gly Lys Leu Leu Gln Leu Gln Glu Val Phe Gln Leu Phe Asp
    270                 275                 280

AAC GCC AAC TGC CCA AGC CTA CAG AAC AAA CCA AAA ATG TTC TTC ATC                 913
Asn Ala Asn Cys Pro Ser Leu Gln Asn Lys Pro Lys Met Phe Phe Ile
285                 290                 295                 300

CAG GCC TGC CGT GGA GAT GAG ACT GAT CGT GGG GTT GAC CAA CAA GAT                 961
Gln Ala Cys Arg Gly Asp Glu Thr Asp Arg Gly Val Asp Gln Gln Asp
                305                 310                 315

GGA AAG AAC CAC GCA GGA TCC CCT GGG TGC GAG GAG AGT GAT GCC GGT                 1009
Gly Lys Asn His Ala Gly Ser Pro Gly Cys Glu Glu Ser Asp Ala Gly
            320                 325                 330

AAA GAA AAG TTG CCG AAG ATG AGA CTG CCC ACG CGC TCA GAC ATG ATA                 1057
Lys Glu Lys Leu Pro Lys Met Arg Leu Pro Thr Arg Ser Asp Met Ile
        335                 340                 345

TGC GGC TAT GCC TGC CTC AAA GGG ACT GCC GCC ATG CGG AAC ACC AAA                 1105
Cys Gly Tyr Ala Cys Leu Lys Gly Thr Ala Ala Met Arg Asn Thr Lys
    350                 355                 360

CGA GGT TCC TGG TAC ATC GAG GCT CTT GCT CAA GTG TTT TCT GAG CGG                 1153
Arg Gly Ser Trp Tyr Ile Glu Ala Leu Ala Gln Val Phe Ser Glu Arg
365                 370                 375                 380

GCT TGT GAT ATG CAC GTG GCC GAC ATG CTG GTT AAG GTG AAC GCA CTT                 1201
Ala Cys Asp Met His Val Ala Asp Met Leu Val Lys Val Asn Ala Leu
                385                 390                 395

ATC AAG GAT CGG GAA GGT TAT GCT CCT GGC ACA GAA TTC CAC CGG TGC                 1249
Ile Lys Asp Arg Glu Gly Tyr Ala Pro Gly Thr Glu Phe His Arg Cys
            400                 405                 410

AAG GAA ATG TCT GAA TAC TGC AGC ACT CTG TGC CGC CAC CTC TAC CTG                 1297
Lys Glu Met Ser Glu Tyr Cys Ser Thr Leu Cys Arg His Leu Tyr Leu
        415                 420                 425

TTC CCA GGA CAC CCT CCC ACA TGATGTCACC TCCCCATCAT CCACGCCA                      1346
Phe Pro Gly His Pro Pro Thr
    430

AGTGGAAGCC ACTGGACCAC AGGAGGTGTG ATAGAGCCTT TGATCTTCAG GATGCACGGT               1406

TTCTGTTCTG CCCCCTCAGG GATGTGGGAA TCTCCCAGAC TTGTTTCCTG GAATTCCAGG               1466
```

```
CCTGTGAAGG GGCTTGGGAC TGATTTCTAA TGGGCACCTT GATGAATCAG CTGTTTTGTT      1526

TCAAAAATTG AGAACCTTTC TGGGTTCTCT TAGAATATGC TCCTGGGCCA GTTGATCCAG      1586

CCTTTATTTT CATTCTCTTG CTTTGGCTAC CTTATCAGTG CTAAAATATA TATTTAGCAA      1646

TATATTTAGA GCTCGGAAAT TATATGAGAA TCACTCTGGC ATTGTCTTAT TACAGAGCAG      1706

GTAGCTGAAG CTGGAGAGGT TTTTTTCCTA GAGTCTCAAA ACTATGAAGT TAGGGAACTG      1766

GAATCCAGAT TTAAGTCAGC TTGTGCCCAA TCCAGTACTC TTTTCACTTC ATCACACCGT      1826

CTGTCAGAAT TTATTCTGTA TATAATCATC CCTTACCACT CCTTGACCTC CACAGGTGTT      1886

GGTGCCACCT ACTTTTTAGT GGCTCTACCT GTTCATTGGC TGTGTGACTT TGAGCAAATT      1946

ATGTAACCTC TTCATGCTTC AGTTTCTTGA TCAGAAGGAA ATAGGGTAAG AATAATACCT      2006

ACTTGATAGA ATTACTGCAA GGATTTACAA TAACATACAA TAACATACAA GTGAAGTGCT      2066

TGGCACAGGT GAAGTGCTGG CACATGCTCA GTAAATGTCA ACTTATTTCT AGTAATAGAC      2126

TGTTTCAGAT ACTTGCTTTC TTTAAGTGTC TAGAGTCATG AAATATTTTT AAAAGGACAG      2186

TTAAAATAAG TGTTTTCTCA AAAAACCTAC ATTATAATTT TCCTTCAGGG GCTCAGGAGG      2246

CAAATTTAGA GCAATGAGTT TCAAATTTGT TCAGAGCTTA GAGTTACCAT GCTTGAGTTT      2306

CCAGACACAT GATTATCTGT CTTATAAATG AGAAACAGTT TTACTAGTAG AAAATGACTT      2366

TATTGGATTT ATATAATATA AATTCACTAT AAGCATACAC ATCCATAAAA AAGCTATATA      2426

GAAGTAAGCC TAATAAACTT GTAAATGGAT GTTATTTTTA ATTTGCATAC TGGGAATTC      2485
```

(2) INFORMATION FOR SEQ ID NO:53:

(i) SEQUENCE CHARACTERISTICS:
        (A) LENGTH: 435 amino acids
        (B) TYPE: amino acid
        (D) TOPOLOGY: linear (ii) MOLECULE TYPE: protein (xi) SEQUENCE DESCRIPTION: SEQ ID NO:53:

```
Met Ala Ala Asp Arg Gly Arg Arg Ile Leu Gly Val Cys Gly Met His
 1               5                  10                  15

Pro His His Gln Glu Thr Leu Lys Lys Asn Arg Val Val Leu Ala Lys
                20                  25                  30

Gln Leu Leu Leu Ser Glu Leu Leu Glu His Leu Leu Glu Lys Asp Ile
            35                  40                  45

Ile Thr Leu Glu Met Arg Glu Leu Ile Gln Ala Lys Val Gly Ser Phe
        50                  55                  60

Ser Gln Asn Val Glu Leu Leu Asn Leu Leu Pro Lys Arg Gly Pro Gln
 65                  70                  75                  80

Ala Phe Asp Ala Phe Cys Glu Ala Leu Arg Glu Thr Lys Gln Gly His
                85                  90                  95

Leu Glu Asp Met Leu Leu Thr Thr Leu Ser Gly Leu Gln His Val Leu
               100                 105                 110

Pro Pro Leu Ser Cys Asp Tyr Asp Leu Ser Leu Pro Phe Pro Val Cys
           115                 120                 125

Glu Ser Cys Pro Leu Tyr Lys Lys Leu Arg Leu Ser Thr Asp Thr Val
       130                 135                 140

Glu His Ser Leu Asp Asn Lys Asp Gly Pro Val Cys Leu Gln Val Lys
145                 150                 155                 160

Pro Cys Thr Pro Glu Phe Tyr Gln Thr His Phe Gln Leu Ala Tyr Arg
               165                 170                 175
```

-continued

```
Leu Gln Ser Arg Pro Arg Gly Leu Ala Leu Val Leu Ser Asn Val His
            180                 185                 190

Phe Thr Gly Glu Lys Glu Leu Glu Phe Arg Ser Gly Gly Asp Val Asp
        195                 200                 205

His Ser Thr Leu Val Thr Leu Phe Lys Leu Leu Gly Tyr Asp Val His
    210                 215                 220

Val Leu Cys Asp Gln Thr Ala Gln Glu Met Gln Glu Lys Leu Gln Asn
225                 230                 235                 240

Phe Ala Gln Leu Pro Ala His Arg Val Thr Asp Ser Cys Ile Val Ala
                245                 250                 255

Leu Leu Ser His Gly Val Glu Gly Ala Ile Tyr Gly Val Asp Gly Lys
            260                 265                 270

Leu Leu Gln Leu Gln Glu Val Phe Gln Leu Phe Asp Asn Ala Asn Cys
        275                 280                 285

Pro Ser Leu Gln Asn Lys Pro Lys Met Phe Phe Ile Gln Ala Cys Arg
    290                 295                 300

Gly Asp Glu Thr Asp Arg Gly Val Asp Gln Gln Asp Gly Lys Asn His
305                 310                 315                 320

Ala Gly Ser Pro Gly Cys Glu Glu Ser Asp Ala Gly Lys Glu Lys Leu
                325                 330                 335

Pro Lys Met Arg Leu Pro Thr Arg Ser Asp Met Ile Cys Gly Tyr Ala
            340                 345                 350

Cys Leu Lys Gly Thr Ala Ala Met Arg Asn Thr Lys Arg Gly Ser Trp
        355                 360                 365

Tyr Ile Glu Ala Leu Ala Gln Val Phe Ser Glu Arg Ala Cys Asp Met
    370                 375                 380

His Val Ala Asp Met Leu Val Lys Val Asn Ala Leu Ile Lys Asp Arg
385                 390                 395                 400

Glu Gly Tyr Ala Pro Gly Thr Glu Phe His Arg Cys Lys Glu Met Ser
                405                 410                 415

Glu Tyr Cys Ser Thr Leu Cys Arg His Leu Tyr Leu Phe Pro Gly His
            420                 425                 430

Pro Pro Thr
```

(2) INFORMATION FOR SEQ ID NO:54:

(i) SEQUENCE CHARACTERISTICS:
        (A) LENGTH: 2174 base pairs
        (B) TYPE: nucleic acid
        (C) STRANDEDNESS: both
        (D) TOPOLOGY: both (ii) MOLECULE TYPE: DNA (ix) FEATURE:
        (A) NAME/KEY: CDS
        (B) LOCATION: 89..1019

(xi) SEQUENCE DESCRIPTION: SEQ ID NO:54:

```
AGAGGGAGGG AACGATTTAA GGAGCGAATA CTACTGGTAA ACTAATGGAA GAAATCTGCT      60

GCACCACTGG ATATTGGGAG TGTGTGGC ATG CAT CCT CAT CAT CAG GAA ACT       112
                              Met His Pro His His Gln Glu Thr
                                1               5

CTA AAA AAG AAC CGA GTG GTG CTA GCC AAA CAG CTG TTG TTG AGC GAA      160
Leu Lys Lys Asn Arg Val Val Leu Ala Lys Gln Leu Leu Leu Ser Glu
 10                  15                  20

TTG TTA GAA CAT CTT CTG GAG AAG GAC ATC ATC ACC TTG GAA ATG AGG      208
Leu Leu Glu His Leu Leu Glu Lys Asp Ile Ile Thr Leu Glu Met Arg
```

```
                                                                    -continued 25                  30                  35                  40
GAG CTC ATC CAG GCC AAA GTG GGC AGT TTC AGC CAG AAT GTG GAA CTC      256
Glu Leu Ile Gln Ala Lys Val Gly Ser Phe Ser Gln Asn Val Glu Leu
                     45                  50                  55

CTC AAC TTG CTG CCT AAG AGG GGT CCC CAA GCT TTT GAT GCC TTC TGT      304
Leu Asn Leu Leu Pro Lys Arg Gly Pro Gln Ala Phe Asp Ala Phe Cys
                 60                  65                  70

GAA GCA CTG AGG GAG ACC AAG CAA GGC CAC CTG GAG GAT ATG TTG CTC      352
Glu Ala Leu Arg Glu Thr Lys Gln Gly His Leu Glu Asp Met Leu Leu
             75                  80                  85

ACC ACC CTT TCT GGG CTT CAG CAT GTA CTC CCA CCG TTG AGC TGT GAC      400
Thr Thr Leu Ser Gly Leu Gln His Val Leu Pro Pro Leu Ser Cys Asp
         90                  95                 100

TAC GAC TTG AGT CTC CCT TTT CCG GTG TGT GAG TCC TGT CCC CTT TAC      448
Tyr Asp Leu Ser Leu Pro Phe Pro Val Cys Glu Ser Cys Pro Leu Tyr
105                 110                 115                 120

AAG AAG CTC CGC CTG TCG ACA GAT ACT GTG GAA CAC TCC CTA GAC AAT      496
Lys Lys Leu Arg Leu Ser Thr Asp Thr Val Glu His Ser Leu Asp Asn
                125                 130                 135

AAA GAT GGT CCT GTC TGC CTT CAG GTG AAG CCT TGC ACT CCT GAA TTT      544
Lys Asp Gly Pro Val Cys Leu Gln Val Lys Pro Cys Thr Pro Glu Phe
            140                 145                 150

TAT CAA ACA CAC TTC CAG CTG GCA TAT AGG TTG CAG TCT CGG CCT CGT      592
Tyr Gln Thr His Phe Gln Leu Ala Tyr Arg Leu Gln Ser Arg Pro Arg
        155                 160                 165

GGC CTA GCA CTG GTG TTG AGC AAT GTG CAC TTC ACT GGA GAG AAA GAA      640
Gly Leu Ala Leu Val Leu Ser Asn Val His Phe Thr Gly Glu Lys Glu
    170                 175                 180

CTG GAA TTT CGC TCT GGA GGG GAT GTG GAC CAC AGT ACT CTA GTC ACC      688
Leu Glu Phe Arg Ser Gly Gly Asp Val Asp His Ser Thr Leu Val Thr
185                 190                 195                 200

CTC TTC AAG CTT TTG GGC TAT GAC GTC CAT GTT CTA TGT GAC CAG ACT      736
Leu Phe Lys Leu Leu Gly Tyr Asp Val His Val Leu Cys Asp Gln Thr
                205                 210                 215

GCA CAG GAA ATG CAA GAG AAA CTG CAG AAT TTT GCA CAG TTA CCT GCA      784
Ala Gln Glu Met Gln Glu Lys Leu Gln Asn Phe Ala Gln Leu Pro Ala
            220                 225                 230

CAC CGA GTC ACG GAC TCC TGC ATC GTG GCA CTC CTC TCG CAT GGT GTG      832
His Arg Val Thr Asp Ser Cys Ile Val Ala Leu Leu Ser His Gly Val
        235                 240                 245

GAG GGC GCC ATC TAT GGT GTG GAT GGG AAA CTG CTC CAG CTC CAA GAG      880
Glu Gly Ala Ile Tyr Gly Val Asp Gly Lys Leu Leu Gln Leu Gln Glu
    250                 255                 260

GTT TTT CAG CTC TTT GAC AAC GCC AAC TGC CCA AGC CTA CAG AAC AAA      928
Val Phe Gln Leu Phe Asp Asn Ala Asn Cys Pro Ser Leu Gln Asn Lys
265                 270                 275                 280

CCA AAA ATG TTC TTC ATC CAG GCC TGC CGT GGA GGT GCT ATT GGA TCC      976
Pro Lys Met Phe Phe Ile Gln Ala Cys Arg Gly Gly Ala Ile Gly Ser
                285                 290                 295

CTT GGG CAC CTC CTT CTG TTC ACT GCT GCC ACC GCC TCT CTT GCT CTA     1024
Leu Gly His Leu Leu Leu Phe Thr Ala Ala Thr Ala Ser Leu Ala Leu
            300                 305                 310

TGAGACTGAT CGTGGGGTTG ACCAACAAGA TGGAAAGAAC CACGCAGGAT CCCCTGGGTG   1084

CGAGGAGAGT GATGCCGGTA AGAAAAGTT GCCGAAGATG AGACTGCCCA CGCGCTCAGA   1144

CATGATATGC GGCTATGCCT GCCTCAAAGG GACTGCCGCC ATGCGGAACA CCAAACGAGG   1204

TTCCTGGTAC ATCGAGGCTC TTGCTCAAGT GTTTTCTGAG CGGGCTTGTG ATATGCACGT   1264

GGCCGACATG CTGGTTAAGG TGAACGCACT TATCAAGGAT CGGGAAGGTT ATGCTCCTGG   1324
```

```
CACAGAATTC CACCGGTGCA AGGAGATGTC TGAATACTGC AGCACTCTGT GCCGCCACCT      1384

CTACCTGTTC CCAGGACACC CTCCCACATG ATGTCACCTC CCCATCATCC ACGCCAAGTG      1444

GAAGCCACTG GACCACAGGA GGTGTGATAG AGCCTTTGAT CTTCAGGATG CACGGTTTCT      1504

GTTCTGCCCC CTCAGGGATG TGGGAATCTT CCAGACTTGT TTCCTGTGCC CATCATCTCT      1564

GCCTTTGAGT GTGGGACTCC AGGCCAGCTC CTTTTCTGTG AAGCCCTTTG CCTGTAGAGC      1624

CAGCCTTGGT TGGACCTATT GCCAGGAATG TTTCAGCTGC AGTTGAAGAG CCTGACAAGT      1684

GAAGTTGTAA ACACAGTGTG GTTATGGGGA GAGGGCATAT AAATTCCCCA TATTTGTGTT      1744

CAGTTCCAGC TTTTGTAGAT GGCACTTTAG TGATTGCTTT TATTACATTA GTTAAGATGT      1804

CTTGAGAGAC CATCTCCTAT CTTTTATTTC ATTCATATCC TCCGCCCTTT TTGTCCTAGA      1864

GTGAGAGTTT GGAAGGTGTC CAAATTTAAT GTAGACATTA TCTTTTGGCT CTGAAGAAGC      1924

AAACATGACT AGAGACGCAC CTTGCTGCAG TGTCCAGAAG CGGCCTGTGC GTTCCCTTCA      1984

GTACTGCAGC GCCACCCAGT GGAAGGACAC TCTTGGCTCG TTTGGGCTCA AGGCACCGCA      2044

GCCTGTCAGC CAACATTGCC TTGCATTTGT ACCTTATTGA TCTTTGCCCA TGGAAGTCTC      2104

AAAGATCTTT CGTTGGTTGT TTCTCTGAGC TTTGTTACTG AAATGAGCCT CGTGGGGAGC      2164

ATCGGAATTC                                                             2174
```

(2) INFORMATION FOR SEQ ID NO:55:

(i) SEQUENCE CHARACTERISTICS:
        (A) LENGTH: 312 amino acids
        (B) TYPE: amino acid
        (D) TOPOLOGY: linear (ii) MOLECULE TYPE: protein (xi) SEQUENCE DESCRIPTION: SEQ ID NO:55:

```
Met His Pro His His Gln Glu Thr Leu Lys Lys Asn Arg Val Val Leu
 1               5                  10                  15

Ala Lys Gln Leu Leu Leu Ser Glu Leu Leu Glu His Leu Leu Glu Lys
            20                  25                  30

Asp Ile Ile Thr Leu Glu Met Arg Glu Leu Ile Gln Ala Lys Val Gly
        35                  40                  45

Ser Phe Ser Gln Asn Val Glu Leu Leu Asn Leu Leu Pro Lys Arg Gly
    50                  55                  60

Pro Gln Ala Phe Asp Ala Phe Cys Glu Ala Leu Arg Glu Thr Lys Gln
65                  70                  75                  80

Gly His Leu Glu Asp Met Leu Leu Thr Thr Leu Ser Gly Leu Gln His
                85                  90                  95

Val Leu Pro Pro Leu Ser Cys Asp Tyr Asp Leu Ser Leu Pro Phe Pro
           100                 105                 110

Val Cys Glu Ser Cys Pro Leu Tyr Lys Lys Leu Arg Leu Ser Thr Asp
       115                 120                 125

Thr Val Glu His Ser Leu Asp Asn Lys Asp Gly Pro Val Cys Leu Gln
   130                 135                 140

Val Lys Pro Cys Thr Pro Glu Phe Tyr Gln Thr His Phe Gln Leu Ala
145                 150                 155                 160

Tyr Arg Leu Gln Ser Arg Pro Arg Gly Leu Ala Leu Val Leu Ser Asn
                165                 170                 175

Val His Phe Thr Gly Glu Lys Glu Leu Glu Phe Arg Ser Gly Gly Asp
           180                 185                 190
```

```
Val Asp His Ser Thr Leu Val Thr Leu Phe Lys Leu Leu Gly Tyr Asp
        195                 200                 205

Val His Val Leu Cys Asp Gln Thr Ala Gln Glu Met Gln Glu Lys Leu
        210                 215                 220

Gln Asn Phe Ala Gln Leu Pro Ala His Arg Val Thr Asp Ser Cys Ile
225                 230                 235                 240

Val Ala Leu Leu Ser His Gly Val Glu Gly Ala Ile Tyr Gly Val Asp
                245                 250                 255

Gly Lys Leu Leu Gln Leu Gln Glu Val Phe Gln Leu Phe Asp Asn Ala
                260                 265                 270

Asn Cys Pro Ser Leu Gln Asn Lys Pro Lys Met Phe Phe Ile Gln Ala
        275                 280                 285

Cys Arg Gly Gly Ala Ile Gly Ser Leu Gly His Leu Leu Leu Phe Thr
        290                 295                 300

Ala Ala Thr Ala Ser Leu Ala Leu
305                 310
```

(2) INFORMATION FOR SEQ ID NO:56:

(i) SEQUENCE CHARACTERISTICS:
        (A) LENGTH: 1402 base pairs
        (B) TYPE: nucleic acid
        (C) STRANDEDNESS: both
        (D) TOPOLOGY: both (ii) MOLECULE TYPE: DNA (ix) FEATURE:
        (A) NAME/KEY: CDS
        (B) LOCATION: 45..1301

(xi) SEQUENCE DESCRIPTION: SEQ ID NO:56:

```
CTTTTTTTTT TTTTTTTTTT TATGTCCTGG AGTCCTGCAC AGCC ATG GCG GCC AGG        56
                                              Met Ala Ala Arg
                                                1

AGG ACA CAT GAA AGA GAT CCA ATC TAC AAG ATC AAA GGT TTG GCC AAG       104
Arg Thr His Glu Arg Asp Pro Ile Tyr Lys Ile Lys Gly Leu Ala Lys
  5                  10                  15                  20

GAC ATG CTG GAT GGG GTT TTT GAT GAC CTG GTG GAG AAG AAT GTT TTA       152
Asp Met Leu Asp Gly Val Phe Asp Asp Leu Val Glu Lys Asn Val Leu
                 25                  30                  35

AAT GGA GAT GAG TTA CTC AAA ATA GGG GAA AGT GCG AGT TTC ATC CTG       200
Asn Gly Asp Glu Leu Leu Lys Ile Gly Glu Ser Ala Ser Phe Ile Leu
             40                  45                  50

AAC AAG GCT GAG AAT CTG GTT GAG AAC TTC TTA GAG AAA ACA GAC ATG       248
Asn Lys Ala Glu Asn Leu Val Glu Asn Phe Leu Glu Lys Thr Asp Met
         55                  60                  65

GCA GGA AAA ATA TTT GCT GGC CAC ATT GCC AAT TCC CAG GAA CAG CTG       296
Ala Gly Lys Ile Phe Ala Gly His Ile Ala Asn Ser Gln Glu Gln Leu
 70                  75                  80

AGT TTA CAA TTT TCT AAT GAT GAG GAT GAT GGA CCT CAG AAG ATA TGT       344
Ser Leu Gln Phe Ser Asn Asp Glu Asp Asp Gly Pro Gln Lys Ile Cys
 85                  90                  95                 100

ACA CCT TCT TCT CCA TCA GAA TCC AAG AGA AAA GTA GAG GAT GAT GAA       392
Thr Pro Ser Ser Pro Ser Glu Ser Lys Arg Lys Val Glu Asp Asp Glu
                105                 110                 115

ATG GAG GTA AAT GCT GGA TTG GCC CAT GAA TCA CAT CTA ATG CTG ACA       440
Met Glu Val Asn Ala Gly Leu Ala His Glu Ser His Leu Met Leu Thr
            120                 125                 130

GCT CCT CAT GGA CTC CAG AGC TCA GAA GTC CAA GAT ACA CTG AAG CTT       488
Ala Pro His Gly Leu Gln Ser Ser Glu Val Gln Asp Thr Leu Lys Leu
```

```
            135                 140                 145
TGT CCA CGT GAT CAG TTT TGT AAG ATA AAG ACA GAA AGG GCA AAA GAG      536
Cys Pro Arg Asp Gln Phe Cys Lys Ile Lys Thr Glu Arg Ala Lys Glu
150                 155                 160

ATA TAT CCA GTG ATG GAG AAG GAG GGA CGA ACA CGT CTG GCT CTC ATC      584
Ile Tyr Pro Val Met Glu Lys Glu Gly Arg Thr Arg Leu Ala Leu Ile
165                 170                 175                 180

ATC TGC AAC AAA AAG TTT GAC TAC CTT TTT GAT AGA GAT AAT GCT GAT      632
Ile Cys Asn Lys Lys Phe Asp Tyr Leu Phe Asp Arg Asp Asn Ala Asp
                185                 190                 195

ACT GAC ATT TTG AAC ATG CAA GAA CTA CTT GAA AAT CTT GGA TAC TCT      680
Thr Asp Ile Leu Asn Met Gln Glu Leu Leu Glu Asn Leu Gly Tyr Ser
                200                 205                 210

GTG GTG TTA AAA GAA AAC CTT ACA GCT CAG GAA ATG GAG ACA GAG TTA      728
Val Val Leu Lys Glu Asn Leu Thr Ala Gln Glu Met Glu Thr Glu Leu
                215                 220                 225

ATG CAG TTT GCT GGC CGT CCA GAG CAC CAG TCC TCA GAC AGC ACA TTC      776
Met Gln Phe Ala Gly Arg Pro Glu His Gln Ser Ser Asp Ser Thr Phe
230                 235                 240

CTG GTG TTT ATG TCC CAT GGC ATC CTG GAA GGA ATC TGT GGG GTG AAG      824
Leu Val Phe Met Ser His Gly Ile Leu Glu Gly Ile Cys Gly Val Lys
245                 250                 255                 260

CAC CGA AAC AAA AAG CCA GAT GTT CTT CAT GAT GAC ACT ATC TTC AAA      872
His Arg Asn Lys Lys Pro Asp Val Leu His Asp Asp Thr Ile Phe Lys
                265                 270                 275

ATT TTC AAC AAC TCT AAC TGT CGG AGT CTG AGA AAC AAA CCC AAG ATT      920
Ile Phe Asn Asn Ser Asn Cys Arg Ser Leu Arg Asn Lys Pro Lys Ile
                280                 285                 290

CTC ATC ATG CAG GCC TGC AGA GGC AGA TAT AAT GGA ACT ATT TGG GTA      968
Leu Ile Met Gln Ala Cys Arg Gly Arg Tyr Asn Gly Thr Ile Trp Val
                295                 300                 305

TCC ACA AAC AAA GGG ATA GCC ACT GCT GAT ACA GAT GAG GAA CGT GTG     1016
Ser Thr Asn Lys Gly Ile Ala Thr Ala Asp Thr Asp Glu Glu Arg Val
                310                 315                 320

TTG AGC TGT AAA TGG AAT AAT AGT ATA ACA AAG GCC CAT GTG GAG ACA     1064
Leu Ser Cys Lys Trp Asn Asn Ser Ile Thr Lys Ala His Val Glu Thr
325                 330                 335                 340

GAT TTC ATT GCT TTC AAA TCT TCT ACC CCA CAT AAT ATT TCT TGG AAG     1112
Asp Phe Ile Ala Phe Lys Ser Ser Thr Pro His Asn Ile Ser Trp Lys
                345                 350                 355

GTA GGC AAG ACT GGT TCC CTC TTC ATT TCC AAA CTC ATT GAC TGC TTC     1160
Val Gly Lys Thr Gly Ser Leu Phe Ile Ser Lys Leu Ile Asp Cys Phe
                360                 365                 370

AAA AAG TAC TGT TGG TGT TAT CAT TTG GAG GAA ATT TTT CGA AAG GTT     1208
Lys Lys Tyr Cys Trp Cys Tyr His Leu Glu Glu Ile Phe Arg Lys Val
                375                 380                 385

CAA CAC TCA TTT GAG GTC CCA GGT GAA CTG ACC CAG ATG CCC ACT ATT     1256
Gln His Ser Phe Glu Val Pro Gly Glu Leu Thr Gln Met Pro Thr Ile
                390                 395                 400

GAG AGA GTA TCC ATG ACA CGC TAT TTC TAC CTT TTT CCC GGG AAT         1301
Glu Arg Val Ser Met Thr Arg Tyr Phe Tyr Leu Phe Pro Gly Asn
405                 410                 415

TAGCACAGGC AACTCTCATG CAGTTCACAG TCAAGTATTG CTGTAGCTGA GAAGAAAAGA   1361

AAATTCCAAG ATCCCAGGAT TTTTAAATGT GTAAAACTTT T                      1402
```

(2) INFORMATION FOR SEQ ID NO:57:

(i) SEQUENCE CHARACTERISTICS:
        (A) LENGTH: 419 amino acids (B) TYPE: amino acid
        (D) TOPOLOGY: linear (ii) MOLECULE TYPE: protein (xi) SEQUENCE DESCRIPTION: SEQ ID NO:57:

Met Ala Ala Arg Arg Thr His Glu Arg Asp Pro Ile Tyr Lys Ile Lys
 1               5                  10                  15

Gly Leu Ala Lys Asp Met Leu Asp Gly Val Phe Asp Leu Val Glu
            20                  25                  30

Lys Asn Val Leu Asn Gly Asp Glu Leu Leu Lys Ile Gly Glu Ser Ala
             35                  40                  45

Ser Phe Ile Leu Asn Lys Ala Glu Asn Leu Val Glu Asn Phe Leu Glu
 50                  55                  60

Lys Thr Asp Met Ala Gly Lys Ile Phe Ala Gly His Ile Ala Asn Ser
 65                  70                  75                  80

Gln Glu Gln Leu Ser Leu Gln Phe Ser Asn Asp Glu Asp Gly Pro
                 85                  90                  95

Gln Lys Ile Cys Thr Pro Ser Ser Pro Ser Glu Ser Lys Arg Lys Val
            100                 105                 110

Glu Asp Asp Glu Met Glu Val Asn Ala Gly Leu Ala His Glu Ser His
            115                 120                 125

Leu Met Leu Thr Ala Pro His Gly Leu Gln Ser Ser Glu Val Gln Asp
130                 135                 140

Thr Leu Lys Leu Cys Pro Arg Asp Gln Phe Cys Lys Ile Lys Thr Glu
145                 150                 155                 160

Arg Ala Lys Glu Ile Tyr Pro Val Met Glu Lys Glu Gly Arg Thr Arg
                165                 170                 175

Leu Ala Leu Ile Ile Cys Asn Lys Lys Phe Asp Tyr Leu Phe Asp Arg
                180                 185                 190

Asp Asn Ala Asp Thr Asp Ile Leu Asn Met Gln Glu Leu Leu Glu Asn
            195                 200                 205

Leu Gly Tyr Ser Val Val Leu Lys Glu Asn Leu Thr Ala Gln Glu Met
            210                 215                 220

Glu Thr Glu Leu Met Gln Phe Ala Gly Arg Pro Glu His Gln Ser Ser
225                 230                 235                 240

Asp Ser Thr Phe Leu Val Phe Met Ser His Gly Ile Leu Glu Gly Ile
                245                 250                 255

Cys Gly Val Lys His Arg Asn Lys Lys Pro Asp Val Leu His Asp Asp
                260                 265                 270

Thr Ile Phe Lys Ile Phe Asn Asn Ser Asn Cys Arg Ser Leu Arg Asn
            275                 280                 285

Lys Pro Lys Ile Leu Ile Met Gln Ala Cys Arg Gly Arg Tyr Asn Gly
290                 295                 300

Thr Ile Trp Val Ser Thr Asn Lys Gly Ile Ala Thr Ala Asp Thr Asp
305                 310                 315                 320

Glu Glu Arg Val Leu Ser Cys Lys Trp Asn Asn Ser Ile Thr Lys Ala
                325                 330                 335

His Val Glu Thr Asp Phe Ile Ala Phe Lys Ser Ser Thr Pro His Asn
            340                 345                 350

Ile Ser Trp Lys Val Gly Lys Thr Gly Ser Leu Phe Ile Ser Lys Leu
            355                 360                 365

Ile Asp Cys Phe Lys Lys Tyr Cys Trp Cys Tyr His Leu Glu Glu Ile
370                 375                 380

-continued

```
Phe Arg Lys Val Gln His Ser Phe Glu Val Pro Gly Glu Leu Thr Gln
385                 390                 395                 400

Met Pro Thr Ile Glu Arg Val Ser Met Thr Arg Tyr Phe Tyr Leu Phe
                405                 410                 415

Pro Gly Asn
```

(2) INFORMATION FOR SEQ ID NO:58:

(i) SEQUENCE CHARACTERISTICS:
        (A) LENGTH: 418 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:58:

```
Met Ala Ala Arg Arg Thr His Glu Arg Asp Pro Ile Tyr Lys Ile Lys
1               5                   10                  15

Gly Leu Ala Lys Asp Met Leu Asp Gly Val Phe Asp Asp Leu Val Glu
                20                  25                  30

Lys Asn Val Leu Asn Gly Asp Glu Leu Leu Lys Ile Gly Glu Ser Ala
                35                  40                  45

Ser Phe Ile Leu Asn Lys Ala Glu Asn Leu Val Glu Asn Phe Leu Glu
50                  55                  60

Lys Thr Asp Met Ala Gly Lys Ile Phe Ala Gly His Ile Ala Asn Ser
65                  70                  75                  80

Gln Glu Gln Leu Ser Leu Gln Phe Ser Asn Asp Glu Asp Asp Gly Pro
                85                  90                  95

Gln Lys Ile Cys Thr Pro Ser Ser Pro Ser Glu Ser Lys Arg Lys Val
                100                 105                 110

Glu Asp Asp Glu Met Glu Val Asn Ala Gly Leu Ala His Glu Ser His
                115                 120                 125

Leu Met Leu Thr Ala Pro His Gly Leu Gln Ser Ser Glu Val Gln Asp
130                 135                 140

Thr Leu Lys Leu Cys Pro Arg Asp Gln Phe Cys Lys Ile Lys Thr Glu
145                 150                 155                 160

Arg Ala Lys Glu Ile Tyr Pro Val Met Glu Lys Glu Gly Arg Thr Arg
                165                 170                 175

Leu Ala Leu Ile Ile Cys Asn Lys Lys Phe Asp Tyr Leu Phe Asp Arg
                180                 185                 190

Asp Asn Ala Asp Thr Asp Ile Leu Asn Met Gln Glu Leu Leu Glu Asn
                195                 200                 205

Leu Gly Tyr Ser Val Val Leu Lys Glu Asn Leu Thr Ala Gln Glu Met
210                 215                 220

Glu Thr Glu Leu Met Gln Phe Ala Gly Arg Pro Glu His Gln Ser Ser
225                 230                 235                 240

Asp Ser Thr Pro Gly Val Tyr Val Pro Trp His Pro Gly Arg Asn Leu
                245                 250                 255

Trp Gly Glu Ala Pro Lys Gln Lys Pro Asp Val Leu His Asp Asp Thr
                260                 265                 270

Ile Phe Lys Ile Phe Asn Asn Ser Asn Cys Arg Ser Leu Arg Asn Lys
                275                 280                 285

Pro Lys Ile Leu Ile Met Gln Ala Cys Arg Gly Arg Tyr Asn Gly Thr
                290                 295                 300

Ile Trp Val Ser Thr Asn Lys Gly Ile Ala Thr Ala Asp Thr Asp Glu
```

-continued

```
305                 310                 315                 320

Glu Arg Val Leu Ser Cys Lys Trp Asn Asn Ser Ile Thr Lys Ala His
                325                 330                 335

Val Glu Thr Asp Phe Ile Ala Phe Lys Ser Ser Thr Pro His Asn Ile
            340                 345                 350

Ser Trp Lys Val Gly Lys Thr Gly Ser Leu Phe Ile Ser Lys Leu Ile
        355                 360                 365

Asp Cys Phe Lys Lys Tyr Cys Trp Cys Tyr His Leu Glu Glu Ile Phe
    370                 375                 380

Arg Lys Val Gln His Ser Phe Glu Val Pro Gly Glu Leu Thr Gln Met
385                 390                 395                 400

Pro Thr Ile Glu Arg Val Ser Met Thr Arg Tyr Phe Tyr Leu Phe Pro
                405                 410                 415

Gly Asn
```

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:59:

ATGCTAACTG TCCAAGTCTA                                         20

(2) INFORMATION FOR SEQ ID NO:60:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:60:

TCCAACAGCA GGAATAGCA                                          19

(2) INFORMATION FOR SEQ ID NO:61:

(i) SEQUENCE CHARACTERISTICS:
        (A) LENGTH: 29 base pairs
        (B) TYPE: nucleic acid
        (C) STRANDEDNESS: both
        (D) TOPOLOGY: both (xi) SEQUENCE DESCRIPTION: SEQ ID NO:61:

TGATCGCCAT CGGGGAAATC GAGGTAGAA                             29

(2) INFORMATION FOR SEQ ID NO:62:

(i) SEQUENCE CHARACTERISTICS:
        (A) LENGTH: 29 base pairs
        (B) TYPE: nucleic acid
        (C) STRANDEDNESS: both
        (D) TOPOLOGY: both (xi) SEQUENCE DESCRIPTION: SEQ ID NO:62:

ATCATATCAT CCAGGCATCG TGCAGAGGG                             29

(2) INFORMATION FOR SEQ ID NO:63:

(i) SEQUENCE CHARACTERISTICS:
        (A) LENGTH: 30 base pairs

```
        (B) TYPE: nucleic acid
        (C) STRANDEDNESS: single
        (D) TOPOLOGY: linear (xi) SEQUENCE DESCRIPTION: SEQ ID NO:63:

GTTGCACTGC TTTCACGATC TCCCGTCTCT                                              30

(2) INFORMATION FOR SEQ ID NO:64:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:64:

TCATCGACTT TTAGATGACT AGAGAACATC                                              30

(2) INFORMATION FOR SEQ ID NO:65:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:65:

GTTTAATTAC CCAAGTTTGA G                                                       21

(2) INFORMATION FOR SEQ ID NO:66:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:66:

CCGGTGACAT TGGACACTC                                                          19

(2) INFORMATION FOR SEQ ID NO:67:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:67:

ACTATTCAAC ACTTG                                                              15

(2) INFORMATION FOR SEQ ID NO:68:

(i) SEQUENCE CHARACTERISTICS:
        (A) LENGTH: 5 amino acids
        (B) TYPE: amino acid
        (D) TOPOLOGY: both (xi) SEQUENCE DESCRIPTION: SEQ ID NO:68:

Gln Ala Cys Arg Gly
1               5

(2) INFORMATION FOR SEQ ID NO:69:

(i) SEQUENCE CHARACTERISTICS:
        (A) LENGTH: 20 base pairs
        (B) TYPE: nucleic acid
```

```
        (C) STRANDEDNESS: both
        (D) TOPOLOGY: both (xi) SEQUENCE DESCRIPTION: SEQ ID NO:69:

CAACCCTGTA ACTCTTGATT                                           20

(2) INFORMATION FOR SEQ ID NO:70:

(i) SEQUENCE CHARACTERISTICS:
        (A) LENGTH: 21 base pairs
        (B) TYPE: nucleic acid
        (C) STRANDEDNESS: both
        (D) TOPOLOGY: both (xi) SEQUENCE DESCRIPTION: SEQ ID NO:70:

ACCTCTTTGG AGCTACCAGA A                                         21

(2) INFORMATION FOR SEQ ID NO:71:

(i) SEQUENCE CHARACTERISTICS:
        (A) LENGTH: 28 base pairs
        (B) TYPE: nucleic acid
        (C) STRANDEDNESS: both
        (D) TOPOLOGY: both (xi) SEQUENCE DESCRIPTION: SEQ ID NO:71:

CCAGATCTAT GCTAACTGTC CAAGTCTA                                  28

(2) INFORMATION FOR SEQ ID NO:72:

(i) SEQUENCE CHARACTERISTICS:
        (A) LENGTH: 28 base pairs
        (B) TYPE: nucleic acid
        (C) STRANDEDNESS: both
        (D) TOPOLOGY: both (xi) SEQUENCE DESCRIPTION: SEQ ID NO:72:

AAGAGCTCCT CCAACAGCAG GAATAGCA                                  28

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:73:

AGAAGCACTT GTCTCTGCTC                                           20

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:74:

TTGGCACCTG ATGGCAATAC                                           20

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: both
```

(D) TOPOLOGY: both (xi) SEQUENCE DESCRIPTION: SEQ ID NO:75:

GATATCCGCA CAAGGAGCTG A                                              21

(2) INFORMATION FOR SEQ ID NO:76:

(i) SEQUENCE CHARACTERISTICS:
            (A) LENGTH: 20 base pairs
            (B) TYPE: nucleic acid
            (C) STRANDEDNESS: both
            (D) TOPOLOGY: both (xi) SEQUENCE DESCRIPTION: SEQ ID NO:76:

CTATAGGTGG GAGGGTGTCC                                                20

(2) INFORMATION FOR SEQ ID NO:77:

(i) SEQUENCE CHARACTERISTICS:
            (A) LENGTH: 23 base pairs
            (B) TYPE: nucleic acid
            (C) STRANDEDNESS: both
            (D) TOPOLOGY: both (xi) SEQUENCE DESCRIPTION: SEQ ID NO:77:

GATATCCAGA GGGAGGGAAC GAT                                            23

(2) INFORMATION FOR SEQ ID NO:78:

(i) SEQUENCE CHARACTERISTICS:
            (A) LENGTH: 23 base pairs
            (B) TYPE: nucleic acid
            (C) STRANDEDNESS: both
            (D) TOPOLOGY: both (xi) SEQUENCE DESCRIPTION: SEQ ID NO:78:

GATATCAGAG CAAGAGAGGC GGT                                            23

(2) INFORMATION FOR SEQ ID NO:79:

(i) SEQUENCE CHARACTERISTICS:
            (A) LENGTH: 21 base pairs
            (B) TYPE: nucleic acid
            (C) STRANDEDNESS: both
            (D) TOPOLOGY: both (xi) SEQUENCE DESCRIPTION: SEQ ID NO:79:

GATATCGTGG GAGGGTGTCC T                                              21

(2) INFORMATION FOR SEQ ID NO:80:

(i) SEQUENCE CHARACTERISTICS:
            (A) LENGTH: 21 base pairs
            (B) TYPE: nucleic acid
            (C) STRANDEDNESS: both
            (D) TOPOLOGY: both (xi) SEQUENCE DESCRIPTION: SEQ ID NO:80:

ATCCAGGCCT CTAGAGGAGA T                                              21

(2) INFORMATION FOR SEQ ID NO:81:

(i) SEQUENCE CHARACTERISTICS:
            (A) LENGTH: 21 base pairs
            (B) TYPE: nucleic acid
            (C) STRANDEDNESS: both
            (D) TOPOLOGY: both (xi) SEQUENCE DESCRIPTION: SEQ ID NO:81:

ATCTCCTCTA GAGGCCTGGA T                                     21

(2) INFORMATION FOR SEQ ID NO:82:

(i) SEQUENCE CHARACTERISTICS:
        (A) LENGTH: 21 base pairs
        (B) TYPE: nucleic acid
        (C) STRANDEDNESS: both
        (D) TOPOLOGY: both (xi) SEQUENCE DESCRIPTION: SEQ ID NO:82:

TGCGGCTATA CGTGCCTCAA A                                     21

(2) INFORMATION FOR SEQ ID NO:83:

(i) SEQUENCE CHARACTERISTICS:
        (A) LENGTH: 21 base pairs
        (B) TYPE: nucleic acid
        (C) STRANDEDNESS: both
        (D) TOPOLOGY: both (xi) SEQUENCE DESCRIPTION: SEQ ID NO:83:

TTTGAGGCAC GTATAGCCGC A                                     21

(2) INFORMATION FOR SEQ ID NO:84:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:84:

CACAGTACTT TCGTCACCCT                                       20

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:85:

AGGGTGACGA AAGTACTGTG                                       20

PROGRAMMED CELL DEATH GENES AND PROTEINS

CROSS-REFERENCE TO RELATED APPLICATIONS

This application is a continuation-in-part application of U.S. Application No. 08/080,850, filed Jun. 24, 1993 now abandoned.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The invention is in the field of molecular biology as related to the control of programmed cell death.

2. Description of the Background Art

Cell death occurs as a normal aspect of animal development as well as in tissue homeostasis and aging (Glucksmann, A., *Biol. Rev. Cambridge Philos. Soc.* 26:59–86 (1950); Ellis et al., *Dev.* 112:591–603 (1991)). Naturally occurring cell death acts to regulate cell number, to facilitate morphogenesis, to remove harmful or otherwise abnormal cells and to eliminate cells that have already performed their function. Such regulated cell death is achieved through a cell-endogenous mechanism of suicide, termed programmed cell death or apoptosis (Wyllie, A. H., in *Cell Death in Biology and Pathology*, Bowen and Lockshin, eds., Chapman and Hall (1981), pp. 9–34). Programmed cell death or apoptosis occurs when a cell activates this internally encoded suicide program as a result of either internal or external signals. The morphological characteristics of apoptosis include plasma membrane blebbing, condensation of nucleoplasm and cytoplasm and degradation of chromosomal DNA at inter-nucleosomal intervals. (Wyllie, A. H., in *Cell Death in Biology and Pathology*, Bowen and Lockshin, eds., Chapman and Hall (1981), pp. 9–34). In many cases, gene expression appears to be required for programmed cell death, since death can be prevented by inhibitors of RNA or protein synthesis (Cohen et al., *J. Immunol.* 32:38–42 (1984); Stanisic et al., *Invest. Urol.* 16:19–22 (1978); Martin et al., *J. Cell Biol.* 106:829–844 (1988)).

The genetic control of programmed cell death has been well-elucidated by the work on programmed cell death in the nematode *C. elegans*. Programmed cell death is characteristic and widespread during *C. elegans* development. Of the 1090 somatic cells formed during the development of the hermaphrodite, 131 undergo programmed cell death. When observed with Nomarski microscopy, the morphological changes of these dying cells follow a characteristic sequence. (Sulston et al., *Dev. Biol.* 82:110–156 (1977); Sulston et al., *Dev. Biol.* 100:64–119 (1983)). Fourteen genes have been identified that function in different steps of the genetic pathway of programmed cell death in this nematode (Hedgecock et al., *Science* 220:1277–1280 (1983); Ellis et al., *Cell* 44:817–829 (1986); Ellis et al., *Dev.* 112:591–603 (1991); Ellis et al., *Genetics* 112:591–603 (1991b); Hengartner et al., *Nature* 356:494–499 (1992); Ellis et al., *Dev.* 112:591–603 (1991)). Two of these genes, ced-3 and ced-4, play essential roles in either the initiation or execution of the cell death program. Recessive mutations in these genes prevent almost all of the cell deaths that normally occur during *C. elegans* development. Additional support for the view that ced-3 and ced-4 cause cell death comes from the genetic analysis of mosaics (Yuan et al., *Dev. Biol.* 138:3341 (1990)). The ced-4 gene encodes a novel protein that is expressed primarily during embryogenesis, the period during which most programmed cell deaths occur (Yuan et al., *Dev.* 116:309–320 (1992)).

A gain-of-function mutation in ced-9 prevents the normal programmed cell death, while mutations that inactivate ced-9 are lethal, suggesting that ced-9 may act by suppressing programmed cell death genes in cells that normally do not undergo programmed cell death (Hengartner, M., et al., *Nature* 356:494–499 (1992)). The ced-9 gene encodes a protein product that shares sequence similarity with the mammalian proto-oncogene and cell death suppressor bcl-2 (Hengartner, M., et al., *Cell* 76:665–676 (1994)). The lethality of ced-9 loss- of-function mutations can be suppressed by mutations in ced-3 and ced-4, indicating that ced-9 acts by suppressing the activity of ced-3 and ced-4. Genetic mosaic analyses indicate that ced-3 and ced-4 likely act in a cell-autonomous fashion within dying cells, suggesting that they might be cytotoxic proteins and/or control certain cytotoxic proteins in the process of programmed cell death (Yuan, J., et al., *Dev. Bio.* 138:33–41 (1990)). The 549 amino acid sequence of the ced-4 protein, deduced from cDNA and genomic clones, contain two regions that are similar to the calcium-binding domain known as the EF-hand (Kretsinger, 1987); however, it is still not clear at present whether calcium plays a role in regulating ced-4 or programmed cell death in *C. elegans*.

SUMMARY OF THE INVENTION

In the present invention, the ced-3 gene has been cloned and sequenced (SEQ ID NO: 1) and the amino acid sequence (SEQ ID NO: 2) of the protein encoded by this gene is disclosed. Structural analysis of the ced-3 gene revealed that it is similar to the enzyme interleukin-1β converting enzyme ("ICE") and that overexpression of the murine interleukin-1β converting enzyme ("mICE") causes programmed cell death in vertebrate cells. Based upon these results, a novel method for controlling programmed cell death in vertebrates by regulating the activity of ICE is claimed.

The amino acid sequence of the ced-3 protein (SEQ ID NO: 2) was also found to be similar to another murine protein, nedd-2 (SEQ ID NO: 40), which is detected during early embryonic brain development, a period when many cells die. The results suggest that ced-3, mICE and nedd-2 are members of a gene family which function to cause programmed cell death.

A new cell death gene, mICE2, has been discovered which appears to be in the same family as ced-3, mICE, and nedd-2. mICE2 is distinguished from other previously identified cell death genes in that it is preferentially expressed in the thymus and placental cells of vertebrates. Thus, the invention is also directed to a newly discovered gene, m!CE2, which is preferentially expressed in thymus and placental cells and which encodes a protein causing programmed cell death.

A comparison of the nucleotide sequences of ced-3 (SEQ ID NO: 34), mICE, human ICE, nedd-2 (SEQ ID NO: 51) and mICE2 (SEQ ID NO: 41) indicates that they are part of a gene family whose members all promote programmed cell death. The identification of this family facilitated the isolation of the newly discovered cell death gene Ice-ced 3 homolog (Ich-1). Ich-1 is homologous with the other cell death genes described above and particularly with nedd2. Based upon its structure and the presence of a QACRG sequence characteristic of the active center of cell death genes, Ich-1 was identified as a new member of the ced-3/ICE family. Thus, the present invention is directed to both the Ich-1 gene sequence (SEQ ID NO: 43) and the Ich-1 protein (SEQ ID NO: 44). Also encompassed are vectors expressing Ich-1 and host cells transformed with such vectors. Alternative splicing results in two distinct Ich-1 mRNA species. Thus, the invention also encompasses these species, proteins produced from them, vectors containing and expressing the genes, and the uses described herein.

The inventors have also identified a new member of the ICE/ced-3 family, Ice-4. Ice-4 has at least two alternative splicing products. A full length cDNA (SEQ ID NO: 56) of one of them from a mouse thymus cDNA library has been identified. It encodes a protein of 418 amino acids that is 38% identical with murine ICE, 42% identical with murine Ice-2, 25% with murine Ich-1, and 24% identical with C. elegans ced-3.

The invention is thus directed to genomic or cDNA nucleic acids having genetic sequences which encode ced-3 (SEQ ID NOs: 1, 34), mICE2 (SEQ ID NO: 41), Ich-1 (SEQ ID NO: 43), and Ice-4 (SEQ ID NO: 56). The invention also provides for vectors and expression vectors containing such genetic sequences, the host cells transformed with such vectors and expression vectors, the recombinant nucleic acid or proteins made in such host/vectors systems and the functional derivatives of these recombinant proteins. The use of the isolated genes or proteins for the purpose promoting cell death is also part of the invention.

The invention is also directed to methods for controlling the programmed death of vertebrate cells by regulating the activity of interleukin-1β converting enzyme, "ICE." Such regulation may take the form of inhibiting the enzyme's activity, e.g. through the use of specific antiproteases such as crmA, in order to prevent cell death. In this way, it may be possible to develop cell lines which remain viable in culture for an extended period of time or indefinitely. Certain cells can only be maintained in culture if they are grown in the presence of growth factors. By blocking cell death, it may be possible to make such cells growth factor independent. Alternatively, ICE activity may be increased in order to promote cell death. Such increased activity may be used in cancer cells to antagonize the effect of oncogenes such as bcl-2.

"Caspase" is the official designation for all members of the ICE family. Therefore, the most recent designation for Ich-2 is "Caspase-1" and for Ich-1 is "caspase-2"

Genetic and Physical Maps of the ced-3 Region on Chromosome IV

Figure 1:
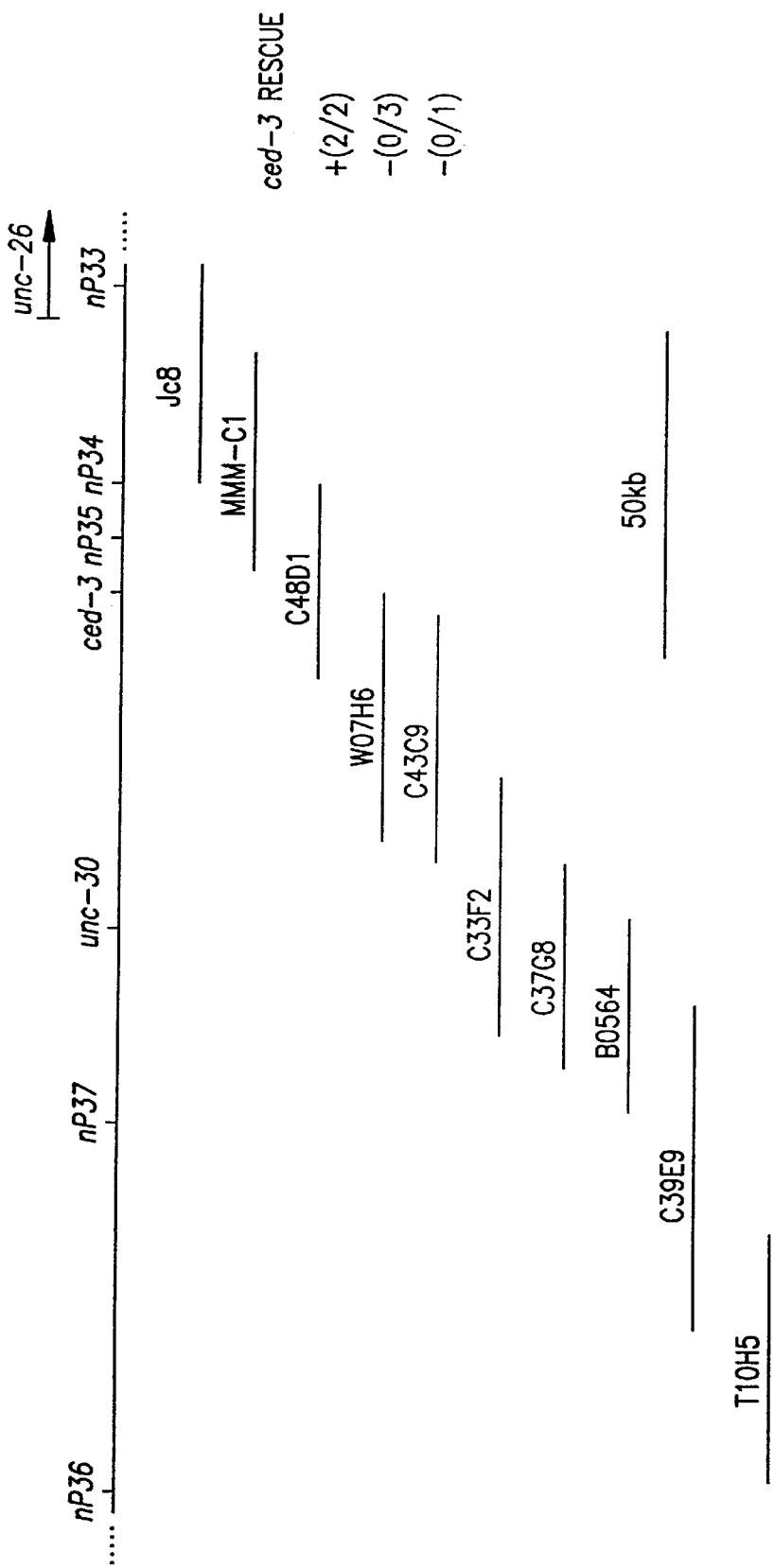
FIGS. 1 and 1A

FIG. 1 shows the genetic map of C. elegans in the region near ced-3 with the cosmid clones representing this region depicted below the map. nP33, nP34, nP35, nP36, and nP37 are restriction fragment length polymorphisms (RFLP) between Bristol and Bergerac wild type C. elegans strains. C43C9, W07H6 and C48D1 are three cosmid clones tested for rescue of the ced phenotype of ced-3(n717) animals. The ability of each cosmid clone to rescue ced-3 mutants and the fraction of independently obtained transgenic lines that were rescued are indicated on the right of the figure (+, rescue; −, no rescue; see text for data). The results indicate that ced-3 is contained in the cosmid C48D1.

Figure 1A:
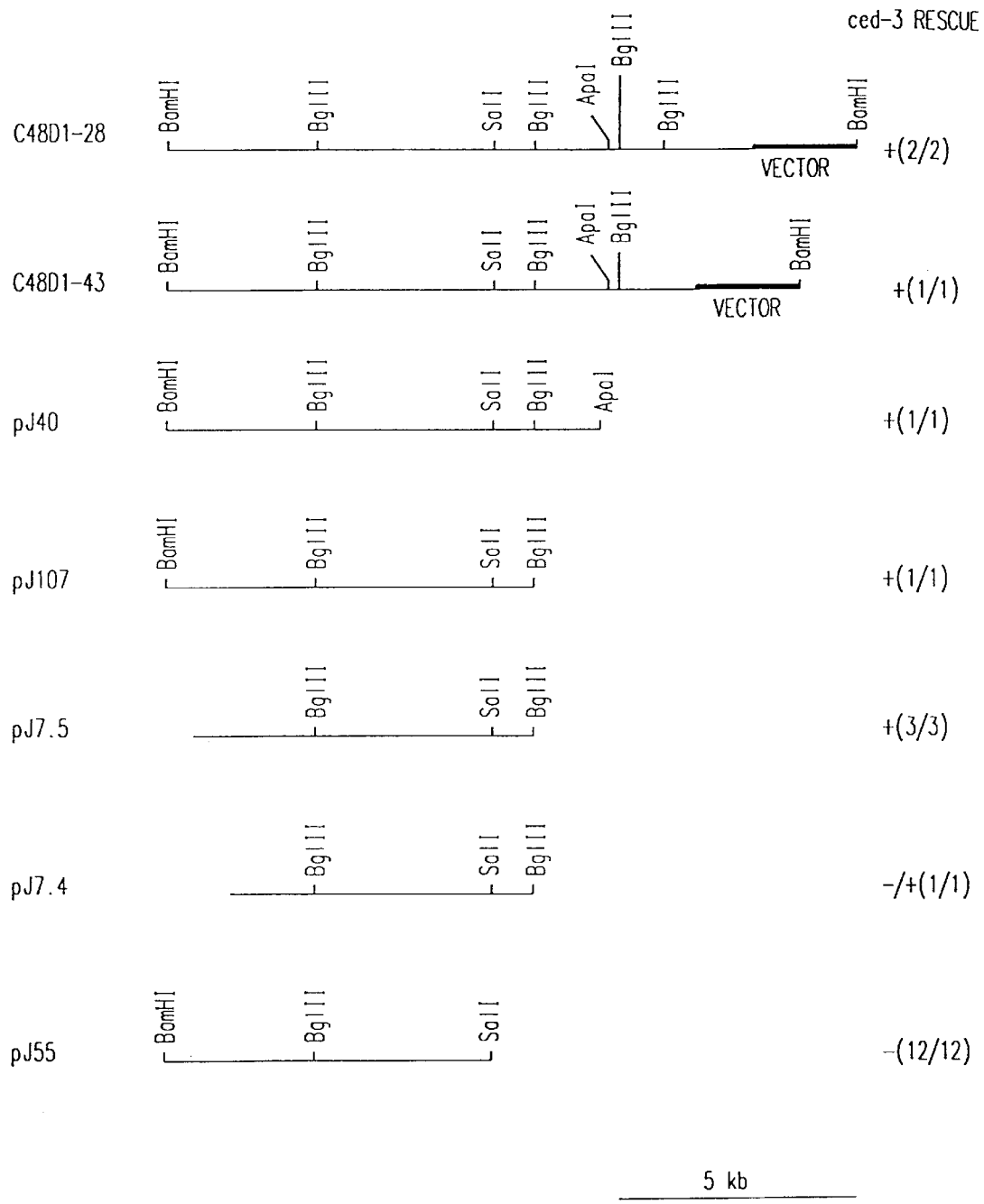

FIG. 1A is a restriction map of C48D1 subclones. C48D1 was digested with BamHI and self-ligated to generate subclone C48D1-28. C48D1-43, pJ40 and pJ107 were generated by partial digesting C48D1-28with BglII. pJ7.5 and pJ7.4 were generated by ExoIII deletion of pJ107. These subclones were assayed for rescue of the ced phenotype of ced-3(n717) animals (+, rescue; −, no rescue; −/+, weak rescue). The numbers in parentheses indicate the fraction of independently obtained transgenic lines that were rescued. The smallest fragment that fully rescued the ced-3 mutant phenotype was the 7.5 kb pJ7.5 subclone.

Figure 2L:
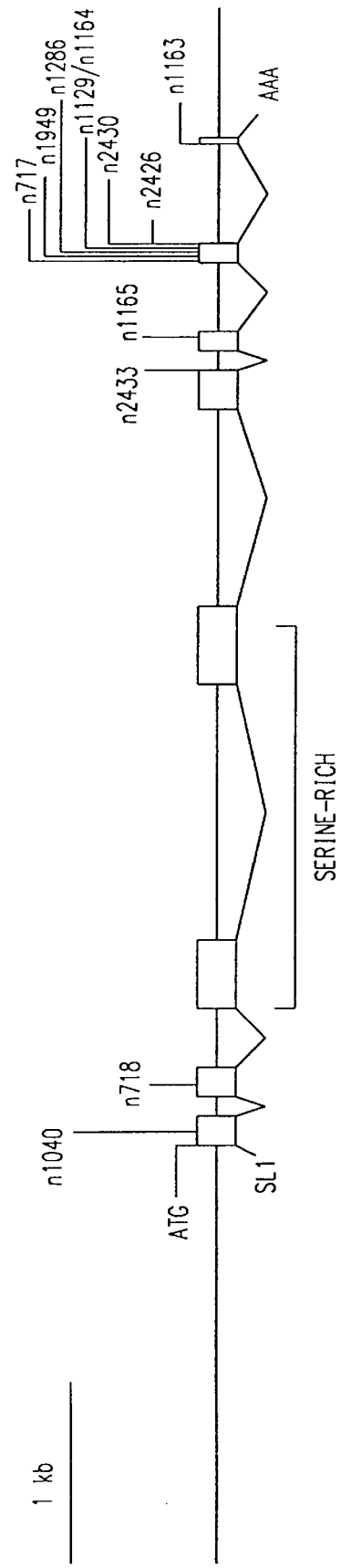

FIG. 2, 2A(i)–FIG. 2A(v), 2B and 2C

Genomic Organization, Nucleotide Sequence, and Deduced Amino Acid Sequence of ced-3

FIG. 2 shows the genomic sequence of the ced-3 region (SEQ ID NO: 1), as obtained from plasmid pJ107. The deduced amino acid sequence of the ced-3 protein (SEQ ID NO: 2) is based on the DNA sequence of ced-3 cDNA pJ87 and upon other experiments described in the text and in Experimental Procedures. The 5' end of pJ87 contains 25 bp of poly-A/T sequence (not shown), which is probably a cloning artifact since it is not present in the genomic sequence. The likely start site of translation is marked with an arrowhead. The SL1 splice acceptor site of the ced-3 transcript is boxed. The positions of 12 ced-3 mutations are indicated. Repetitive elements are indicated as arrows above the relevant sequences. Numbers on the left indicate nucleotide positions, beginning with the start of pJ107. Numbers below the amino acid sequence indicate codon positions. Five types of imperfect repeats were found: repeat 1, also found in fem-1 (Spence et al., Cell 60:981–990 (1990)) and hlh-1 (Krause et al., Cell 63:907–919 (1990)); repeat 2, novel; repeat 3, also found in lin-12 and fem-1; repeat 4, also found in lin-12; and repeat 5, novel. Numbers on the sides of the figure indicate nucleotide positions, beginning with the start of pJ107. Numbers under the amino acid sequence indicate codon positions.

FIG. 2A(i)–FIG. 2A(iv) FIG. 2A(v) contains a comparison of ced-3 with previously characterized repetitive elements contain comparisons of the repetitive elements in ced-3 with the repetitive elements in the genes ced-3, fem-1, hlh-1, lin-12, glp-1, and the cosmids B0303 and ZK643 (see text for references). In the case of inverted repeats, each arm of a repeat ("for" or "rev" for "forward" or "reverse", respectively) was compared to both its partner and to individual arms of the other repeats. 2A(i): Repeat 1 (SEQ ID NOs: 3–11); 2A(ii): Repeat 2 (SEQ ID NOs: 12–14); 2A(iii): Repeat 3 (SEQ ID NOs: 15–27); 2A(iv): Repeat 4 (SEQ ID NOs: 28–30); and 2A(v): Repeat 5 (SEQ ID NOs: 31–33). The different ced-3 sequences which appear in the comparisons are different repeats of the same repetitive element. The numbers "1a", "1b" etc. are different repeats of the same class of repetitive element.

FIG. 2B shows the locations of the introns (lines) and exons (open boxes) of the ced-3 gene as well as the positions of 12 ced-3 mutations analyzed. The serine-rich region, the trans-spliced leader (SL1), the possible start of translation (ATG) and polyadenlyation (AAA) site are also indicated.

FIG. 2C shows the cDNA sequence (SEQ ID NO: 34) and deduced amino acid sequence (SEQ ID NO: 35) of ced-3 as obtained from plasmid pJ87.

Figure 3:
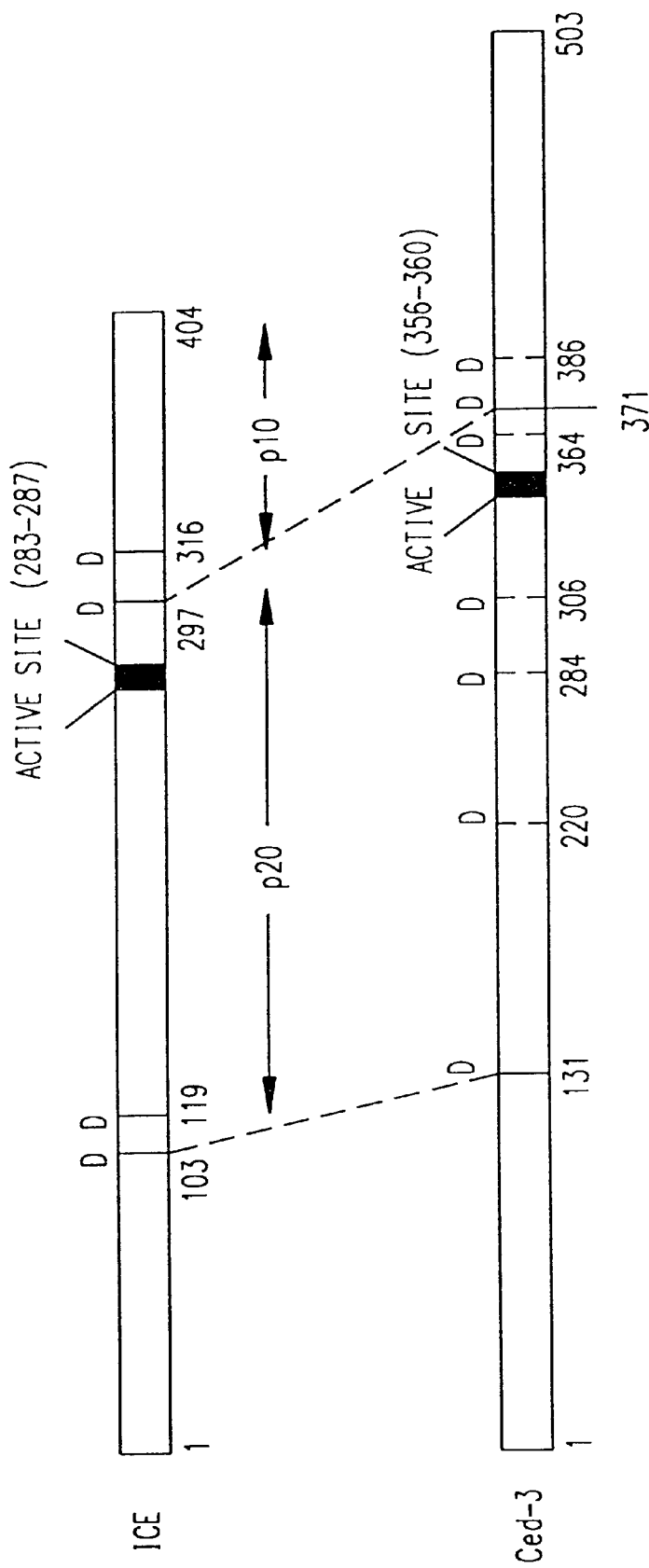
Figure 3A:
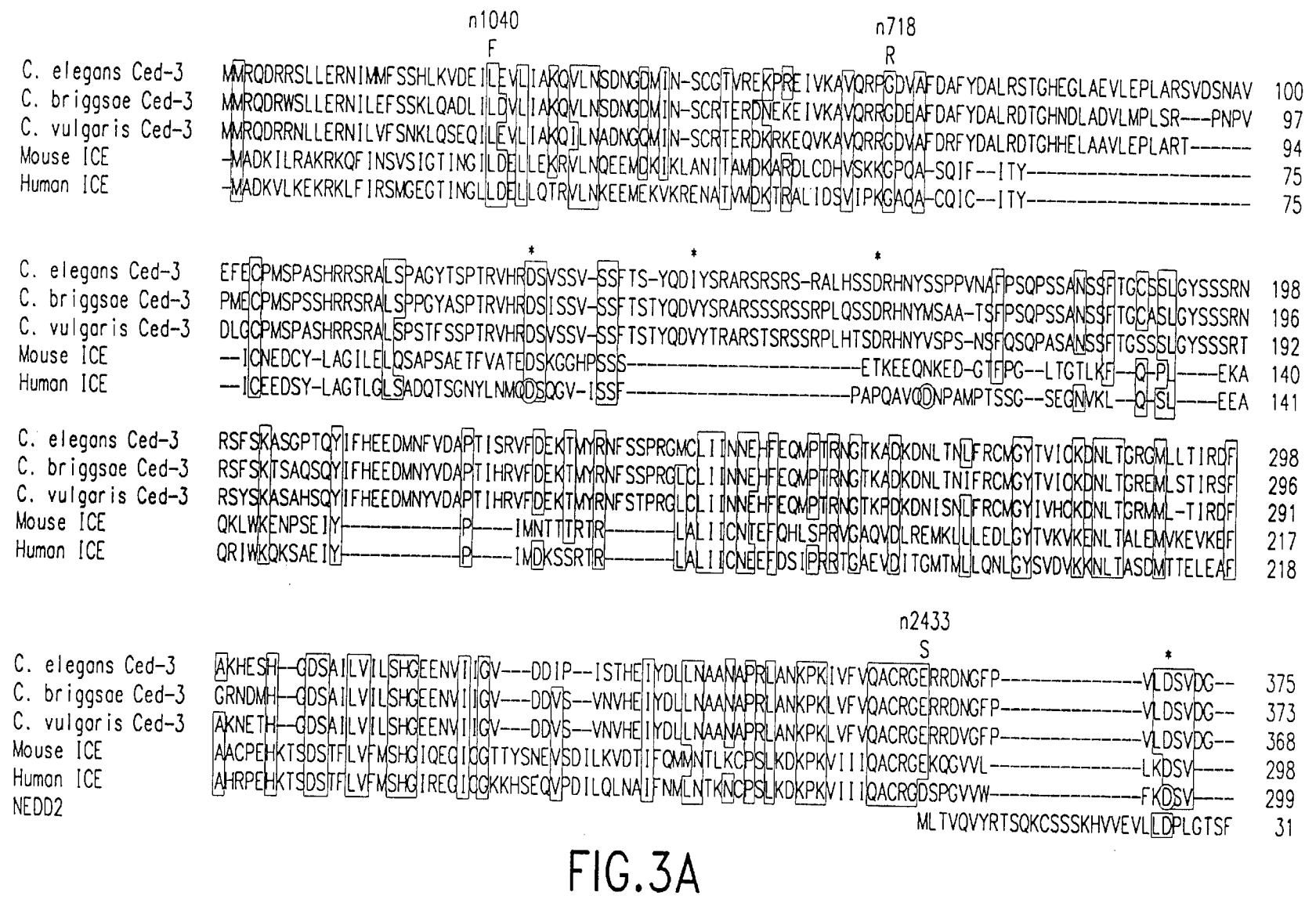
Figure 3B:
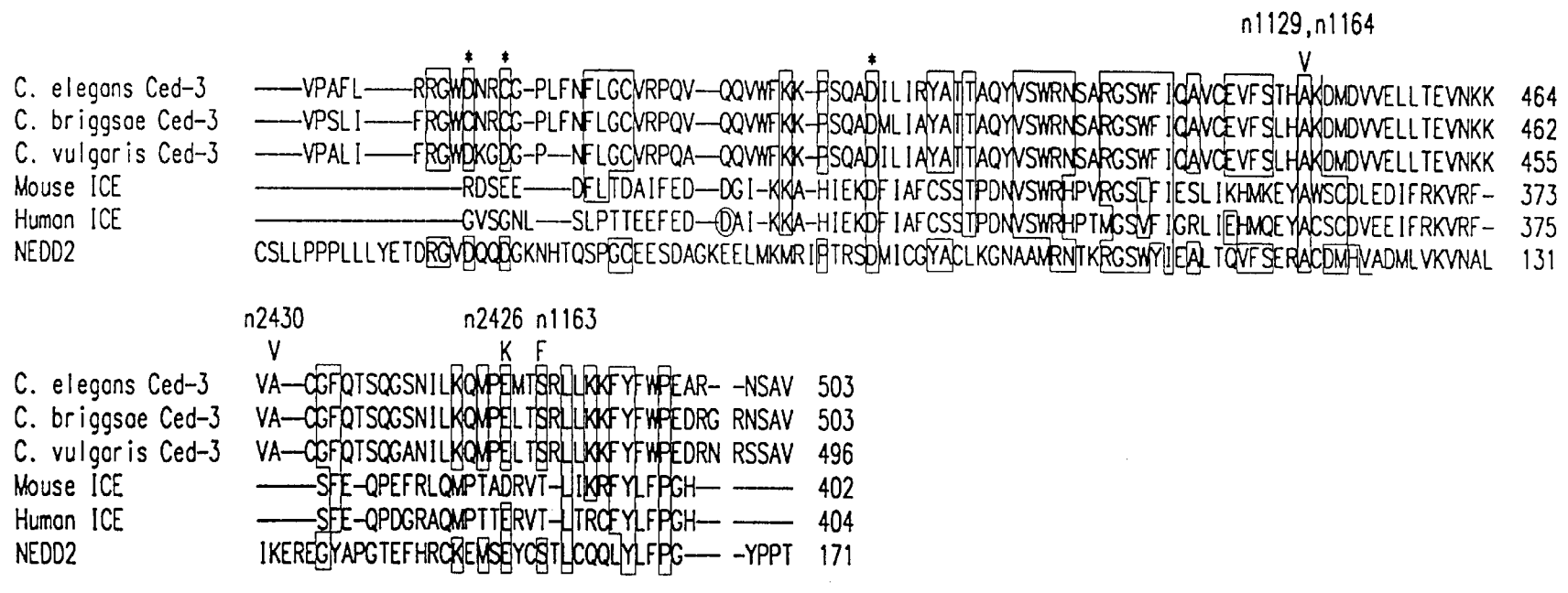

FIGS. 3 and 3A

Structure of the ced-3 Protein

FIG. 3 shows a comparison of structural features of ced-3 with those of the human interleukin-1β converting enzyme (ICE) gene. The predicted proteins corresponding to the ICE proenzyme and ced-3 are represented. The active site in ICE and the predicted active site in ced-3 are indicated by the black rectangles. The four known cleavage sites in ICE flanking the processed ICE subunits (p24, which was detected in low quantities when ICE was purified (Thornberry et al., 1992), p20, and p10) and two conserved presumptive cleavage sites in the ced-3 protein are indicated with solid lines and linked with dotted lines. Five other potential cleavage sites in the ced-3 protein are indicated with dashed lines. The positions of the aspartate (D) residues at potential cleavage sites are indicated below each diagram.

FIG. 3A contains a comparison of the amino acid sequences of the ced-3 proteins from C. elegans (SEQ ID NO: 35), C. briggsae (SEQ ID NO: 36) and C. vulgaris (SEQ ID NO: 37) and the human (SEQ ID NO: 39) and mouse (SEQ ID NO: 38) ICE and mouse nedd-2 proteins (SEQ ID NO: 40). Amino acids are numbered to the right of each protein. Dashes indicate gaps in the sequence made to allow optimal alignment. Residues that are conserved among more than half of the proteins are boxed. Missense ced-3 mutations are indicated above the comparison blocks showing the residue in the mutant ced-3 protein and the allele name. Asterisks indicate potential aspartate self-cleavage sites in the ced-3 protein. Circles indicate known aspartate self-cleavage sites in human ICE. Residues indicated in boldface correspond to the highly conserved pentapeptide containing the active cysteine in ICE.

FIG. 4

Construction of Expression Cassettes of mICE-lacZ and ced-3-lacZ Fusion Genes

Figure 4:
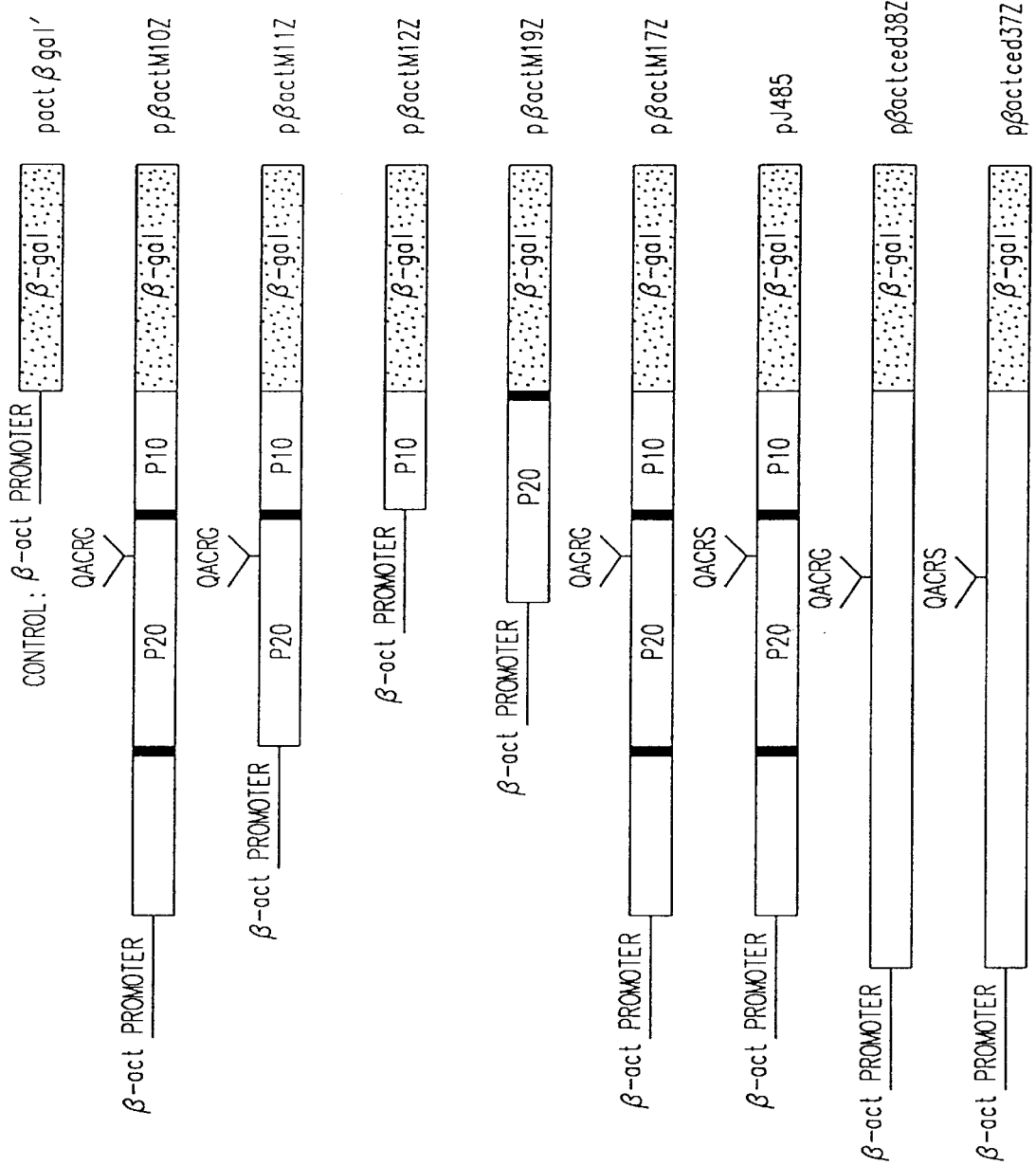

FIG. 4 shows several expression cassettes used in studying the cellular effects of ICE and ced-3 gene expression. The cassettes are as follows: pβactM10Z contains intact mICE fused to the E. coli lacZ gene (mICE-lacZ). pβactM11Z contains the P20 and P10 subunits of mICE fused to the E. coli lacZ gene (P20/P10-lacZ). pβactM19Z contains the P20 subunit of mICE fused to the E. coli lacZ gene (P20-lacZ). pβactM12Z contains the P10 subunit of mICE fused to the E. coli lacZ gene (P10-lacZ). pβactced38Z contains the C. elegans ced-3 gene fused to the lacZ gene (ced-3-lacZ). pJ485 and pβactced37Z contain a Gly to Ser mutation at the active domain pentapeptide "QACRG" in mICE and ced-3 respectively. pβactM17Z contains a Cys to Gly mutation at the active domain pentapeptide "QACRG" in mICE. pactβgal' is a control plasmid (Maekawa et al., Oncogene 6:627–632 (1991)). All plasmids use the β-actin promoter.

FIG. 5

Genetic Pathways of Programmed Cell Death in the Nematode C. elegans and in Vertebrates In vertebrates, bcl-2 blocks the activity of ICE thereby preventing programmed cell death. Enzymatically active ICE causes vertebrate cell death. In C. elegans, ced-9 blocks the action of ced-3/ced-4. Active ced-3 together with active ced-4 causes cell death.

FIG. 6 mICE2 cDNA Sequence and Deduced Amino Acid Sequence

FIG. 6 shows the nucleotide sequence of the mICE2 cDNA sequence (SEQ ID NO: 41) and the amino acid sequence (SEQ ID NO: 42) deduced therefrom.

FIGS. 7 and 7A mICE2 Amino Acid Sequence

FIGS. 7 and 7A contain a comparison of the amino acid sequences of murine interleukin-1β converting enzyme (mICE1) (SEQ ID NO: 38), human interleukin-1β converting enzyme (hICE) (SEQ ID NO: 39), mICE2 (SEQ ID NO: 42) and ced-3 (SEQ ID NO: 35).

FIG. 8

Ich-1 cDNA Sequence and Deduced Amino Acid Sequence

FIG. 8 shows the nucleotide sequence of the Ich-1 cDNA sequence (SEQ ID NO: 43) and the amino acid sequence (SEQ ID NO: 44) deduced therefrom.

FIG. 9

Potential QACRG Coding Region in the Mouse nedd2 cDNA

The reading frame proposed by Kumar et al. (Biochem. & Biophys. Res. Comm. 185:1155–1161 (1992)) is b. In reading frame a, a potential QACRG coding region is underlined (SEQ ID NOs: 45–50).

FIGS. 10–10C

Comparison of Mouse nedd2 and Ich-1 cDNA Sequences

FIGS. 10–10C contains a comparison of the mouse nedd2 cDNA sequence (top strand) (SEQ ID NO: 51) and the Ich-1 cDNA sequence (bottom strand) (SEQ ID NO: 43). The coding region for nedd2 starts at basepair 1177.

FIGS. 11 and 11A

Comparison of the Amino Acid Sequences of ced-3, ICE and Ich-1

FIG. 11 contains a comparison of the amino acid sequences of ced-3 (SEQ ID NO: 35) and Ich-1 (SEQ ID NO: 44). There is a 52% similarity between the sequences and a 28% identity.

FIG. 11A contains a comparison of the amino acid sequences of ICE (SEQ ID NO: 39) and Ich-1 (SEQ ID NO: 44). There is a 52% similarity between the sequences and a 27% identity.

FIG. 12A

The cDNA Sequence of Ich-$1_L$ (SEQ ID NO: 52) and the Deduced Amino Acid Sequence of Ich-$1_L$ Protein Product (SEQ ID NO: 53)

The putative active domain is underlined.

FIG. 12B

The cDNA Sequence of Ich-$1_S$ (SEQ ID NO: 54) and the Deduced Amino Acid Sequence of Ich-$1_S$ Protein Product (SEQ ID NO: 55)

The intron sequence is underlined.

FIG. 13

The Schematic Diagram of Ich-$1_L$ and Ich-$1_S$

FIG. 14

A comparison of the [Ich-1] Ich-$1_S$ (SEQ ID NO: 55) and Ich-$1_L$ (SEQ ID NO: 53) protein sequence (SEQ ID NOs: 55 and 53) with the mouse nedd-2 (SEQ ID NO: 40) protein, the human interleukin-1β-converting enzyme (ICE) protein (SEQ ID NO: 39), the mouse interleukin-1β-converting enzyme (mICE) protein (SEQ ID NO: 38) and *C. elegans* ced-3 protein (SEQ ID NO: 35). Amino acids are numbered to the right of each sequence. Any residues in nedd-2 (SEQ ID NO: 40), ice (SEQ ID NO: 39) and ced-3 (SEQ ID NO: 35) that are identical with Ich-1 (SEQ ID NOs: 55 and 53) protein are highlighted.

FIG. 15

Stable Expression of Ich-1$_S$ Prevents Rat-1 Cells Induced by Serum Removal

Stable transfectants of Rat-1 cells expressing bcl-2, crmA or Ich-1$_S$ were prepared as described in Experimental Procedures. Independent clones of both Ich-1$_S$ positive and Ich-1$_S$ negative were used. At time 0, exponentially growing cells were washed with serum-DMEM and dead cells were counted over time by trypan blue staining.

FIG. 16

The cDNA Sequence (SEQ ID NO: 56) and Putative Ice-4 Protein Sequence (SEQ ID NO: 57)

The putative first Met is marked with a dot.

FIG. 17

Comparison of Amino Acid Sequences of Ice-4 (SEQ ID NO: 58) with ICE (SEQ ID NO: 38), Ice-2 (SEQ ID NO: 42), Ich-1 (SEQ ID NO: 44) and ced-3 (SEQ ID NO: 35)

DEFINITIONS

In the description that follows, a number of terms used in recombinant DNA (rDNA) technology or in the research area of programmed cell death are extensively utilized. In order to provide a clear and consistent understanding of the specification and claims, including the scope to be given such terms, the following definitions are provided.

Gene. A DNA sequence containing a template for a RNA polymerase. The RNA transcribed from a gene may or may not code for a protein. RNA that codes for a protein is termed messenger RNA (mRNA).

A "complementary DNA" or "cDNA" gene includes recombinant genes synthesized by reverse transcription of mRNA and from which intervening sequences (introns) have been removed.

Cloning vector. A plasmid or phage DNA or other DNA sequence which is able to replicate autonomously in a host cell, and which is characterized by one or a small number of endonuclease recognition sites at which such DNA sequences may be cut in a determinable fashion without loss of an essential biological function of the vehicle, and into which DNA may be spliced in order to bring about its replication and cloning. The cloning vector may further contain a marker suitable for use in the identification of cells transformed with the cloning vehicle. Markers, for example, are tetracycline resistance or ampicillin resistance. The term "cloning vehicle" is sometimes used for "cloning vector."

Expression vector. A vector similar to a cloning vector but which is capable of expressing a gene which has been cloned into it, after transformation into a host. The cloned gene is usually placed under the control of (i.e., operably linked to) certain control sequences such as promoter sequences. Control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Programmed cell death. The process in which cell death is genetically programmed. Programmed cell death allows organisms to get rid of cells that have served a developmental purpose but which are no longer beneficial.

Functional Derivative. A "functional derivative" of mICE2, Ich-1 (Ich-1$_L$ and Ich-1$_S$), or Ice-4 is a protein which possesses a biological activity that is substantially similar to the biological activity of the non-recombinant. A functional derivative of may or may not contain post-translational modifications such as covalently linked carbohydrate, depending on the necessity of such modifications for the performance of a specific function. The term "functional derivative" is intended to include the "fragments," "variants," "analogues," or "chemical derivatives" of a molecule.

Fragment. A "fragment" is meant to refer to any variant of the molecule, such as the peptide core, or a variant of the peptide core.

DETAILED DESCRIPTION OF THE PREFERRED EMBODIMENTS

Description

The present invention relates, inter alia, to isolated DNA encoding the ced-3 protein of *C. elegans* (SEQ ID NO: 35), mICE2 (SEQ ID NO: 42), Ich-1 (SEQ ID NO: 44), and Ice-4 (SEQ ID NO: 58). The invention also encompasses nucleic acids having the cDNA sequence of ced-3 (SEQ ID NOs: 1, 34), mICE-2 (SEQ ID NO: 44), Ich-1 (SEQ ID NO: 43), and Ice-4 (SEQ ID NO: 56). The invention also encompasses related sequences in other species that can be isolated without undue experimentation. It will be appreciated that trivial variations in the claimed sequences and fragments derived from the full-length genomic and cDNA genes are encompassed by the invention as well. The invention also encompasses protein sequences from ced-3 (SEQ ID NO: 35), Ich-1 (SEQ ID NO: 44), and Ice-4 (SEQ ID NO: 58). It should also be understood that by Ich-1 is intended both Ich-1$_S$ and ICh-1$_L$.

ced-3

The genomic sequence (SEQ ID NOs: 1, 34) of the claimed gene encoding ced-3 is shown in FIG. 2. The gene is 7,656 base pairs in length and contains seven introns ranging in size from 54 base pairs to 1,195 base pairs. The four largest introns as well as sequences 5' to the START codon contain repetitive elements, some of which have been previously characterized in the non-coding regions of other *C. elegans* genes such as fem-1 (Spence et al., *Cell* 60:981–990 (1990)) and hlh-I (Krause et al., *Cell* 63:907–919 (1990)). A comparison of the repetitive elements in ced-3 with previously characterized repetitive elements is shown in FIGS. 2A(i)–2A(v) (SEQ ID NOs: 3–33). The START codon of the ced-3 (SEQ ID NO: 34) protein is the methionine at position 2232 of the genomic sequence shown in FIG. 2.

The cDNA sequence of ced-3 shown in FIG. 2C. The cDNA is 2,482 base pairs in length with an open reading frame encoding 503 amino acids and 953 base pairs of 3' untranslated sequence. The last 380 base pairs of the 3' sequence are not essential for the expression of the ced-3 protein.

In addition to encompassing the genomic and cDNA sequences (SEQ ID NO: 1) of ced-3 from *C. elegans*, the present invention also encompasses related sequences in other nematode species which can be isolated without undue experimentation. For example, the inventors have shown that ced-3 genes from *C. briggsae* and *C. vulgaris* may be isolated using the ced-3 cDNA from *C. elegans* as a probe (see Example 1).

The invention also encompasses protein products from the ced-3 gene, gene variants, derivatives, and related sequences. As deduced from the DNA sequence, the ced-3 protein is 503 amino acids (SEQ ID NOs: 2, 35) in length and contains a serine-rich middle region of about 100 amino acids. The amino acid sequence (SEQ ID NOs: 2, 35) comprising the claimed ced-3 protein is shown in FIG. 2 and FIG. 2C. A comparison of the ced-3 protein of *C. elegans* with the inferred ced-3 protein sequences (SEQ ID NOs: 36, 37) from the related nematode species *C. briggsae* and *C. vulgaris* indicates that the non-serine-rich region is highly conserved and that the serine-rich region is more variable. The non-serine-rich portion of the ced-3 protein is also homologous with interleukin-1β converting enzyme (ICE), a cysteine protease that can cleave the inactive 31 kD precursor of IL-1β to generate the active cytokine (Cerretti et al., *Science* 256:97–100 (1992); Thornberry et al., *Nature* 356:768–774 (1992)). The C-terminal portions of both the ced-3 and ICE proteins are similar to the mouse nedd-2 protein, which is encoded by an mRNA expressed during mouse embryonic brain development and down-regulated in the adult brain (Kumar et al., *Biochem. & Biophys. Res. Comm.* 185:1155–1161 (1992)). The results suggest that ced-3 acts as a cysteine protease in controlling the onset of programmed cell death in *C. elegans* and that members of the ced-3/ICE/nedd-2 gene family function in programmed cell death in a wide variety of species.

mICE-2

The cDNA sequence (SEQ ID NO: 41) and deduced amino acid sequence (SEQ ID NO: 42) of mICE2 are shown in FIG. 6. As expected, mICE2 shows homology to both human and murine ICE as well as to *C. elegans* ced-3 (see FIGS. 7 and 7A). In contrast to other cell-death genes that have been identified, mICE2 is preferentially expressed in the thymus and placenta. Example 3 describes how the gene was obtained by screening a mouse thymus cDNA library with a DNA probe derived from human ICE under conditions of low stringency. Given the amino acid sequence and cDNA sequence shown in FIG. 6 (SEQ ID NOs: 41, 42), preferred methods of obtaining the mICE2 gene (either genomic or cDNA) are described below.

Ich-1 nedd2, ICE, mICE2 and ced-3 are all members of the same gene family. This suggested that new genes might be isolated based upon their homology to identified family members.

nedd2 is a mouse gene which is preferentially expressed during early embryonic brain development (Kumar et al., *Biochem. Biophys. Res. Commun.* 185:1155–1161 (1992)). Since many neurons die during early embryonic brain development, it is possible that nedd-2 is a cell death gene.

Ich-1 is 2492 base pairs in length and contains an open reading frame of 441 amino acids (FIG. 8). The C-terminal 130 amino acids of Ich-1 are over 87% identical to mouse nedd2. However, Ich-1 contains a much longer open reading frame and has the pentapeptide QACRG which is the active center of the proteins of the ced-3/ICE family. The results indicate that the cDNA isolated by Kumar may not have been synthesized from a fully processed mRNA and that the 5' 1147 base pairs which Kumar reported for nedd2 cDNA may actually represent the sequence of an intron. The sequence reported by Kumar contains a region which could potentially code for QACRG but these amino acids are encoded in a different reading frame than that indicated by Kumar (FIG. 9) (SEQ ID NOs: 46, 48, 50). This suggests that Kumar made an error in sequencing.

The coding regions of nedd2 and n37 are highly homologous (FIG. 10) (SEQ ID NOs: 51, 43). The amino acid sequence of the deduced n37 protein shares 28% identity with ced-3 and 27% identity with ICE (FIG. 11) (SEQ ID NO: 44). The n37 protein was named Ich-1.

Ich-1 mRNA is alternatively spliced into two different forms. One mRNA species encodes a protein product of 435 amino acids (SEQ ID NO: 53), designated Ich-1$_L$, which contains amino acid sequence homologous to both P20 and P10 subunits of ICE as well as entire ced-3 protein. The other mRNA encodes a 312 amino-acid truncated version of Ich-1 protein, named Ich-1$_S$, that terminates 21 amino acid residues after the QACRG active domain of Ich-1. Expression of Ich-1$_L$ and Ich-1$_S$ has opposite effects on cell death. Overexpression of Ich-1$_L$ induces Rat-1 fibroblast cells to die in culture, while overexpression of the Ich-1$_S$ suppresses Rat-1 cell death induced by serum deprivation. Results herein suggest that Ich-1 may play an important role in both positive and negative regulation of programmed cell death in vertebrate animals.

Ice-4

Ice-4 was identified based on its sequence homology with ICE and other isolated ICE homologs. Since the Ice-4 clone isolated by PCR only contains the coding region for the C-terminal half of the Ice-4 protein, a mouse thymus cDNA library was screened using the Ice-4 insert. Among 2 million clones screened, 9 positive clones were isolated. The sequence (SEQ ID NO: 56) herein is from one clone that contains the complete coding region for Ice-4 gene.

Methods of Making ced-3

There are many standard procedures for cloning genes which are well-known in the art and which can be used to obtain the ced-3 gene (see e.g., Sambrook et al., *Molecular Cloning, a Laboratory Manual,* 2nd edition, vol. 1–3, Cold Spring Harbor Laboratory Press, 1989). In Example 1, a detailed description is provided of two preferred procedures. The first preferred procedure does not require the availability of ced-3 gene sequence information and is based upon a method described by Ruvkun et al. (*Molecular Genetics of Caenorhabditis Elegans Heterochromic Gene lin-14* 121: 501–516 (1988)). In brief, Bristol and Bergerac strains of nematode are crossed and restriction fragment length polymorphism mapping is performed on the DNA of the resulting inbred strain. Restriction fragments closely linked to ced-3 are identified and then used as probes to screen cosmid libraries for cosmids carrying all or part of the ced-3 gene. Positive cosmids are injected into a nematode strain in which ced-3 has been mutated. Cosmids carrying active ced-3 genes are identified by their ability to rescue the ced-3 mutant phenotype A second method for cloning ced-3 genes relies upon the sequence information which has been disclosed herein.

Specifically, DNA probes are constructed based upon the sequence of the ced-3 gene (SEQ ID NO: 1) of *C. elegans*. These probes are labelled and used to screen DNA libraries from nematodes or other species. Procedures for carrying out such cloning and screening are described more fully below in connection with the cloning and expression of mICE2, Ich-1, and Ice-4, and are well-known in the art (see, e.g., Sambrook et al., *Molecular Cloning, a Laboratory Manual*, 2nd edition (1988)). When hybridizations are carried out under conditions of high stringency, genes are identified which contain sequences corresponding exactly to that of the probe. In this way, the exact same sequence as described by the inventors herein may be obtained. Alternatively, hybridizations may be carried out under conditions of low stringency in order to identify genes in other species which are homologous to ced-3 but which contain structural variations (see Example 1 for a description of how such hybridizations may be used to obtain the ced-3 genes from *C. briggsae* and *C. vulgaris*).

The results in Example 2 demonstrate that the products of cell-death genes may be tolerated by cells provided they are expressed at low levels. Therefore, the ced-3 protein may be obtained by incorporating the ced-3 cDNA (SEQ ID NO: 34) described above into any of a number of expression vectors well-known in the art and transferring these vectors into appropriate hosts (see Sambrook et al., *Molecular Cloning, a Laboratory Manual*, vol. 3 (1988)). As described below in connection with the expression of mICE2, Ich-1, and Ice-4, expression systems may be utilized in which cells are grown under conditions in which a recombinant gene is not expressed and, after cells reach a desired density, expression may be induced. In this way, the tendency of cells which express ced-3 to die may be circumvented.

mICE2, Ich-1, and Ice-4

DNA encoding mICE2 (SEQ ID NO: 41), Ich-1 (SEQ ID NO: 43), and Ice-4 (SEQ ID NO: 56) may be obtained from either genomic DNA or from cDNA. Genomic DNA may include naturally occurring introns. Moreover, such genomic DNA may be obtained in association with the 5' promoter region of the sequences and/or with the 3' transcriptional termination region. Further, such genomic DNA may be obtained in association with the genetic sequences which encode the 5' non-translated region of the mICE2, Ich-1, and Ice-4 mRNA and/or with the genetic sequences which encode the 3' non-translated region. To the extent that a host cell can recognize the transcriptional and/or translational regulatory signals associated with the expression of the mRNA and protein, then the 5' and/or 3' non-transcribed regions of the native gene, and/or, the 5' and/or 3' non-translated regions of the mRNA, may be retained and employed for transcriptional and translational regulation.

Genomic DNA can be extracted and purified from any cell containing mouse chromosomes by means well known in the art (for example, see *Guide to Molecular Cloning Techniques*, S. L. Berger et al., eds., Academic Press (1987)). Alternatively, mRNA can be isolated from any cell which expresses the genes, and used to produce cDNA by means well known in the art (Id.). The preferred sources for mICE2 are thymus or placental cells. The mRNA coding for any of the proteins (i.e., mICE2, Ich-1, or Ice-4) may be enriched by techniques commonly used to enrich mRNA preparations for specific sequences, such as sucrose gradient centrifugation, or both.

For cloning into a vector, DNA prepared as described above (either human genomic DNA or preferably cDNA) is randomly sheared or enzymatically cleaved, and ligated into appropriate vectors to form a recombinant gene library. A DNA sequence encoding the protein or its functional derivatives may be inserted into a DNA vector in accordance with conventional techniques. Techniques for such manipulations are disclosed by Sambrook, et al., supra, and are well known in the art.

In a preferred method, oligonucleotide probes specific for the gene are designed from the cDNA sequences shown in the FIGS. 6, 8, 12A, 12B, and 16 (SEQ ID NOs: 41, 43, 52, 54). The oligonucleotide may be synthesized by means well known in the art (see, for example, *Synthesis and Application of DNA and RNA*, S. A. Narang, ed., 1987, Academic Press, San Diego, Calif.) and employed as a probe to identify and isolate the cloned gene by techniques known in the art. Techniques of nucleic acid hybridization and clone identification are disclosed by Maniatis, T., et al. (In: *Molecular Cloning, A Laboratory Manual*, Cold Spring Harbor Laboratories, Cold Spring Harbor, N.Y. (1982)), and by Hames, B. D., et al. (In: *Nucleic Acid Hybridization, A Practical Approach*, IRL Press, Washington, DC (1985)). Those members of the above-described gene library which are found to be capable of such hybridization are then analyzed to determine the extent and nature of the coding sequences which they contain.

To facilitate the detection of the desired coding sequence, the above-described DNA probe is labeled with a detectable group. This group can be any material having a detectable physical or chemical property. Such materials are well-known in the field of nucleic acid hybridization and any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby, P. J. W., et al., *J. Mol. Biol.* 113:237 (1977) or by T4 DNA polymerase replacement synthesis as described in, for example, Deen, K. C., et al., *Anal. Biochem.* 135:456 (1983).

Alternatively, oligonucleotide probes may be labeled with a non-radioactive marker such as biotin, an enzyme or a fluorescent group. See, for example, Leary, J. J., et al., *Proc. Natl. Acad. Sci. USA* 80:4045 (1983); Renz, M., et al., *Nucl. Acids Res.* 12:3435 (1984); and Renz, M., *EMBO J.* 6:817 (1983).

For Ich-1, the isolation shown in the Examples was as follows. Two primers were used in the polymerase chain reaction to amplify nedd2 cDNA from embryonic day 15 mouse brain cDNA (Sambrook et al., *Molecular Cloning, a Laboratory Manual*, vol. 3 (1988)). One primer had the sequence (SEQ ID NO: 59): ATGCTAACTGTC-CAAGTCTA and the other primer had the sequence (SEQ ID NO: 60): TCCAACAGCAGGAATAGCA. The cDNA thus amplified was cloned using standard methodology. The cloned mouse nedd2 cDNA (SEQ ID NO: 51) was used as a probe to screen a human fetal brain cDNA library purchased from Stratagene. Such methods of screening and isolating clones are well known in the art (Maniatis, T., et al., *Molecular Cloning, A Laboratory Manual*, Cold Spring Harbor Laboratories, Cold Spring Harbor, N.Y. (1982)); Hames, B. D., et al., *Nucleic Acid Hybridization, A Practical Approach*, IRL Press, Washington, DC (1985)). A human nedd-2 cDNA clone was isolated that encodes a protein much longer than the mouse nedd-2 and contains amino acid sequences homologous to the entire ICE and ced-3 proteins. The isolated clone was given the name Ice--ced 3 homolog or Ich-1.

The Ich-1 cDNA may be obtained using the nucleic acid sequence information given in FIGS. 8, 12A, or 12B (SEQ ID NOs: 43, 52, 54). DNA probes constructed from this sequence can be labeled and used to screen human gene libraries as described herein. Also as discussed herein, Ich-1 may be cloned into expression vectors and expressed in systems in which host cells are grown under conditions in which recombinant genes are not expressed and, after cells reach a desired density, expression is induced. In this way, a tendency of cells which express Ich-1 to die may be circumvented.

One method of making Ice-4 is as follows. mRNA was isolated from embryonic day 14 mouse embryos using Invitrogens' microfast track mRNA isolation kit. The isolated mRNA was reverse transcribed to generate template for PCR amplification. The degenerate PCR primers were: cIceB (SEQ ID NO: 61) {TG(ATCG)CC(ATCG)GGGAA(ATCG)AGGTAGAA} and cTceAs (SEQ ID NO: 62) {ATCAT(ATC)ATCCAGGC(ATCG)TGCAG(AG)GG}. The PCR cycles were set up as follows: 1. 94° C., 3 min; 2. 94° C., 1 min; 3. 48° C., 2 min; 4. 72° C., 3 min; 5. return to "2" 4 cycles; 6. 94° C., 1 min; 7. 55° C., 2 min; 8. 72° C., 3 min; 9. return to "6" 34 cycles; 10. 72° C., 10 min; 11. end. Such PCR generated a band about 400 bp, the predicted size of ICE homologs. The PCR products were cloned into T-tailed blunt-ended pBSKII plasmid vector (Stratagene). Plasmids that contain an insert were analyzed by DNA sequencing.

The Ice-4 cDNA may also be obtained using the nucleic acid sequence information given in FIG. 16 (SEQ ID NO: 56). DNA probes constructed from this sequence can be labeled and used to screen human gene libraries as described herein. Also as discussed herein, Ice-4 may be cloned into expression vectors and expressed in systems in which host cells are grown under conditions in which recombinant genes are not expressed and, after cells reach a desired density, expression is induced.

The methods discussed herein are capable of identifying genetic sequences which encode mICE2, Ich-1, and Ice-4. In order to further characterize such genetic sequences, and, in order to produce the recombinant protein, it is desirable to express the proteins which these sequences encode.

To express any of the genes herein (mICE2, Ich-1, Ice-4, and derivatives), transcriptional and translational signals recognizable by an appropriate host are necessary. The cloned coding sequences, obtained through the methods described herein, may be operably linked to sequences controlling transcriptional expression in an expression vector and introduced into a host cell, either prokaryote or eukaryote, to produce recombinant protein or a functional derivative thereof. Depending upon which strand of the sequence is operably linked to the sequences controlling transcriptional expression, it is also possible to express antisense RNA or a functional derivative thereof.

Expression of the protein in different hosts may result in different post-translational modifications which may alter the properties of the protein. Preferably, the present invention encompasses the expression of mICE2, Ich-1, and Ice-4 or a functional derivative thereof, in eukaryotic cells, and especially mammalian, insect and yeast cells. Especially preferred eukaryotic hosts are mammalian cells either in vivo, or in tissue culture. Mammalian cells provide post-translational modifications which should be similar or identical to those found in the native protein. Preferred mammalian host cells include rat-1 fibroblasts, mouse bone marrow derived mast cells, mouse mast cells immortalized with Kirsten sarcoma virus, or normal mouse mast cells that have been co-cultured with mouse fibroblasts. Razin et al., *J. of Immun.* 132:1479 (1984); Levi-Schaffer et al., *Proc. Natl. Acad. Sci.* (*USA*) 83:6485 (1986) and Reynolds et al., "Immortalization of Murine Connective Tissue-type Mast Cells at Multiple Stages of Their Differentiation by Coculture of Splenocytes with Fibroblasts that Produce Kirsten Sarcoma Virus," *J. Biol. Chem.* 263:12783–12791 (1988).

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide. An operable linkage is a linkage in which a coding sequence is connected to a regulatory sequence (or sequences) in such a way as to place expression of the coding sequence under the influence or control of the regulatory sequence. Two DNA sequences (e.g. the coding sequence of protein and a promoter) are said to be operably linked if induction of promoter function results in the transcription of the coding sequence and if the nature of the linkage between the two DNA sequences does not (1) result in the introduction of a frame-shift mutation; (2) interfere with the ability of regulatory sequences to direct the expression of the coding sequence, antisense RNA, or protein; or (3) interfere with the ability of the coding sequence template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene.

Expression of proteins of the invention in eukaryotic hosts requires the use of regulatory regions functional in such hosts, and preferably eukaryotic regulatory systems. A wide variety of transcriptional and translational regulatory sequences can be employed, depending upon the nature of the eukaryotic host. The transcriptional and translational regulatory signals can also be derived from the genomic sequences of viruses which infect eukaryotic cells, such as adenovirus, bovine papilloma virus, Simian virus, herpes virus, or the like. Preferably, these regulatory signals are associated with a particular gene which is capable of a high level of expression in the host cell.

In eukaryotes, where transcription is not linked to translation, control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA capable of translation are preferred, and especially, strong promoters such as the promoter for actin, collagen, myosin, etc., can be employed provided they also function as promoters in the host cell. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); in yeast, the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)) or a glycolytic gene promoter may be used.

It is known that translation of eukaryotic mRNA is initiated at the codon which encodes the first methionine. For this reason, it is preferable to ensure that the linkage between a eukaryotic promoter and a DNA sequence which encodes the proteins of the invention or functional derivatives thereof, does not contain any intervening codons which are capable of encoding a methionine. The presence of such codons results either in the formation of a fusion protein or a frame-shift mutation.

If desired, a fusion product of the proteins may be constructed. For example, the sequence coding for the proteins may be linked to a signal sequence which will allow secretion of the protein from, or the compartmentalization of the protein in, a particular host. Such signal sequences may be designed with or without specific protease sites such that the signal peptide sequence is amenable to subsequent removal. Alternatively, the native signal sequence for this protein may be used.

Transcriptional initiation regulatory signals can be selected which allow for repression or activation, so that expression of operably linked genes can be modulated. Of interest are regulatory signals which are temperature-sensitive so that by varying the temperature, expression can be repressed or initiated, or are subject to chemical regulation, e.g., metabolite.

If desired, the non-transcribed and/or non-translated regions 3' to the sequence coding for the proteins can be obtained by the above-described cloning methods. The 3'-non-transcribed region may be retained for transcriptional termination regulatory sequence elements; the 3'-non-translated region may be retained for translational termination regulatory sequence elements, or for those elements which direct polyadenylation in eukaryotic cells. Where native expression control signals do not function satisfactorily in a host cell, functional sequences may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert the DNA construct into the host cell chromosomal DNA, or to allow it to exist in extrachromosomal form. If the protein encoding sequence and an operably linked promoter are introduced into a recipient eukaryotic cell as a non-replicating DNA (or RNA) molecule, the expression of the protein may occur through the transient expression of the introduced sequence.

In a preferred embodiment, genetically stable transformants may be constructed with vector systems, or transformation systems, whereby mICE2, Ich-1, or Ice-4 DNA is integrated into the host chromosome. Such integration may occur de novo within the cell or, in a most preferred embodiment, through the aid of a cotransformed vector which functionally inserts itself into the host chromosome, for example, retroviral vectors, transposons or other DNA elements which promote integration of DNA sequences in chromosomes.

Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transfection. In another embodiment, the introduced sequence is incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40, and, in yeast, plasmids containing the 2-micron circle, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology. A Comprehensive Treatise*, Vol. 3, *Gene Expression*, Academic Press, NY, pp. 563–608 (1980)), and are commercially available.

Once the vector or DNA sequence containing the construct(s) is prepared for expression, the DNA construct(s) is introduced into an appropriate host cell by any of a variety of suitable means, including transfection. After the introduction of the vector, recipient cells are grown in a medium which selects for the growth of vector-containing cells. Expression of the cloned gene sequence(s) results in the production of the protein, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like). The latter is preferred for the expression of the proteins of the invention. By growing cells under conditions in which the proteins are not expressed, cell death may be avoided. When a high cell density is reached, expression of the proteins may be induced and the recombinant protein harvested immediately before death occurs.

The expressed protein is isolated and purified in accordance with conventional procedures, such as extraction, precipitation, gel filtration chromatography, affinity chromatography, electrophoresis, or the like.

The mICE2, Ich-1, and Ice-4 sequences (SEQ ID NO: 41, 43, 56), obtained through the methods above, will provide sequences which not only encode these proteins but which also encode antisense RNA directed against mICE2, Ich-1, and Ice-4; the antisense DNA sequence will be that sequence found on the opposite strand of the strand transcribing the mRNA. The antisense DNA strand may also be operably linked to a promoter in an expression vector such that transformation with this vector results in a host capable of expression of the antisense RNA in the transformed cell. Antisense DNA and RNA may be used to interact with endogenous mICE2, Ich-1, or Ice-4 DNA or RNA in a manner which inhibits or represses transcription or translation of the genes in a highly specific manner. Use of antisense nucleic acid to block gene expression is discussed in Lichtenstein, C., *Nature* 333:801–802 (1988).

Methods of Using ced-3

The ced-3 gene (as well as ced-3 homologs and other members of the ced-3 gene family) may be used for a number of distinct purposes. First, portions of the gene may be used as a probe for identifying genes homologous to ced-3 in other strains of nematode (see Example 1) as well as in other species (see Examples 2 and 3). Such probes may also be used to determine whether the ced-3 gene or homologs of ced-3 are being expressed in cells.

The cell death genes will be used in the development of therapeutic methods for diseases and conditions characterized by cell death. Among diseases and conditions which could potentially be treated are neural and muscular degenerative diseases, myocardial infarction, stroke, virally induced cell death and aging. The discovery that ced-3 is related to ICE suggests that cell death genes may play an important role in inflammation (IL-1β is known to be involved in the inflammatory response). Thus therapeutics based upon ced-3 and related cell death genes may also be developed.

mICE2, Ich-1, and Ice-4 mICE2, Ich-1, and Ice-4 will have the same uses as those described in connection with ced-3 (above) and ICE (see below). The gene sequences may be used to construct antisense DNA and RNA oligonucleotides, which, in turn, may be used to prevent programmed cell death in thymus or placental cells. Techniques for inhibiting the expression of genes using antisense DNA or RNA are well-known in the art (Lichtenstein, C., *Nature* 333:801–802 (1988)). Portions of the claimed DNA sequence may also be used as probes for determining the level of expression. Similarly the protein may be used to generate antibodies that can be used in assaying cellular expression.

Portions of the mICE2, Ich-1, and Ice-4 genes described above may be used for determining the level of expression of the proteins (mICE2 in thymus or placental cells as well as in other tissues and organs). Such methods may be useful in determining if these cells have undergone a neoplastic transformation. Probes based upon the gene sequences may be used to isolate similar genes involved in cell death. A portion of the gene may be used in homologous recombination experiments to repair defective genes in cells or, alternatively, to develop strains of mice that are deficient in the gene. Antisense constructs may be transfected into cells (placental or thymus cells for mICE2) in order to develop cells which may be maintained in culture for an extended period of time or indefinitely. Alternatively antisense constructs may be used in cell culture or in vivo to block cell death.

The protein may be used for the purpose of generating polyclonal or monoclonal antibodies using standard techniques well known in the art (Klein, J. *Immunology: The Science of Cell-Noncell Discrimination*, John Wiley & Sons, N.Y. (1982); Kennett et al., *Monoclonal Antibodies, Hybridoma: A New Dimension in Biological Analyses*, Plenum Press, N.Y. (1980); Campbell, A., "Monoclonal Antibody Technology," In: *Laboratory Techniques in Biochemistry and Molecular Biology* 13, Burdon et al. eds., Elseiver, Amsterdam (1984); Harlow and Lane, Antibodies, *A Laboratory Manual*, Cold Spring Harbor Laboratory, N.Y. (1988)). Such antibodies may be used in assays for determining the expression of the genes. Purified protein would serve as the standard in such assays.

Based upon the sequences of FIG. 6 (SEQ ID NO: 41), probes may be used to determine whether the mICE2 gene or homologs of mICE2 are being expressed in cells. Such probes may be utilized in assays for correlating mICE2 expression with cellular conditions, e.g. neoplastic transformation, as well as for the purpose of isolating other genes which are homologous to mICE2.

mICE2 will be used in the development of therapeutic methods for diseases and conditions characterized by cell death. The diseases and conditions which could potentially be treated include neural and muscular degenerative diseases, myocardial infarction, stroke, virally induced cell death and aging.

Antisense nucleic acids based upon the sequences shown in FIG. 6 (SEQ ID NO: 41) may be used to inhibit mICE2 expression. Such inhibition will be useful in blocking cell death in cultured cells.

The mICE2 protein may be used to generate polyclonal or monoclonal antibodies using methods well known in the art (Klein, J. *Immunology: The Science of Cell-Noncell Discrimination*, John Wiley & Sons, N.Y. (1982); Kennett et al., *Monoclonal Antibodies, Hybridoma: A New Dimension in Biological Analyses*, Plenum Press, N.Y. (1980); Campbell, A., "Monoclonal Antibody Technology," In: *Laboratory Techniques in Biochemistry and Molecular Biology* 13, Burdon et al. eds., Elseiver, Amsterdam (1984); Harlow and Lane, Antibodies, *A Laboratory Manual*, Cold Spring Harbor Laboratory, N.Y. (1988)). The antibodies may be used in assays for determining the expression of mICE2. Purified mICE2 protein would serve as the standard in such assays.

Based upon the sequences of FIGS. 8, 12A, and 12B (SEQ ID NOs: 43, 52, 54), probes may be used to determine whether the Ich-1 gene or homologs of Ich-1 are being expressed in cells. Such probes may be utilized in assays for correlating Ich-1 expression with cellular conditions, e.g. neoplastic transformation, as well as for the purpose of isolating other genes which are homologous to Ich-1.

Ich-1 will be used in the development of therapeutic methods for diseases and conditions characterized by cell death. The diseases and conditions which could potentially be treated include neural and muscular degenerative diseases, myocardial infarction, stroke, virally induced cell death and aging.

Antisense nucleic acids based upon the sequences shown in FIGS. 8, 12A, and 12B (SEQ ID NOs: 43, 52, 54), may be used to inhibit Ich-1 expression. Such inhibition will be useful in blocking cell death in cultured cells.

The Ich-1 protein may be used to generate polyclonal or monoclonal antibodies using methods well known in the art (Klein, J. *Immunology: The Science of Cell-Noncell Discrimination*, John Wiley & Sons, N.Y. (1982); Kennett et al., *Monoclonal Antibodies, Hybridoma: A New Dimension in Biological Analyses*, Plenum Press, N.Y. (1980); Campbell, A., "Monoclonal Antibody Technology," In: *Laboratory Techniques in Biochemistry and Molecular Biology* 13, Burdon et al. eds., Elseiver, Amsterdam (1984); Harlow and Lane, Antibodies, *A Laboratory Manual*, Cold Spring Harbor Laboratory, N.Y. (1988)). The antibodies may be used in assays for determining the expression of Ich-1. Purified Ich-1 protein would serve as the standard in such assays.

Based upon the sequence of FIG. 16 (SEQ ID NO: 56), probes may be used to determine whether the Ice-4 gene or homologs of Ice-4 are being expressed in cells. Such probes may be utilized in assays for correlating Ice-4 expression with cellular conditions, e.g. neoplastic transformation, as well as for the purpose of isolating other genes which are homologous to Ice-4.

Ice-4 will be used in the development of therapeutic methods for diseases and conditions characterized by cell death. The diseases and conditions which could potentially be treated include neural and muscular degenerative diseases, myocardial infarction, stroke, virally induced cell death and aging.

Antisense nucleic acids based upon the sequence shown in FIG. 16 may be used to inhibit Ice-4 expression. Such inhibition will be useful in blocking cell death in cultured cells.

The Ice-4 protein may be used to generate polyclonal or monoclonal antibodies using methods well known in the art (Klein, J. *Immunology. The Science of Cell-Noncell Discrimination*, John Wiley & Sons, N.Y. (1982); Kennett et al., *Monoclonal Antibodies, Hybridoma: A New Dimension in Biological Analyses*, Plenum Press, N.Y. (1980); Campbell, A., "Monoclonal Antibody Technology," In: *Laboratory Techniques in Biochemistry and Molecular Biology* 13, Burdon et al. eds., Elseiver, Amsterdam (1984); Harlow and Lane, *Antibodies, A Laboratory Manual*, Cold Spring Harbor Laboratory, N.Y. (1988)). The antibodies may be used in assays for determining the expression of Ice-4. Purified Ice-4 protein would serve as the standard in such assays.

Method for Preventing Programmed Cell Death in Vertebrate Cells by Inhibiting the Enzymatic Activity of Interleukin-1β Converting Enzyme (ICE)

The present invention is directed to preventing the programmed death of vertebrate cells by inhibiting the action of ICE. The detailed structural analysis performed on the ced-3 gene from C. elegans revealed a homology to human and murine ICE which is especially strong at the QACRG active domain of ICE (see FIG. 3A) (SEQ ID NOs: 38, 39). ICE is a cysteine protease that cleaves inactive pro-interleukin-β into active interleukin-1β.

In order to determine if ICE functions as a cell death gene in vertebrates, the mouse ICE gene was cloned, inserted into an expression vector and then transfected into rat cells. A close correlation was found between ICE expression and cell death (see Example 2).

Further support for the function of ICE as a cell death gene was obtained from inhibition studies. The cowpox gene crmA encodes a protein that specifically inhibits ICE activity (Ray et al., *Cell* 69:597–604 (1992)). In order to determine whether cell death can be prevented by inhibiting the enzymatic action of ICE, cell lines were established which produced a high level of crib protein. When these cells were transfected with ICE, it was found that a large percentage of the cells expressing ICE maintained a healthy morphology and did not undergo programmed cell death.

Evidence that ICE has a physiological role as a vertebrate cell death gene was also obtained by examining cells engineered to over-express bcl-2, an oncogene known to inhibit programmed cell death and to be overexpressed in many follicular and B cell lymphomas. It was found that cells expressing bcl-2 did not undergo cell death despite the synthesis of high levels of ICE. These results suggest that bcl-2 may promote malignancy by inhibiting the action of ICE.

Any method of specifically regulating the action of ICE in order to control programmed cell death in vertebrates is encompassed by the present invention. This would include not only inhibitors specific to ICE, e.g. crmA, or the inhibitors described by Thornberry et al., *Nature* 356:768–774 (1992), but also any method which specifically prevented the expression of the ICE gene. Thus, antisense RNA or DNA comprised of nucleotide sequences complementary to ICE and capable of inhibiting the transcription or translation of ICE are within the scope of the invention (see Lichtenstein, C., *Nature* 333:801–802 (1988)).

The ability to prevent vertebrate programmed cell death is of use in developing cells which can be maintained for an indefinite period of time in culture. For example, cells over-expressing crmA may be used as hosts for expressing recombinant proteins. The ability to prevent programmed cell death may allow cells to live independent of normally required growth factors. It has been found that microinjecting crmA mRNA or a crmA-expressing nucleic acid construct into cells allows chicken sympathetic neurons to live in vitro after the removal of neural growth factor.

Alternatively, the expression of ICE may be increased in order to cause programmed cell death. For example, homologous recombination may be used to replace a defective region of an ICE gene with its normal counterpart. In this way, it may be possible to prevent the uncontrolled growth of certain malignant cells. Methods of increasing ICE activity may be used to kill undesired organisms such as parasites. crmA is a viral protein which is important for cowpox infection. This suggests that the prevention of cell death may be important for successful infection and that, by the promotion of ICE expression, may provide a means for blocking infection.

Having now generally described this invention, the same will be further described by reference to certain specific examples which are provided herein for purposes of illustration only and are not intended to be limiting unless otherwise specified. All references cited throughout the specification are incorporated by reference in their entirety.

EXAMPLE 1

Experimental Procedures

General Methods and Strains

The techniques used for culturing C. elegans have been described by Brenner (Brenner, S., *Genetics* 77:71–94 (1974)). All strains were grown at 20° C. The wild-type parent strains were C. elegans variety Bristol strain N2, Bergerac strain EM1002 (Emmons et al., *Cell* 32:55–65 (1983)), C. briggsae and C. vulgaris. The genetic markers used are described below. These markers have been previously described (Brenner, S., *Genetics* 77:71–94 (1974)); and Hodgkin et al., *Genetics in the Nematode Caenorhabditis Elgens* (Wood et al. eds.) pp.491–584, Cold Spring Harbor, N.Y. (1988)). Genetic nomenclature follows the standard system (Horvitz et al., *Mol. Gen. Genet.* 175:129–133 (1979)).

LG I: ced-1 (ei 735); unc-54 (r323)

LG VI: unc-31 (e928), unc-30 (el91), ced-3 (n717, n718, n1040, n1129, n11634, n1164, n1165, n1286, n1949, n2426, n2430, n2433), unc-26 (e205), dpy-4 (e1166)

LG V: eg-1(n986); unc-76 (e911)

LG X: dpy-3(e27)

Isolation of additional alleles of ced-3

A non-complementation screen was designed to isolate new alleles of ced-3. Because animals heterozygous for ced3(n717) in trans to a deficiency are viable (Ellis et al., Cell 44:817–829 (1986)), it was expected that animals carrying a complete loss-of-function mutant ced-3 allele in trans to ced-3(n717) would be viable even if homozygotes for the allele were inviable. EMS mutagenized egl L4 males were mated with ced-3(n717) unc-26(e205); egl-1(n487); dpy-3(e27) hermaphrodites. egl-1 was used as a marker in this screen. Dominant mutations in egl-1 cause the two hermaphrodite-specific neurons, the HSNs, to undergo programmed cell death (Trent et al., *Genetics* 104:619–647 (1983)). The HSNs are required for normal egg-laying, and egl-1(n986) hermaphrodites, which lack HSNs are egg-laying defective (Trent et al., *Genetics* 104:619–647)). The mutant phenotype of egl-1 is suppressed in a ced-3; egl-1 strain because mutations in ced-3 block programmed cell deaths. egl-1 males were mutagenized with EMS and crossed with ced3(n717) unc-26(e205); egl-1(n487); dpy-3 (e27). Most cross progeny were egg-laying defective because they were heterozygous for ced-3 and homozygous for egl-1. Rare egglaying competent animals were picked, those animals being candidates for carrying new alleles of ced-3. Four such animals were isolated from about 10,000 Fl cross progeny of EMS-mutagenized animals. These new mutations were made homozygous to confirm that they carried mutations of ced-3.

RFLP mapping

Two cosmid libraries were used extensively in this work—a Sau3A I partial digest genomic library of 7000 clones in the vector pHC79 and a Sau3A I partial digest genomic library of 6000 clones in the vector pJB8 (Coulson et al., *Proc. Natl. Acad. Sci. U.S.A.* 83:7821–7825 (1986).

Bristol (N2) and Bergerac (EM1002) DNA was digested with various restriction enzymes and probed with different cosmids to look for RFLPs. nP33 is a HindIII RFLP detected by the "right" end of Jc8. The "right" end of Jc8 was made by digesting Jc8 with EcoRI and self-ligating. nP34 is a HindIII RFLP detected by the "left" end of Jc8. The "left" end of Jc8 was made by digesting Jc8 by SalI and self ligating. nP36 and nP37 are both HindIII RFLPs detected by T1OH5 and B0564, respectively.

Germ line transformation

The procedure used for microinjection basically follows that of A. Fire (Fire, A., *EMBO J.* 5:2673–2680 (1986)). Cosmid DNA was twice CsCl gradient purified. Miniprep DNA was used when deleted cosmids were injected and was prepared from 1.5 ml overnight bacteria culture in super-broth. Superbroth was prepared by combining 12 g Bacto tryptone, 24 g yeast extract, 8 ml 50% glycerol and 900 ml $H_2O$. The mixture was autoclaved and then 100 ml of 0.17 M $KH_2PO_4$ and 0.72 M $K_2HPO_4$ were added. The bacterial culture was extracted by the alkaline lysis method as described in Maniatis et al. (*Molecular Cloning, A Laboratory Manual*, Cold Spring Harbor Press (1983)). DNA was treated with RNase A (37°, 30 min) and then with protease K (55°, 30 min). The preparation was phenol- and then chloroform-extracted, precipitated twice (first in 0.3 M Na acetate and second in 0.1 M K acetate, pH 7.2), and resuspended in 5 l injection buffer as described by A. Fire (Fire, A., *EMBO J.* 5:2673–2680 (1986)). The DNA concentration for injection was in the range of 100 μg to 1 mg per ml.

All transformation experiments used the ced-1(e1735); unc-31(e928) ced-3(n717) strain. unc-31 was used as a marker for co-transformation (Kim et al., *Genes & Dev.* 4:357–371 (1990)). ced-1 was present to facilitate scoring of the ced-3 phenotype. The mutations in ced-1 block the engulfment process of cell death, which makes the corpses of the dead cells persist much longer than that in the wild-type (Hedgecock et al., *Science* 220:1277–1280 (1983)). ced-3 phenotype was scored as the number of dead cells present in the head of young L1 animals. The cosmid C10D8 or the plasmid subclones of C10D8 were mixed with C14G10 (unc-31(+)-containing) at a ratio of 2:1 or 3:1 to increase the chances that an Unc-31(+) transformant would contain the cosmid or plasmid being tested. Usually, 20–30 animals were injected in one experiment. Non-Unc F1 progeny of injected animals were isolated three to four days later. About ½ to ⅓ of the non-Unc progeny transmitted the non-Unc phenotype to F2 and established a line of transfomants. The young L1 progeny of such non-Unc transformants were checked for the number of dead cells present in the head using Nomarski optics.

Determination of ced-3 transcript initiation site.

Two primers, Pexi (SEQ ID NO: 63): (5'GTTGCACTGCTTTCACGATCTCCCGTCTCT3') and Pex2 (SEQ ID NO: 64): (5'TCATCGACTTTTAGATG-ACTAGAGAACATC3'), were used for primer extension. The primers for RT-PCR are: SL1 (SEQ ID NO: 65) (5'GTTTAATTACCCAAGTTTGAG3') and log-5 (SEQ ID NO: 66) (5'CCGGTGACATTGGACACTC3'). The products are reamplified using the primers SL1 and oligo10 (SEQ ID NO: 67) (5'ACTATTCAACACTTG3'). A product of the expected length was cloned into the PCR1000 vector (invitrogen) and sequenced.

Determination and analysis of DNA sequence

For DNA sequencing, serial deletions were made according to a procedure developed by Henikoff (Heinkoff, S., *Gene* 28:351–359 (1984)). DNA sequences were determined using Sequenase and protocols obtained from US Biochemicals with minor modifications.

The ced-3 amino acid sequence (SEQ ID NO: 2) was compared with amino acid sequences in the GenBank, PIR and SWISS-PROT databases at the National Center for Biotechnology Information (NCBI) using the blast network service.

Cloning of ced-3 genes from other nematode species *C. briggsae* and *C. vulgaris* ced-3 genes were isolated from corresponding phage genomic libraries using the ced-3 cDNA subclone pJ118 insert as a probe under low stringency conditions (5×SSPE, 20% Formamide, 0.02% Ficoll, 0.02% BSA, 0.02% polyvinylpyrrolidone, 1% SDS) at 40° C. overnight and washed in 1×SSPE and 0.5% SDS twice at room temperature and twice at 42° C. for 20 min each time.

Results ced-3 is not essential for viability

All previously described ced-3 alleles were isolated in screens designed to detect viable mutants in which programmed cell death did not occur (Ellis et al., *Cell* 44:817–829 (1986)). Such screens might systematically have missed classes of ced-3 mutations that result in inviability. Since animals with the genotype of ced-3/deficiency are viable (Ellis et al., *Cell* 44:817–829 (1986)), a noncomplementation-screening scheme was designed that would allow the isolation of recessive lethal alleles of ced-3. Four new ced-3 alleles (n1163, n1164, n1165, and n1286) were obtained which were viable as homozygotes. These new alleles were isolated at a frequency of about 1 in 2500 mutagenized haploid genomes, approximately the frequency expected for the generation of null mutations in an average *C. elegans* gene (Brenner, S., *Genetics* 77:71–94 (1974); Meneely et al., *Genetics* 92:99–105 (1990); Greenwald et al., *Genetics* 96:147–160 (1980)).

These results suggest that animals that lack ced-3 gene activity are viable. In support of this hypothesis, molecular analysis has revealed that three ced-3 mutations are nonsense mutations that prematurely terminate ced-3 protein translation and one alters a highly conserved splice acceptor site (see below). These mutations would be expected to eliminate ced-3 activity completely. Based upon these considerations, it was concluded that ced-3 gene activity is not essential for viability.

ced-3 is contained within a 7.5 kb genomic fragment

The ced-3 gene was cloned using the approach of Ruvkun et al. (*Molecular Genetics of the Caenorhabditis Elgens Heterochronic Gene lin-*14 121:501–516 (1988)). Briefly (for further details, see Experimental Procedures), the *C. elegans* Bristol strain N2 contains 30 dispersed copies of the transposable element Tc1, whereas the Bergerac strain contains more than 400 copies (Emmons et al., *Cell* 32:55–65 (1983); Finney, M., Ph.D. Thesis "The Genetics and Molecular Biology of unc-86, a *Caenorhabditis elgens* Cell Lineage Gene," Cambridge, Mass. (1987)). By crossing Bristol and Bergerac strains, a series of recombinant inbred strains were generated in which chromosomal material was mostly derived from the Bristol strain with varying amounts of Bergerac-specific chromosome IV-derived material in the region of the ced-3 gene. By probing DNA from these strains with plasmid pCe2001 which contains Tc1 (Emmons et al., *Cell* 32:55–65 (1983),) a 5.1 kb EcoRI Tc1-containing restriction fragment specific to the Bristol strain (restriction fragment length polymorphism nP35) and closely linked to ced-3 was identified.

Cosmids that contained this 5.1 kb restriction fragment were identified and it was found that these cosmids overlapped an existing cosmid contig that had been defined as part of the *C. elegans* genome project (Coulson et al., *Proc. Natl. Acad. Sci.* 83:7821–7825 (1986). Four other Bristol-Bergerac restriction fragment length polymorphisms were defined by cosmids in this contig (nP33, np34, nP36, nP37). By mapping these restriction fragment length polymorphisms with respect to the genes unc-30, ced-3 and unc-26, the physical contig was oriented with respect to the genetic map and the region containing the ced-3 gene was narrowed to an interval spanned by three cosmids (FIG. 1). By mapping these RFLPs between Bristol and Bergerac strains with respect to the genes unc-30, ced-3 and unc-26, the physical contig was oriented with respect to the genetic map.

On Southern blot, three of three+Berg unc-26 recombinants showed the Bristol nP33 pattern while two of two ced-3+Berg recombinants showed the Bergerac pattern (data not shown). Thus, nP33 maps very close or to the right of unc-26. For nP34, two of two ced-3+Berg recombinants and two of three+Berg unc-26 recombinants showed the Bergerac pattern; one of the three+Berg unc-26 recombinant showed the Bristol pattern (data not shown). The genetic distance between ced-3 and unc-26 is about 0.2 mu. Thus, nP34 maps between ced-3 and unc-26, about 0.1 mu to the right of ced-3. Similar experiments mapped nP35, the 5.1 kb Bristol specific Tc1 element, to about 0.1 mu to the right of ced-3 (data not shown).

In order to map n36 and n37, Bristol unc-30 ced-3/++ males were crossed with Bergerac hermaphrodites. From the progeny of heterozygotes of genotype unc-30 ced-3 (Bristol)/++(Bergerac), Unc-30 non-ced-3 and non-Unc-30 ced-3 animals were picked and DNA was prepared from these strains. nP36 maps very close or to the right of unc-30 since two of two unc-30+Berg recombinants showed Bristol pattern and two of two+Berg ced-3 recombinants showed the Bergerac pattern (data not shown). Similarly, nP37 maps very close or to the right of unc-30 since four of the four+Berg ced-3 showed Bergerac pattern and six of six unc-30+Berg recombinants showed the Bristol pattern (data not shown). These experiments narrowed the region containing the ced-3 gene to an interval spanned by the three cosmids (FIG. 1*a*).

Cosmids that were candidates for containing the ced-3 gene were microinjected (Fire, A., *EMBO J.* 5:2673–2680 (1986)) into ced-3 mutant animals to test for rescue of the mutant phenotype. Specifically, cosmid C14G10, which contains the wild-type unc-31 gene and a candidate cosmid were coinjected into ced-1(e1375); unc-31(e928) ced-3 (n717) hermaphrodites. Non-unc progeny were isolated and observed to see if the non-Unc phenotype was transmitted to the next generation, thus establishing a line of transformed animals. Young L1 progeny of such transformant lines were examined for the presence of cell deaths using Nomarski optics to see whether the ced-3 phenotype was complemented (see Experimental Procedures). Cosmid C14G10 alone does not confer ced-3 activity when injected into a ced-3 mutant.

unc-31 was used as a marker for co-transformation (Kim et al., *Genes & Devel.* 4:357–371 (1990)). ced-1 was present to facilitate scoring of the ced-3 phenotype. Mutations in ced-1 block the engulfment process of programmed cell death, causing the corpses of dead cells to persist much longer than in the wild-type (Hedgecock et al., *Science* 220:1277–1280 (1983)). Thus, the presence of a corpse indicates a cell that has undergone programmed cell death. The ced-3 phenotype was scored as the number of corpses present in the head of young L1 animals.

As indicated in FIG. 1, of the three cosmids injected (C43C9, W07H6 and C48D1), only C48D1 rescued the ced-3 mutant phenotype. Both non-Unc transformed lines obtained, nIs1 and nEx2, were rescued. Specifically, L1 ced-1 animals contain an average of 23 cell corpses in the head, and L1 ced-1; ced3 animals contain an average of 0.3 cell corpses in the head (Ellis et al., *Cell* 44:817–829 (1986)). By contrast, ced-1; unc-31 ced-3; nIs1; and ced-1; unc-31 ced-3; nEx2 animals contained an average of 16.4 and 14.5 cell corpses in the head, respectively. From these results, it was concluded that C48D1 contains the ced-3 gene.

To locate ced-3 more precisely within the cosmid C48D1, this cosmid was subcloned and the subclones tested for their ability to rescue the ced-3 mutant phenotype (FIG. 1A). From these experiments, ced-3 was localized to a DNA fragment of 7.5 kb (pJ7.5).

A 2.8 kb ced-3 transcript is expressed primarily during embryogenesis and independently of ced-4 function The 7.6 kb pJ107 subclone of C48D1 (FIG. 1A) was used as a probe in a northern blot of polyA+RNA derived from the wild-type *C. elegans* strain N2. This probe hybridized to a 2.8 kb transcript. Although this transcript is present in 11 different EMS-induced ced-3 mutant strains, subsequent analysis has shown that all 11 tested ced-3 mutant alleles contain mutations in the genomic DNA that encodes this mRNA (see below), thus establishing this RNA as a ced-3 transcript.

The developmental expression pattern of ced-3 was determined by hybridizing a northern blot of RNA from animals at different stages of development with the ced-3 cDNA subclone pJ 118 (see below). The ced-3 transcript was found to be most abundant during embryogenesis, when most programmed cell deaths occur, but was also detected during the L1 through L4 larval stages. It is present in relatively high levels in young adults.

Since ced-3 and ced-4 are both required for programmed cell death in *C. elegans*, and since both are highly expressed during embryonic development (Yuan et al., *Dev.* 116:309–320 (1992), the possibility existed that one of the genes might regulate the mRNA level of the other. Previous studies have revealed that ced-3 does not regulate ced-4 mRNA levels (Yuan et al., *Dev.* 116:309–320 (1992)). To determine if ced-4 regulates ced-3 mRNA levels, a northern blot of RNA prepared from ced-4 mutant embryos was probed with the ced-3 cDNA subclone pJ118. It was found that the amount and size of the ced-3 transcript was normal in the ced-4 mutants n1162, n1416, n1894 and n1920. Thus, ced-4 does not appear to affect the steady-state levels of ced-3 mRNA.

ced-3 cDNA and Genomic Sequences

To isolate ced-3 cDNA clones, ced-3 genomic DNA pJ40 (FIG. 1A) was used as a probe to screen a cDNA library of the *C. elegans* wild-type strain N2 (Kim et al., *Genes & Dev.* 4:357–371 (1990)). The 2.5 kb cDNA clone pJ87 was isolated in this way. On northern blots, pJ87 hybridized to a 2.8 kb transcript and on Southern blots, it hybridized only to bands to which pJ40 hybridizes (data not shown). Thus, pJ87 represents an mRNA transcribed entirely from pJ40 which can rescue the ced-3 mutant phenotype when microinjected into ced-3 mutant animals. To confirm that pJ87 contains the ced-3 cDNA, a frameshift mutation in the SaiI site of pJ40 was made corresponding to the SalI site in the pJ87 cDNA. Constructs containing the frameshift mutation failed to rescue the ced-3 phenotype when microinjected into ced-3 mutant animals (6 transformant lines; data not shown), suggesting that ced-3 activity had been eliminated by mutagenizing a region of genomic DNA that corresponds to the pJ87 cDNA.

The DNA sequence of pJ87 is shown in FIG. 2C. pJ87 contains an insert of 2482 bp with an open reading frame of 503 amino acids. It has 953 bp of 3' untranslated sequence, not all of which is essential for ced-3 expression; genomic constructs that do not contain 380 bp of the 3'-most region (pJ107 and its derivatives, see FIG. 1a) were capable of rescuing ced-3 mutant phenotype. The cDNA ends with a poly-A sequence, suggesting that the complete 3' end of the ced-3 transcript is present.

To confirm the DNA sequence obtained from the ced-3 cDNA and to study the structure of the ced-3 gene, the genomic sequence of the ced-3 gene from the plasmid pJ107 was determined. The insert in pJ107 is 7656 bp in length (FIG. 2 ) (SEQ ID NO: 1).

To determine the location and nature of the 5' end of the ced-3 transcript, a combination of primer extension and amplification using the polymerase chain reaction (PCR) was used. Two primers, Pexi (SEQ ID NO: 63) and Pex2 (SEQ ID NO: 64), were used for primer extension. The Pex1 reaction yielded two major bands, whereas the Pex2 reaction gave one band. The Pex2 band corresponds in size to the smaller band from the Pex1 reaction, and agrees in length with a possible transcript that is trans-spliced to a *C. elegans* splice leader (Bektesh et al., *Genes and Dev.* 2:1277–1283 (1988)) at a consensus splice acceptor at position 2166 of the genomic sequence. The nature of the larger Pex1 band is unclear.

To confirm these observations, wild-type total RNA was reverse-transcribed and then amplified using the primers SL1 (SEQ ID NO: 65) and log-5 (SEQ ID NO: 66) followed by reamplification using the primers SL1 (SEQ ID NO: 65) and oligo10 (SEQ ID NO: 67). A product of the expected length was cloned into the PCR1000 vector (invitrogen) and sequenced. The sequence obtained confirmed the presence of a ced-3 message trans-spliced to SL1 at position 2166 of the genomic sequence. These experiments suggest that a ced-3 transcript is trans-spliced to the *C. elegans* splice leader SL1 (Bektesh et al., *Genes and Dev.* 2:1277–1283 (1988)) at a consensus splice acceptor at position 2166 of the genomic sequence. Based upon these observations, it is concluded that the start codon of ced-3 protein is the methionine encoded at position 2232 of the genomic sequence (SEQ ID NO: 1) and that the ced-3 protein is 503 amino acids (SEQ ID NO: 2) in length.

The predicted ced-3 protein is hydrophilic (256/503 residues are charged or polar) and does not contain any obvious potential trans-membrane domains. One region of the ced-3 protein is rich in serines: from amino acid 107 to amino acid 205, 32 of 99 amino acids are serine residues.

The sequences of 12 EMS-induced ced-3 mutations (Table 1) were determined. Eight are missense mutations, three are nonsense mutations, and one alters a conserved G at the splice acceptor site of intron 6. Interestingly, nine of these 12 mutations alter residues within the last 100 amino acids of the protein, and none occurs within the serine-rich region.

TABLE 1

Sites of mutations in the ced-3 gene

| Allele | Mutation | Nucleotide | Codon | Consequence |
|---|---|---|---|---|
| n717 | G to A | 6297 | | Altered splicing |
| n718 | G to A | 2487 | 65 | G to R |
| n1040 | C to T | 2310 | 27 | L to F |
| n1129 & n164 | C to T | 6434 | 449 | A to V |
| n1163 | C to T | 7020 | 486 | S to F |
| n1165 | C to T | 5940 | 403 | Nonsense |
| n1286 | G to A | 6371 | 428 | Nonsense |
| n1949 | C to T | 6222 | 412 | Nonsense |
| n2426 | G to A | 6535 | 483 | E to K |
| n2430 | C to T | 6485 | 466 | A to V |
| n2433 | G to A | 5757 | 360 | G to S |

Nucleotide and codon positions correspond to the numbering in FIG. 2.

To identify functionally important regions of the ced-3 protein, the genomic sequences of the ced-3 genes from the related nematode species *C. briggsae* and *C. vulgaris* were cloned and sequenced. Sequence comparison of the three ced-3 genes showed that the relatively non-serine-rich regions of the proteins are more conserved than are serine-rich regions (FIG. 3A) (SEQ ID NOs: 35, 36, 37). All 12 EMS-induced ced-3 mutations altered residues that are conserved among the three species. These results suggest that the non-serine-rich region is important for ced-3 function and that the serine rich region is either unimportant or that residues within it are functionally redundant.

ced-3 protein is similar to the mammalian ICE and Nedd-2 proteins

A search of the GenBank, PIR and SWISS-PROT databases revealed that the non-serine-rich regions of the ced-3 protein are similar to human and murine interleukin-1β (IL-1β) convertases (ICE) (FIG. 3A) (SEQ ID NOs: 35–39). ICE is a cysteine protease that cleaves the inactive 31 KD precursor of IL-1β between $Asp^{116}$ and $Ala^{117}$ releasing a carboxy-terminal 153 amino-acid peptide known as mature IL-1β (Kostura et al., *Proc. Natl. Acad. Sci., USA* 86:5227–5231 (1989); Black et al., *FEBS Lett.* 247:386–390 (1989)). The most highly conserved region among the proteins shown in FIG. 3A consists of amino acids 246–360 of the ced-3 protein and amino acids 166–287 of the human ICE protein: 49 residues are identical (43% identity). The active site cysteine of human ICE is located at cysteine 285 (Thornberry et al., *Nature* 356:768–774 (1992)). The five-amino-acid peptide (QACRG) around this active cysteine is the longest conserved peptide among the murine and human ICE proteins and ced-3 proteins from nematodes.

Human ICE is composed of two subunits (p20 and p10) that appear to be proteolytically cleaved from a single proenzyme by the mature enzyme (Thornberry et al., *Nature* 356:768–774 (1992)). Two cleavage sites in the proenzyme, Asp-Ser at positions 103 and 297 of ICE, are conserved in ced-3 (position 131 and 371, respectively).

The C-terminal portion of the ced-3 protein and the p10 subunit of ICE are similar to the protein product of the murine nedd-2 gene, which is highly expressed during embryonic brain development and is down-regulated in adult brain (Kumar et al., *Biochem and Biophy. Res. Comm.* 185:1155–1161 (1992)). The ced-3 and nedd-2 proteins, and the ICE and nedd-2 proteins are 27% identical (FIG. 3A). The nedd-2 protein does not contain the QACRG peptide at the active site of ICE (FIG. 3A). Seven of eight point mutations that were analyzed (n718, n1040, n1129, n1164, n2430, n2426 & n2433) result in alterations of amino acids that are conserved or semi-conserved among the three nematode ced-3 proteins, ICE and the nedd-2 protein. In particular, the mutation, n2433, introduces a Gly to Ser change near the putative active cysteine (FIG. 2, Table 1).

Discussion

The genes ced-3 and ced-4 are the only genes known to be required for programmed cell death to occur in *C. elegans* (Ellis et al., *Cell* 44:817–829 (1986)). Genetic and molecular studies have revealed that the ced-3 gene shares a number of features with ced-4. Like ced-4 (see Yuan et al., *Dev.* 116:309–320 (1992)), ced-3 is not required for viability. It appears to encode a single mRNA which is expressed mostly in the embryo, the stage during which 113 of the 131 programmed cell death occur. Furthermore, just as ced-3 gene function is not required for ced-4 gene expression (Yuan et al., *Dev.* 116:309–320 (1992)), ced-4 gene function is not required for ced-3 gene expression. Thus, these two genes do not appear to control the onset of programmed cell death by acting sequentially in a transcriptional regulatory cascade. Unlike ced-4 (Yuan et al., *Dev. Biol.* 138:33–41 (1992)), ced-3 is expressed at a substantial level in young adults, this observation suggests that ced-3 expression might not be limited to cells undergoing programmed cell death.

The ced-4 protein is novel in sequence, and the only hint concerning its function is that two regions of the protein show some similarity to the EF-hand motif, which binds calcium (Yuan et al., *Dev.* 116:309–320 (1992)). For this reason it has been suggested that the ced-4 protein and hence programmed cell death in *C. elegans* might be regulated by calcium. However, no direct evidence for this hypothesis has yet been obtained. The ced-3 protein similarly contains a region that offers a clue about possible biochemical function: a region of 99 amino acids contains 32 serines. Since serines are common phosphorylation sites (Edelman et al., *Ann. Rev. Biochem.* 56:567–613 (1987)), it is possible that the ced-3 protein and hence programmed cell death in *C. elegans* is regulated by phosphorylation. Phosphorylation has previously been suggested to function in cell death. McConkey et al. (McConkey et al., *J. Immunol.* 145:1227–1230 (1990)) have shown that several agents that can elevate cytosolic cAMP level induce thymocyte death, suggesting that protein kinase A may mediate cell death by phosphorylating certain proteins. Although the precise sequence of the serine-rich region varies among the three Caenorhabditis species studied, the relatively high number of serines is conserved in *C. elegans, C. briggsae* and *C. vulgaris*. None of the mutations in ced-3 affect the serine-rich region. These observations are consistent with the hypothesis that the presence of serines is more important than the precise amino acid sequence within this region.

Much more striking than the presence of the serine-rich region in the ced-3 protein is the similarity between the non-serine-rich regions of ced-3 and the human and murine interleukin-1β converting enzyme (ICE). Human ICE is a substrate-specific protease that cleaves 31 KD prointerleukin-1β at Asp116- Ala$^{117}$ to produce the mature 17.5 kD interleukin-1β (IL-1β). IL-1β is a cytokine involved in mediating a wide range of biological responses including inflammation, septic shock, wound healing, hematopoiesis and growth of certain leukemias (Dinarello, C. A., *Blood* 77:1627–1652 (1991); diGiovine et al., *Today* 11:13 (1990)). A specific inhibitor of ICE, the crmA gene product of Cowpox virus, prevents the proteolytic activation of interleukin-1β (Ray et al., *Cell* 69:597–604 (1992)) and inhibits host inflammatory response (Ray et al., *Cell* 69:597–604 (1992)). Cowpox virus carrying a deleted crmA gene is unable to suppress the inflammatory response of chick embryos, resulting in a reduction in the number of virus-infected cells and less damage to the host (Palumbo et al., *Virology* 171:262–273 (1989)). This observation indicates the importance of ICE in bringing about the inflammatory response.

The carboxy half of the ced-3 protein is the region most similar to ICE. A stretch of 115 residues (amino acids 246–360 of ced-3) is 43% identical between the ced-3 and ICE proteins. This region contains a conserved pentapeptide QACRG (positions 361–365 of the ced-3 protein), which surrounds the active cysteine of ICE. Specific modification of this cysteine in human ICE results in complete loss of activity (Thronberry et al., *Nature* 356:768–774 (1992)). The ced-3 mutation n2433 alters the conserved glycine in this pentapeptide and eliminates ced-3 function, suggesting that this glycine is important for ced-3 activity and might be an integral part of the active site of ICE. Interestingly, the mutations n718 (position 67 of ced-3) and n1040 (position 27 of ced-3) eliminate ced-3 function in vivo yet they contain alterations in conserved residues which are outside of mature P20 subunit of ICE (Thronberry et al., *Nature* 356:768–774 (1992)). Perhaps these residues have a non-catalytic role in both ced-3 and ICE function, e.g. they may maintain a proper conformation for proteolytic activation. The ICE precursor (p45) is proteolytically cleaved at 4 sites of ICE (Asp103, Asp119, Asp297 and Asp316) to generate p24, p20, and p10 (Thronberry et al., *Nature* 356:768–774 (1992)). At least two of the cleavage sites are conserved in ced-3 indicating that the ced-3 product might be processed as well.

The similarity between the ced-3 and ICE proteins strongly suggests that ced-3 might function as a cysteine protease in controlling programmed cell death by proteolytically activating or inactivating a substrate protein. One potential substrate for ced-3 might be the product of the ced-4 gene which contains 6 Asp residues that might be the target of ced-3 protein (Asp25, Asp151, Asp185, Asp192, Asp459 and Asp541). Alternatively, the ced-3 protein might directly cause cell death by proteolytically cleaving certain proteins or subcellular structures that are crucial for cell viability.

ced-3 and ICE are part of a novel protein family. Thornberry et al. suggested that the sequence GDSPG at position 287 of ICE resembles a GX(S/C)XG motif found in serine and cysteine protease active sites (*Nature* 356:768–774 (1992)). However, in the three nematode ced-3 proteins examined, only the first glycine of this sequence is conserved and in mouse ICE the S/C is missing. This suggests that the ced-3/ICE family shares little sequence similarity with known protease families.

The similarity between ced-3 and ICE suggests, not only that ced-3 functions as a cysteine protease, but also that ICE functions in programmed cell death in vertebrates. Consistent with this hypothesis, it has been observed that after murine peritoneal macrophages are stimulated with lipopolysaccharide (LPS) and induced to undergo programmed cell death by exposure to extracellular ATP, mature active IL-1β is released into the culture supernatant. In contrast, when cells are injured by scraping, IL-1β is released exclusively as the inactive proform (Hogoquist et al., *Proc. Natl. Acad. USA* 88:8485–8489 (1991)). These results suggest that ICE is activated upon induction of programmed cell death. ICE transcript has been detected in cells that do not make IL-1β (Cerretti et al., *Science* 256:97–100 (1992)), suggesting that other ICE substrates exist. This suggests that ICE could mediate programmed cell death by cleaving a substrate other than IL-1β.

The carboxy-terminal portions of both the ced-3 protein and the p10 subunit of ICE are similar to the protein encoded by the murine nedd-2 gene, which is expressed preferentially during early embryonic brain development (Kumar et al., *Biochem and Biophy. Res. Comm.* 185:1155–1161 (1992)). Since the nedd-2 protein lacks the QACRG active domain, it might function to regulate an ICE or ICE-like p20 subunits. Interestingly, four ced-3 mutations alter residues conserved between the nedd-2 and ced-3 proteins and nedd-2 gene expression is high during embryonic brain development, when much programmed cell death occurs. These observations suggest that nedd-2 might function in programmed cell death.

The *C. elegans* gene ced-9 protects cells from undergoing programmed cell death by directly or indirectly antagonizing the activities of ced-3 and ced-4 (Hengartner et al., *Nature* 356:494499 (1992)). The vertebrate gene bcl-2 acts in a way functionally similar to ced-9. Overexpression of bcl-2 protects or delays the onset of apoptotic cell death in a variety of vertebrate cell types as well as in *C. elegans* (Vaux et al., *Science* 258:1955–1957 (1992); Nunez et al., *J. Immun.* 144:3602–3610 (1990); Vaux et al., *Science* 258:1955–1957 (1992); Sentman et al., *Cell* 67:879–888 (1992); Strasser et al., *Cell* 67:889–899 (1991)). Thus, if ICE or another ced-3/ICE family member is involved in vertebrate programmed cell death, it is possible that bcl-2 could act by modulating its activity. The fact that bcl-2 is a dominant oncogene (overexpression of bcl-2 as a result of chromosomal translocation occurs in 85% of follicular and 20% of diffuse B cell lymphomas, Fukuhara et al., *Cancer Res.* 39:3119 (1979); Levine et al., *Blood* 66:1414 (1985); Yunis et al., *N. Engl. J. Med.* 316:79–84 (1987)) suggests that ICE and other ced-31ICE family members might be recessive oncogenes. The elimination of such cell death genes would prevent normal cell death and promote malignancy, just as does overexpression of bcl-2.

EXAMPLE 2

The mouse homolog of human ICE from a mouse thymus cDNA library (Stratagene) was cloned by low stringency hybridization using human ICE as a probe. This clone, named "mICE", is identical to the clone isolated by Net et al. (*J. Immun.* 149:3245–3259 (1992)) except that base pair 166 is an A and, as a result, Asn is encoded rather than Asp. This may be a DNA polymorphism since the isolated clone was from a thymus cDNA library (Stratagene) of mouse B6/CBAFIJ (C57Black×CBA) strain while Nett's clone was from a WEH13 cell cDNA library (Stratagene). Subsequent experiments have shown that this DNA polymorphism is in a region which is not essential for ICE function (see below). Thus, the presence of Asn rather than Asp should have no effect on the results obtained.

In order to circumvent the difficulty of establishing a permanent cell line that expresses ICE in high levels, a transient expression system was developed to determine if overexpression of mICE kills cells. mICE cDNA (SEQ ID NO: 41) was fused with the *E. coli* lac-Z gene and the product so produced was placed under the control of chicken β-actin promoter (FIG. 4). The active ICE protein is known to have two subunits, P20 and P10, which are processed from a precursor peptide (Thornberry et al., *Nature* 356:768–774 (1992)). To test the function of the subunits, two additional fusion genes were made, P20/P10-lacZ and P10-lacZ.

The constructs shown in FIG. 4 were transfected into rat 1 cells by calcium phosphate precipitation. 24 hours after transfection, cells were fixed and X-gal was added to begin the color reaction. It was found that, after 3 hours of color development, most blue cells transfected with intact mICE-lacZ or P20/P10-lacZ were round, whereas most blue cells transfected with P10-lacZ or the control lac-Z construct were normal, flat cells (Table 2). Similar results were obtained with another cell line, NG108-15 neuronal cells. Healthy living rat cells are flat and well-attached to plates whereas dying cells are round and often float into the medium.

TABLE 2

Overexpression of mICE causes rat-1 cells to undergo programmed cell death. The constructs shown in FIG. 4 are transiently transfected into rat-1 cells, rat-1 cells expressing bc1-2 (rat-1/bcl-2) or rat-1 cells expressing crmA (rat-1/crmA). 24 hrs after transfection, cells are fixed and stained with X-gal for 3 hrs. The data shown are the percentage of round blue cells among total number of blue cells. The data are collected from at least three different experiments.

| Construct    | rat-1          | rat-1/bc1-2    | rat-1/crmA     |
|--------------|----------------|----------------|----------------|
| pActbGal'    | 1.44 ± 0.18    | 2.22 ± 0.53    | 2.89 ± 0.79    |
| pβActM10Z    | 80.81 ± 2.33   | 9.91 ± 2.08    | 18.83 ± 2.86   |
| pβActM11Z    | 93.33 ± 2.68   | 13.83 ± 4.23   | 24.48 ± 2.78   |
| pβactM19Z    | 2.18 ± 0.54    | —              | —              |
| pβActM12Z    | 2.44 ± 0.98    | 3.33 ± 1.45    | 2.55 ± 0.32    |
| pβact17Z     | 2.70 ± 1.07    | —              | —              |
| pJ485        | 1.32 ± 0.78    | —              | —              |
| pβActced38Z  | 46.73 ± 4.65   | 35.28 ± 1.36   | 34.40 ± 2.38   |
| pβActced37Z  | 3.67 ± 1.39    | —              | —              |

Methods: a: Construction of bcl-2 expressing vector (pJ415): pJ415 was constructed by first inserting 5', the 400 bp BglII/BamHI crmA fragment into the BamHI site of the pBabe/puro vector and then inserting the remaining 1 kb BamHI crmA fragment into the 3' BamHI site in the sense direction. b: Construction of the bcl-2 expressing vector (pJ436): pJ436 was constructed by inserting an EcoRI/SalI bcl-2 fragment into the EcoRI/SalI sites of the pBabe/puro vector. c: Establishing Rat-1 cell lines that overexpress crmA and bcl-2: pJ415 and pJ436 were electroporated into ΨCRE retroviral packaging cells (Danos et al., Proc. Natl. Acad. Sci. U.S.A. 85:6460–6464 (1988)) using a BioRad electroporating apparatus. Supernatant either from overnight transiently transfected ΨCRE cells or from stable lines of ΨCRE cells expressing either crmA or bcl-2 were used to infect Rat-1 cells overnight in the presence of 8 μg/ml of polybrene. Resistant cells were selected using 30 ug/ml puromycin for about 10 days. Resistant colonies were cloned and checked for expression using both Northern and Western blots. Bcl-2 antibodies were from S. J. Korsmeyer and from DAKO. crmA antisera was made by immunizing rabbits with anm E. coli-expressed crmA fusion protein (pJ434). pJ434 was made by inserting an EcoRI/SalI fragment of crmA cDNA into EcoRI/SalI sites of pET21a (Novagen) and fusion protein was expressed in the E. coli BL21 (DE3) strain. Multiple lines that express either bcl-2 or crmA were checked for suppression of mICE induced cell death and all showed similar results.

When cells were stained with rhodamine-coupled anti-β galactosidase antibody and Hoechst dye, it was found that galactosidase-positive round cells had condensed and fragmented nuclei. Such nuclei are indicative of programmed cell death. When observed in an electron microscope, the X-gal reaction product was electron dense, allowing ICE-lacZ expressing cells to be distinguished from other cells (Snyder et al., Cell 68:33–51 (1992)). The chimeric gene expressing cells showed condensed chromatin and membrane blebbing. These are characteristics of cells undergoing programmed cell death (Wyllie, A. H., in Cell Death in Biology and Pathology, 9–34 (1981); Oberhammer et al., Proc. Natl. Acad. Sci. U.S.A. 89:5408–5412 (1992); Jacobson et al., Nature 361:365–369 (1993)). Thus, the results indicate that overexpression of mICE induces programmed cell death and induction depends on both P20 and P10 subunits.

When color development in rat-1 cells transfected with mICE-lacZ or P20/P10-lacZ is allowed to proceed for 24 hours, a greater number of flat cells turn blue. This result indicates that a lower level of ICE activity can be tolerated by cells.

If mICE is a vertebrate homolog of ced-3, then ced-3 might also be expected to cause cell death in vertebrates. This hypothesis was tested by making a ced-3-lacZ fusion construct and examining its ability to cause cell death using the assay as described above. As expected, the expression of ced-3 caused the death of rat cells (Table 2).

If mICE functions in a similar way to ced-3, another prediction is that mutations eliminating ced-3 activity in C. elegans should also eliminate its activity in vertebrates. This hypothesis was tested by mutating the Gly residue in the pentapeptide active domain of ICE, QACRG, to Ser. It was found that this mutation eliminated the ability of both mICE and ced-3 to cause rat cell death (Table 2).

The cowpox gene crmA encodes a 38 kD protein that can specifically inhibit ICE activity (Ray et al., Cell 69:597–604 (1992)). To demonstrate that cell death caused by overexpression of mICE is due to the enzymatic activity of ICE protein, rat-1 cells were infected with a pBabe retroviral construct (Morgenstern et al., Nucl. Acids Res. 18:3587–3596 (1990)) expressing crmA and cell lines were identified which produce a high level of crmA protein. When the mICE-lacZ construct was transfected into these cell lines, it was found that a large percentage of blue cells had a healthy, flat morphology (Table 2). In addition, a point mutation that changes the Cys residue in the active site pentapeptide, QACRG to a Gly eliminates the ability of ICE to cause cell death (construct pβactM17Z, FIG. 4, Table 2). This result indicates that the proteolytic activity of ICE is essential to its ability to kill cells.

In mammals, bcl-2 prevents certain cells from undergoing programmed cell death (Vaux et al., Nature 335:440–442 (1988); Nunez et al., J. Immun. 144:3602–3610 (1990); Strasser et al., Cell 67:889–899 (1991); Sentman et al., Cell 67:879–888 (1991)). Expression of bcl-2 in the nematode C. elegans has been shown to partially prevent programmed cell death. Thus, bcl-2 is functionally similar to the C. elegans ced-9 gene (Vaux et al., Science 258:1955–1957 (1992); Hengartner et al., nature 356:494–499 (1992)).

Figure 5:
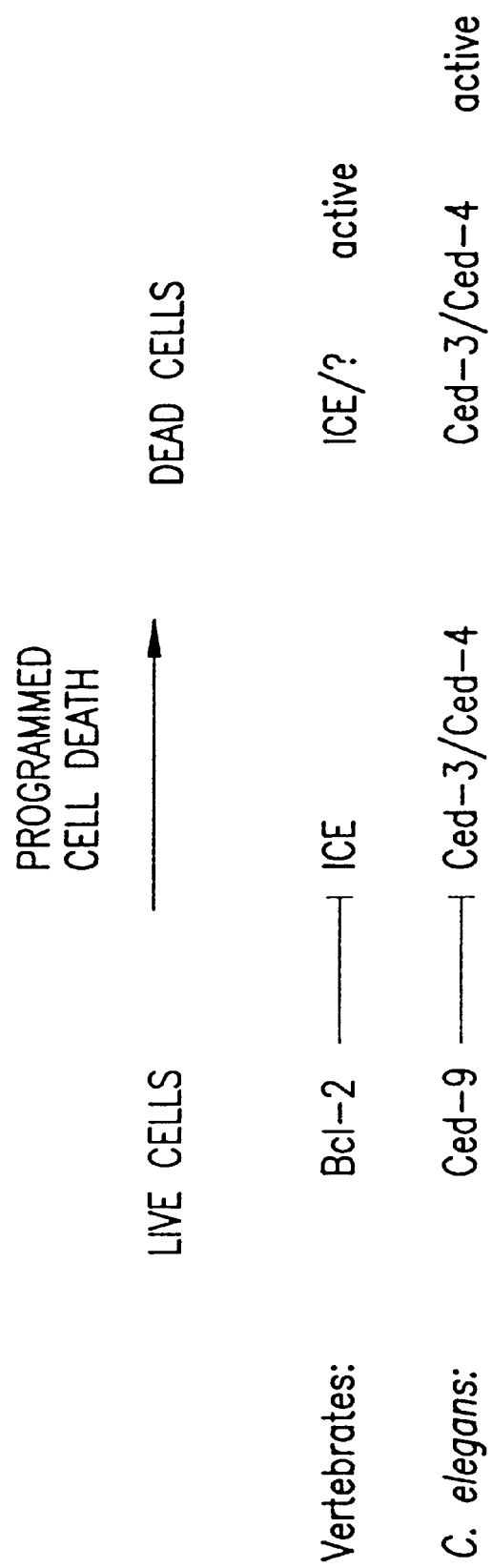

Rat-1 cells were infected with the pBabe retroviral construct expressing bcl-2. Transfection of the mICE-lacZ fusion construct into the cells lines overexpressing bcl-2 showed that a high percentage of blue cells were now healthy (Table 2). Thus, cell death induced by overexpression of mICE can be suppressed by bcl-2. This result indicates that cell death induced by overexpression of mICE is probably caused by activation of a normal programmed cell death mechanism. The amino acid sequence of ICE (SEQ ID NO: 38) is similar to C. elegans ced-3 (SEQ ID NO: 35), which functions in initiating programmed cell death during development. Thus, vertebrate animals may have a genetic pathway of programmed cell death similar to that of C. elegans (FIG. 5).

EXAMPLE 3

As described above, the genes in the ICE/ced-3 family would be expected to function during the initiation of programmed cell death. In order to identify additional members of this gene family, cDNA encoding human interleukin-1β converting enzyme (ICE) was used to screen a mouse thymus cDNA library (Stratagene) under conditions of low stringency. Using this procedure, a new gene was identified and named "mICE2" (see FIG. 6 for the cDNA sequence (SEQ ID NO: 41) and deduced amino acid sequence (SEQ ID NO: 42) of mICE2).

FIGS. 7 and 7A (SEQ ID NOs: 35, 38, 39, 42) shows that the protein encoded by mICE2 contains significant homology to both human and murine interleukin-1β converting enzyme (ICE), as well as to the C. elegans cell death gene, ced-3. The sequence homology indicates that mICE2, like mICE, is a vertebrate cell death gene.

Northern blot analyses showed that, unlike mICE, which is broadly expressed during embryonic development, the expression of mICE2 is restricted to the thymus and placenta, areas where cell death frequently occurs. In addition, it was found that the expression of mICE2 in the thymus can be induced by dexmethosome, an agent which causes thymus regression. It is concluded that mICE2 is a thymus/placenta specific vertebrate cell death gene.

EXAMPLE 4

Extensive cell death occurs in the developing nervous system (Oppenheim, R. W., Ann. Rev. Neurosci. 145:453–501 (1991)). Many neurons die during the period of synapse formation. During this critical period, the survival of neurons depends on the availability of neural trophic factors. The survival of isolated primary neurons in vitro depends critically on the presence of such trophic factors (Davies, A. M., Development 100: 185–208 (1987)). Removal of such factors induces neuronal cell death, usually within 48 hrs. The death of the sympathetic neurons and sensory neurons whose survival depends on one or more members of the nerve growth factor family (nerve growth factor, brain-derived neurotrophic factor, and neurotrophin-3) can be rescued by microinjection of bcl-2 expression vector (Garcia, I., et al., Science 258:302–304 (1993); Allsopp et al., 1993). To examine if the genes in the Ice/ced-3 family may be responsible for neuronal cell death, the ability of crmA to inhibit the death of chicken dorsal root ganglionic neurons induced by NGF removal was examined. It was found that microinjection of an expression vector containing crmA inhibits the death of DRG neurons as effectively as that of a bcl-2 expression vector (Gagliardini, V., et al., *Science* 263:826–828 (1994)). This result demonstrated that the genes in the Ice/ced-3 family may play a key role in regulating neuronal cell death during development.

EXAMPLE 5

Results

Cloning of Ich-1

The protein product of the *C. elegans* cell death gene, ced-3, is homologous to the product of the mouse gene, nedd-2, isolated by Kumar et al. as part of a group of genes that are down regulated during late mouse brain development (Kumar et al., *Biochem. Biophys. Res. Commun.* 185:1155–1161 (1992); Yuan, J., et al., *Cell* 75:641–752 (1993)). The nedd-2 cDNA in the data bank has an open reading frame of 171 amino acids and has long 3' and 5' untranslated regions. This 171-amino acid nedd-2 protein does not contain the active domain, QACRG, of ICE and ced-3 proteins and is homologous only to the P10 subunit of mammalian interleukin-1β converting enzyme (ICE) and the C-terminal part of the ced-3 protein. While analyzing nedd-2 cDNA, the inventors discovered that it contains the sequence that can potentially encode a QACRG pentapeptide, but that the sequence is in another reading frame. The inventors considered the possibility that the nedd-2 cDNA isolated by Kumar et al. contains cloning artifacts and that another nedd-2 transcript could encode a protein homologous to both the P20 and P10 subunits of ICE.

A mouse nedd-2 probe was made by polymerase chain reaction (PCR). Using this mouse nedd-2 probe, three cDNA libraries were screened: a mouse embryonic day 11.5 cDNA library from CLONTECH (one million clones screened), a human fetal brain cDNA library from James Gusella's laboratory (10 million clones screened) and a human fetal brain cDNA library from Stratagene (one million clones screened). The longest positive cDNA clones were obtained from the Stratagene cDNA library. From the Stratagene library, two cDNA species (pBSH37 and pBSH30) were identified that encode two closely related proteins homologous to the mouse nedd-2 protein. The insert of pBSH37 (2.5 kb) encodes a protein that contains amino acid sequence similarities to both the P20 and P10 subunits of ICE and entire ced-3 protein. The insert of pBSH30 (2.2 kb) contains a 61 bp additional sequence one basepair after the sequence encoding QACRG which causes an early termination of protein translation. The Northern blot analysis showed that expression patterns of this human gene are different from the expression of nedd-2 reported by Kumar et al. (see below); thus, the sequences were renamed Ich-$1_L$ (pBSH37) (FIG. 12A) (SEQ ID NOs: 52, 53) and Ich-$1_S$ (SEQ ID NOs: 54, 55) (pBSH30) (FIG. 12B).

Ich-$1_S$ cDNA (SEQ ID NO: 54) differs from Ich-$1_L$ (SEQ ID NO: 52) at two locations. The first difference is at the beginning of the coding region. The putative first methionine of Ich-$1_S$ is 15 amino acids downstream from the first methionine of Ich-$1_L$ because the beginning 35 bp of Ich-$1_S$ is different from Ich-$1_L$ and includes a stop codon (FIG. 12B) (SEQ ID NO: 55). PCR analysis using primers specific to the first 35 bp of Ich-1 and the Ich-$1_S$-specific intron (see below) and human placenta cDNA as template amplified a DNA fragment of predicted size, suggesting that the 35 bp Ich-$1_S$-specific sequence (SEQ ID NO: 54) is not a cloning artifact and is present in the endogenous Ich-$1_S$ mRNA (data not shown).

The second difference is after the active domain QACRG (SEQ ID NO: 68). Ich-$1_S$ begins to differ from Ich-$1_L$ one basepair after the coding region of the active site QACRG. The difference is caused by an insertion of 61 bp sequence, which results in a termination codon 21 amino acids downstream from the insertion. The last two identical basepairs of Ich-$1_S$ (SEQ ID NO: 54) and Ich-$1_L$ (SEQ ID NO: 52) are AG, the general eukaryotic splicing donor consensus sequence (Mount, 1982).

Figure 13:
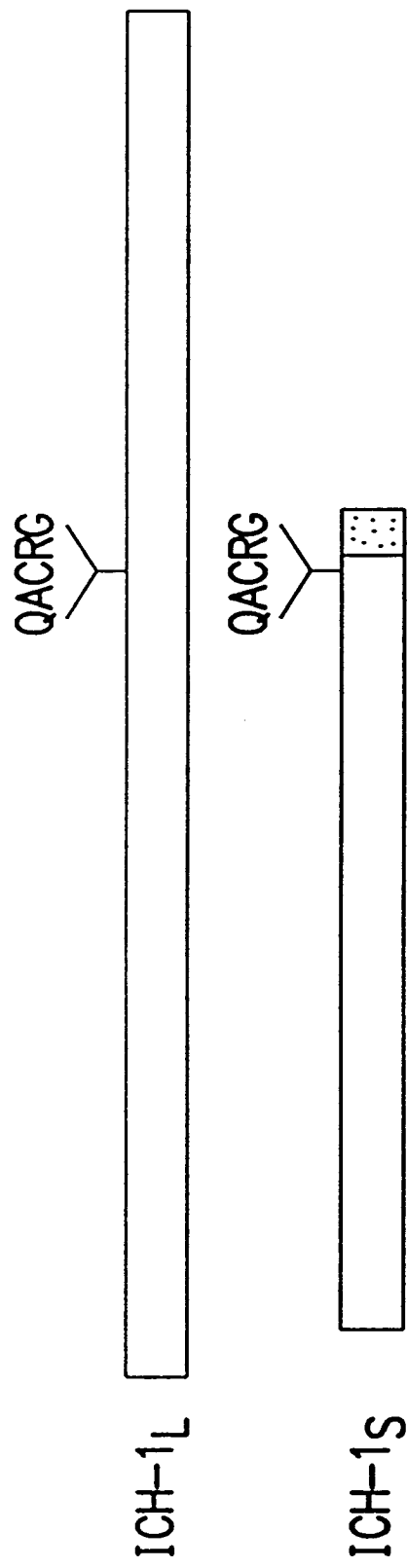

Mouse genomic DNA of Ich-1 was cloned. Analysis of mouse genomic Ich-1 DNA showed that the 61 bp is from an intron, whose sequence is identical between human and mouse Ich-1. This difference between Ich-$1_S$ and Ich-$1_L$ is caused by alternative use of two different 5' splicing donor sequences. A schematic diagram of Ich-$1_L$ and Ich-$1_S$ is shown in FIG. 13. As the result of an insertion of an intron between coding regions, the open reading frame of Ich-$1_S$ is broken into two: the first one encodes a 312 amino acid peptide homologous to the P20 subunit of ICE only and the second encodes a 235 amino acid peptide homologous to a part of the P20 subunit and the P10 subunit of ICE. The second is almost identical to the mouse nedd-2 protein (FIGS. 12 and 13). The data suggest that only the first reading frame is translated in cells (see below).

Ich-$1_L$ protein contains similarities to both ICE (27% identity and 52% similarity) and ced-3 (28% identity and 52% similarity) (FIG. 14) (SEQ ID NOs: 35, 38, 39, 53, 55). Thus, the homology between Ich-1 and ced-3, Ich-1 and ICE is about equal.

Ich-1 is expressed in many tissues and THP-1 cells which express interleukin-1β converting enzyme To characterize the function of Ich-1, the expression pattern of Ich-1 was examined. Northern blot analysis of human fetal heart, brain, lung, liver and kidney tissue using the insert of pBSH37 as a probe hybridizing to both Ich-$1_S$ and Ich-$1_L$ transcripts, revealed that 4 kb Ich-1 mRNA is expressed at low level in about same amount in all tissues examined. When the same Northern blot was analyzed using Ich-$1_S$ 61 bp intron as a probe (which hybridizes to Ich-$1_S$ transcript only), it showed that Ich-$1_S$ was expressed in a larger amount in the embryonic heart and brain than in the lung, liver and kidney. This result suggests that in the embryonic lung, liver and kidney, Ich-$1_L$ is expressed in a larger amount than Ich-$1_S$. In Northern blot analysis of adult RNA with pBSH37 probe, Ich-1 is detected in all the tissues examined: its level is higher in placenta, lung, kidney, pancreas than in heart, brain, liver and skeletal muscle.

To examine whether Ich-1 and ICE are expressed in the same cells, a Northern blot of THP-1 cells was analyzed. Ice expression has been detected in these cells (Thornberry, N. A., et al., *Nature* 356:768–774 (1992); Cerretti, D. P., et al., *Science* 256:97–100 (1992)). The inventors found that Ich-1 can be detected in THP-1 cells. Thus, Ich-1 and ICE are both expressed in THP-1 cells.

Using quantitative RT-PCR, we examined the expression of ICE and Ich-1 in the normal living T-cell hybridoma DO11.10 cells (Haskins, K., et al., *Exp. Med.* 157:1149–1169 (1983)) as well as dying DO11.10 cells in serum-deprived condition. Similar to THP-1 cells, the expression of both ICE and Ich-1 can be detected in DO11.10 cells. Interestingly, the expression levels of both Ich-$1_L$ and ICE appear to increase in dying DO11.10 cells under serum-deprived condition.

Overexpression of Ich-$1_L$ induces rat-1 fibroblast death

To examine the function of Ich-$1_L$, the same transient expression system used for ICE (Miura, M., et al., *Cell* 75:653–660 (1993)) was used to determine if overexpression of Ich-1 induces programmed cell death. The human Ich-$1_L$ cDNA was fused with the *Escherichia coli* lacZ gene and the fused gene was placed under the control of the chicken β-actin promotor (pβactH37Z). This fusion gene was transfected into Rat-1 cells by lipofectamine mediated gene transfer and the expression of the gene was examined using the X-gal reaction. Results showed that most of the blue (X-Gal-positive) Rat-1 cells transfected with pβactH37Z were round. These results are similar to those obtained with cells transfected with mIce-lacZ fusion sequence (Table 1). In contrast, most blue cells transfected with vector alone were flat and healthy. Live Rat-1 cells are flat while dying Rat-1 cells are round and eventually detached from plates. This result suggests that the expression of Ich-$1_L$ induces Rat-1 cells to die.

To examine whether the cell death induced by Ich-1 has any cell type specificity and to compare its effect with that of ICE, mIce-lacZ and Ich-1-lacZ fusion constructs were transfected to HeLa cells, NG108-15 cells, and COS cells. The cell killing effect was assayed as before (Table 1). The results showed that compared to controls, the cytotoxic effect of Ich-1 and ICE exhibit certain cell type specificities. Expression of either Ich-1 or ICE kill Rat-1 cells and HeLa cells effectively (>90% dead). NG108 cells are more resistant to Ich-1 and ICE expression than Rat-1 cells and HeLa cells (68–80% dead). Expression of either Ich-1 or ICE cannot kill COS cells (Table 1).

To examine the nuclear morphology of the cell death induced by Ich-1 expression, the Ich-$1_L$-lacZ Rat-1 cell transfectants were stained with a rhodamine-coupled anti-β-galactosidase antibody and Hoechst dye. Results showed that β-galactosidase-positive round cells have condensed and fragmented nuclei. This is one of the characteristics of cells undergoing apoptosis. Thus, the results suggest that overexpression of Ich-$1_L$, like that of ICE, causes Rat-1 cells to undergo programmed cell death.

To determine if cell death caused by overexpression of Ich-$1_L$ is specific, three mutant Ich-$1_L$ fusion proteins were made: the first was a Ser→Cys 303 in the active site of Ich-1, the second was a Thr→Ala 352 in the putative P10 subunit and the third with a Phe→Leu 212 in the putative P20 subunit (FIG. 14). The Ala 352 in P10 and Leu 212 in P20 are two amino acid residues of ced-3 that are conserved in Ich-1 but not in ICE. The mutant Ich-$1_L$-lacZ fusion constructs were transfected into Rat-1 cells and the expression was examined by X-gal reaction as before.

The analysis revealed that the S303C and T352A mutations eliminated the activity of Ich-1 completely (Table 1) while F212L mutation caused a reduction of cell killing activity of Ich-$1_L$ (Table 1). These results suggest that the ability of Ich-1 to cause cell death depends upon its enzymatic activity and that only some characteristics of ced-3 are conserved in Ich-1.

The cell death induced by overexpression of Ice can be inhibited by bcl-2 and crmA (Miura, M., et al., *Cell* 75:653–660 (1993)). To examine if the cell death induced by expression of Ich-1 could also be inhibited by bcl-2 and crmA, Ich-$1_L$-lacZ fusion construct was transfected into Rat-1 cells that overexpress either bcl-2 or crmA(Miura, M., et al., *Cell* 75:653–660 (1993)). Cell death was assayed as described for Table 1. The results showed that the cell death induced by overexpression of Ich-1 could be inhibited effectively by bcl-2 but only marginally by crmA.

Expression of Ich-$1_S$ protects Rat-1 fibroblast death

Since Ich-$1_S$ contains two open reading frames, it was important to determine which reading frame is functionally translated. Ich-$1_S$ was translated in the presence of $^{35}$S-methionine using in vitro transcribed RNA in a reticulocyte lysate as described in Experimental Procedures. The translated products were run on an SDS-polyacrylamide gel with molecular weight standards. Ich-$1_S$ antisense RNA was used as a negative control. Results showed that only the first reading frame was translated.

Second, *E. coli* lacZ gene was fused to the ends of first (pβactH30Z1) and second (pβactH30Z2) open reading frames. The constructs were separately transfected into Rat-1 cells and the cells were assayed for color using the X-gal reaction. Results showed that only when LacZ gene was fused to the end of the first open reading frame (but not the second open reading frame) could blue cells be detected. Thus, it is most likely that only the first open reading frame of Ich-$1_S$ homolog is used in vivo.

To characterize the function of Ich-$1_S$, the ability of pβactH30Z1 to cause cell death was examined. pβactH30Z1 was transfected in Rat-1 cells and the X-gal reaction was developed as before. The analysis showed that the expression of pβactH30Z1 did not cause cell death (Table 1).

Figure 15:
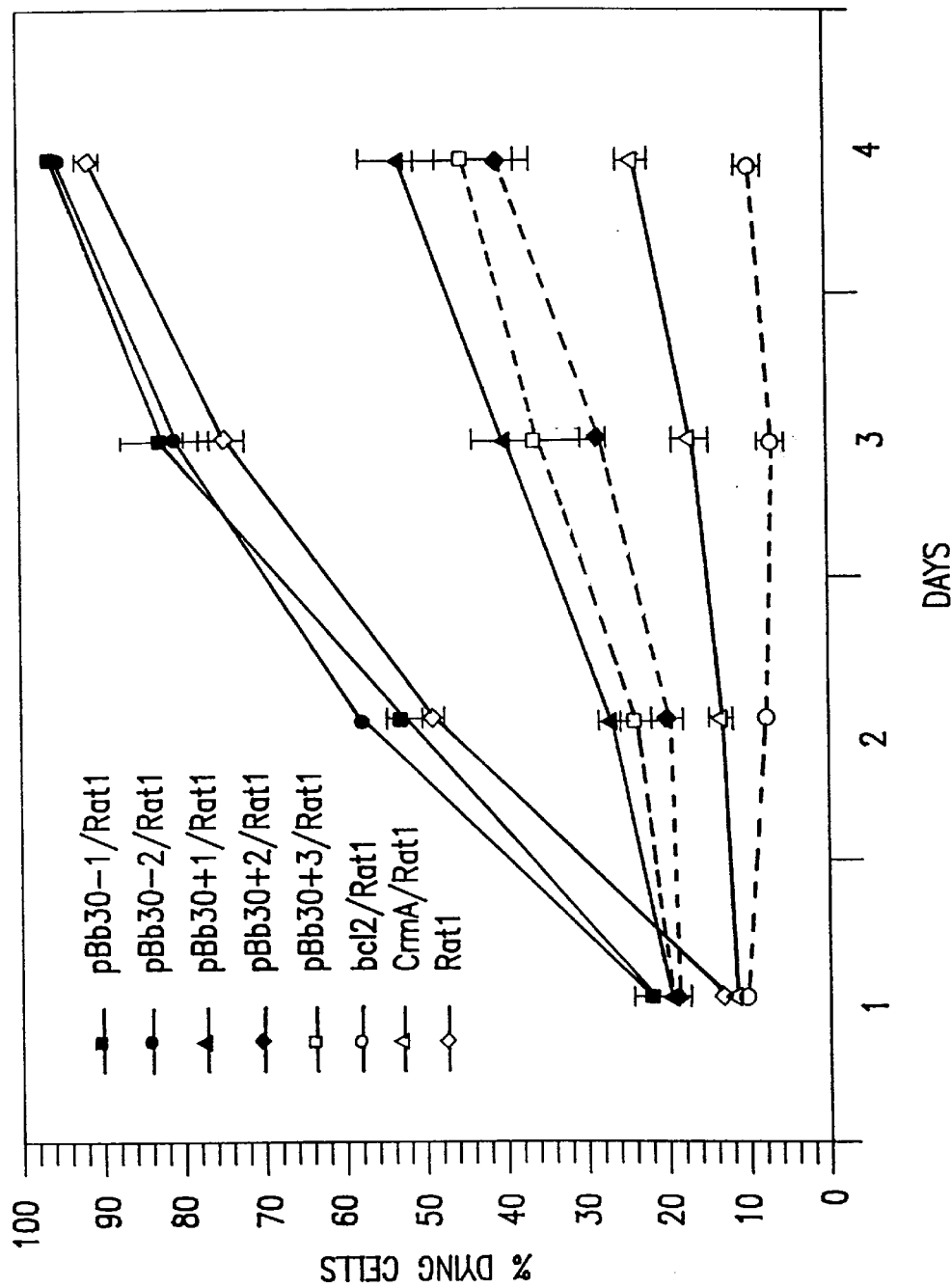

To examine if Ich-$1_S$ has any protective effect against cell death, a stable Rat-1 cell line that express Ich-$1_S$ was established. The cDNA Ich-$1_S$ was cloned into pBabepuro retroviral expression vector (Morgenstern et al., *Nucl. Acids Res.* 18:3587–3596 (1990)) and transfected into Rat-1 cells. The stable transfectants were selected in puromycin and individual clones were assayed for expression of Ich-$1_S$, by Northern blot analysis. The clones that expressed Ich-$1_S$ were used for analysis and the clones that did not express Ich-$1_S$ were used as negative controls together with untransfected Rat-1 cells. When plated in non-confluent density and washed carefully, Rat-1 cells would die in serum-free medium. Under these conditions, Rat-1 cells expressing bcl-2 or crmA were resistant to death (FIG. 15). When the ability of the stable Rat-1 cell lines that express human Ich-$1_S$ was tested under serum-free conditions, it was found that they are more resistant to serum deprivation than parental Rat-1 cells and negative control transfectants not expressing Ich-$1_S$ (FIG. 15). These experiments suggest that Ich-$1_S$ may have the ability to prevent cell death.

Since Ich-$1_S$ may prevent cell death by inhibiting ICh-$1_L$, the inventors examined whether Rat-1 cells express Ich-1. Using mouse Ich-1 cDNA as a probe, an mRNA species predictive of the Ich-1 transcript was detected in Rat-1 cells under low stringency conditions.

Discussion

The isolation and characterization of Ich-1, a mammalian gene belonging to the cell death gene family of Ice/ced-3, has been described. Two distinct Ich-1 mRNA species have been identified (Ich-$1_L$ and Ich-$1_S$). These two cDNAs (SEQ ID NOs: 52, 54) differ in both 5' regions around translation initiation and in the middle region. The difference in the middle is the result of alternative use of two different 5' splicing donor sites.

The Ich-1 gene is expressed at low levels in both embryonic and adult tissues tested. Ich-$1_S$ is expressed at higher levels than Ich-$1_L$ in embryonic heart and brain. The converse is true in embryonic lung, liver and kidney. The expression of both ICE and Ich-1 can be detected in THP-1 cells and DO11. 10 cells. The expression of both ICE and Ich-$1_L$ appear to increase in dying cells under serum deprived conditions. Overexpression of Ich-$1_L$ in rat fibroblast cells caused programmed cell death. This suggests that Ich-1 is also a programmed cell death gene. Overexpression of Ich-$1_S$ did not cause cell death. Stable expression of Ich-$1_S$ prevented Rat-1 cell death induced by serum deprivation. The collective results show that Ich-1 encodes protein products that regulate cell death positively and negatively.

The mouse nedd-2 gene was originally isolated by Kumar et al. (*Biochem. & Biophy. Res. Comm.* 185:1155–1161

(1992)). The nedd-2 gene was identified as having a transcript of 3.7 kb that is abundantly expressed in embryonic day 10 mouse brain and almost undetectable in adult brain. The nedd-2 cDNA isolated contained an open reading frame of 171 amino acids and long 5' and 3' untranslated regions with stop codons in all reading frames. The 171-amino-acid open reading frame is homologous to P10 subunit of ICE and the C-terminal part of ced-3 protein (Yuan, J., et al., *Cell* 75:641–752 (1993)).

In the Northern blot analysis described herein, the Ich-1 expression in human fetal brain is not high compared to other tissues tested (heart, lung, liver and kidney). Part of the difference could be explained by the different developmental stages tested: mouse EIO versus human 20–26 week old fetuses. However, Ich-1 expression can be detected in human adult tissues.

In the studies herein, amplification of the 5' untranslated regions of the mouse nedd-2 cDNA that Kumar reported was not achieved. It is possible that the 5' untranslated region in the Kumar clone was a product of incompletely processed nedd-2 mRNA. Both Ich-1 mRNAs are about 4 kb; since the cDNA clones described herein are 2.5 kb and 2.2 kb for Ich-$1_L$ (SEQ ID NO: 52) and Ich-$1_S$ (SEQ ID NO: 54), respectively, these cDNAs are incomplete. However, since they are fully functional in the assay reported herein, the complete coding regions should be encoded in these two cDNAs.

Ich-1 is a new member of the ICE/ced-3 family of cell death genes. Thus, unlike *C. elegans*, mammals must have multiple members of ICE/ced-3. Ich-1 is even slightly more homologous to ced-3 protein than ICE. The cell death induced by overexpression of Ich-1 was poorly inhibited by crmA. This result is similar to that with ced-3 (Miura, M., et al., *Cell* 75:653–660 (1993)).

The two amino acid residues of ced-3 protein that are conserved in Ich-1 but not in ICE were mutagenized. Results showed that T352A completely eliminated the ability of Ich-1 to cause cell death, despite the fact that the corresponding amino acid in ICE is a Ser, while F212L caused a reduction of the cell killing activity. These data also suggest that Ich-1 may be mechanistically more similar to ced-3 than ICE, and Ich-1 and ICE may have evolved independently from ced-3.

The overexpression of ICE and Ich-1 can kill Rat-1 cells and HeLa cells effectively but NG108 cells only moderately. The possibility that the activity of β-actin promoter is lower in NG108 cells cannot be ruled out. However, an interesting possibility is that NG108 cells express a higher level of ICE and Ich-1 inhibitors. COS cells are completely resistant to the cell killing activity of ICE and Ich-1. COS cells may lack either the activator or the substrates of ICE and Ich-1. This result also suggests that the cytotoxic effects of ICE and Ich-1 have certain specificity and are unlikely to be caused by random cleavage activities of proteases.

Ich-1 can make a protein product that either prevents or causes cell death depending on how the mRNA is processed. Similar regulation has been observed with bcl-x, a bcl-2 related gene (Boise et al., 1993). The bcl-x transcripts can also be processed in two different ways: the larger mRNA, bcl-$x_L$, encodes a bcl-2 related protein product that can inhibit cell death induced by growth factor withdrawal when overexpressed in an IL-3-dependent cell line. Alternative splicing of bcl-x transcripts can generate another smaller transcript. bcl-$x_S$, encodes an internal truncated version of bcl-x protein that inhibits the ability of bcl-2 to enhance the survival of growth factor-deprived cells. Control of the RNA splicing could prove to be an important differential regulatory check point in programmed cell death.

How does Ich-$1_S$ act to prevent cell death? It could act either by inactivating the activator of cell death or by directly inactivating Ich-$1_L$. Since Rat-1 cells appear to express Ich-1, these two possibilities cannot be distinguished at present. In the transient transfection assay, the expression of Ich-$1_L$-lacZ fusion gene and the Ice-lacZ fusion gene kill the stable Ich-$1_S$ expressing cells as efficiently as the control Rat-1 cells (L. Wang, unpublished data). Thus, unlike crmA or bcl-2, the inhibition of cell death by Ich-$1_S$ may be highly dosage-dependent. This is probably why the expression of Ich-$1_S$ provided only partial protection to the cell death of Rat-1 cells induced by serum deprivation: only those cells expressing high levels of Ich-$1_S$ are protected.

crmA has the ability to suppress cell death induced by overexpression of Ich-$1_L$. The amino acid sequence of crmA protein is homologous to the members of the serpin and superfamily (Pickup et al., 1986), which usually inhibit serine proteases by acting as pseudosubstrates. The nature of interaction of ICE and crmA protein is not fully understood but it is likely to be similar to the interaction of other serpin and serine proteases. The inhibition of ICE family members by crmA may depend upon both the affinity and relative concentration of ICEs and crmA protein. The fact that crmA can suppress a certain percentage of cell deaths induced by overexpression of the Ich-$1_L$ suggests that crmA and Ich-1 can bind to each other although their affinity may below. It is possible that when Ich-1 concentration is lower, crmA may be able to suppress a much larger percentage of cell death induced by Ich-1. Microinjection of crmA expression construct can effectively suppress the death of dorsal root ganglia neurons induced by nerve growth factor deprivation (Gagliardini, V., et al., *Science* 263:826–828 (1994)). One or more ICE/ced-3 family members may be responsible for neuronal cell death. When crmA expression construct is microinjected into neurons, the transient concentration of crmA protein may be very high. Thus, it is possible that crmA may be able to suppress multiple members of ICE/ced-3 family under such conditions despite the fact that their affinity to crmA is not very high.

Since the expression of Ich-1 and Ice can be detected in the same cells, the results described herein suggest that multiple members of Ice/ced-3 family may contribute to cell death induced by a single signal. There are three possible ways that Ice and Ich-1 may act to cause cell death (FIG. 16). First, Ich-1 may activate Ice, directly or indirectly, to cause cell death. Second, ICE may inactivate Ich-1, directly or indirectly, to cause cell death. Third, ICE and Ich-1 may act in parallel to cause cell death. In the first scenario, the inhibitor of ICE should inhibit cell death induced by Ich-1. In the second scenario, the inhibitor of Ich-1 should inhibit the cell death induced by ICE. To test this hypothesis, specific inhibitors for each member of ICH are necessary. For the reasons discussed above, it seems likely that crmA can inhibit other members of ICE/ced-3 family as well. These models can be tested directly by "knock-out" mutant mice in which a specific member of the ICE/ced-3 family is mutated.

Experimental Procedures

Cloning and Construction of Plasmids

The mouse nedd-2 cDNA was isolated using embryonic mouse brain cDNA and the primer pairs specific for the 5' and 3' untranslated regions and the coding region. Primers nedd2/1 (SEQ ID NO: 69) (5'-CAACCCTGTAACT-CTTGATT-3') and nedd2/2 (SEQ ID NO: 70) (5'-ACCTCTTTGGAGCTACCAGAA-3') were used for amplifying the 5' untranslated region. Primers nedd2/3 (SEQ ID NO: 71) (5'-CCAGATCTATGCTAACTGTCCAAGTCTA-3') and nedd2/4 (SEQ ID NO: 72) (5'AAGAGCTCCTCCAACAGCAGGAATAGCA-3') were used for amplifying the nedd-2 coding region. Primer nedd2/5 (SEQ ID NO: 73) (AGAA-GCACTTGTCTCTGCTC) and nedd2/6 (SEQ ID NO: 74) (5'TTGGCACCTGATGGCAATAC-3') were used for amplifying the 3' untranslated region. 0.5 kb PCR product of nedd-2 coding region was cloned into pBluescript plasmid vector to be used as a probe (Stratagene).

A human fetal brain cDNA library (Stratagene) was screened with murine nedd-2 cDNA probe at low stringency. The filters were hybridized in 5×SSPE, 30% formamide, 1×Denhardt's solution, 1% SDS at 42° C. overnight and washed in 1×SSPE and 0.5% SDS, twice at room temperature and twice at 45° C. (20 min). The human Ich-$1_S$ (pBSH30) was isolated from the positive clones using a BamHI-SalI fragment of the murine nedd-2 cDNA, a 76 bp fragment which contains the 61 bp intron, as a probe under the same hybridization and washing conditions described above. The phage clones (pBSH37 for Ich-$1_L$, pBSH30 for Ich-$1_S$) were excised in vivo to obtain plasmids by an in vivo excision protocol (Stratagene). To construct expression constructs, PCR was performed using synthetic primers. H1 (SEQ ID NO: 75) (5'-GATATCCGCACAAGGAGCTGA-3') and H2 (SEQ ID NO: 76) (5'-CTATAGGT-GGGAGGGTGTCC-3') were used for Ich-$1_L$ construction. H3 (SEQ ID NO: 77) (5'-GATATCCAGAGGGA-GGGAACGAT-3'), corresponding to sequences in the 5' region of Ich-$1_S$ cDNA and H4 (SEQ ID NO: 78) (5'-GATATCAGAGCAAGAGAGGCGGT-3'), corresponding to the sequences in the 3' region of the first open reading frame (ORF) of Ich-$1_S$ were used for the first ORF of Ich-$1_S$ construction. H3 and H5 (SEQ ID NO: 79) (5'-GATATCGTGGGAGGGTGTCCT-3'), corresponding to the sequences in the 3' region of the second ORF of Ich-$1_S$ were used for the second ORF of Ich-$1_S$ construction. pBSH37 and pBSH30 were used as templates where appropriate. The three PCR products were inserted into the EcoRV site of pBluescript II, and the inserts were isolated by digestion with SmaI and KpnI and cloned into SmaI-KpnI sites of BSLacZ (Miura, M., et al., *Cell* 75:653–660 (1993)). NotI linkers were added to the KpnI site by digesting with KpnI, blunt-ending by T4 polymerase and ligating in the presence of excess NotI linker. These constructs, BSh37Z, BSh30Z1 and BSh30Z2, were digested with NotI and individually cloned into pβactstneoB (which uses chicken β-actin promoter) (Miyawaki, A., et al., *Neuron* 5:11–18 (1990)). The final plasmids were designated pβactH37Z, pβactH30Z1 and pβactH30Z2, respectively. pBabeH30 plasmid, used for establishing stable Rat-1 cell line carrying Ich-$1_S$, was constructed by inserting the full length Ich-$1_S$ cDNA into the SalI site of pBabe/puro vector (Morgenstern, J. P., et al., *Nucl. Acids Res.* 18:3587–3596 (1990)).

To mutagenize Cys 303 to a Ser residue in the active domain of Ich-$1_L$, Ala 352 to a Thr residue in the P10 subunit of Ich-$1_L$ and Leu 212 to a Phe residue in the P20 subunit of Ich-$1_L$, primers containing mutant sites were synthesized as follows:

HM1 (SEQ ID NO: 80) 5'-ATCCAGGCCTCTAGAGG-AGAT-3'

HM2 (SEQ ID NO: 81) 5'-ATCTCCTCTAGAGGCCT-GGAT-3'

HM3 (SEQ ID NO: 82) 5'-TGCGGCTATACGTGCCT-CAAA-3'

HM4 (SEQ ID NO: 83) 5'-TTTGAGGCACGTATAGC-CGCA-3'

HM5 (SEQ ID NO: 84) 5'-CACAGTACTTTCGTCACCCT-3'

HM6 (SEQ ID NO: 85) 5'-AGGGTGACGAAAGTAC-TGTG-3'

(HM1 is corresponding with HM2, HM3 is corresponding with HM4, HM5 is corresponding with HM6). PCRs were performed in two steps. To make the Cys 303 to Ser mutation, in the first round of PCR, the fragments from the N-terminal to mutation site of Ich-$1_L$ and from the mutant site to C-terminal of Ich-$1_L$ were synthesized using two primer pairs, T3 and HM1, HM2 and T7, and PBSH37 as a template. In the second round PCR, the two PCR fragments generated in the first reaction were used as templates and T7 and T3 were used as primers. Two such rounds of PCR generated a full length Ich-$1_L$ mutant. The other two mutations were generated in similar way using T3 and HM3, HM4 and T7 for Ala 352 to Thr mutation, and T3 and HM5, HM6 and T7 for Leu 212 to Phe mutation as primers for first PCR. The PCR products were inserted into the EcoRV site of pBluescript II and sequenced. The mutant cDNA inserts were cloned into expression vectors as described above. The mutated clones were designated pβactH37ZCS, pβactH37ZAT and pβactH37LF.

Cell Culture and Functional Studies

All cells were maintained in Dulbecco's modified Eagle's medium (DMEM) supplemented with 10% fetal calf serum (FCS). The day before transfection, cells were seeded at a density of about $2.5 \times 10^5$ in each of the 6-well dishes. For each well, 0.7–1 μg of LacZ chimeric construct and 10 μg of lipofectamine reagent were used according to a protocol from GIBCO BRL (Gaithersburg, Md.). The cells were incubated for 3 hr in serum-free medium containing DNA and lipofectamine. Then an equal volume of growth medium containing 20% serum was added without removing the transfection mixture and incubation was continued for 24 hr. The expression of the chimeric gene in cells in culture was detected as previously described (Miura, M., et al., *Cell* 75:653–660 (1993)).

To establish Rat-1 cell lines overexpressing Ich-$1_S$, pBabeH30 was transfected into Rat-1 cells using lipofectamine mediated gene transfer. Resistant cells were selected using 3 μg/ml puromycin for about 10 days. Cells were assayed for expression of Ich-$1_S$ by Northern blot analysis. To examine whether Ich-$1_S$ can render Rat-1 cells resistant to apoptosis in the condition of serum deprivation, the Rat-1 cells overexpressing Ich-$1_S$, untransfected control Rat-1 cells, transfected negative control Rat-1 cells and Rat-1 cells overexpressing bcl-2 or crmA were seeded in 24-well dish at $5 \times 10^4$ cells in 500 μl of DMEM containing 10% FCS for 24 hr, and then washed once with serum-free DMEM and transferred into 500 μl of serum-free DMEM. The cells were harvested at daily intervals and stained with 0.4% trypan blue for 5 min. at room temperature. The numbers of dead and living cells were counted using a haemocytometer.

RNA Analysis

The Multiple Tissue Northern (MTN) blots membrane of human fetal and adult tissues (CLONTECH) were probed using human Ich-$1_L$ cDNA or the intron of Ich-$1_S$ cDNA (for fetal tissue) under conditions of 5×SSPE, 10×Denhardt's solution, 50% formamide, 2% SDS, 100 μg/ml salmon sperm DNA at 42° C. for overnight. The blots were washed twice in 2×SSPE, 0.05% SDS at room temperature and twice in 0.1×SSPE, 0. 1% SDS for 20 min. at 50° C. for 20 min each.

In Vitro Transcription and Translation of Ice-ced $3_S$ homolog

To determine which open reading frame of Ich-$1_S$ homolog was expressed, pBluescript plasmid containing Ich-1$_S$ (pBSH30) was linearized at the 3' multiple cloning site with XhoI, purified, and transcribed with T3 RNA polymerase for 2 hr at 37° C. using a protocol from Stratagene. The plasmid was also linearized at the 5' multiple cloning site with NotI, purified, and transcribed with T7 polymerase as an antisense control. The resulting runoff transcripts were extracted with phenol-chloroform and ethanol precipitated. In vitro translation was performed with rabbit reticulocyte lysate (Promega) in the presence of $^{35}$S-methionine for 1 hr. at 30° C. 5 µl lysate was mixed with equal volume of 2×SDS gel loading buffer and subjected to SDS-polyacrylamide gel electrophoresis (12%). The gel was dried and exposed to X-ray film.

TABLE 1

| Expression cassettes | COS | HeLa | NG108-15 | Rat-1 | Rat-1/ bcl-2 | Rat-1/ crmA |
|---|---|---|---|---|---|---|
| pactbβgal' | 1.3 + 0.1(983) | 2.9 ± 0.2(1020) | 4.2 ± 0.2(1535) | 2.9 ± 0.2(1470) | 3.4 ± 0.2(1446) | 3.7 ± 0.1(1459) |
| pβactM10Z | 11.0 ± 0.2(1080) | 93.9 ± 0.3(1003) | 80.2 ± 0.5(1545) | 94.2 ± 1.1(978) | 28.8 ± 0.5(691) | 45.8 ± 1.6(233) |
| pβactH37Z | 8.3 ± 0.9(1053) | 91.4 ± 0.2(1076) | 68.7 ± 1.5(1605) | 92.1 ± 0.3(1079) | 21.5 ± 3.2(1335) | 80.7 ± 0.9(1010) |
| pβactH37ZCS | ND | 5.6 ± 0.1(1039) | 5.9 ± 0.9(707) | 4.1 ± 0.2(1477) | ND | ND |
| pβactH37ZAT | ND | 8.2 ± 0.7(435) | 5.2 ± 0.2(640) | 5.4 ± 0.3(1356) | ND | ND |
| pβactH37ZLF | ND | 75.8 ± 2.2(1404) | 39.9 ± 3.8(1193) | 77.4 ± 0.4(1704) | ND | ND |
| pβactH30Z1 | 1.3 ± 0.2(676) | 0.0 ± 0.0(40) | 0.0 ± 0.0(61) | 1.8 ± 0.4(785) | ND | ND |

Table 1. The constructs as described in the text were transiently transfected into Rat-1 cells, Rat-1 cells expressing human bcl-2, Rat-1 cells expressing cowpox virus crmA gene, HeLa cells, NG108-15 cells and COS cells. Cells were fixed lightly 24 hr after transfection and stained with X-Gal for 3 hr. The data (mean ± SEM) shown are the percentage of round blue cells among total number of blue cells counted.
The number in the parentheses are the number of blue cells counted. The data were collected from at least three independent experiments.
ND = not determined.

What is claimed is:

1. A substantially pure protein comprising the amino acid sequence of humane Ich-1$_L$ (Caspase-2$_L$) as shown in FIG. 12A (SEQ ID NO: 53.

2. A purified protein comprising the amino acid sequence of humane Ich-1$_S$ (Caspase-2$_S$) as shown in FIG. 12B (SEQ ID No: 55).

3. A composition comprising the protein of claim 1, wherein said protein is purified from transformed host cells expressing a DNA sequence encoding the amino acid sequence of humane Ich-1$_L$ (Caspase-2$_L$) as shown in FIG. 12A (SEQ ID No: 53).

4. A composition comprising the protein of claim 2, wherein said protein is purified from transformed host cell expressing a DNA sequence encoding the amino acid sequence of human Ich-1$_S$ (Caspase-2$_S$) as shown in FIG. 12B (SEQ ID No: 55).

5. The composition of claim 3, wherein said host cells are selected from the group consisting of mammalian, insect and yeast cells.

6. The composition of claim 1, wherein said host cells are selected from the group consisting of mammalian, insect and yeast cells.

* * * * *